US006844367B1

(12) United States Patent
Zhu et al.

(10) Patent No.: US 6,844,367 B1
(45) Date of Patent: Jan. 18, 2005

(54) BENZAMIDES AND RELATED INHIBITORS OF FACTOR XA

(75) Inventors: Bing-Yan Zhu, Belmont, CA (US); Penglie Zhang, South San Francisco, CA (US); Lingyan Wang, South San Francisco, CA (US); Wenrong Huang, Cupertino, CA (US); Erick A. Goldman, San Francisco, CA (US); Wenhao Li, South San Francisco, CA (US); Jingmei Zuckett, San Mateo, CA (US); Yonghong Song, Foster City, CA (US); Robert M. Scarborough, Half Moon Bay, CA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 30 days.

(21) Appl. No.: 09/663,420

(22) Filed: Sep. 15, 2000

Related U.S. Application Data

(60) Provisional application No. 60/185,746, filed on Feb. 29, 2000, and provisional application No. 60/154,332, filed on Sep. 17, 1999.

(51) Int. Cl.[7] .................. A61K 31/166; G07C 233/64
(52) U.S. Cl. ....................... 514/620; 564/157
(58) Field of Search ................. 564/157, 309, 564/155; 514/620, 353, 617, 619

(56) References Cited

U.S. PATENT DOCUMENTS

| | | | | |
|---|---|---|---|---|
| 4,514,416 A | 4/1985 | Fujii et al. | ........... | 549/442 |
| 4,912,001 A | 3/1990 | Kouno et al. | ........... | 430/71 |
| 4,971,957 A | 11/1990 | Tsutsumi et al. | ........... | 514/79 |
| 5,569,768 A | 10/1996 | Boyd et al. | ........... | 548/253 |
| 5,576,343 A | 11/1996 | Nagahara et al. | ........... | 514/422 |
| 5,872,115 A | 2/1999 | Binet et al. | ........... | 514/211 |
| 6,140,351 A | 10/2000 | Arnaiz et al. | ........... | 514/336 |

FOREIGN PATENT DOCUMENTS

| | | | |
|---|---|---|---|
| CH | 520657 | * | 3/1972 |
| EP | 077534 | * | 4/1983 |
| EP | 540 051 A1 | | 5/1993 |
| EP | 0 937 711 A | | 8/1999 |
| GB | 2220206 A | * | 1/1990 |
| JP | 59-181257 | | 10/1984 |
| JP | 418675 | | 7/1992 |
| JP | 11302177 | | 11/1999 |
| WO | 96/28427 | | 9/1996 |
| WO | 97/29067 | | 8/1997 |
| WO | 98/06694 | | 2/1998 |
| WO | 98/09630 | | 3/1998 |
| WO | 98/28269 | | 7/1998 |
| WO | 98/28282 | | 7/1998 |
| WO | 98/57934 | | 12/1998 |
| WO | 99/00121 | | 1/1999 |
| WO | 99/00126 | | 1/1999 |
| WO | 99/00127 | | 1/1999 |
| WO | 99/00128 | | 1/1999 |
| WO | 99/32477 | | 7/1999 |
| WO | WO 99/42439 A1 | | 8/1999 |
| WO | 00/34237 | | 6/2000 |
| WO | 00/34238 | | 6/2000 |
| WO | 00/34258 | | 6/2000 |
| WO | 00/34260 | | 6/2000 |
| WO | 00/34261 | | 6/2000 |
| WO | 00/34268 | | 6/2000 |
| WO | 00/34269 | | 6/2000 |
| WO | 00/39118 | | 7/2000 |

OTHER PUBLICATIONS

Michael R. Wiley et al., "Structure–Based Design of Potent, Amidine–Derived Inhibitors of Factor Xa: Evaluation of Selectively, Anticoagulant Activity, and Antithrombotic Activity", *J. Med. Chem.*, vol. 43, pp. 883–899 (2000).

Ying K. Yee et al., "N[2]–Aroylanthranilamide Inhibitors of Human Factor Xa", *J. Med. Chem.*, vol. 43, pp. 873–882 (2000).

David K. Herron et al., "1,2–Dibenzamidobenzene Inhibitors of Human Factor Xa", *J. Med. Chem.*, vol. 43, pp. 859–872 (2000).

W. E. Bachmann et al., "Reduction by Magnesium + Magnesium Halide, XIII. The Reaction Between Epoxy Ketones and Grignard Reagents", *Journal of the American Chemical Society*, vol. 56, No. 7, pp. 1559–1560 (1934).

Takashi Keumi et al., "2–(Trifluoromethylsulfonyloxy)pyridine as a Reagent for the Ketone Synthesis from Carboxylic Acids and Aromatic Hydrocarbons", *Bull. Chem. Soc. Jpn.*, vol. 61, No. 2, pp. 455–459 (1988).

"Dictionary of Organic Compounds, 5th Ed., vol. 5," Chapman and Hall, New York, NY, US (1982), compounds T–00160, T–00161, T–00162, p. 5119 (1982).

Herbert J. Sipe, Jr. et al., "An Improved Synthesis of Aryl Sulfones", *Synthesis*, No. 3, pp. 283–284 (1984).

Richard Kuhn et al., "Addition von Maleinsaure–anhydride an Polyene. (Uber konjugierte Doppelbindungen XIV," *Berichte Der Deutschen Chemischen* Gesellschaft, vol. 63, pp 2662–2679 (1930).

Hey, D., *J. Chem. Soc.* 16, 1513–18 (1967).

El–Zanfally, S., *Egypt. J. Pharm. Sci.* vol. 17(1), 29–34 (1978).

Bing–Yan Zhu et al., *Annual Reports in Medicinal Chemistry*, 35, pp. 83–102 (2000).

John D. Young et al., "Interannular Interactions in Para–Substituted Diphenylmethane Anion Radicals," *J. Am. Chem. Soc.*, 94:25, Dec. 1972.

(List continued on next page.)

*Primary Examiner*—Zinna Northington Davis
(74) *Attorney, Agent, or Firm*—Townsend and Townsend and Crew LLP

(57) ABSTRACT

Novel benzamide compounds, their salts and compositions related thereto having activity against mammalian factor Xa are disclosed. The compounds are useful in vitro or in vivo for preventing or treating coagulation disorders.

10 Claims, No Drawings

OTHER PUBLICATIONS

Hitomi Suzuki et al., "Selective Reduction with Lithium Aluminum Hydride/Diphosphorus Tetraiodide. A Mild Conversion of Aromatic Ketones to Parent Hydrocarbons," *Chemistry Letters*, pp. 909–910, 1983.

St. Goldschmidt and P. Modderman, "Biophenyl Derivatives II. Basic 4–Biphenyl Compounds," *Recueil*, 69, 1109–1117 (1950).

W. F. Cockburn et al., "Molecular Rearrangement of Tertiary Amines. Part I.," *J. Chem. Soc.*, No. 8, pp. 3340–3346 (1960).

Hamilton, A., "Intra– and Intermolecular Hydrogen Bonding Control of Supermolecular Structure," *NATO ASI Ser., Ser. C.* (*Computational Approaches In Supramolecular Chemistry*) vol. 426, 101–8, (1994)

El–Nagdy, S., *Asian J. Chem.* 2(4):368–78 (1990).

Kulkarni, *J. Indain Chem. Soc.* 61(8):720–1 (1984).

* cited by examiner

BENZAMIDES AND RELATED INHIBITORS OF FACTOR XA

CROSS REFERENCE TO RELATED APPLICATIONS

This application claims benefit of priority under 35 U.S.C.§ 119(e) to U.S. Provisional Application No. 60/185,746 filed on Feb. 29, 2000 and U.S. Provisional Application No. 60/154,332 Sep. 17, 1999, each of which is herein incorporated in its entirety by reference.

FIELD OF THE INVENTION

This invention relates to novel compounds which are potent and highly selective inhibitors of isolated factor Xa or when assembled in the prothrombinase complex. These compounds show selectivity for factor Xa versus other proteases of the coagulation (e.g. thrombin, fVIIa, fIXa) or the fibrinolytic cascades (e.g. plasminogen activators, plasmin). In another aspect, the present invention relates to novel monoamidino-containing compounds, their pharmaceutically acceptable salts, and pharmaceutically acceptable compositions thereof which are useful as potent and specific inhibitors of blood coagulation in mammals. In yet another aspect, the invention relates to methods for using these inhibitors as therapeutic agents for disease states in mammals characterized by coagulation disorders.

BACKGROUND OF THE INVENTION

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction or other disruption. Although platelets and blood coagulation are both involved in thrombus formation, certain components of the coagulation cascade are primarily responsible for the amplification or acceleration of the processes involved in platelet aggregation and fibrin deposition.

Thrombin is a key enzyme in the coagulation cascade as well as in hemostasis. Thrombin plays a central role in thrombosis through its ability to catalyze the conversion of fibrinogen into fibrin and through its potent platelet activation activity. Direct or indirect inhibition of thrombin activity has been the focus of a variety of recent anticoagulant strategies as reviewed by Claeson, G., "Synthetic Peptides and Peptidomimetics as Substrates and Inhibitors of Thrombin and Other Proteases in the Blood Coagulation System", Blood Coag. Fibrinol. 5, 411–436 (1994). Several classes of anticoagulants currently used in the clinic directly or indirectly affect thrombin (i.e. heparins, low-molecular weight heparins, heparin-like compounds and coumarins).

A prothrombinase complex, including Factor Xa (a serine protease, the activated form of its Factor X precursor and a member of the calcium ion binding, gamma carboxyglutamyl (Gla)-containing, vitamin K dependent, blood coagulation glycoprotein family), converts the zymogen prothrombin into the active procoagulant thrombin. Unlike thrombin, which acts on a variety of protein substrates as well as at a specific receptor, factor Xa appears to have a single physiologic substrate, namely prothrombin. Since one molecule of factor Xa may be able to generate up to 138 molecules of thrombin (Elodi et al., Thromb. Res. 15, 617–619 (1979)), direct inhibition of factor Xa as a way of indirectly inhibiting the formation of thrombin may be an efficient anticoagulant strategy. Therefore, it has been suggested that compounds which selectively inhibit factor Xa may be useful as in vitro diagnostic agents, or for therapeutic administration in certain thrombotic disorders, see e.g. WO 94/13693.

Polypeptides derived from hematophagous organisms have been reported which are highly potent and specific inhibitors of factor Xa U.S. Pat. No. 4,588,587 describes anticoagulant activity in the saliva of the Mexican leech, *Haementeria officinalis*. A principal component of this saliva was shown to be the polypeptide factor Xa inhibitor, antistasin (ATS), by Nutt, E. et al., "The Amino Acid Sequence of Antistasin, a Potent Inhibitor of Factor Xa Reveals a Repeated Internal Structure", J. Biol. Chem., 263, 10162–10167 (1988). Another potent and highly specific inhibitor of Factor Xa, called tick anticoagulant peptide (TAP), has been isolated from the whole body extract of the soft tick *Ornithidoros moubata*, as reported by Waxman, L., et al., "Tick Anticoagulant Peptide (TAP) is a Novel Inhibitor of Blood Coagulation Factor Xa" Science, 248, 593–596 (1990).

Factor Xa inhibitory compounds which are not large polypeptide-type inhibitors have also been reported including: Tidwell, R. R. et al., "Strategies for Anticoagulation With Synthetic Protease Inhibitors. Xa Inhibitors Versus Thrombin Inhibitors", Thromb. Res., 19, 339–349 (1980); Turner, A. D. et al., "p-Amidino Esters as Irreversible Inhibitors of Factor IXa and Xa and Thrombin", Biochemistry, 25, 4929–4935 (1986); Hitomi, Y. et al., "Inhibitory Effect of New Synthetic Protease Inhibitor (FUT-175) on the Coagulation System", Haemostasis, 15, 164–168 (1985); Sturzebecher, J. et al., "Synthetic Inhibitors of Bovine Factor Xa and Thrombin. Comparison of Their Anticoagulant Efficiency", Thromb. Res., 54, 245–252 (1989); Kam, C. M. et al., "Mechanism Based Isocoumarin Inhibitors for Trypsin and Blood Coagulation Serine Proteases: New Anticoagulants", Biochemistry, 27, 2547–2557 (1988); Hauptmann, J. et al., "Comparison of the Anticoagulant and Antithrombotic Effects of Synthetic Thrombin and Factor Xa Inhibitors", Thromb. Haemost., 63, 220–223 (1990); and the like.

Others have reported Factor Xa inhibitors which are small molecule organic compounds, such as nitrogen containing heterocyclic compounds which have amidino substituent groups, wherein two functional groups of the compounds can bind to Factor Xa at two of its active sites. For example, WO 98/28269 describes pyrazole compounds having a terminal C(=NH)—NH$_2$ group; WO 97/21437 describes benzimidazole compounds substituted by a basic radical which are connected to a naththyl group via a straight or branched chain alkylene, —C(=O) or —S(=O)$_2$ bridging group; WO 99/10316 describes compounds having a 4-phenyl-N-alkylamidino-piperidine and 4-phenoxy-N-alkylamidino-piperidine group connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamide or carboxamide bridging group.

There exists a need for effective therapeutic agents for the regulation of hemostasis, and for the prevention and treatment of thrombus formation and other pathological processes in the vasculature induced by thrombin such as restenosis and inflammation. In particular, there continues to be a need for compounds which selectively inhibit factor Xa or its precursors. Compounds that have different combinations of bridging groups and functional groups than compounds previously discovered are needed, particularly compounds which selectively or preferentially bind to Factor Xa. Compounds with a higher degree of binding to Factor Xa than to thrombin are desired, especially those compounds having good bioavailability and/or solubility.

SUMMARY OF THE INVENTION

The present invention relates to novel compounds which inhibit factor Xa, their pharmaceutically acceptable isomers, salts, hydrates, solvates and prodrug derivatives, and pharmaceutically acceptable compositions thereof which have particular biological properties and are useful as potent and specific inhibitors of blood coagulation in mammals. In another aspect, the invention relates to methods of using these inhibitors as diagnostic reagents or as therapeutic agents for disease states in mammals characterized by undesired thrombosis or which have coagulation disorders, such as in the treatment or prevention of any thrombotically mediated acute coronary or cerebrovascular syndrome, any thrombotic syndrome occurring in the venous system, any coagulopathy, and any thrombotic complications associated with extracorporeal circulation or instrumentation, and for the inhibition of coagulation in biological samples.

In certain embodiments, this invention relates to novel compounds which are potent and highly selective inhibitors of isolated factor Xa when assembled in the prothrombinase complex. These compounds show selectivity for factor Xa versus other proteases of the coagulation cascade (e.g. thrombin, etc.) or the fibrinolytic cascade, and are useful as diagnostic reagents as well as antithrombotic agents.

In one embodiment, the present invention relates to a compound according to the formula:

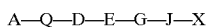

wherein:

A is selected from:
(a) $C_1$-$C_6$-alkyl;
(b) $C_3$-$C_8$-cycloalkyl;
(c) —N($R^1$,$R^2$), N($R^1$,$R^2$)—C(=N$R^3$)—, N($R^1$,$R^2$)—C(=N$R^3$)—N($R^4$)—, $R^1$—C(=N$R^3$)—, $R^1$—C(=N$R^3$)—N($R^4$)—;
(d) phenyl, which is independently substituted with 0–2 R substitutuents;
(e) naphthyl, which is independently substituted with 0–2 R substitutuents; and
a monocyclic or fused bicyclic heterocyclic ring system having from 5 to 10 ring atoms, wherein 1–4 ring atoms of the ring system are selected from N, O and S, and wherein the ring system may be substituted with 0–2 R substitutuents;

R is selected from:
H, halo, —CN, —$CO_2R^1$, —C(=O)—N($R^1$,$R^2$), —($CH_2$)$_m$—$CO_2R^1$, —($CH_2$)$_m$—C(=O)—N($R^1$, $R^2$), —$NO_2$, —$SO_2$N($R^1$,$R^2$), —$SO_2R^1$, —($CH_2$)$_m$N$R^1R^2$, —($CH_2$)$_m$—C(=N$R^3$)—$R^1$, —($CH_2$)$_m$—C(=N$R^3$)—N($R^1$,$R^2$), —($CH_2$)$_m$—N($R^4$)—C(=NR)—N($R^1$,$R^2$), —($CH_2$)$_m$N$R^1$— group appended to a 3 to 6 membered heterocyclic ring containing from 1–4 heteroatoms selected from N, O and S, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$CF_3$, —$OR^2$, and a 5–6 membered heterocyclic system containing from 1–4 heteroatoms selected from N, O and S, wherein from 1–4 hydrogen atoms on the heterocyclic system may be independently replaced with a member selected from the group consisting of halo, —$C_1$-$C_4$-alkyl, —$C_{1-4}$alkyl-CN, —$C_{2-6}$alkenyl, —$C_{2-6}$alkynyl, —$C_{3-8}$cycloalkyl, —$C_{0-4}$alkyl$C_{3-8}$cycloalkyl and —$NO_2$;

m is an integer of 0–2;

$R^1$, $R^2$, $R^3$ and $R^4$ are independently selected from the group consisting of:
H, —$OR^5$, —N(—$R^5$, —$R^6$), —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, $C_{2-6}$alkynyl, —$C_{3-8}$cycloalkyl, —$C_{0-4}$alkyl$C_{3-8}$cycloalkyl, —CN, and —$NO_2$; or,
$R^1$ and $R^2$, or $R^2$ and $R^3$ taken together can form a 3–8 membered cycloalkyl or a heterocyclic ring system, wherein the heterocyclic ring system may have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, $C_1$-$C_4$-alkyl, —CN—$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl and —$NO_2$;

$R^5$ and $R^6$ are independently selected from the group consisting of:
H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, $C_{3-8}$cycloalkyl, —$C_{0-4}$alkyl$C_{3-8}$cycloalkyl, —CN, and —$NO_2$; or
$R^5$ and $R^6$ taken together can form a 3–8 membered cycloalkyl or a heterocyclic ring system, wherein the heterocyclic ring system may have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, —$C_1$-$C_4$-alkyl, —CN—$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl and —$NO_2$;

Q is a member selected from the group consisting of:
a direct link, —$CH_2$—, —C(=O)—, —O—, —N($R^7$)—, —N($R^7$)$CH_2$—, —$CH_2$N($R^7$)—, —C(=N$R^7$)—, —C(—O)—N($R^7$)—, —N($R^7$)—C(=O)—, —S—, —SO—, —$SO_2$—, —$SO_2$—N($R^7$)— and —N($R^7$)$SO_2$—;

$R^7$ is selected from:
H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$ alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$;

D is a direct link or is a member selected from the group consisting of:

(a) phenyl, which is independently substituted with 0–2 $R^{1a}$ substitutuents;
(b) naphthyl, which is independently substituted with 0–2 $R^{1a}$ substitutuents; and
(c) a monocyclic or fused bicyclic heterocyclic ring system having from 5 to 10 ring atoms, wherein 1–4 ring atoms of the ring system are selected from N, O and S, and wherein the ring system may be substituted from 0–2 $R^{1a}$ substitutuents;

$R^{1a}$ is selected from:
halo, $—C_{1-4}$alkyl, $—C_{2-6}$alkenyl, $—C_{2-6}$alkynyl, $—C_{3-8}$ cycloalkyl, $—C_{0-4}$alkyl$C^{3-8}$cycloalkyl, $—CN$, $—NO_2$, $—(CH_2)_nNR^{2a}R^{3a}$, $—(CH_2)_n CO_2R^{2a}$, $—(CH_2)_n CONR^{2a}R^{3a}$, $—SO_2NR^{2a}R^{3a}$, $—SO_2R^{2a}$, $—CF_3$, $—OR^{2a}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $—C_{1-4}$alkyl, $—C_{2-6}$alkenyl, $—C_{2-6}$alkynyl, $—C_{3-8}$ cycloalkyl, $—C_{0-4}$alkyl$C_{3-8}$cycloalkyl, $—CN$ and $—NO_2$;

$R^{2a}$ and $R^{3a}$ are independently selected from the group consisting of:
H, $—C_{1-4}$alkyl, $—C_{2-6}$alkenyl, $—C_{2-6}$alkynyl, $—C_{3-8}$ cycloalkyl, $—C_{0-4}$alkyl$C_{3-8}$cycloalkyl, $—C_{0-4}$ alkylphenyl and $—C_{0-4}$alkylnaphthyl, wherein from 1–4 hydrogen atoms on the ring atoms of the phenyl and naphthyl moieties may be independently replaced with a member selected from the group consisting of halo, $—C_{1-4}$alkyl, $—C_{2-6}$alkenyl, $—C_{2-6}$alkynyl, $—C_{3-8}$cycloalkyl, $—C_{0-4}$alkyl$C_{3-8}$ cycloalkyl, $—CN$ and $—NO_2$;

n is an integer of 0–2;

E is a direct link or a member selected from the group consisting of:
$—C_{1-2}$-alkyl-, $—O—$, $—S—$, $—SO—$, $—SO_2—$, $—C_{0-1}$-alkyl-C(=O), $—C_{0-1}$-alkyl-C(=O)—N(—$R^8$)—$C_{0-1}$-alkyl-, $—C_{0-1}$-alkyl-N(—$R^8$)—C(=O)—$C_{0-1}$-alkyl-, $—N(—R^8)—C(=O)—N(—R^8)—$ and $—C_{0-1}$-alkyl-N(—$R^8$)—;

$R^8$ is a member selected from the group consisting of:
H; $—C_{1-4}$-alkyl; $—C_{0-4}$-alkylaryl; $—C_{0-4}$-alkylheteroaryl; $—C_{1-4}$-alkyl-C(=O)—OH, $—C_{1-4}$-alkyl-C(=O)—O—$C_{1-4}$-alkyl, and $—C_{1-4}$-alkyl-C(=O)—N(—$R^{2b}$, —$R^{3b}$);

$R^{2b}$ and $R^{3b}$ are each a member independently selected from the group consisting of:
H, $—C_{1-4}$-alkyl, $—C_{0-4}$-alkyl-aryl; $—C_{0-4}$-alkyl-heterocyclic group, and $R^{2b}$ and $R^{3b}$ together with the N atom to which they are attached can form a 5–8 membered heterocyclic ring containing 1–4 heteroatoms selected from N, O and S, wherein the heterocyclic ring may be substituted with 0–2 $R^{1c}$ groups;

$R^{1c}$ is a member selected from the group consisting of:
Halo; $—C_{1-4}$-alkyl; $—CN$, $—NO_2$; $—C(=O)—N(—R^{2c}, —R^{3c})$; $—C(=O)—OR^{2c}$; $(CH_2)_q—N(R^{2c}, 13 R^{3c})$; $—SO_2—N(—R^{2c}, —R^{3c})$; $—SO_2R^{2c}$; $—CF_3$ and $—(CH_2)_q—OR^{2c}$;

$R^{2c}$ and $R^{3c}$ are each independently a member selected from the group consisting of:
H; $—C_{1-4}$-alkyl and $—C_{1-4}$-alkyl-aryl;

q is an integer of 0–2;

G is a member selected from the group consisting of:
(a) $C_2$-alkenyl or $C_{3-8}$-cycloalkenyl, wherein the alkenyl and cycloalkenyl attachment points are the alkenyl carbon atoms and wherein the $—C_2$-alkenyl or $—C_{3-8}$-cycloalkenyl are substituted with 0–4 $R^{1d}$ groups;
(b) a phenylene group wherein the ring carbon atoms of the phenylene group are substituted with 0–4 $R^{1d}$ groups;
(c) a 3–8 membered a saturated, partially unsaturated or aromatic monocyclic-heterocyclic ring system containing 1–4 heteroatoms selected from N, O and S, wherein 0–2 ring atoms of the heterocyclic ring may be substituted with 0–4 $R^{1d}$ groups; and,
(d) an 8–10 membered fused heterocyclic bicyclic ring system, containing 1–4 heteroatoms selected from N, O and S, wherein 0–2 ring atoms of the fused bicyclic ring system may be substituted with 0–4 $R^{1d}$ groups;

$R^{1d}$ is a member selected from the group consisting of:
H, halo; $C_{1-6}$-alkyl, carbocyclic aryl, $—CN$; $—NO_2$; $—(CH_2)_{0-6}—NR^{2d3d}$; $SO_2NR^{2d}R^{3d}$; $—SO_2R^{2d}$; $—CF_3$; $—(CH_2)_{0-6}—OR^{2d}$; $—O—(CH_2)_{1-6}OR^{2d}$; $—O—(CH_2)_{1-6}—C(=O)—O—R^{2d}$; $—O—(CH_2)_{1-6}—C(=O)—N(R^{2d},R^{3d})$; $—N(R^{5a})—(CH_2)_{1-6}—OR^{2d}$; $—N(R^{5a})—(CH_2)_{1-6}—N(R^{2d}, R^{3d})$; $—C(=O)—N(R^{2d},R^{3d})$; $—N(R^{5a})—(CH_2)_{1-6}—C(=O)—N(R^{2d},R^{3d})$; $—N(—(CH_2)_{1-6}—OR^{2d})_2$; $—N(R^{5a})—(CH_2)1-6—OR^{2d}$; $—N(R^{5a})—C(=O)—R^{2d}$; $—N(R^{5a})—SO_2—R^{2d}$; $—(CH_2)_{0-6}—C(=O)—O—R^{2d}$; $—(CH_2)_{0-6}—C(=O)—N(R^{2d},R^{3d})$; $—(CH_2)_{0-6}—C(=NR^{2d})—N(R^{3d},R^{4d}$; $—(CH_2)_{0.6}—N(R^{5a})C(=NR^{2d}—N(R^{3d}R^{4d})$; a $—(CH_2)_{0-6}—N(R^{3d})C_{5-6}$ membered saturated, partially unsaturated or aromatic heterocyclic ring containing 1–4 heteroatoms selected from N, O and S, and a $—(CH_2)_{0-6}$-5–6 membered saturated, partially unsaturated or aromatic heterocyclic ring containing 1–4 heteroatoms selected from N, O and S;

$R^{5a}$, $R^{2d}$, $R^{3d}$ and $R^{4d}$ are each independently a member selected from the group consisting of:
H, $C_{1-6}$-alkyl and $C_{1-6}$-alkylaryl, $—CN$; $—NO_2$; carbocylic aryl, $—CN$; $—NO_2$; or
$R^{2d}$ and $R^{3d}$ taken together with the N atoms they are independently attached form a 5–7 membered saturated, partially unsaturated or aromatic heterocyclic ring; or
$R^{3d}$ and $R^{4d}$ taken together with the N atom to which they are attached form a 5–8 membered saturated, partially unsaturated or aromatic heterocyclic ring containing 1–4 heteroatoms selected from N, O and S;

J is a direct link or is a member selected from the group consisting of:
$—N(—R^9)—C(=O)—$; $—C(=O)—N(—R^9)—$; $—O—$; $—S—$; $—SO—$; $—SO_2—$; $—CH_2—$; $—N(—R^9)—$; and $—N(—R^9)—SO_2—$;

$R^9$ is a member selected from the group consisting of:
H; $—C_{1-4}$-alkyl; $—C_{0-4}$-alkyl-carbocyclic aryl; $—(CH_2)_{0-4}$-5–6 membered saturated, partially unsaturated or aromatic heterocyclic ring containing 1–4 heteroatoms selected from N, O and S; $—(CH_2)_{1-6}—C(=O)—O—C_{1-4}$-alkyl; and $—CH_2)_{1-6}—C(=O)—N(R^{6a}, R^{6b})$;

$R^{6a}$ and $R^{6b}$ are each a member independently selected from the group consisting of:
H and $—C_{1-6}$-alkyl;

X is a member selected from the group consisting of:
(a) phenyl substituted with 0–3 $R^{1e}$ groups;

(b) naphthyl substituted with 0–3 $R^{1e}$ groups and (c) a 6-membered aromatic heterocyclic ring system containing 1–3 N atoms and having 0–3 ring atoms substituted with 0–3 $R^{1e}$ groups; and (d) an 8–10 membered fused aromatic heterocyclic bicyclic ring system containing 1–4 heteroatoms selected from, N, O and S and 0–3 ring atoms of the fused heterocyclic bicyclic ring system are substituted with 0–3 $R^{1e}$ groups;

$R^{1e}$ is a member independently selected from the group consisting of:

Halo; $CF_3$; —$C_{1-4}$-alkyl; carbocyclic aryl; —$C_{0-2}$-alkyl-CN; —O—$R^{2e}$; —$C_{0-2}$-alkyl-C(=O)—O—$R^{2e}$; —$C_{0-2}$-alkyl-C(=O)—N($R^{2e}$,$R^{3e}$); —$C_{0-2}$-alkyl-$NO_2$; —$C_{0-2}$-alkyl-N($R^{2e}$,$R^3$); —$C_{0-2}$-alkyl-$SO_2$—N($R^{2e}$,$R^{3e}$); —$C_{0-2}$-alkyl-$SO_2$—$R^2$—$R^{2e}$; trihaloalkyl; —O—$C_{0-2}$-alkyl-O—$R^{2e}$; —$C_{0-2}$-alkyl-O—$R^{2e}$; —O—$C_{1-4}$-alkyl-C(=O)—N($R^{2e}$, $R^{3e}$); —O—$C_{1-4}$-alkyl-C(=O)—O—$R^{2e}$; —$C_{0-2}$-alkyl-N($R^{2e}$)—C(=O)—$R^{3e}$; —$C_{0-2}$-alkyl-N(—$R^{2e}$)—$SO_2$—$R^{3e}$; —$CH_2$—N($R^{2e}$)—C(=O)—$R^{3e}$; —$CH_2$—N($R^{2e}$)—$SO_2$—$R^{3e}$; —$(CH_2)_{0-6}$—$NR^{2e}R^{3e}$; —C(=O)—N($R^{2e}$,$R^{3e}$); —N(—$(CH_2)_{1-6}$—$OR^{1O}$)—$(CH_2)_{1-6}$—$OR^{2e}$)_2; —N($R^{1O}$)—$(CH_2)_{1-6}$—$OR^{2e}$; —N($R^{10}$)—C(=O)—$R^{2e}$; —N($R^{10}$)—$SO_2$—$R^{2e}$; —C(=N($R^{10}$))—N($R^{2e}$,$R^{3e}$); and a —$(CH_2)$0-6-5-6 membered saturated, partially unsaturated or aromatic heterocyclic ring containing 1–4 heteroatoms selected from N, O and S;

$R^{10}$, $R^{2e}$ and $R^{3e}$ are each independently a member selected from the group consisting of:

H; —$C_{1-4}$-alkyl; —$C_{0-2}$-alkyl-O—$R^{1g}$; —$C_{0-2}$-alkyl-N(—$R^{1g}$, —$R^{2g}$); —$C_{1-4}$-alkyl-carbocyclic aryl; —$C_{1-4}$-alkyl-heterocyclic; and $R^{10}$ and $R^{2e}$, or $R^{2e}$ and $R^{3e}$ together with the N atom to which they are attached can form 5–8 membered heterocyclic ring containing 1–4 heteroatoms selected from N, O and S which can be substituted with 0–2 $R^{1g}$ groups;

$R^{1g}$ and $R^{2g}$ are independently a member selected from the group of:

H; halo; —$C_{1-4}$-alkyl, a carbocyclic aryl group; a saturated, partially unsaturated or aromatic heterocyclic group; —CN; —C(=O)—N($R^{3g}$)$R^{4g}$; —C(=O)—$OR^{3g}$; —$NO_2$; —$(CH_2)_p$—$NR^{3g}R^{4g}$; —$SO_2NR^{3g}R^{4g}$; —$SO_2R^{3g}$; —$CF_3$; and —$(CH_2)_p$$OR^{3g}$;

p is an integer of 0–2;

$R^{3g}$ and $R^{4g}$ are each independently selected from the group consisting of:

H; $C_{1-4}$-alkyl and —$C_{0-4}$-alkyl-carbocyclic aryl;

and all pharmaceutically acceptable isomers, salts, hydrates, solvates and prodrug derivatives thereof.

In certain aspects of this invention, compounds are provided which are useful as diagnostic reagents. In another aspect, the present invention includes pharmaceutical compositions comprising a pharmaceutically effective amount of the compounds of this invention and a pharmaceutically acceptable carrier. In yet another aspect, the present invention includes methods comprising using the above compounds and pharmaceutical compositions for preventing or treating disease states characterized by undesired thrombosis or disorders of the blood coagulation process in mammals, or for preventing coagulation in stored blood products and samples. Optionally, the methods of this invention comprise administering the pharmaceutical composition in combination with an additional therapeutic agent such as an antithrombotic and/or a thrombolytic agent and/or an anticoagulant.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified alkenyl and alkinyl each refer to radicals having from 2–12 carbon atoms.

The term "alkyl" refers to saturated aliphatic groups including straight-chain, branched-chain and cyclic groups having the number of carbon atoms specified, or if no number is specified, having up to 12 carbon atoms. The term "cycloalkyl" as used herein refers to a mono-, bi-, or tricyclic aliphatic ring having 3 to 14 carbon atoms and preferably 3 to 7 carbon atoms.

As used herein, the terms "carbocyclic ring structure" and "$C_{3-16}$ carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is aromatic ring ("aryl") having six ring atoms; a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), 2.2.2] bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from loweralkoxy, loweralkyl, loweralkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, napthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

As used herein, the term "heterocyclic ring" or "heterocyclic ring system" is intended to mean a substituted or unsubstituted member selected from the group consisting of stable monocyclic ring having from 5–7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as non-aromatic rings which can be saturated, partially saturated or fully saturated non-aromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom, Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be replaced by one or more of the indicated substituents if such replacement (s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more that 1 O or S ring atoms in the same ring of a given heterocyclic ring structure.

Examples of monocylic and bicyclic heterocylic ring systems, in alphabetical order, are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocylic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The term "methylene" refers to —$CH_2$—.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

Preferred Embodiments

In a preferred embodiment the present invention provides a compound according to the formula:

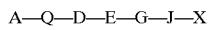

wherein:

A is selected from:
(a) $C_1$–$C_6$-alkyl;
(b) $C_3$–$C_8$-cycloalkyl;
(c) —N($R^1$,$R^2$), N($R^1$,$R^2$)—C(=N$R^3$)—, N($R^1$,$R^2$)—C(=N$R^3$)—N($R^4$)—, $R^1$—C(=N$R^3$)—, $R^1$—C(=N$R^3$)—N($R^4$)—;
(d) phenyl, which is independently substituted with 0–2 R substitutuents;
(e) naphthyl, which is independently substituted with 0–2 R substitutuents; and
(f) a monocyclic or fused bicyclic heterocyclic ring system having from 5 to 10 ring atoms, wherein 1–4 ring atoms of the ring system are selected from N, O and S, and wherein the ring system may be substituted with 0–2 R substitutuents;

R is selected from:
H, halo, —CN, —$CO_2R^1$, —C(=O)—N($R^1$,$R^2$, —$(CH_2)_m$—$CO_2R^1$, —$(CH_2)_m$—C(=O)—N($R^1$,$R^2$), —$NO_2$, —$SO_2N(R^1,R^2)$, —$SO_2R^1$, —$(CH_2)_m$N$R^1R^2$, —$(CH_2)_m$—C(=N$R^3$)—$R^1$, —$(CH_2)_m$—C(=N$R^3$)—N($R^1,R^2$), —$(CH_2)_m$—N($R^4$)—C(=N$R^3$)—N($R^1,R^2$), —$(CH_2)_m$N$R^1$—$C_{3-6}$heterocyclics, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —$CF_3$, —$OR^2$, and a 5–6 membered heterocyclic system containing from 1–4 heteroatoms selected from N, O and S, wherein from 1–4 hydrogen atoms on the heterocyclic system may be independently replaced with a member selected from the group consisting of halo, $C_1$–$C_4$-alkyl, CN-$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl and —$NO_2$;

m is an integer of 0–2;

$R^1$, $R^2$, $R^3$ and $R^4$ are independently selected from the group consisting of:
H, —$OR^5$, —N(—$R^5$, —$R^6$), —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$; or $R^1$ and $R^2$, or $R^2$ and $R^3$ taken together can form a 3–8 membered cycloalkyl or a heterocyclic ring system, wherein the heterocyclic ring system may have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, $C_1$–$C_4$-alkyl, —CN—$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl and —$NO_2$;

$R^5$ and $R^6$ are independently selected from the group consisting of:
H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$ alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$ cycloalkyl, —CN, and —$NO_2$; or $R^5$ and $R^6$ taken together can form a 3–8 membered cycloalkyl or a heterocyclic ring system, wherein the heterocyclic ring system may have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, $C_1$–$C_4$-alkyl, —CN—$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl and —$NO_2$;

Q is a member selected from the group consisting of:
a direct link, —$CH_2$—, —C(=O)—, —O—, —N($R^7$)—, —N($R^7$)($CH_2$)—, —$CH_2$N($R^7$)—, —C(=N$R^7$)—, —C(=O)—N($R^7$)—, —N($R^7$)—C(=O)—, —S—, —SO—, —$SO_2$—, —$SO_2$—N($R^7$)— and —N($R^7$)—$SO_2$—;

$R^7$ is selected from:
H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$ alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$ cycloalkyl, —CN, and —$NO_2$;

D is a direct link or is a member selected from the group consisting of:
(a) phenyl, which is independently substituted with 0–2 $R^{1a}$ substitutuents;
(b) naphthyl, which is independently substituted with 0–2 $R^{1a}$ substitutuents; and
(c) a monocyclic or fused bicyclic heterocyclic ring system having from 5 to 10 ring atoms, wherein 1–4 ring atoms of the ring system are selected from N, O and S, and wherein the ring system may be substituted from 0–2 $R^{1a}$ substitutuents;

$R^{1a}$ is selected from:
halo, —$C_{1-4}$alkyl, —$C_{2-6}$alkenyl, —$C_{2-6}$alkynyl, —$C_{3-8}$ cycloalkyl, —$C_{0-4}$alkyl$C_{3-8}$cycloalkyl, —CN, —$NO_2$, —$(CH_2)NR^{2a}NR^{3a}$, —$(CH_2)_n CO_2R^{2a}$, —$(CH_2)_nCONR^{2a}R^{3a}$, —$SO_2NR^{2a}R^{3a}$, —$SO_2R^{2a}$, —$CF_3$, —$OR^{2a}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, —$C_{1-4}$alkyl, —$C_{2-6}$alkenyl, —$C_{2-6}$alkynyl, —$C_{3-8}$ cycloalkyl, —$C_{0-4}$alkyl$C_{3-8}$cycloalkyl, —CN and —$NO_2$;

$R^{2a}$ and $R^{3a}$ are independently selected from the group consisting of:
H, —$C_{1-4}$alkyl, —$C_{2-6}$alkenyl, —$C_{2-6}$alkynyl, —$C_{3-8}$ cycloalkyl, —$C_{0-4}$alkyl$C_{3-8}$cycloalkyl, —$C_{0-4}$ alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN and —$NO_2$;

n is an integer of 0–2;

E is a direct link or a member selected from the group consisting of:
—$C_{1-2}$-alkyl-, —O—, —S—, —SO—, —$SO_2$—, —$C_{0-1}$-alkyl-C(=O), —$C_{0-1}$-alkyl-C(=O)—N(—$R^8$)—$C_{0-1}$-alkyl-, —$C_{0-1}$-alkyl-N(—$R^8$)—C(=O)—$C_{0-1}$-alkyl-, —N(—$R^8$)—C(=O)—N(—$R^8$)— and —$C_{0-1}$-alkyl-N(—$R^8$)—;

$R^8$ is a member selected from the group consisting of:
H; —$C_{1-4}$-alkyl; —$C_{0-4}$-alkylaryl; —$C_{0-4}$-alkylheteroaryl; —$C_{1-4}$-alkyl-C(=O)—OH, —$C_{1-4}$-alkyl-C(=O)—O—$C_{1-4}$-alkyl, and —$C_{1-4}$-alkyl-C(=O)—N(—$R^{2b}$, —$R^{3b}$);

$R^{2b}$ and $R^{3b}$ are each a member independently selected from the group consisting of:
H, —$C_{1-4}$-alkyl, —$C_{0-4}$-alkyl-aryl; —$C_{0-4}$-alkyl-heterocyclic group, and $R^{2b}$ and $R^{3b}$ together with the N atom to which they are attached can form a 5–8 membered heterocyclic ring containing 1–4 heteroatoms selected from N, O and S, wherein the heterocyclic ring may be substituted with 0–2 $R^{1c}$ groups;

$R^{1c}$ is a member selected from the group consisting of:
Halo; —$C_{1-4}$-alkyl; —CN, —$NO_2$; —C(=O)—N(—$R^{2c}$,—$R^{3c}$; —C(=O)—$OR^{2c}$; —$(CH_2)_q$—N(—$R^{2c}$, —$R^{3c}$); —$SO_2$—N(—$R^{2c}$, —$R^{3c}$); —$SO_2R^{2c}$; —$CF_3$ and $CH_2)_q$—$OR^{2c}$;

$R^{2c}$ and $R^{3c}$ are each independently a member selected from the group consisting of:
H; —$C_{1-4}$-alkyl and —$C_{1-4}$-alkyl-aryl;

q is an integer of 0–2;

G is a member selected from the group consisting of:
(a) $C_2$-alkenyl or $C_{3-8}$-cycloalkenyl, wherein the alkenyl and cycloalkenyl attachment points are the alkenyl carbon atoms and wherein $C_2$-alkenyl or $C_{3-8}$-cycloalkenyl are substituted with 0–4 $R^{1d}$ groups;
(b) a phenylene group wherein the ring carbon atoms of the phenylene group are substituted with 0–4 $R^{1d}$ groups;
(c) a 3–8 membered a saturated, partially unsaturated or aromatic monocyclic-heterocyclic ring system containing 1–4 heteroatoms selected from N, O and S, wherein 0–4 ring atoms of the heterocyclic ring may be substituted with 0–4 $R^{1d}$ groups; and,
(d) an 8–10 membered fused heterocyclic bicyclic ring system, containing 1–4 heteroatoms selected from N, O, and S, wherein 0–4 ring atoms of the fused bicyclic ring system may be substituted with 0–4 $R^{1d}$ groups;

$R^{1d}$ is a member selected from the group consisting of:
H, halo; $C_{1-6}$-alkyl, carbocylic aryl, —CN; —$NO_2$; —$(CH_2)_{0-6}$—$NR^{2d}R^{3d}$; —$SO_2NR^{2d}R^{3d}$; —$SO_2R^{2d}$; —$CF_3$; —$(CH_2)_{0-6}$—O—$OR^{2d}$; —O—$(CH_2)_{1-6}$ $OR^{2d}$; —O—$(CH_2)_{1-6}$—C(=O)—O—$R^{2d}$; —O—$(CH_2)_{1-6}$—C(=O)—N($R^{2d}$,$R^{3d}$); —N($R^{5a}$)—$(CH_2)_{1-6}$—$OR^{2d}$; —N($R^{5a}$)—$(CH_2)$1-6—N($R^{2d}$, $R^{3d}$); —C(=O)—N($R^{2d}$,$R^{3d}$); —N($R^{5a}$)—$(CH_2)$1-6—C(=O)—N($R^{2d}$,$R^{3d}$); —N(—$(CH_{21-6}$—$OR^{2d}$)_2$; —N($R^{5a}$)—$(CH_2)_{1-6}$—$OR^{2d}$; —N($R^{5a}$)—C(=O)—$R^{2d}$; —N($R^{5a}$)—$SO_2$—$R^{2d}$; —$(CH_2)_{0-6}$—C(=O)—O—$R^{2d}$; —$(CH_2)_{0-6}$—C(=O)—N($R^{2d}$,$R^{3d}$); —$(CH_2)_{0-6}$—C(=$NR^{2d}$)—N($R^{3d}$,$R^{4d}$); —$(CH_2)_{0-6}$—N($R^{5a}$)C(=$NR^{2d}$)—N($R^{3d}$,$R^{4d}$); and —$(CH_2)_{0-6}$—N(—$R^{3d}$)— group attached directly by its nitrogen atom to a carbon atom of a 5 to 6 membered saturated, partially unsaturated or aromatic heterocyclic ring containing 1–4 heteroatoms selected from N, O and S, and a —$(CH_2)_{0-6}$— group attached to a 5–6 membered saturated, partially unsaturated or aromatic heterocyclic ring containing 1–4 heteroatoms selected from N, O and S;

$R^{5a}$, $R^{2d}$, $R^{3d}$ and $R^{4d}$ are each independently a member selected from the group consisting of:
H, $C_{1-4}$-alkyl and $C_{1-6}$-alkylaryl, —CN; —$NO_2$; carbocylic aryl, —CN; —$NO_2$; or
$R^{2d}$ and $R^{3d}$ taken together with the N atoms they are independently attached form a 5–7 membered saturated, partially unsaturated or aromatic heterocyclic ring; or
$R^{3d}$ and $R^{3d}$ taken together with the N atom to which they are attached form a 5–8 membered saturated, partially unsaturated or aromatic heterocyclic ring containing 1–4 heteroatoms selected from N, O and S;

J is a direct link or is a member selected from the group consisting of:
—N(—$R^9$)—C(=O)—; —C(=O)—N(—$R^9$)—; —O—; —S—; —SO—; —$SO_2$—; —$CH_2$—; —N(—$R^9$)—; and —N(—$R^9$)—$SO_2$—;

$R^9$ is a member selected from the group consisting of:
H; —$C_{1-4}$-alkyl; —$C_{0-4}$-alkyl-carbocyclic aryl; —$(CH_2)_{0-4}$-5–6 membered saturated, partially unsaturated or aromatic heterocyclic ring containing 1–4 heteroatoms selected from N, O and S; —(CH$_2$)$_{1-6}$—C(=O)—O—C$_{1-4}$-alkyl; and —(CH$_2$)$_{1-6}$—C(=O)—N(R$^{6a}$,R$^{6b}$);

R$^{6a}$ and R$^{6b}$ are each a member independently selected from the group consisting of: H and —C$_{1-6}$-alkyl;

X is a member selected from the group consisting of:
(a) phenyl substituted with 0–3 R$^{1e}$ groups;
(b) naphthyl substituted with 0–3 R$^{1e}$ groups and
(c) a 6-membered aromatic heterocyclic ring system containing 1–3 N atoms and having 0–3 ring atoms substituted with 0–3 R$^{1e}$ groups; and
(d) an 8–10 membered fused aromatic heterocyclic bicyclic ring system containing 1–4 heteroatoms selected from N, O and S and 0–3 ring atoms of the fused heterocyclic bicyclic ring system are substituted with 0–3 R$^{1e}$ groups;

R$^{1e}$ is a member independently selected from the group consisting of:
Halo; CF$_3$; —C$_{1-4}$-alkyl; carbocyclic aryl; —C$_{0-2}$-alkyl-CN; —O—R$^{2e}$; —C$_{0-2}$-alkyl-C(=O)—O—R$^{2e}$; —C$_{0-2}$-alkyl-C(=O)—N(R$^{2e}$,R$^{3e}$); —C$_{0-2}$-alkyl-NO$_2$; —C$_{0-2}$-alkyl-N(R$^{2e}$,R$^{3e}$); —C$_{0-2}$-alkyl-SO$_2$—N(R$^{2e,R3e}$); —C$_{0-2}$-alkyl-SO$_2$—R$^{2e}$; trihaloalkyl; —O—C$_{0-2}$-alkyl-O—R$^{2e}$; —C$_{0-2}$-alkyl-O—R$^{2e}$; —O—C$_{1-4}$-alkyl-C(=O)—N(R$^{2e}$, R$^{3e}$); —O—C$_{1-4}$-alkyl-C(=O)—O—R$^{2e}$; —C$_{0-2}$-alkyl-N(—R$^{2e}$)—C(=O)—R$^{3e}$; —C$_{0-2}$-alkyl-N(—R$^{2e}$)—SO$_2$—R$^{3e}$; —CH$_2$—N(R$^{2e}$)—C(=O)—R$^{3e}$; —CH$_2$—N(R$^{2e}$)—SO$_2$—R$^{3e}$; —(CH$_2$)$_{0-6}$—NR$^{2e}$R$^{3e}$; —C(=O)—N(R$^{2e}$,R$^{3e}$); —N(—CH$_2$)$_{1-6}$—OR$^{2e}_2$; —N(R$^{10}$)—(CH$_2$)$_{1-6}$—OR$^{2e}$; —N(R$^{10}$)—C(=O)—R$^{2e}$; —N(R$^{10}$)—SO$_2$—R$^{2e}$; —C(=N(R$^{10}$))—N(R$^{2e}$,R$^{3e}$); and a —(CH$_2$)$_{0-6}$-5-6 membered saturated, partially unsaturated or aromatic heterocyclic ring containing 1–4 heteroatoms selected from N, O and S;

R$^{10}$, R$^{2e}$ and R$^{3e}$ are each independently a member selected from the group consisting of:
H; —C$_{1-4}$-alkyl; —C$_{0-2}$alkyl-O—R$^{1g}$; —C$_{0-2}$-alkyl-N(—R$^{1g}$, —R$^{2g}$); —C$_{1-4}$-alkyl-carbocyclic aryl; —C$_{1-4}$-alkyl-heterocyclic; and R$^{10}$ and R$^{2e}$, or R$^{2e}$ and R$^{3e}$ together with the N atom to which they are attached can form 5–8 membered heterocyclic ring containing 1–4 heteroatoms selected from N, O and S which can be substituted with 0–2 R$^{1g}$ groups;

R$^{1g}$ and R$^{2g}$ are independently a member selected from the group of:
H; halo; —C$_{1-4}$-alkyl, a carbocyclic aryl group; a saturated, partially unsaturated or aromatic heterocyclic group; —CN; —C(=O)—N(R$^{3g}$)R$^{4g}$; —C(=O)—OR$^{3g}$; —NO$_2$; —(CH$_2$)$_p$—NR$^{3g}$R$^{4g}$; —SO$_2$NR$^{3g}$R$^{4g}$; —SO$_2$R$^{3g}$; —CF$_3$; and —(CH$_2$)$_p$OR$^{3g}$;

p is an integer of 0–2;

R$^{3g}$ and R$^{4g}$ are each independently selected from the group consisting of:
H; C$_{1-4}$-alkyl and —C$_{0-4}$-alkyl-carbocyclic aryl;
and all pharmaceutically acceptable isomers, salts, hydrates, solvates and prodrug derivatives thereof In a further preferred embodiment the present invention provides a compound according to the formula:

A—Q—D—E—G—J—X wherein:

A is selected from:
(a) C$_1$–C$_6$-alkyl;
(b) C$_3$–C$_8$-cycloalkyl;
(c) —N(R$^1$,R$^2$), N(R$^1$,R$^2$)—C(=NR$^3$)—, N(R$^1$,R$^2$)—C(=NR$^3$)—N(R$^4$)—, R$^1$—C(=NR$^3$)—, R$^1$—C(=NR$^3$)—N(R$^4$)—;
(d) phenyl, which is independently substituted with 0–2 R substitutuents;
(e) naphthyl, which is independently substituted with 0–2 R substitutuents; and
(f) monocyclic or fused bicyclic heterocyclic ring system having from 5 to 10 ring atoms, wherein 1–4 ring atoms of the ring system are selected from N, O and S, and wherein the ring system may be substituted with 0–2 R substitutuents;

R is selected from:
H, halo, —CN, —CO$_2$R$^1$, —C(=O)—N(R$^1$,R$^2$), —(CH$_2$)$_m$—CO$_2$R$^1$, —(CH$_2$)$_m$—C(=O)—N(R$^1$,R$^2$), —NO$_2$, —SO$_2$N(R$^1$,R$^2$), —SO$_2$R$^1$, —(CH$_2$)$_m$NR$^1$R$^2$, —(CH$_2$)$_m$—C(=NR$^3$)—R$^1$, —(CH$_2$)$_m$—C(=NR)—N(R$^1$,R$^2$), —(CH$_2$)$_m$—N(R$^4$)—C(=NR$^3$)—N(R$^1$,R$^2$, —(CH$_2$)$_m$NR$^1$— group attached to a 3–6 membered heterocylic ring having from 1 to 3 heteroatoms selected from the group consisting of N, O and S, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CF$_3$, —OR$^2$, and a 5–6 membered heterocyclic aromatic or partially saturated system, including imidazoline, containing from 1–4 heteroatoms selected from N, O and S, wherein from 1–4 hydrogen atoms on the heterocyclic system may be independently replaced with a member selected from the group consisting of halo, -methyl, —C$_2$—C$_4$-alkyl, —CN, —C$_{2-6}$alkenyl, —C$_{2-6}$alkynyl, —C$_{3-8}$cycloalkyl, —C$_{0-4}$alkylC$_{3-8}$cycloalkyl and —NO$_2$;

m is an integer of 0–2;

R$^1$, R$^2$, R$^3$ and R$^4$ are independently selected from the group consisting of:
H, —OR$^5$, —N(—R$^5$, —R$^6$), —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —C$_{0-4}$alkylphenyl and —C$_{0-4}$alkylnaphthyl, wherein from 1–4 hydrogen atoms on the ring atoms of the phenyl and naphthyl moieties may be independently replaced with a member selected from the group consisting of halo, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CN, and —NO$_2$; or.

R$^1$ and R$^2$, or R$^2$ and R$^3$ taken together can form a 3–8 membered cycloalkyl or a heterocyclic ring system, wherein the heterocyclic ring system may have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, C$_1$–C$_4$-alkyl, —CN—C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl and NO$_2$;

R$^5$ and R$^6$ are independently selected from the group consisting of:
H, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —C$_{0-4}$alkylphenyl and —C$_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$; or $R^5$ and $R^6$ taken together can form a 3–8 membered cycloalkyl or a heterocyclic ring system, wherein the heterocyclic ring system may have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, $C_1$–$C_4$-alkyl, —CN—$C_{1-4}$alkyl, —$C_{2-6}$alkenyl, —$C_{2-6}$ alkynyl, —$C_{3-8}$cycloalkyl, —$C_{0-4}$alkyl$C_{3-8}$cycloalkyl and —$NO_2$;

Q is a member selected from the group consisting of:
a direct link, —$CH_2$—, —C(=O)—, —O—, —NH—, —NMe-, —NHCH$_2$—, —NMeCH$_2$—, —$CH_2$NH—, —C(=NH)—, —C(=O)—NH—, —NH—C(=O)—, —$CH_2$NMe-, —C(=NMe)—;

D is a direct link or is a member selected from the group consisting of:
(a) phenyl, which is independently substituted with 0–2 $R^{1a}$ substitutuents;
(b) naphthyl, which is independently substituted with 0–2 $R^{1a}$ substitutuents; and
a monocyclic or fused bicyclic heterocyclic ring system having from 5 to 10 ring atoms, wherein 1–4 ring atoms of the ring system are selected from N, O and S, and wherein the ring system may be substituted from 02 $R^{1a}$ substitutuents;

$R^{1a}$ is selected from:
halo, —$C_{1-4}$alkyl, —$C_{2-4}$alkenyl, —$C_{2-6}$alkynyl, —$C_{3-8}$ cycloalkyl, —$C_{0-4}$alkyl$C_{3-8}$cycloalkyl, —CN, —$NO_2$, —$(CH_2)_n$NR$^{2a}$R$^{3a}$, —$(CH_2)_n$$CO_2$R$^{2a}$, —$(CH_2)_n$CONR$^{2a}$R$^{3a}$, —$SO_2$NR$^{2a}$R$^{3a}$, —$SO_2$R$^{2a}$, —CF$_3$, —OR$^{2a}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, —$C_{1-4}$alkyl, —$C_{2-6}$alkenyl, —$C_{2-6}$alkynyl; —$C_{3-8}$ cycloalkyl, —$C_{0-4}$alkyl$C_{3-8}$cycloalkyl, —CN and —$NO_2$;

$R^{2a}$ and $R^{3a}$ are independently selected from the group consisting of:
H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$ cycloalkyl, —CN and —$NO_2$;

n is an integer of 0–2;

E is a member selected from the group consisting of:
a direct link, —O—, —NH—, —$CH_2$NH—, —NHCH$_2$—, —NMe-, —NH—C(=O)—NH—, —C(=O)—NH—, —NH—C(=O)—;

G is a member selected from the group consisting of:
(a) a $C_2$-alkenyl group or a $C_{3-8}$-cycloalkenyl group, wherein the alkenyl group and cycloalkenyl group attachment points are the alkenyl carbon atoms and wherein the $C_2$-alkenyl group or $C_{3-8}$-cycloalkenyl group is substituted with 0–4 $R^{1d}$ groups;

(b) a phenylene group wherein the ring carbon atoms of the phenylene group are substituted with 0–4 $R^{1d}$ groups;
(c) a 3–8 membered a saturated, partially unsaturated or aromatic monocyclic-heterocyclic ring system containing 1–4 heteroatoms selected from N, O and S, wherein 0–4 ring atoms of the heterocyclic ring may be substituted with 0–4 $R^{1d}$ groups; and,
(d) an 8–10 membered fused heterocyclic bicyclic ring system, containing 1–4 heteroatoms selected from N, O and S, wherein 0–4 ring atoms of the fused bicyclic ring system may be substituted with 0–4 $R^{1d}$ groups;

$R^{1d}$ is a member selected from the group consisting of:
H, halo; $C_{1-6}$-alkyl, carbocylic aryl, —CN; —$NO_2$; —$(CH_2)_{0-6}$—NR$^{2d}$R$^{3d}$; —$SO_2$NR$^{2d}$R$^{3d}$; $SO_2$R$^{2d}$; —CF$_3$; —$(CH_2)_{0-6}$—OR$^{2d}$; —O—$(CH_2)_{1-6}$OR$^{2d}$; —O—$(CH_2)_{1-6}$—C(=O)—O—R$^{2d}$; —O—$(CH_2)_{1-6}$—C(=O)—N(R$^{2d}$,R$^{3d}$); —N(R$^{5a}$)—$(CH_2)_{1-6}$—OR$^{2d}$; —N(R$^{5a}$)—$(CH_2)_{1-6}$—N(R$^{2d}$,R$^{3d}$); —C(=O)—N(R$^{2d}$,R$^{3d}$); —N(R$^{5a}$)—$(CH_2)_{1-6}$—C(=O)—N(R$^{2d}$,R$^{3d}$); —N(—$(CH_2)_{1-6}$—OR$^{2d}$)$_2$; —N(R$^{5a}$)—$(CH_2)_{1-6}$—OR$^{2d}$; —N(R$^{5a}$)—C(=O)—R$^{2d}$; —N(R$^{5a}$)—$SO_2$—R$^{2d}$; —$(CH_2)_{0-6}$—C(=O)—O—R$^{2d}$; —$(CH_2)_{0-6}$—C(=O)—N(R$^{2d}$,R$^{3d}$); —$(CH_2)_{0-6}$—C(=NR$^{2d}$)—N(R$^{3d}$,R$^{4d}$); —$(CH_2)_{0-6}$—N(R$^{5a}$)C(=NR)—N(R$^{3d}$,R$^{4d}$); and a —$(CH_2)_{0-6}$—N(R$^{3d}$) group which is attached via the nitrogen atom to a carbon atom of a 5 to 6 membered saturated, partially unsaturated or aromatic heterocyclic ring containing 1–4 heteroatoms selected from N, O and S, and a —$(CH_2)_{0-6}$— group attached to a 5–6 membered saturated, partially unsaturated or aromatic heterocyclic ring containing 1–4 heteroatoms selected from N, O and S;

$R^{5a}$, $R^{2d}$, $R^{3d}$ and $R^{4d}$ are each independently a member selected from the group consisting of:
H, $C_{1-4}$-alkyl and $C_{1-6}$-alkylaryl, —CN; —$NO_2$; carbocylic aryl, —CN; —$NO_2$; or $R^{2d}$ and $R^{3d}$ taken together with the N atoms they are independently attached form a 5–7 membered saturated, partially unsaturated or aromatic heterocyclic ring; or $R^{3d}$ and $R^{4d}$ taken together with the N atom to which they are attached form a 5–8 membered saturated, partially unsaturated or aromatic heterocyclic ring containing 1–4 heteroatoms selected from N, O and S;

J is a member selected from the group consisting of:
a direct link, —O—, —NH—, —NMe-, —C(=O)—NH—, —NH—C(=O)—;

X is a member selected from the group consisting of:
(a) phenyl substituted with 0–3 $R^{1e}$ groups;
(b) naphthyl substituted with 0–3 $R^{1e}$ groups and
(c) a 6-membered aromatic heterocyclic ring system containing 1–3 N atoms and having 0–3 ring atoms substituted with 0–3 $R^{1e}$ groups; and
(d) an 8–10 membered fused aromatic heterocyclic bicyclic ring system containing 1–4 heteroatoms selected from N, O and S and 0–3 ring atoms of the fused heterocyclic bicyclic ring system are substituted with 0–3 $R^{1e}$ groups;

$R^{1e}$ is a member independently selected from the group consisting of:
Halo; CF$_3$; —$C_{1-4}$-alkyl; carbocylic aryl; —$C_{0-2}$-alkyl-CN; —O—R$^{2e}$; —$C_{0-2}$-alkyl-C(=O)—O—

$R^{2e}$; —$C_{0-2}$-alkyl-C(=O)—N($R^{2e}$,$R^{3e}$); —$C_{0-2}$-alkyl-NO$_2$; —$C_{0-2}$-alkyl-N($R^{2e}$,$R^{3e}$); —$C_{0-2}$-alkyl-SO$_2$—N($R^{2e}$,$R^{3e}$); —$C_{0-2}$-alkyl-SO$_2$—$R^{2e}$; trihaloalkyl; —O—$C_{0-2}$-alkyl-O—$R^{2e}$; —$C_{0-2}$-alkyl-O—$R^{2e}$; —O—$C_{1-4}$-alkyl-C(=O)—N($R^{2e}$, $R^{3e}$); —O—$C_{1-4}$-alkyl-C(=O)—O—$R^{2e}$; —$C_{0-2}$-alkyl-N($R^{2e}$)—C(=O)—$R^{3e}$; —$C_{0-2}$-alkyl-N(—$R^{2e}$)—SO$_2$—$R^{3e}$; —CH$_2$—N($R^{2e}$)—C(=O)—$R^{3e}$; —CH$_2$—N($R^{2e}$)—SO$_2$—$R^{3e}$; —(CH$_2$)$_{0-6}$—NR$^{2e}$R$^{3e}$; —C(=O)—N($R^{2e}$,$R^{3e}$); —N(—(CH$_2$)$_{1-6}$—OR$^{2e}$)$_2$; —N($R^{10}$)—(CH$_2$)$_{1-6}$—OR$^{2e}$; —N($R^{10}$)—C(=O)—$R^{2e}$; —N($R^{10}$)—SO$_2$—$R^{2e}$; —C(=N($R^{10}$))—N($R^{2e}$,$R^{3e}$); and a —(CH$_2$)$_{0-6}$-5–6 membered saturated, partially unsaturated or aromatic heterocyclic ring containing 1–4 heteroatoms selected from N, O and S;

$R^{10}$, $R^{2e}$ and $R^{3e}$ are each independently a member selected from the group consisting of:
H; —$C_{1-4}$-alkyl; —$C_{0-2}$-alkyl-O—$R^{1g}$; —$C_{0-2}$-alkyl-N(—$R^{1g}$,—$R^{2g}$); —$C_{1-4}$-alkyl-carbocyclic aryl; $C_{1-4}$-alkyl-heterocyclic; and $R^{10}$ and $R^{2e}$, or $R^{2e}$ and $R^{3e}$ together with the N atom to which they are attached can form 5–8 membered heterocyclic ring containing 1–4 heteroatoms selected from N, O and S which can be substituted with 0–2 $R^{1g}$ groups;

$R^{1g}$ and $R^{2g}$ are independently a member selected from the group of:
H; halo; —$C_{1-4}$-alkyl a carbocyclic aryl group; a saturated, partially unsaturated or aromatic heterocyclic group; —CN; —C(=O)—N($R^{3g}$,$R^{4g}$); —C(=O)—OR$^{3g}$; —NO$_2$; —(CH$_2$)$_p$—NR$^{3g}$R$^{4g}$; —SO$_2$NR$^{3g}$R$^{4g}$; —SO$_2$R$^{3g}$; —CF$_3$; and —(CH$_2$)$_p$OR$^{3g}$;

p is an integer of 0–2;

$R^{3g}$ and $R^{4g}$ are each independently selected from the group consisting of:
H; $C_{1-4}$-alkyl and —$C_{0-4}$-alkyl-carbocyclic aryl;
and all pharmaceutically acceptable isomers, salts, hydrates, solvates and prodrug derivatives thereof In a still further preferred embodiment the present invention provides a compound according to the formula:

A—Q—D—E—G—J—X wherein:

A is a member selected from the group consisting of:

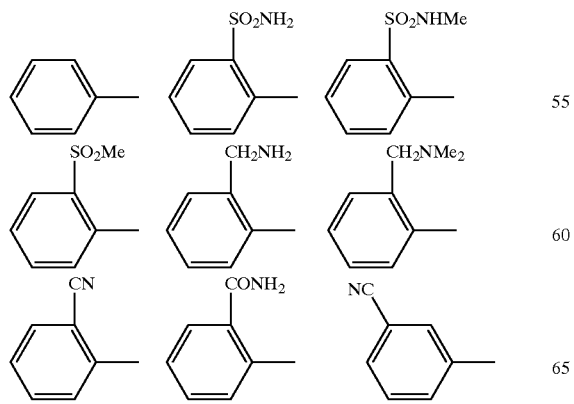

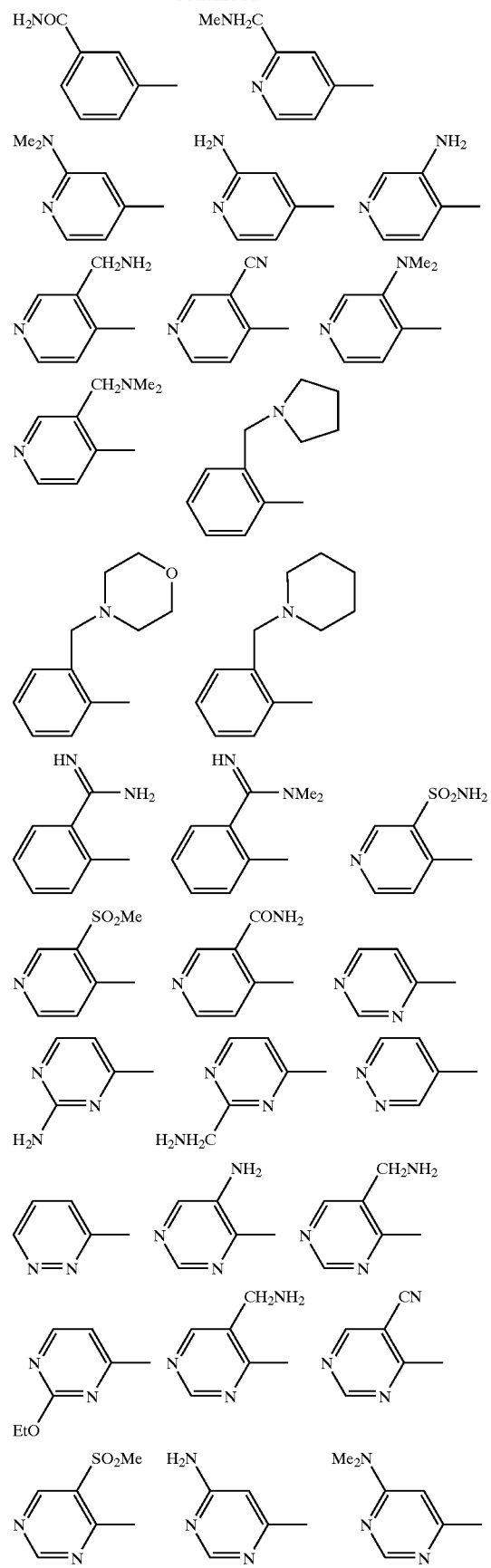

-continued
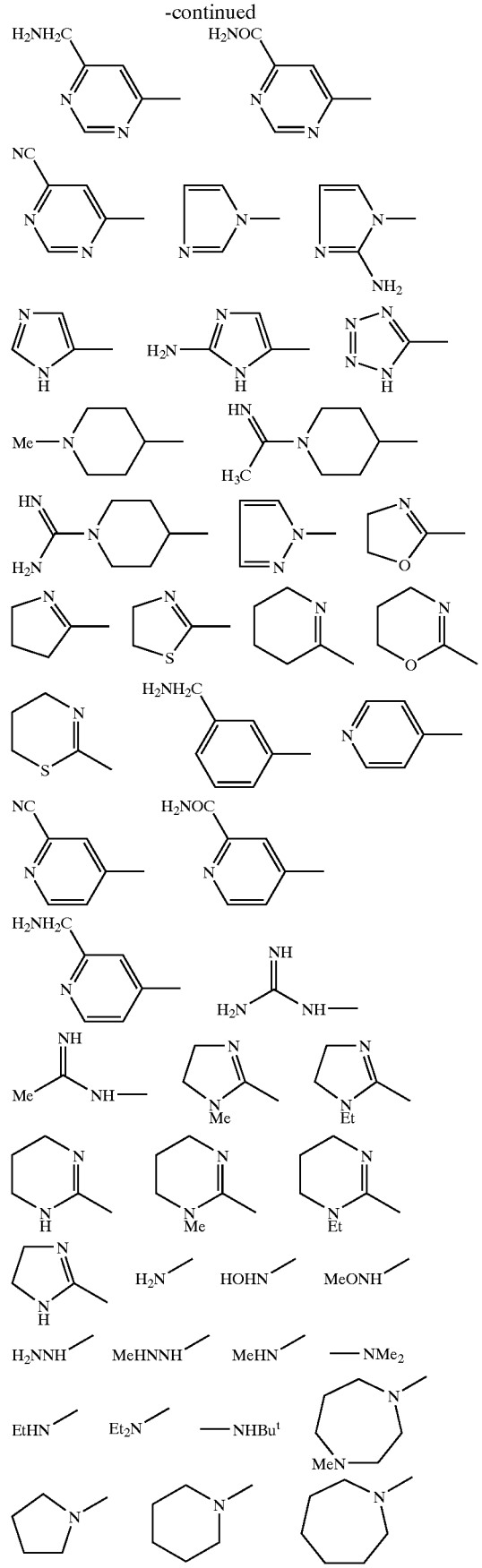
-continued
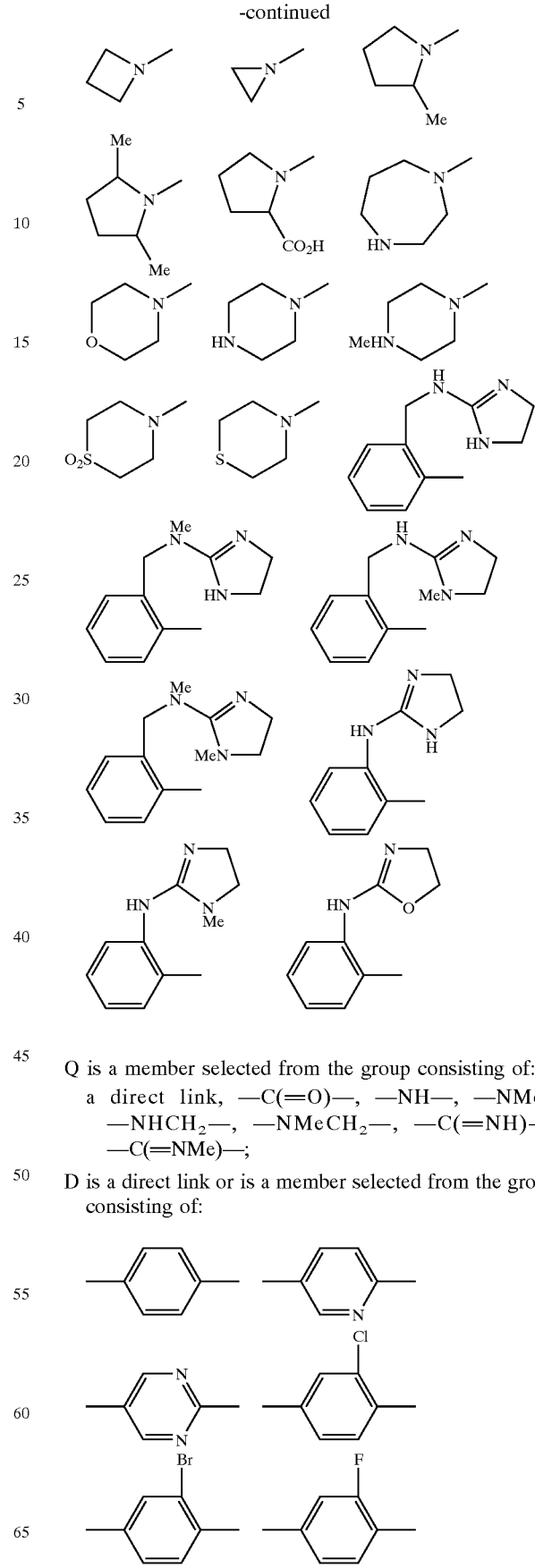
Q is a member selected from the group consisting of:
  a direct link, —C(=O)—, —NH—, —NMe-, —NHCH$_2$—, —NMeCH$_2$—, —C(=NH)—, —C(=NMe)—;
D is a direct link or is a member selected from the group consisting of:
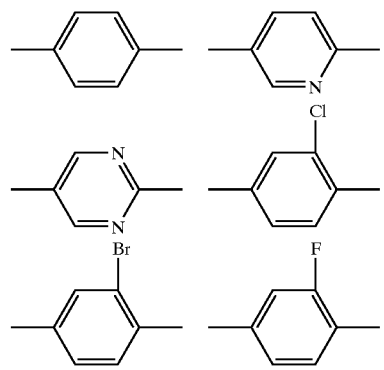

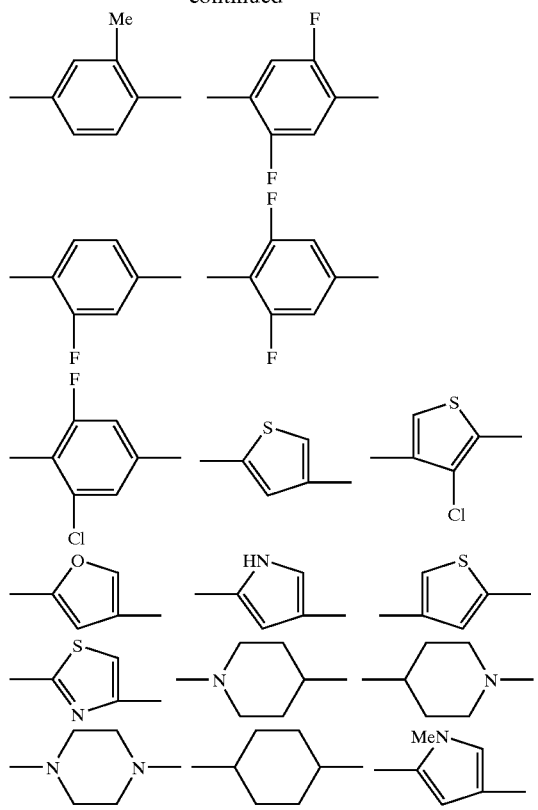
E is a member selected from the group consisting of:
a direct link, —CH₂NH—, —C(=O)—NH—, —NH—C(=O)—;
G is a member selected from the group consisting of:
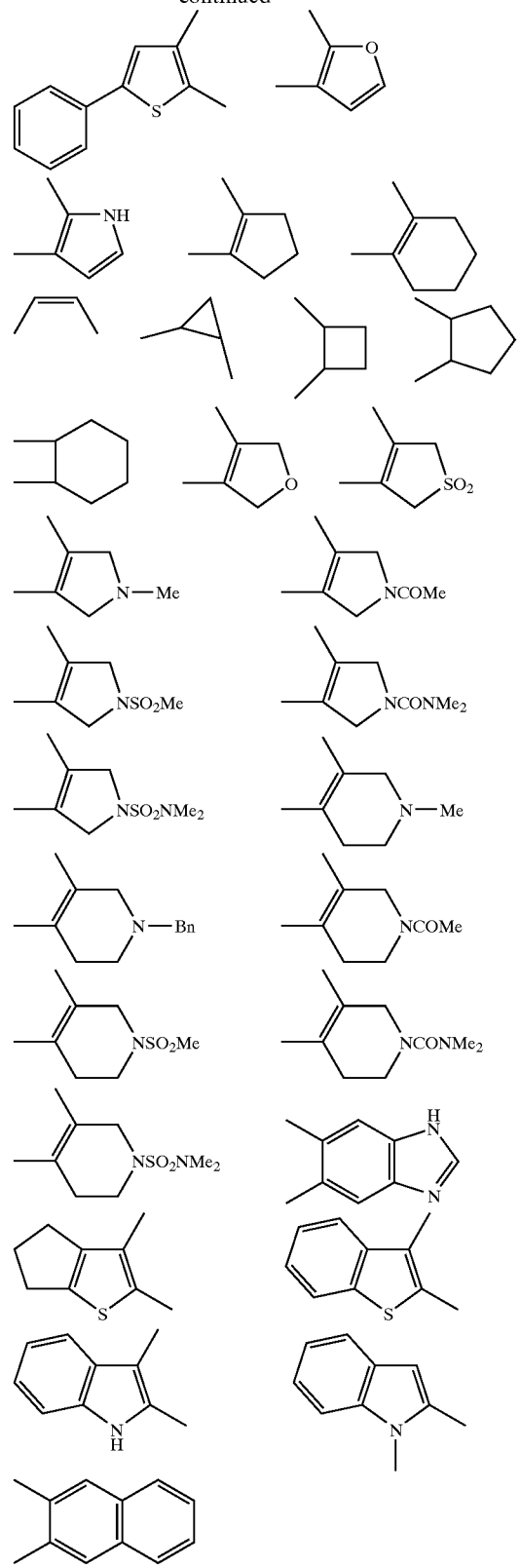
G is substituted by 0–4 $R^{1d}$ groups and each $R^{1d}$ group is independently selected from the group consisting of:
H, —CH₃, —CF₃, —Cl, —F, —Br, —NH₂, —NMe₂, —OH, —OMe, —NHSO₂Me, —NO₂, —CN, —C(=O)—OMe, —CO₂H, —CONH₂, —SO₂NH₂, —SO₂CH₃, —NHC(=O)Me, —C(=O)N(-Me)₂, —CH₂NH₂, —CH₂N(-Me)₂, —CH₂OH, —OCH₂CO₂H, —OCH₂C(=O)—OMe, —OCH₂C(=O)—NH₂ and —OCH₂C(=O)N(-Me)₂.
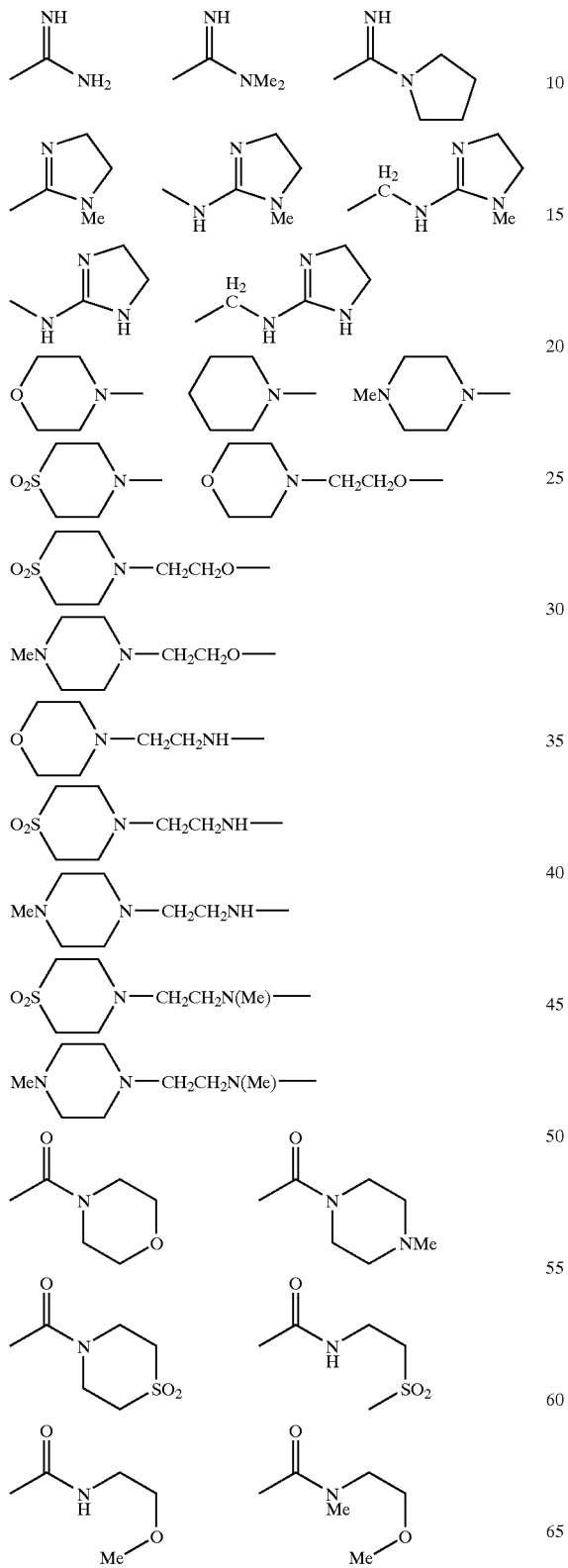
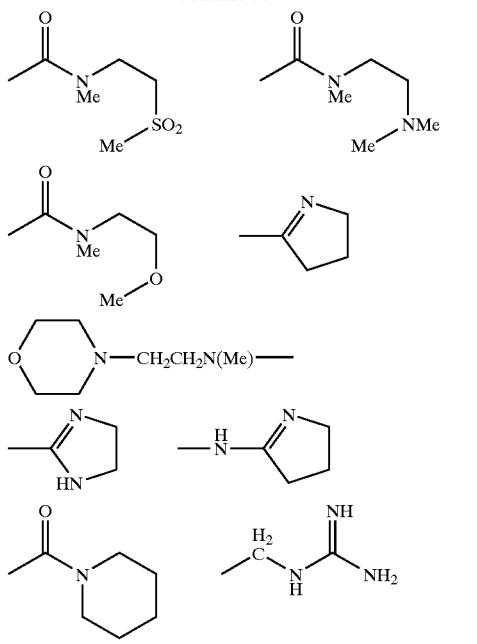
J is a member selected from the group consisting of:
a direct link, —O—, —NH—, —C(=O)—NH— and —NH—C(=O)—;
X is a member selected from the group consisting of:
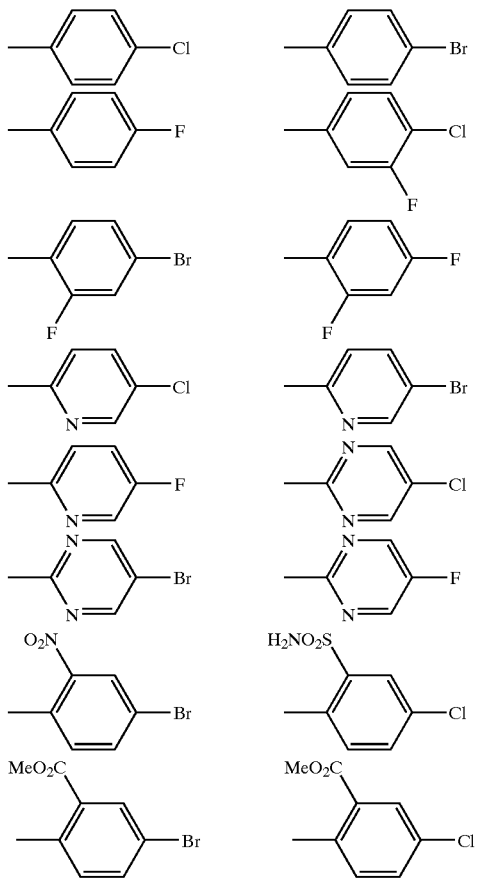

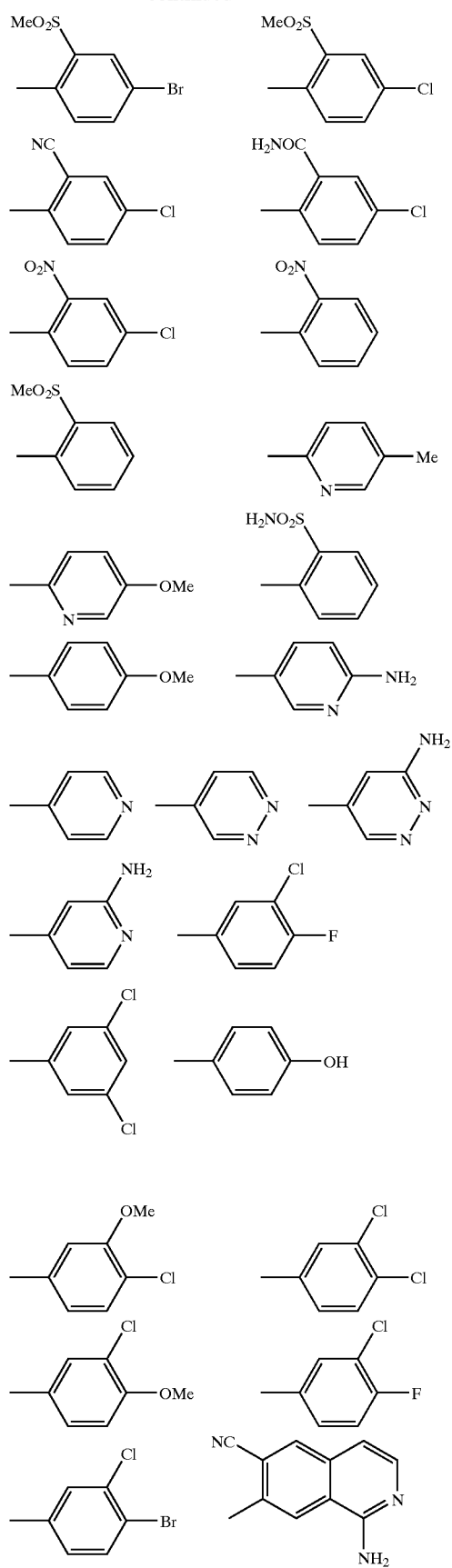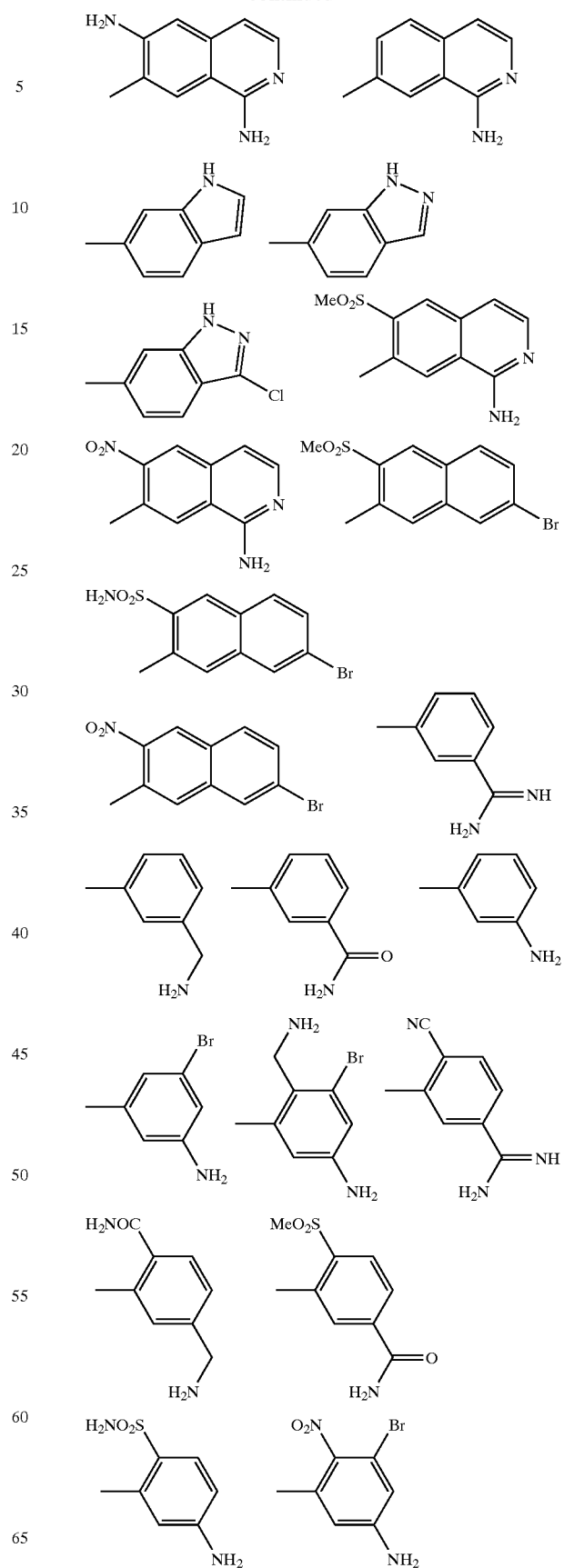

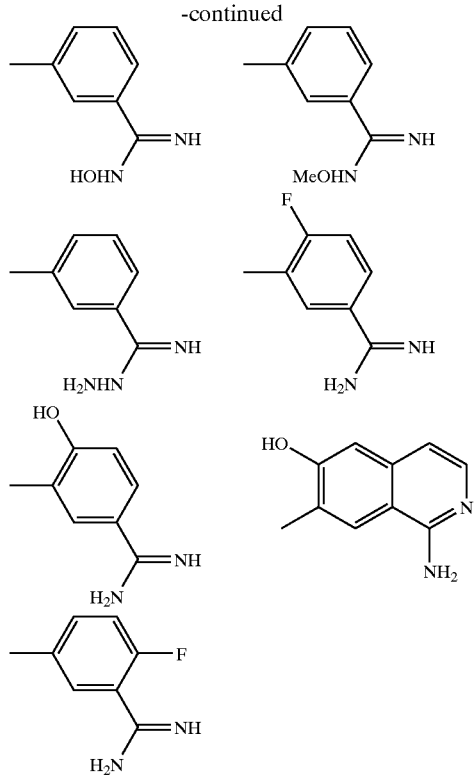

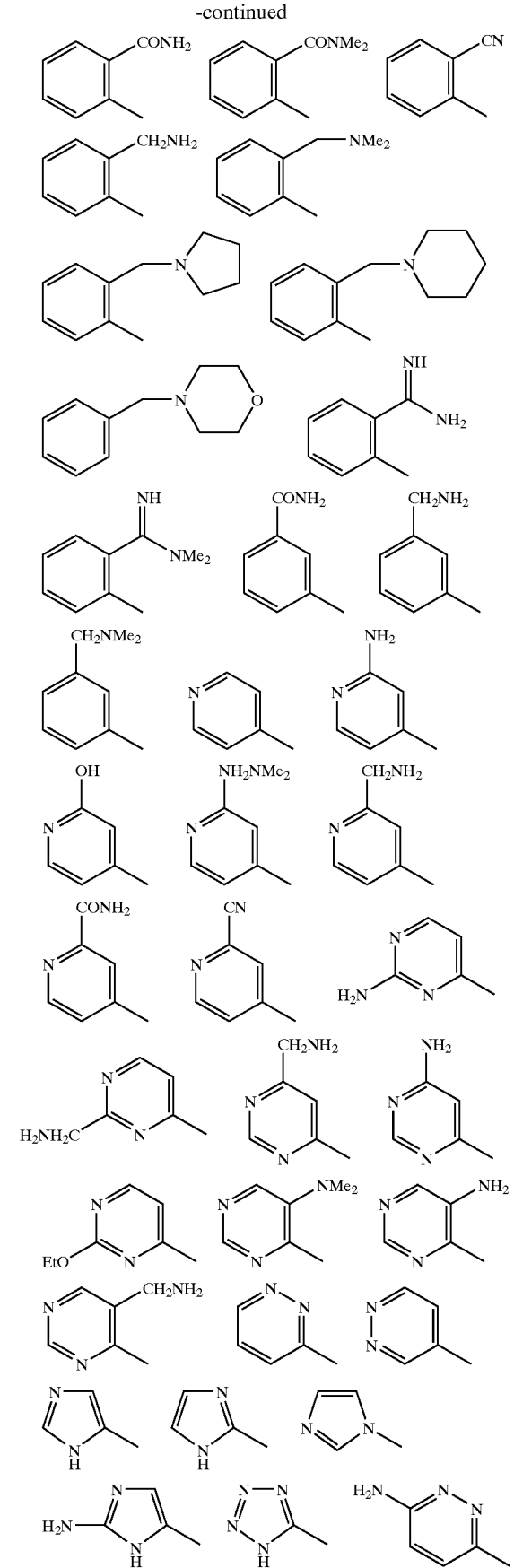

and all pharmaceutically acceptable isomers, salts, hydrates, solvates and prodrug derivatives thereof.

In another further preferred embodiment the present invention provides a compound according to the formula:

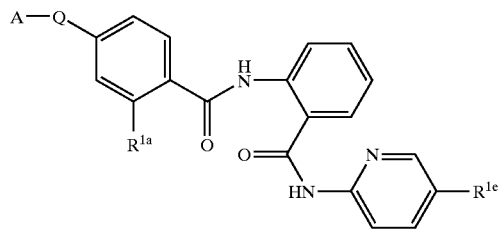

wherein:

$R^{1a}$ is a member selected from the group consisting of: H, —F, —Cl and —Br;

$R^{1e}$ is a member selected from the group consisting of: H, —F, —Cl, —Br, —OMe, —OH, -Me, —CF$_3$ and —CH$_2$NH$_2$; and A—Q is a member selected from the group consisting of:

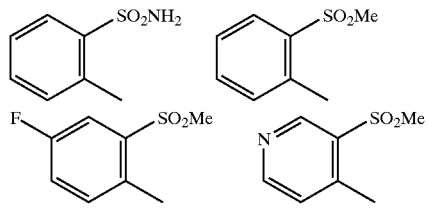

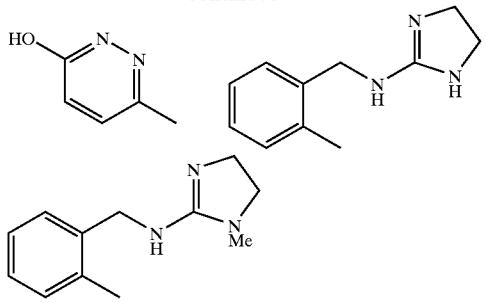

and all pharmaceutically acceptable isomers, salts, hydrates, solvates and prodrug derivatives thereof.

In another further preferred embodiment the present invention provides a compound according to the formula:

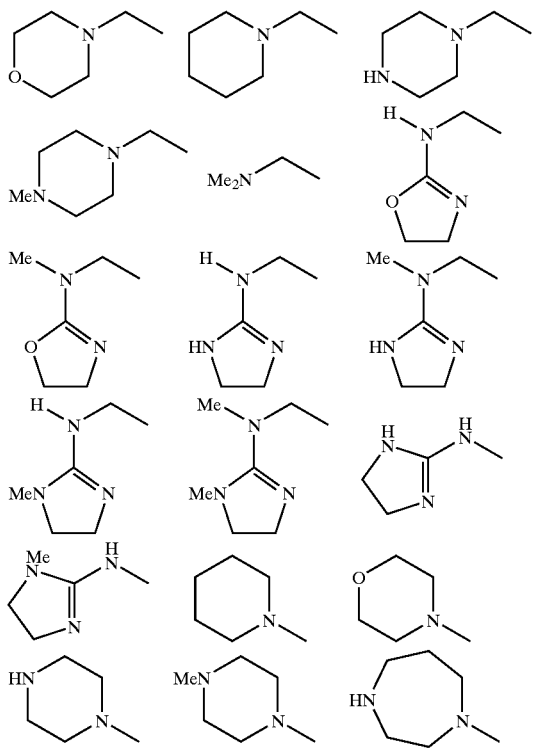

wherein:

$R^{1a}$ is a member selected from the group consisting of: H, —F, —Cl and —Br;

$R^{1e}$ is a member selected from the group consisting of: H, —F, —Cl, —Br, —OMe, —OH, -Me, —CF, and —CH$_2$NH$_2$; and A—Q is a member selected from the group consisting of:

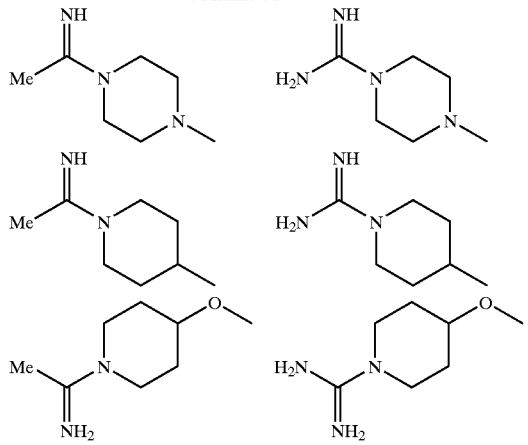

and all pharmaceutically acceptable isomers, salts, hydrates, solvates and prodrug derivatives thereof.

In another flirter preferred embodiment the present invention provides a compound according to the formula:

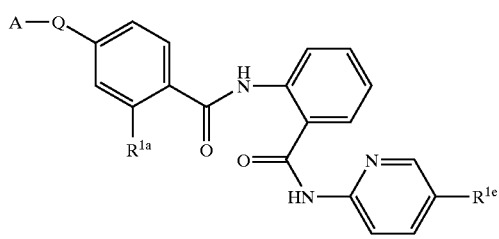

wherein:

$R^{1a}$ is a member selected from the group consisting of: H, —F, —Cl and —Br;

$R^{1e}$ is a member selected from the group consisting of: H, —F, —Cl, —Br, —OMe, —OH, -Me, —CF$_3$ and —CH$_2$NH$_2$;

A—Q is a member selected from the group consisting of:

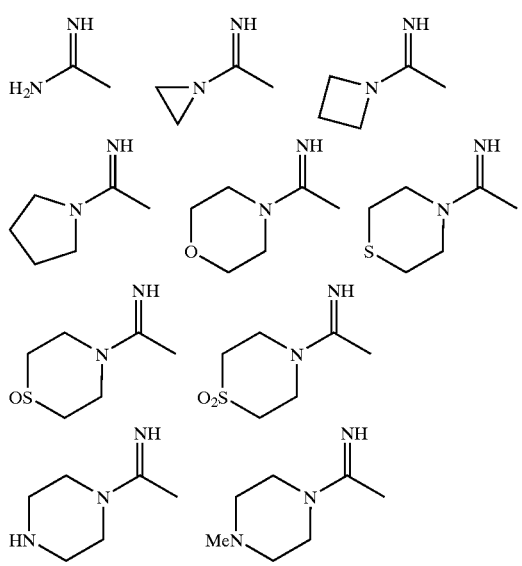

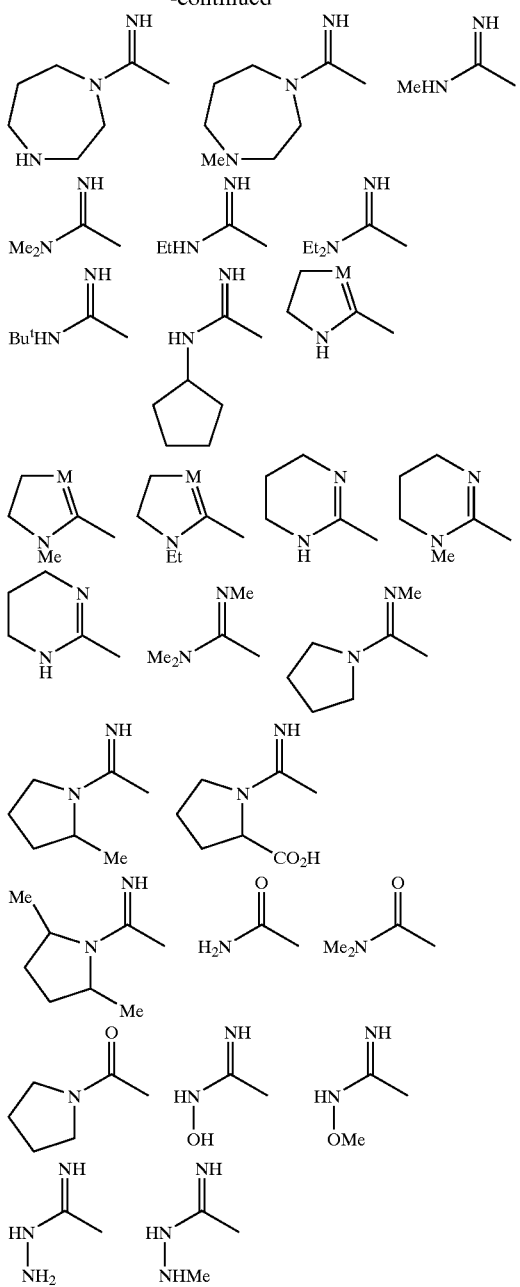

and all pharmaceutically acceptable isomers, salts, hydrates, solvates and prodrug derivatives thereof.

In another further preferred embodiment the present invention provides a compound according to the formula:

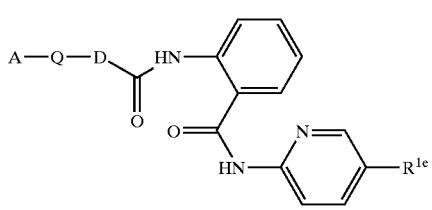

wherein:

$R^{1e}$ is a member selected from the group consisting of: H, —F, —Cl, —Br, —OMe, —OH, -Me, —$CF_3$ and —$CH_2NH_2$;

A—Q is a member selected from the group consisting of:

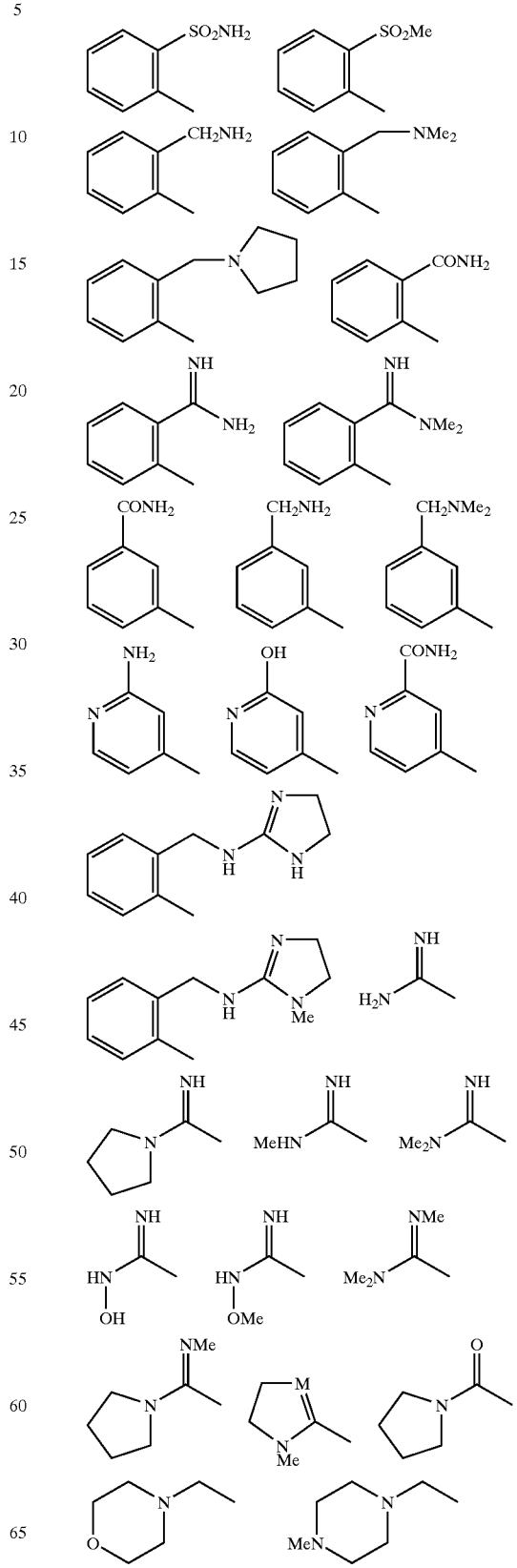

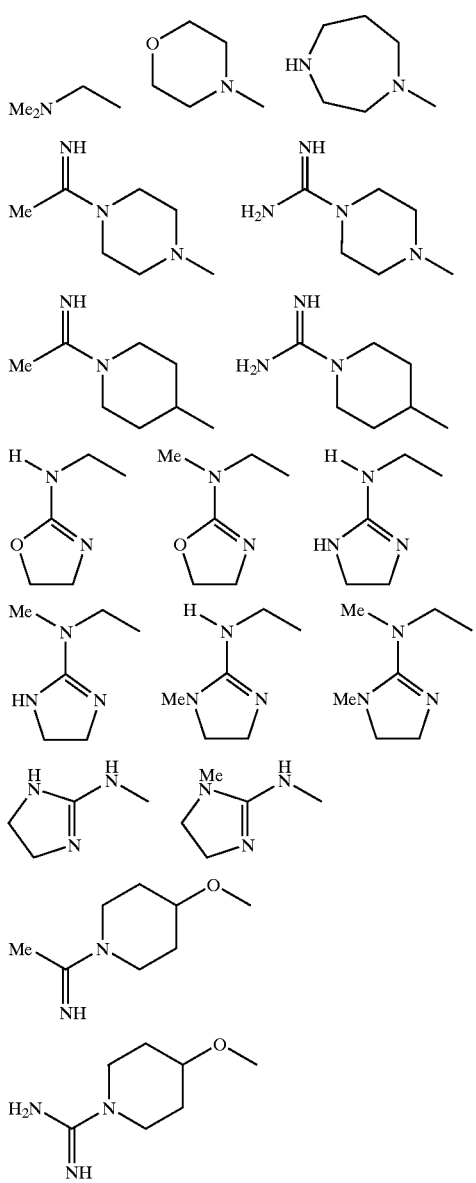
D is a member selected from the group consisting of:
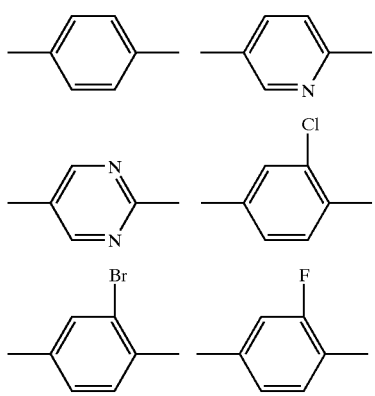
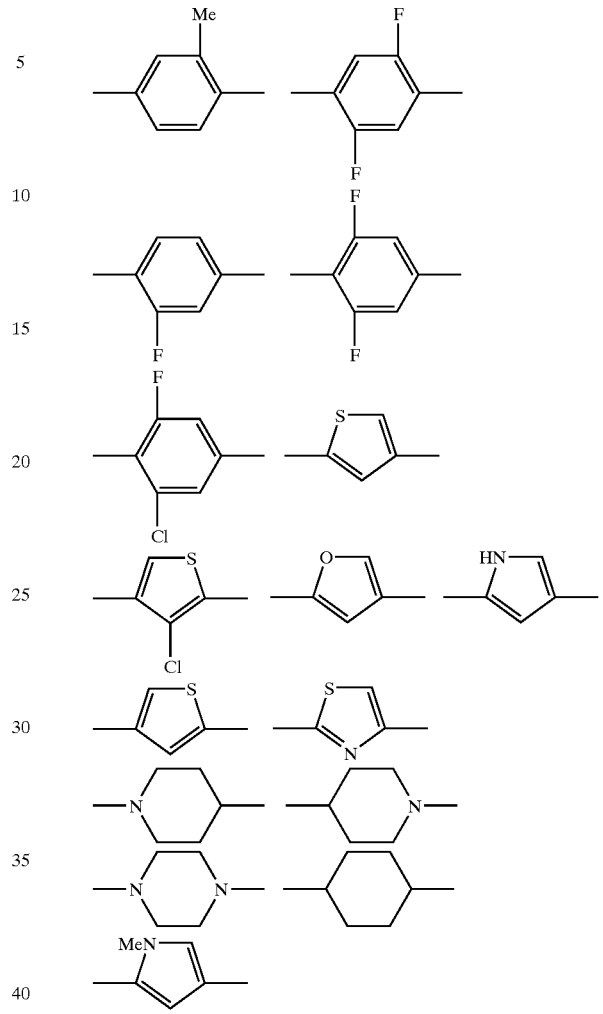
and all pharmaceutically acceptable isomers, salts, hydrates, solvates and prodrug derivatives thereof
In another preferred embodiment the present invention provides a compound according to the formula:
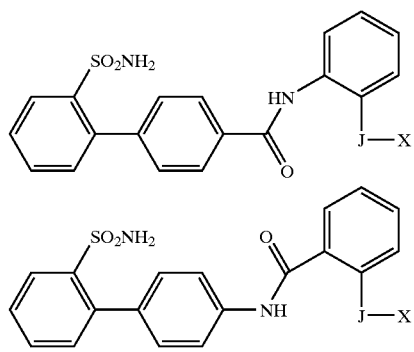
wherein:
J is a member selected from the group consisting of:
—NHC(=O)—, —C(=O)NH—;

X is a member selected from the group consisting of:
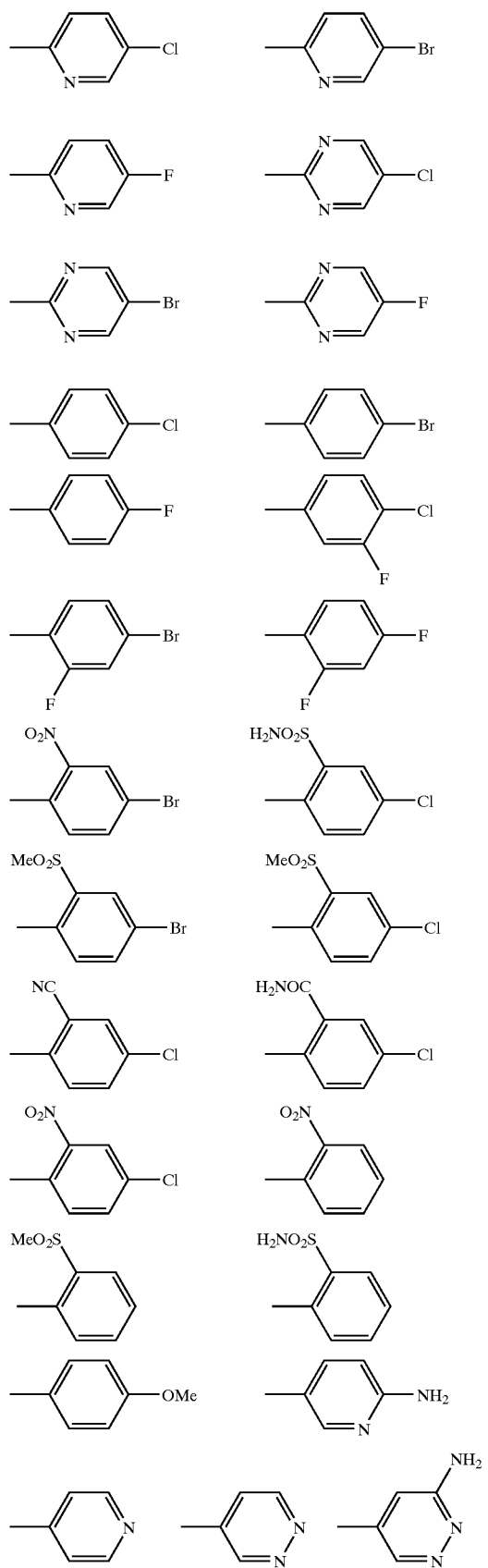
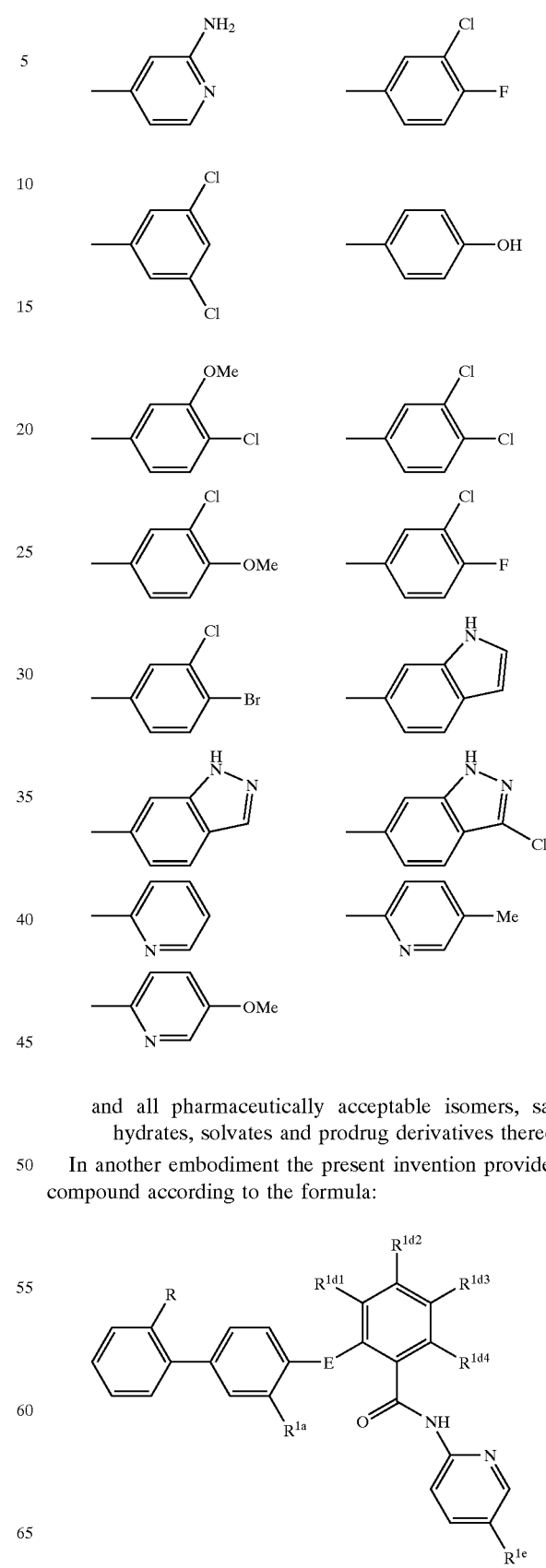
and all pharmaceutically acceptable isomers, salts, hydrates, solvates and prodrug derivatives thereof
In another embodiment the present invention provides a compound according to the formula:
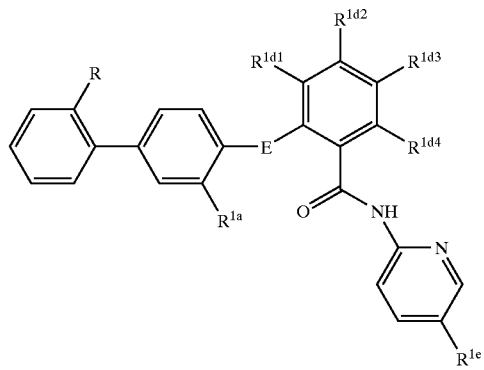

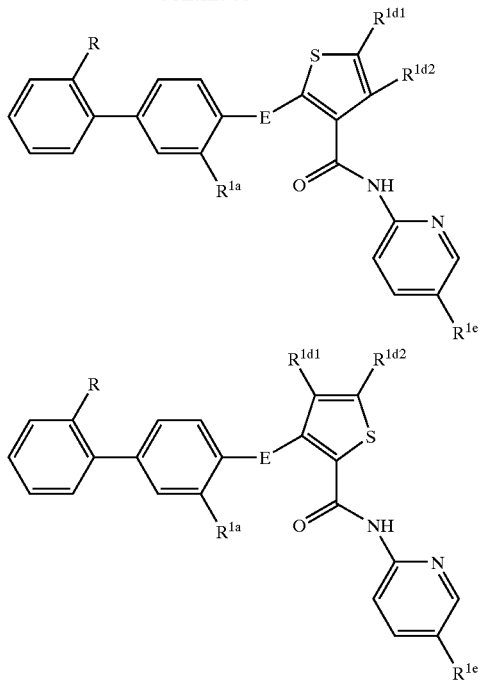

wherein:
- R is a member selected from the group of:
  —SO₂—NH₂ and —SO₂Me;
- R$^{1a}$ is a member selected from the group of:
  H, —F, —Cl and Br;
- E is a member selected from the group consisting of:
  —NHC(=O)— and —C(=O)NH—;
- R$^{1d1}$, R$^{1d2}$, and R$^{1d4}$ are independently a member selected from the group of:
  H, —F, —Cl, —Br, -Me, —NO₂, —OH, —OMe, —NH₂, —NHAc, —NHSO₂Me, —CH₂OH and —CH₂NH₂;
- R$^{1d3}$ is a member selected from the group of:
  H, —CH₃, —CF₃, —Cl, —F, —Br, —NH₂, —N(-Me)₂, —OH, —OMe, —NHSO₂Me, —NO₂, —CN, —C(=O)—OMe, —CO₂H, —C(=O)—NH₂, —SO₂NH₂, —SO₂CH₃, —NHC(=O)Me, —C(=O)—N(-Me)₂, —CH₂NH₂, —CH₂—N(-Me)₂, —CH₂OH, —OCH₂CO₂H, —OCH₂C(=O)—OMe, —OCH₂C(=O)—NH₂, and —OCH₂C(=O)—N(-Me)₂,

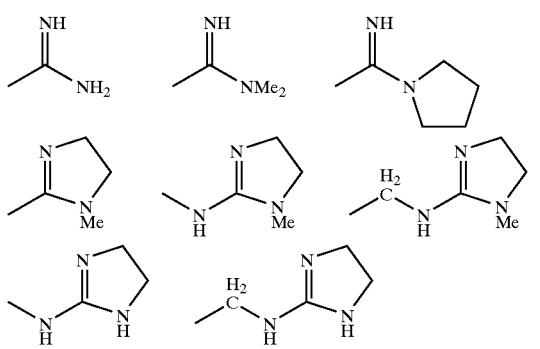

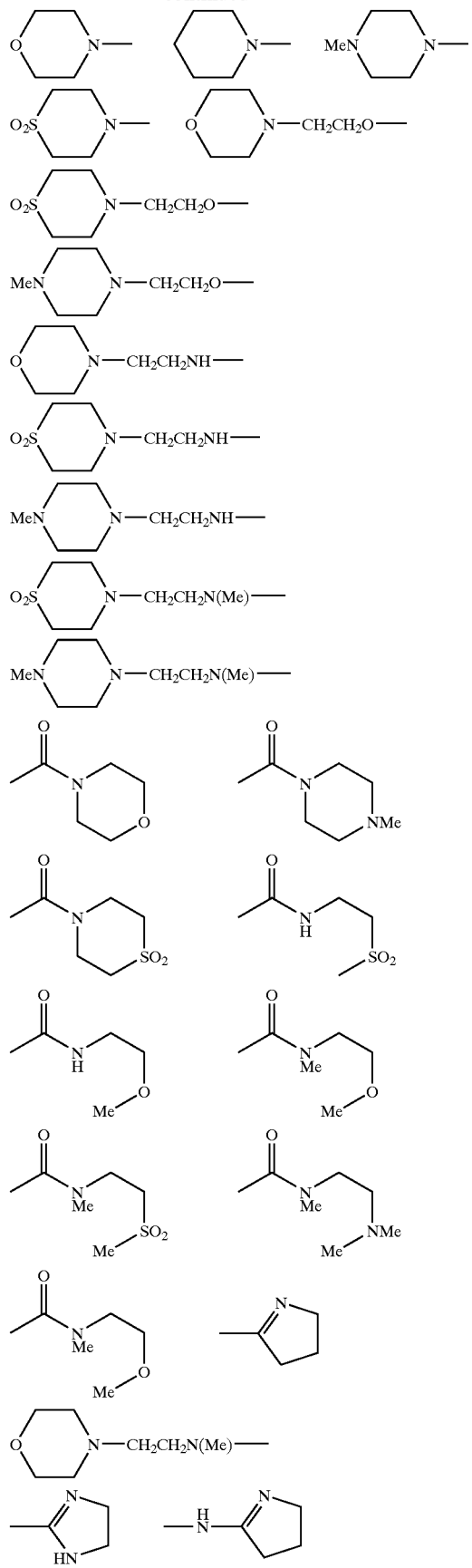

-continued

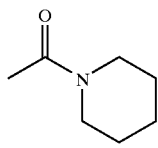 

$R^{1e}$ is a member selected from the group of:
F, —Cl, —Br, —OH, -Me and —Ome,
and all pharmaceutically acceptable isomers, salts, hydrates, solvates and prodrug derivatives thereof.

In another further preferred embodiment the present invention provides a compound according to the formula:

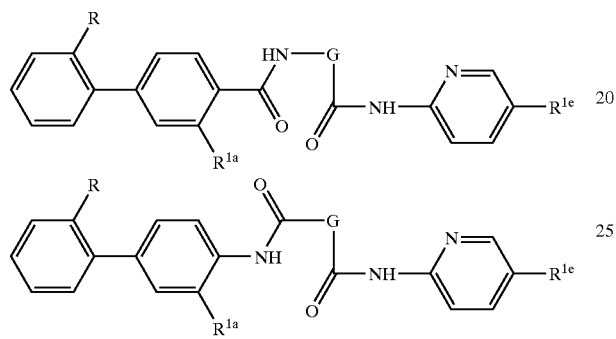

wherein:

R is a member selected from the group consisting of:
—SO$_2$NH$_2$, —SO$_2$Me;

$R^{1a}$ is a member selected from the group consisting of:
H, —F, —Cl and Br;

$R^{1e}$ is a member selected from the group consisting of:
H, —F, —Cl, —Br, —OMe, —OH, -Me, —CF, and —CH$_2$NH$_2$; and G is a member selected from the group consisting of:

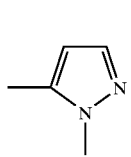 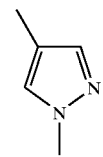 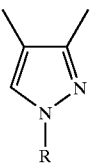

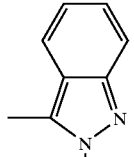 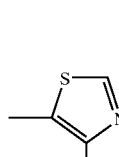 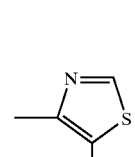

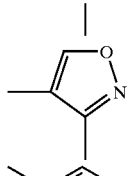 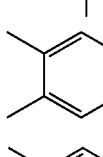 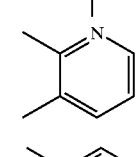

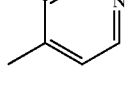 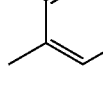 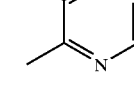

-continued

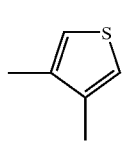 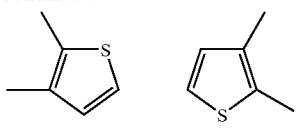

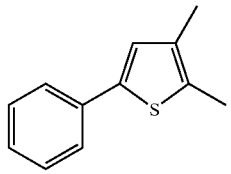 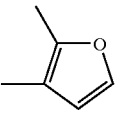

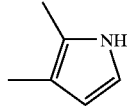 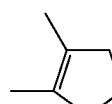 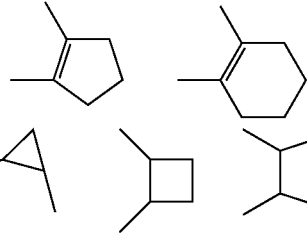

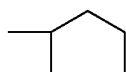 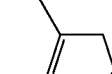 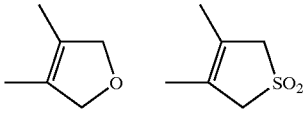

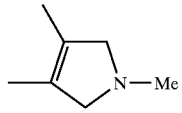  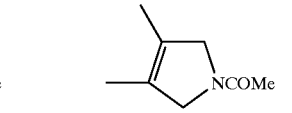

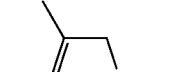  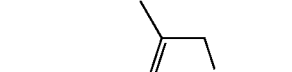

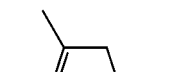  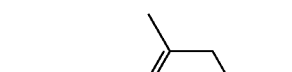

  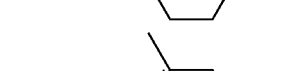

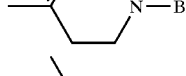  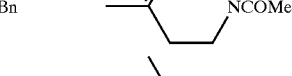

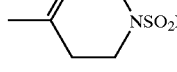  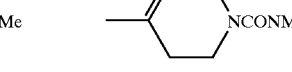

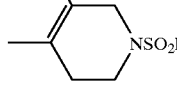 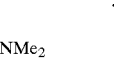 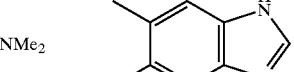

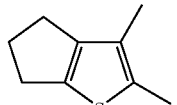  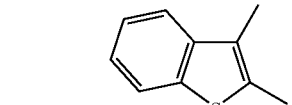

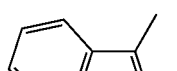  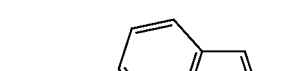

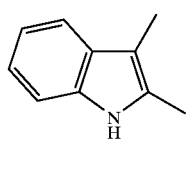 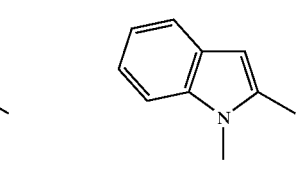

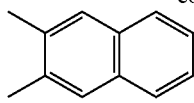

wherein each G group may be substituted by 0–4 $R^{1d}$ groups and each such $R^{1d}$ group is independently selected from the group consisting of:

H, —$CH_3$, —$CF_3$, —Cl, —F, —Br, —$NH_2$, —N(-Me)$_2$, —OH, —OMe, —$NHSO_2Me$, —$NO_2$, —CN, —C(=O)—OMe, —$CO_2H$, —C(=O)—$NH_2$, —$SO_2NH_2$, —$SO_2CH_3$, —NH—C(=O)-Me, —C(=O)—N(-Me)$_2$, —$CH_2NH_2$, —$CH_2$—N(-Me)$_2$, —$CH_2OH$, —$OCH_2CO_2H$, —$OCH_2CO_2Me$, —$OCH_2C$(=O)—$NH_2$, —$OCH_2C$(=O)—N(-Me)$_2$

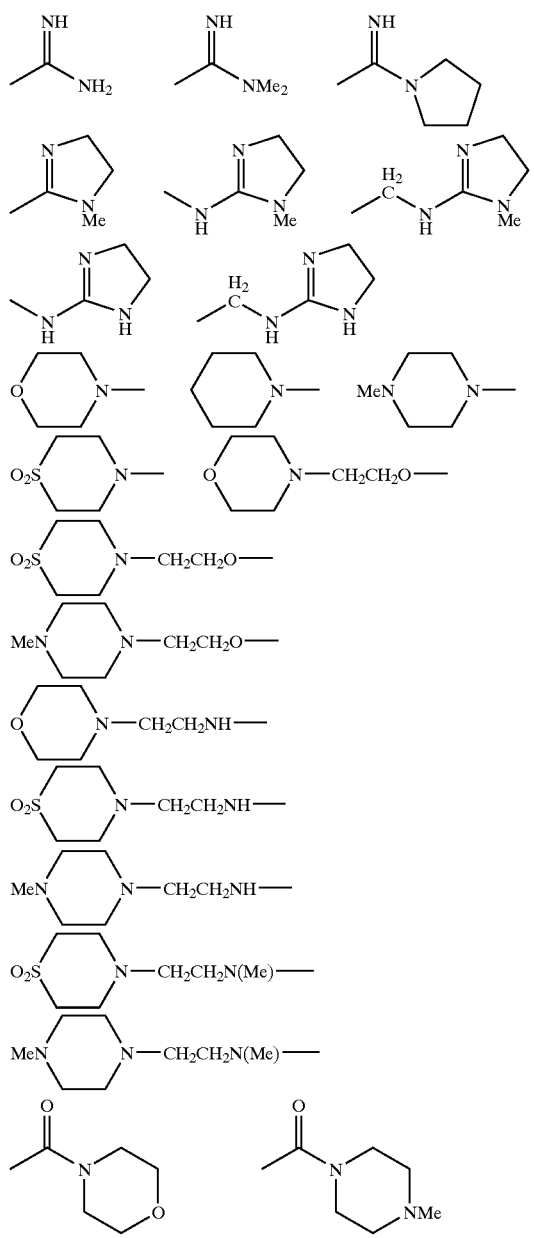

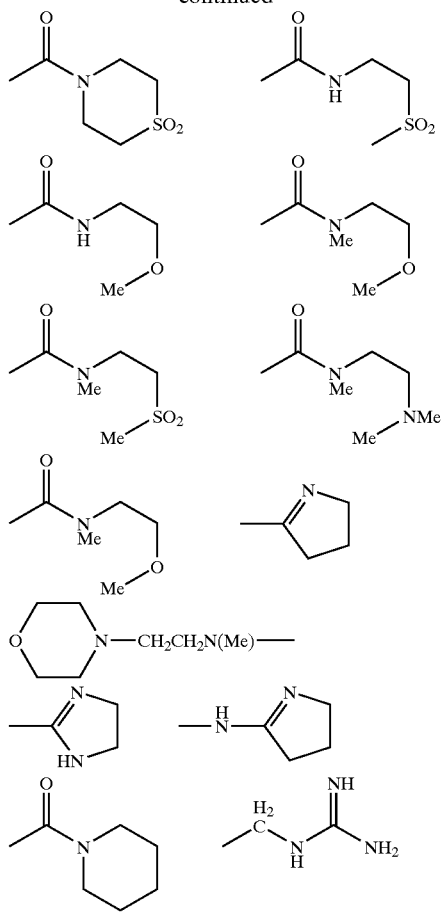

and all pharmaceutically acceptable isomers, hydrates, solvates and prodrug derivatives thereof In another further preferred embodiment the present invention provides a compound according to the formula:

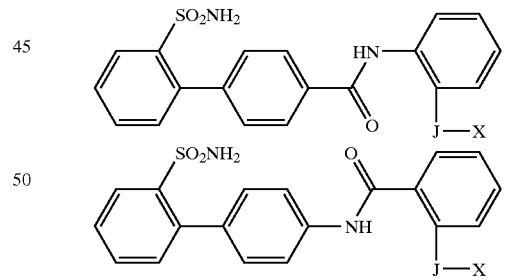

wherein:

J—X are collectively a member selected from the group consisting of:

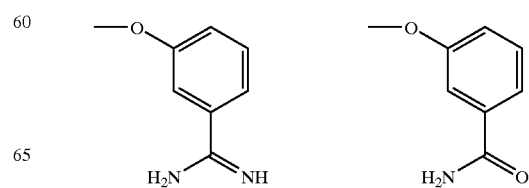

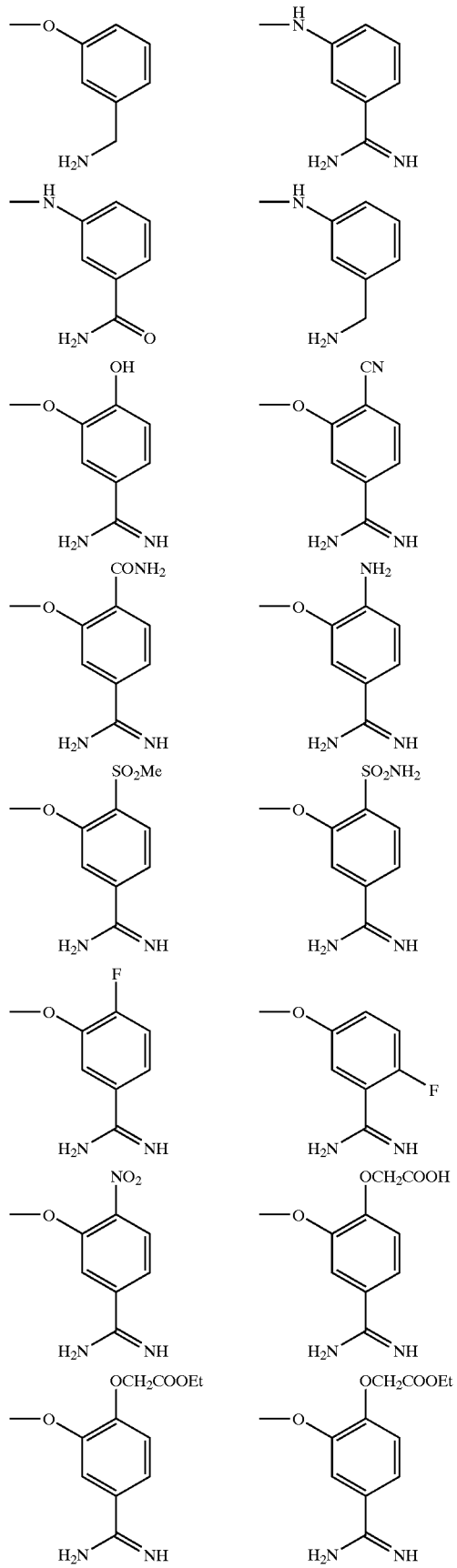
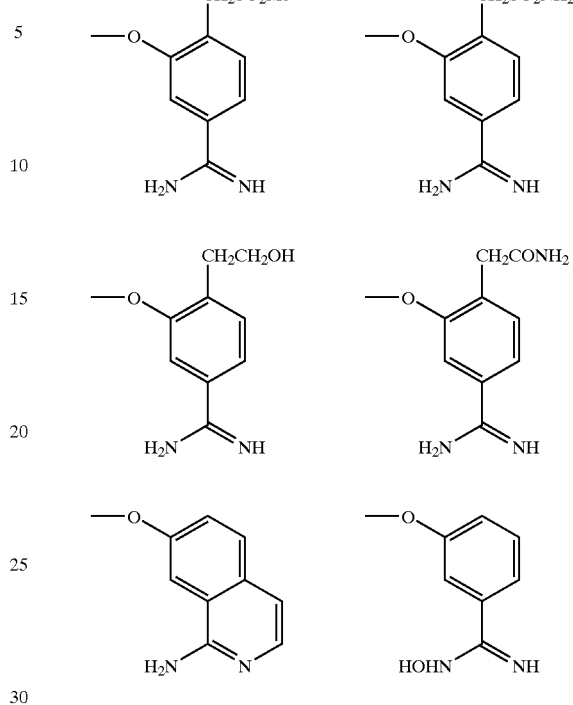
and all pharmaceutically acceptable isomers, salts, hydrates, solvates and prodrug derivatives thereof.
In another further preferred embodiment the present invention provides a compound according to the formula:
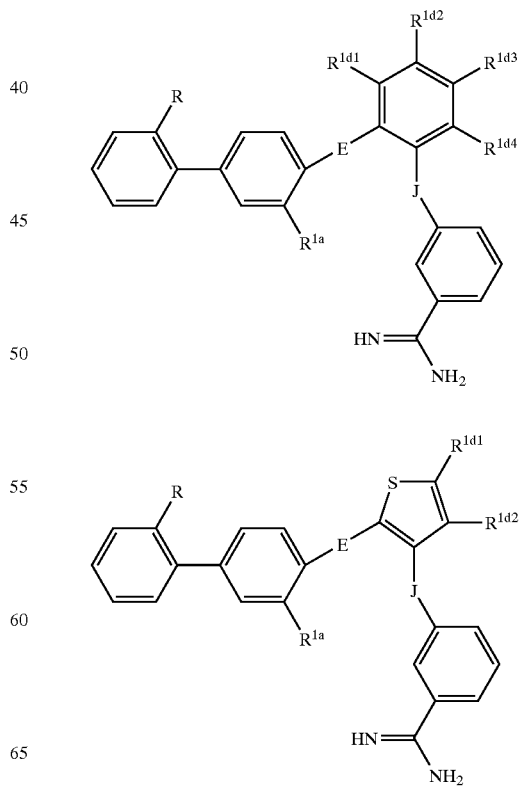

47

-continued

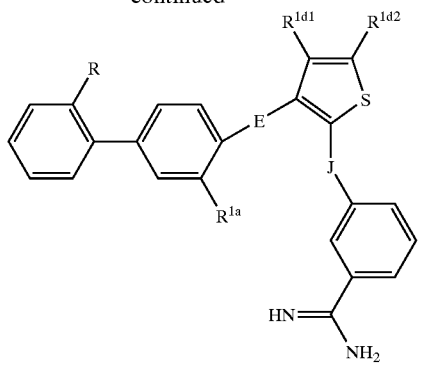

wherein:
R is a member selected from the group of:
—SO$_2$NH$_2$, and —SO$_2$Me;
R$^{1a}$ is a member selected from the group of:
H, —F, —Cl and Br;
E is a member selected from the group consisting of:
—NHC(=O)— and —C(=O)NH—;
J is a member selected from the group consisting of:
—NHC(=O)— and —C(=O)NH—, O;
R$^{1d1}$, R$^{1d2}$, and R$^{1d}$4 are independently a member selected from the group of:
H, —F, —Cl, —Br, -Me, —NO$_2$, —OH, —OMe, —NH$_2$, —NHAc, —NHSO$_2$Me, —CH$_2$OH, —CH$_2$NH$_2$;
R$^{1d3}$ is a member selected from the group of:
H, —CH$_3$, —CF$_3$, —Cl, —F, —Br, —NH$_2$, —N(-Me)$_2$, —OH, —OMe, —NHSO$_2$Me, —NO$_2$, —CN, —CO$_2$Me, —CO$_2$H, —C(=O)—NH$_2$, —SO$_2$NH$_2$, —SO$_2$CH$_3$, —NHC(=O)-Me, —C(=O)—N (-Me)$_2$, —CH$_2$NH$_2$, —CH$_2$—N(-Me)$_2$, —CH$_2$OH, —OCH$_2$CO$_2$H, —OCH$_2$C(=O)—OMe, —OCH$_2$C(=O)—NH$_2$, —OCH$_2$C(=O)—N(-Me)$_2$,

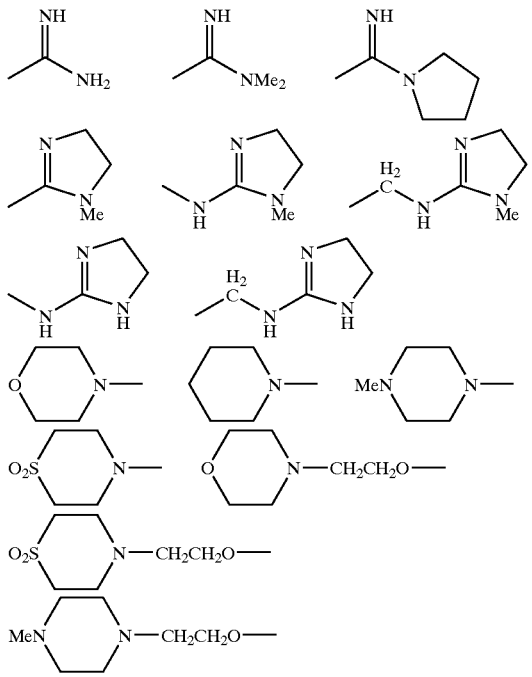

48

-continued

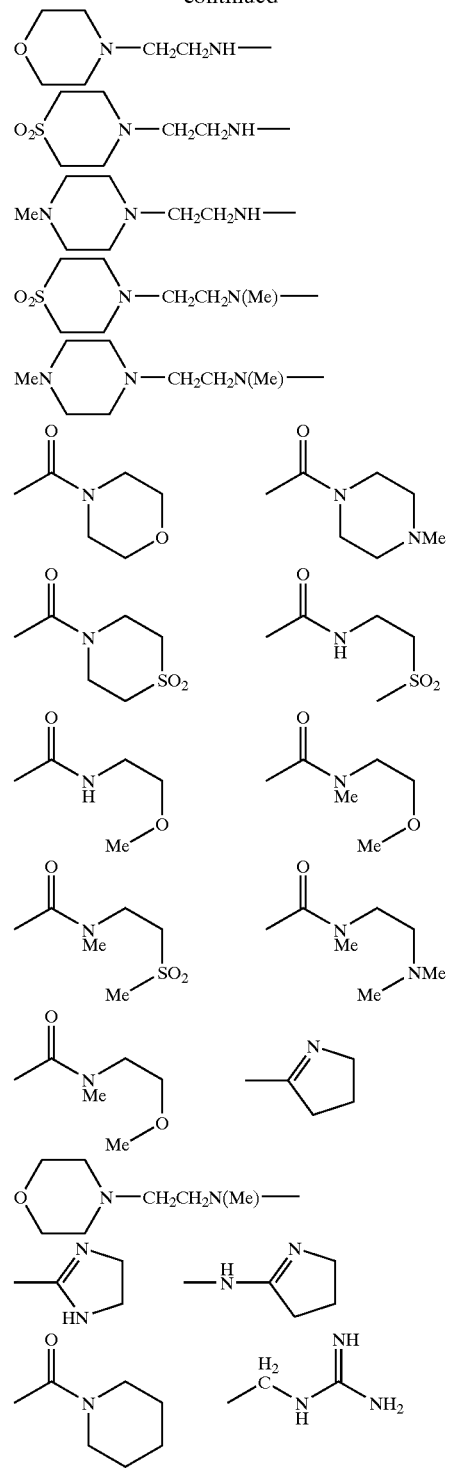

R$^{1e}$ is a member selected from the group of
F, —Cl, —Br, —OH, -Me and —OMe;
and all pharmaceutically acceptable isomers, salts, hydrates, solvates and prodrug derivatives thereof.

In another preferred embodiment the present invention provides a compound of the following formulae, which illustrate the compounds having preferred substituents for G, particularly when G is a pyrazole ring structure.

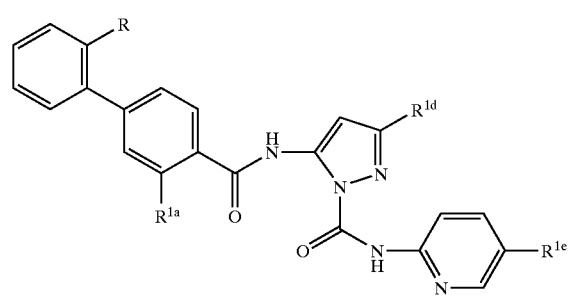
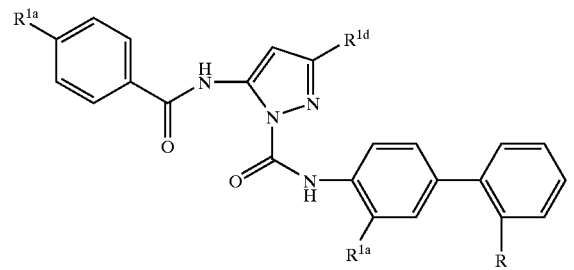
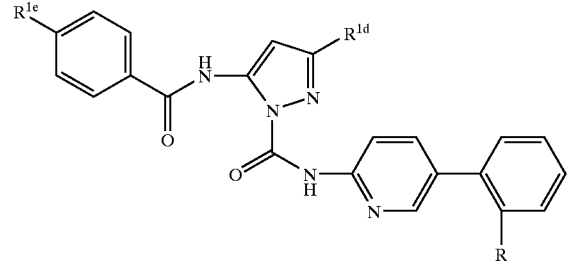
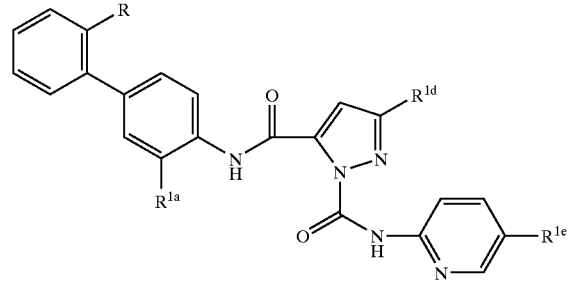
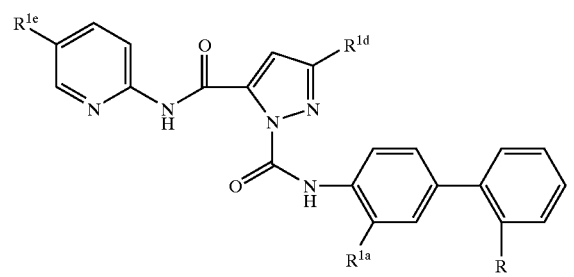
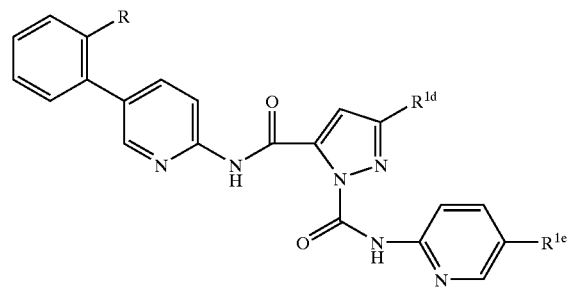
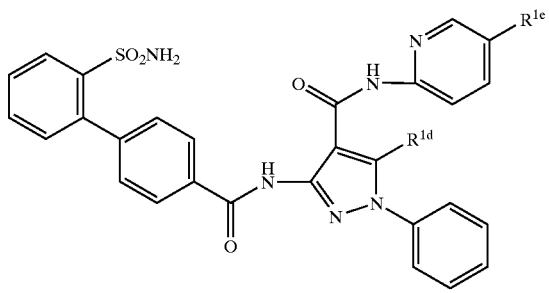
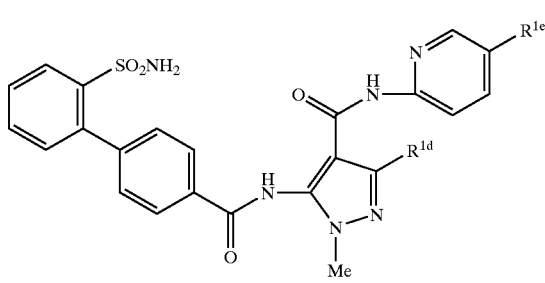
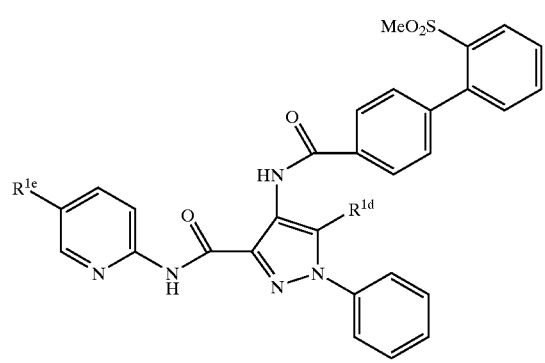
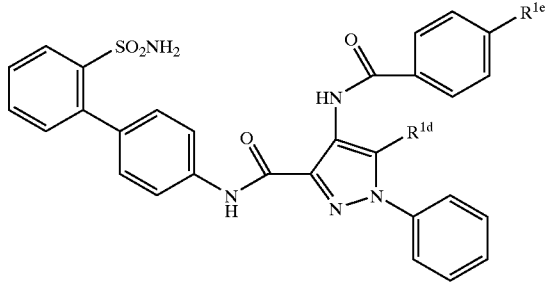
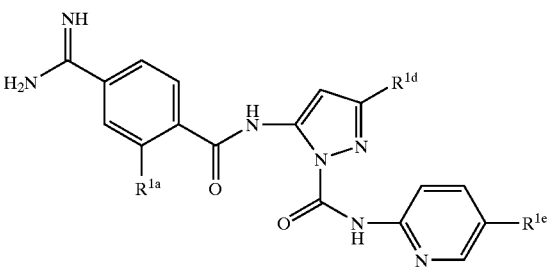

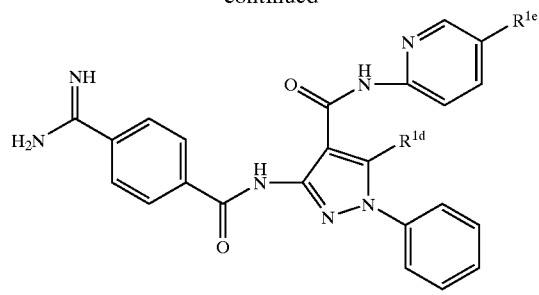

wherein:

R is a member selected from the group of:
—SO$_2$—NH$_2$, and —SO$_2$Me;

R$^{1a}$ is a member selected from the group of:
H, —F, —Cl, and Br;

R$^{1d}$ is a member selected from the group consisting of:
—H, —CH$_3$, —CF$_3$, —CN, —SO$_2$NH$_2$ and —SO$_2$CH$_3$; and R$^{1e}$ is a member selected from the group of:
—Cl, and —Br;

and all pharmaceutically acceptable isomers, salts, hydrates, solvates and prodrug derivatives thereof.

In another preferred embodiment the present invention provides a compound of the following formulae, which illustrate the compounds having preferred substituents for A—Q taken collectively when the remainder of the compound structure has the one of the following two formulae:

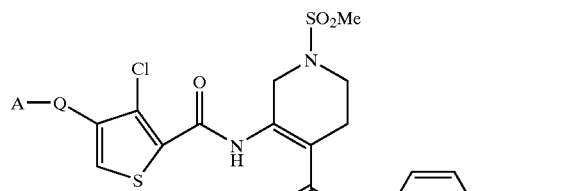

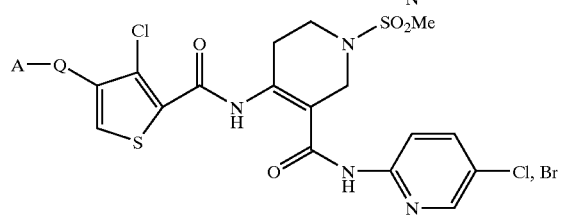

wherein:

A—Q taken together are a member selected from the group consisting of:

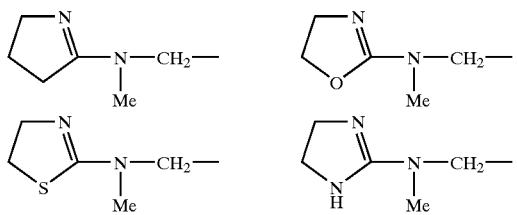

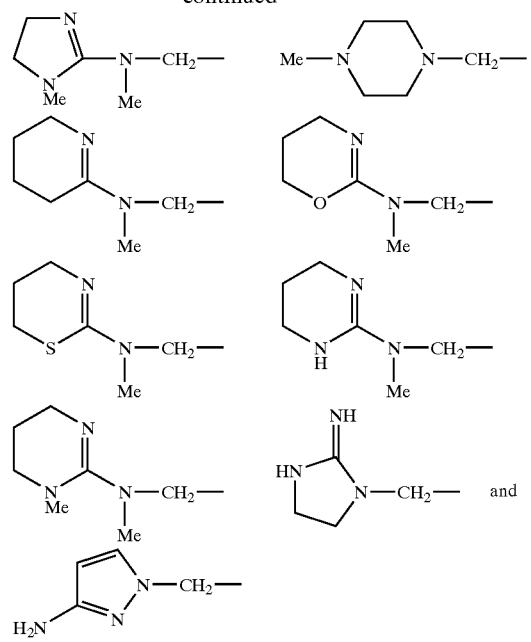

and all pharmaceutically acceptable isomers, salts, hydrates, solvates and prodrug derivatives thereof.

In another preferred embodiment the present invention provides a compound according to the formula:

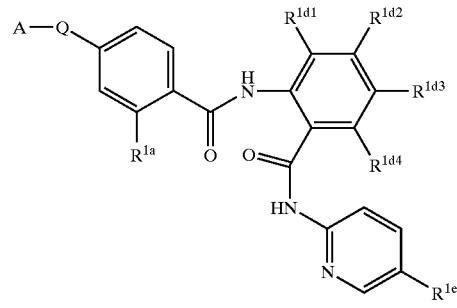

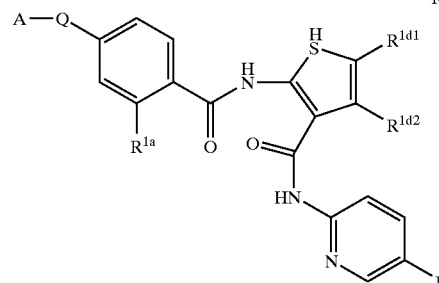

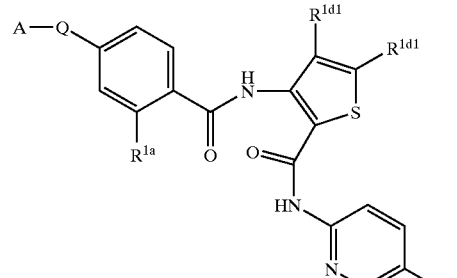

wherein:

A—Q is a member selected from the group of:

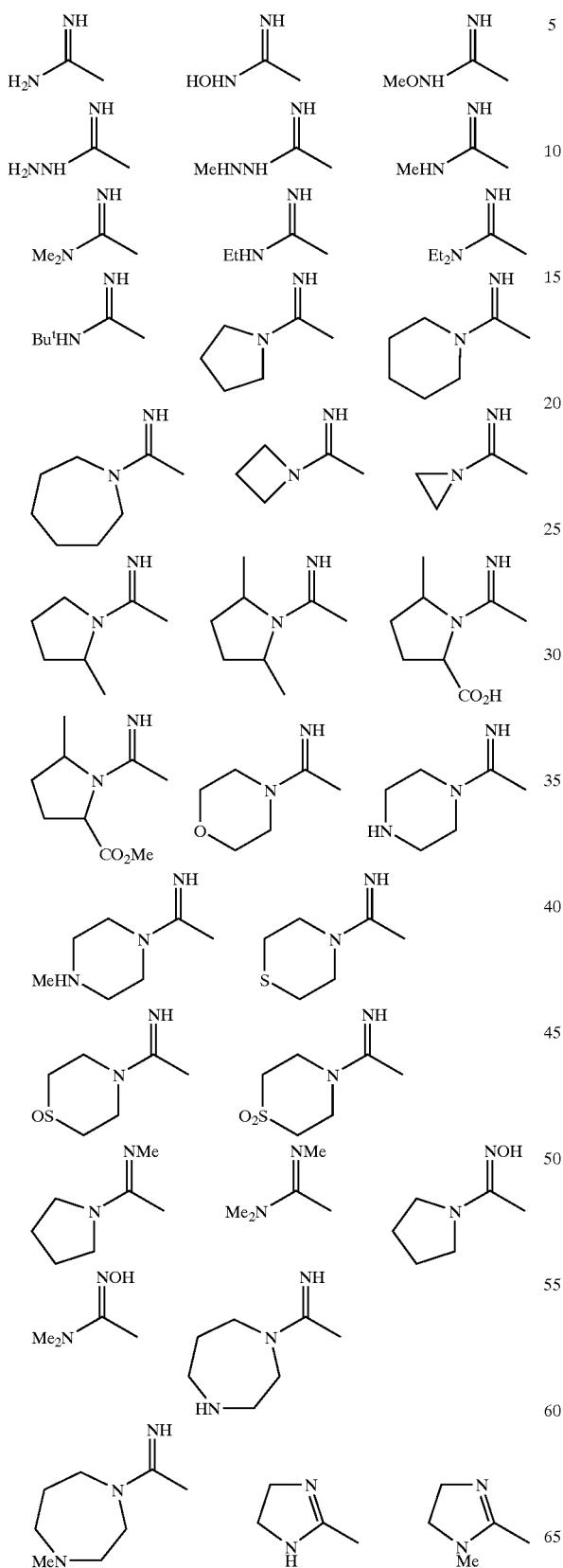
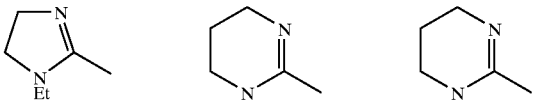
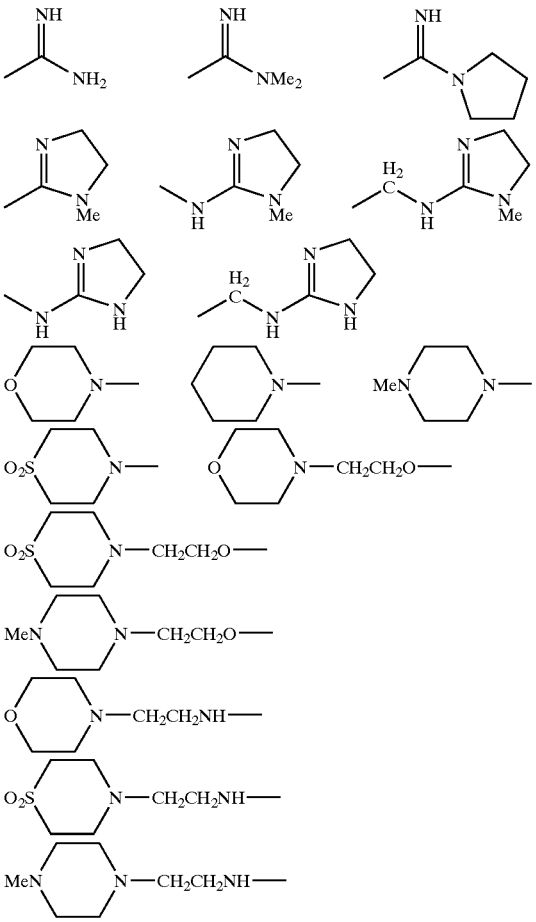

$R^{1a}$ is a member selected from the group of:
H, —F, —Cl and Br;

$R^{1d1, R1d2}$, and $R^{1d4}$ are independently a member selected from the group of:
H, —F, —Cl, —Br, -Me, —NO$_2$, —OH, —OMe, —NH$_2$, —NHAc, —NHSO$_2$Me, —CH$_2$OH, —CH$_2$NH$_2$ $R^{1d3}$ is a member selected from the group of:
H, —CH$_3$, —CF$_3$, —Cl, —F, —Br, —NH$_2$, —N(-Me)$_2$, —OH, —OMe, —NHSO$_2$Me, —NO$_2$, —CN, —C(=O)—OMe, —CO$_2$H, —C(=O)—NH$_2$, —SO$_2$NH$_2$, —SO$_2$CH$_3$, —NHC(=O)-Me, —C(=O)—N(Me)$_2$, —CH$_2$NH$_2$, —CH$_2$—N(-Me)$_2$, —CH$_2$OH, —OCH$_2$CO$_2$H, —OCH$_2$C(=O)—OMe, —OCH$_2$C(=O)—NH$_2$, —OCH$_2$C(=O)—N(-Me)$_2$.

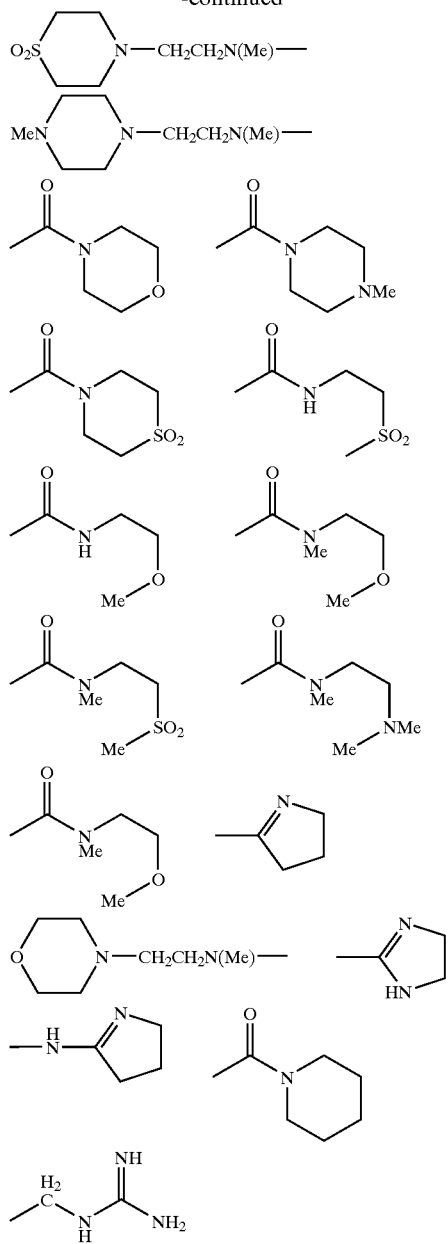
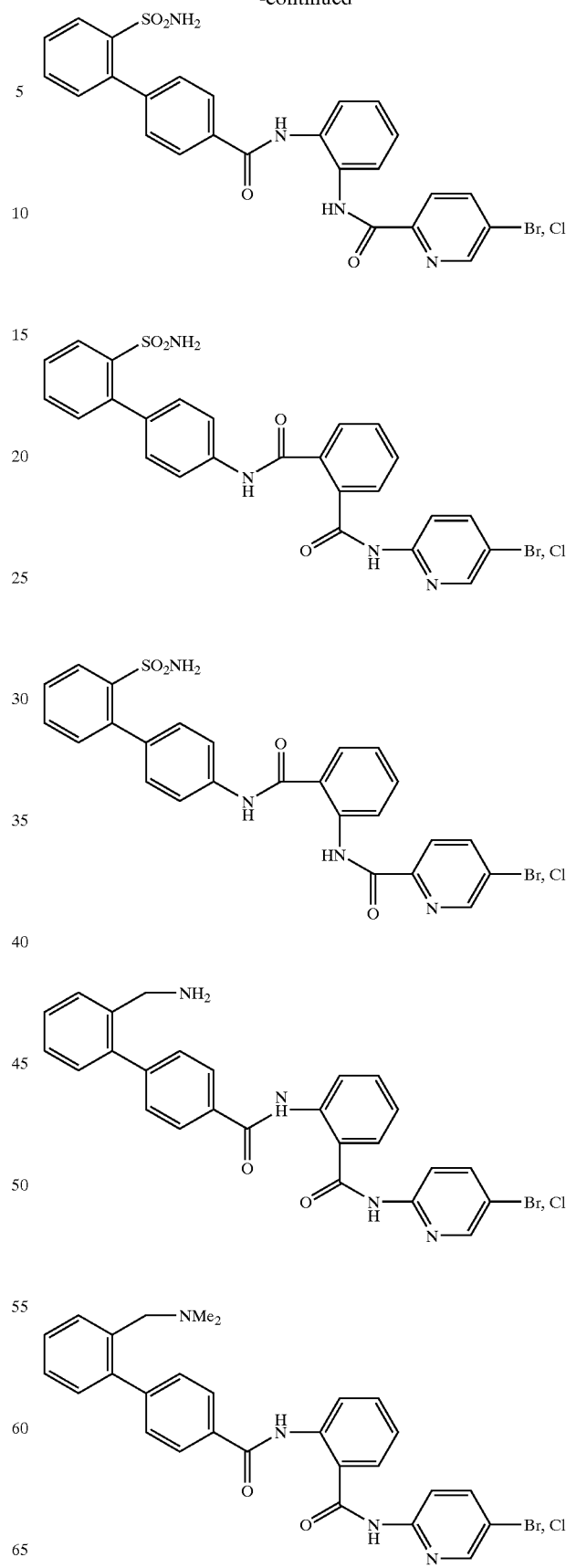
R$^{1e}$ is a member selected from the group of:
F, —Cl, —Br, —OH, Me, and —OMe;
and all pharmaceutically acceptable isomers, salts, hydrates, solvates and prodrug derivatives thereof.
In another further preferred embodiment the present invention provides the following compounds:
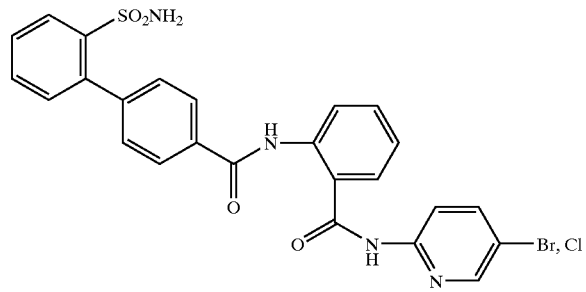
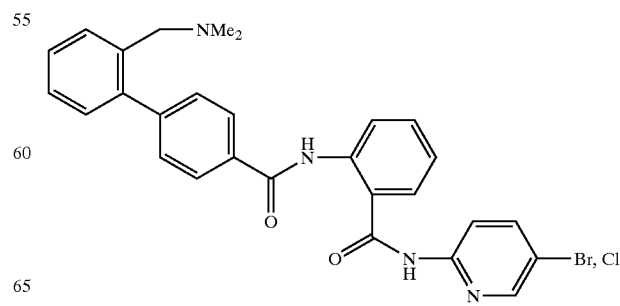

57
-continued
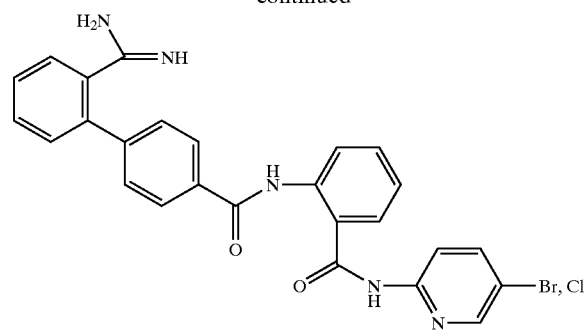
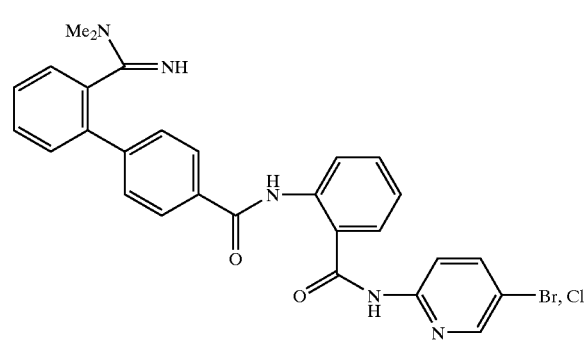
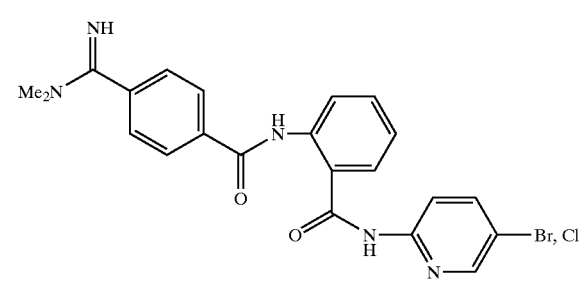
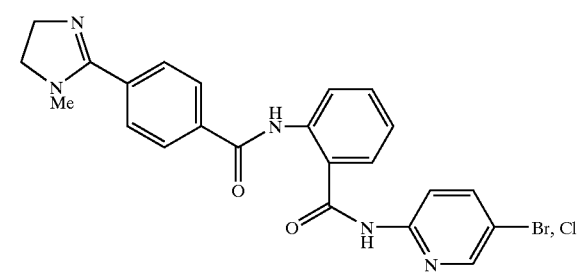
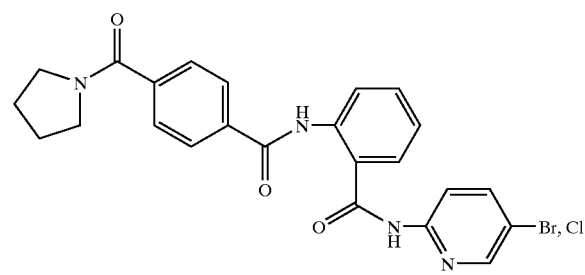
58
-continued
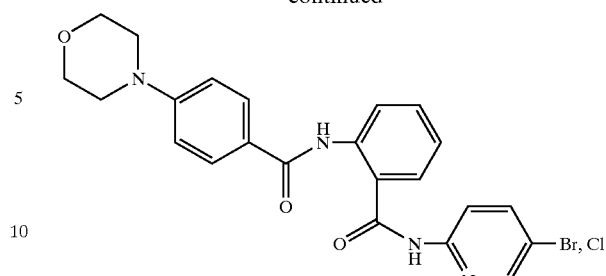
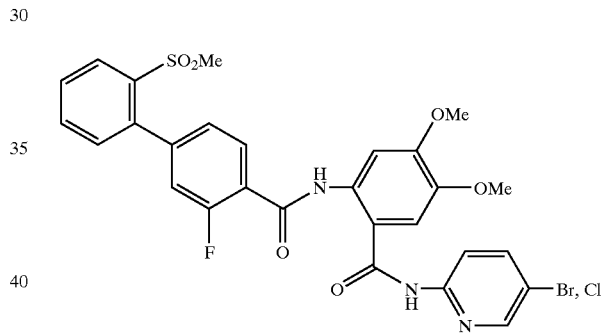
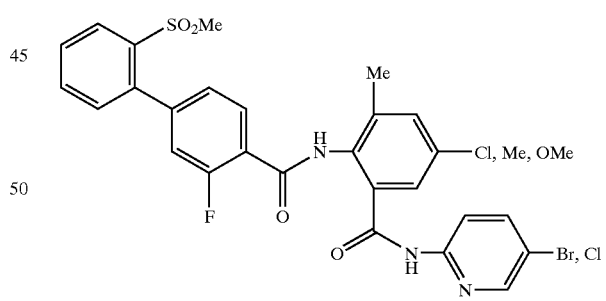
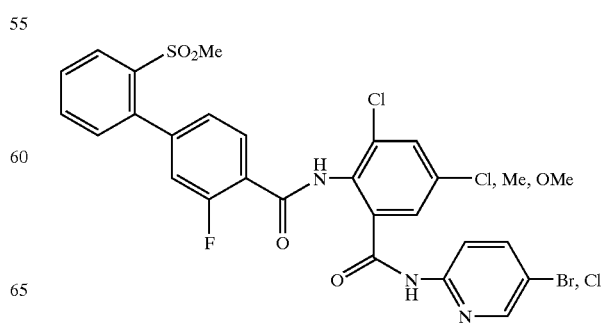

-continued
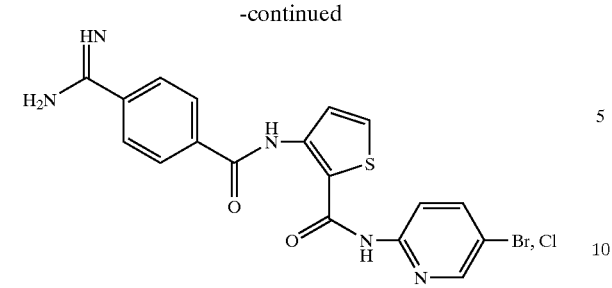
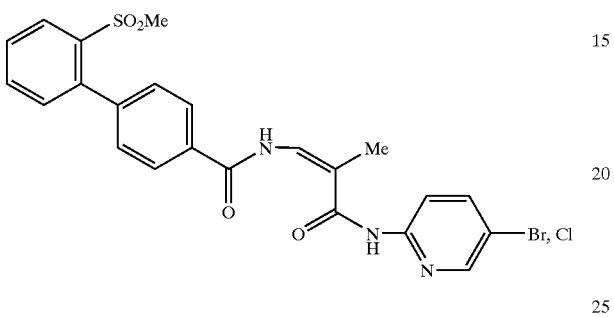
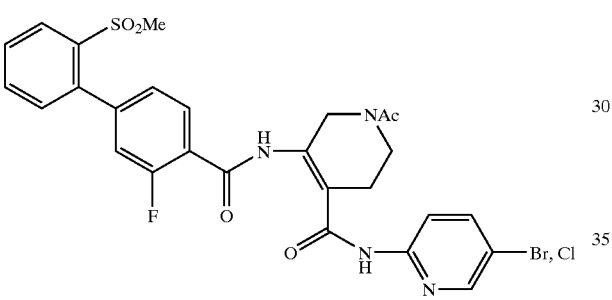
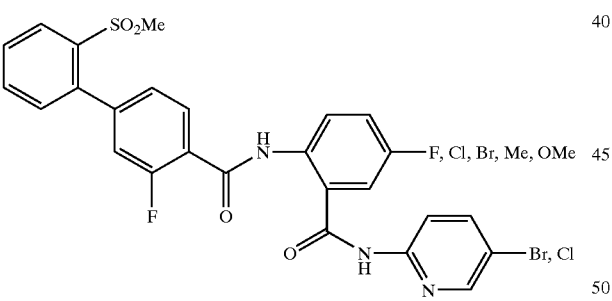
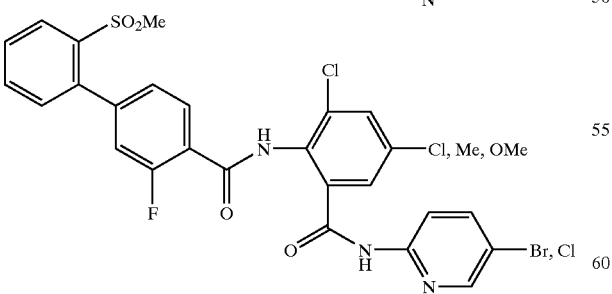
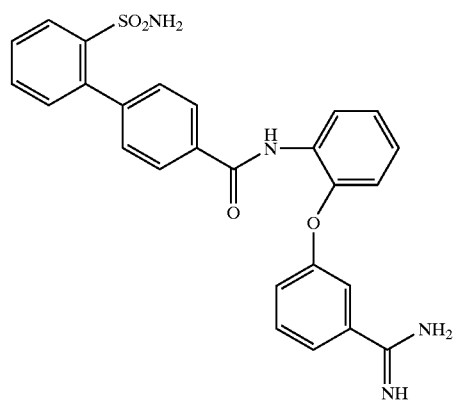
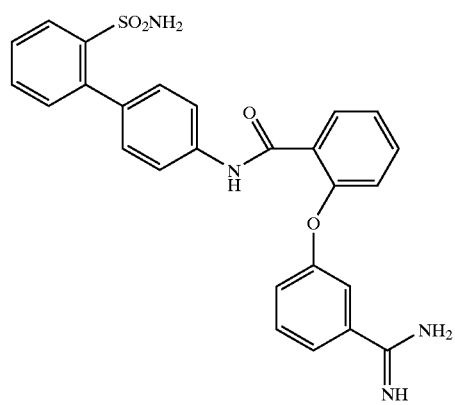
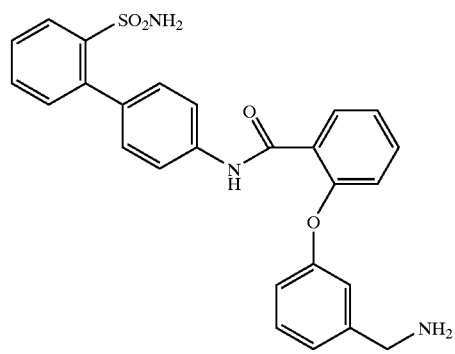
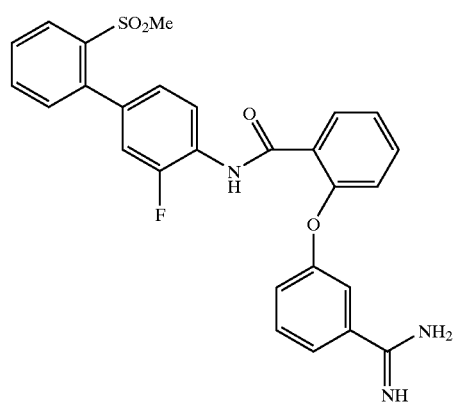
and all pharmaceutically acceptable isomers, salts, hydrates, solvates and prodrug derivatives thereof.
In another further preferred embodiment the present invention provides the following compounds;

-continued
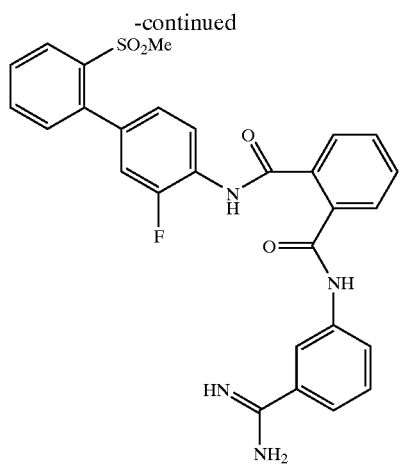
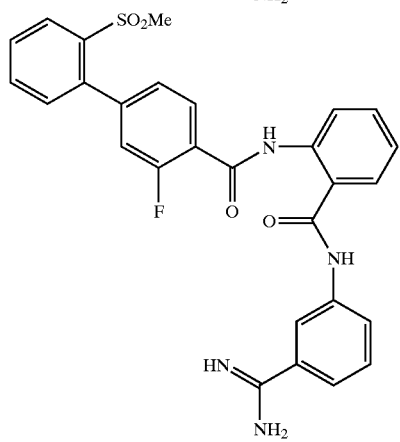
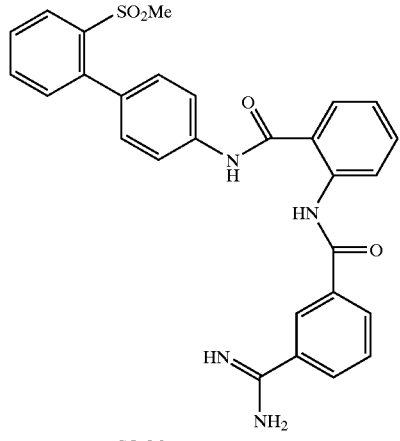
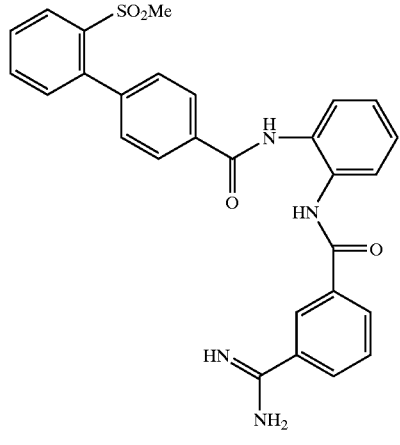
-continued
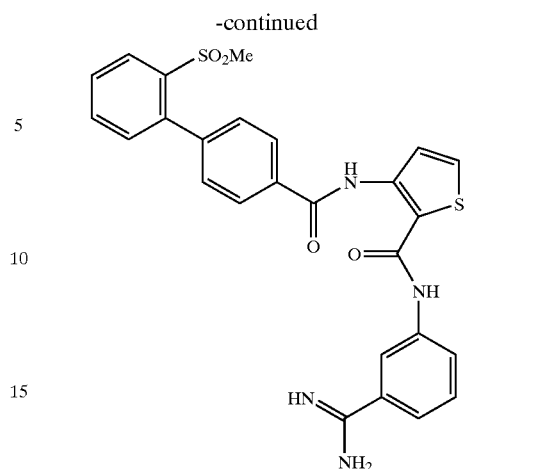
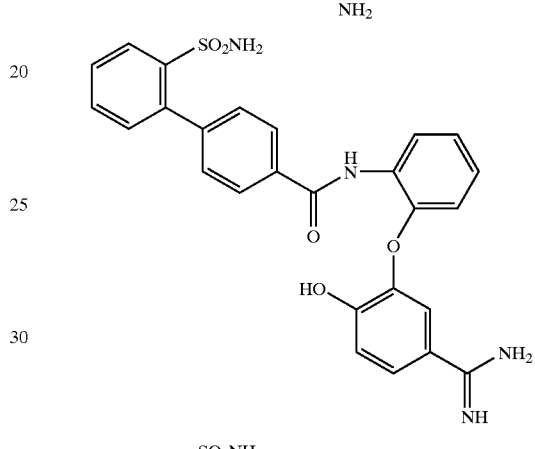
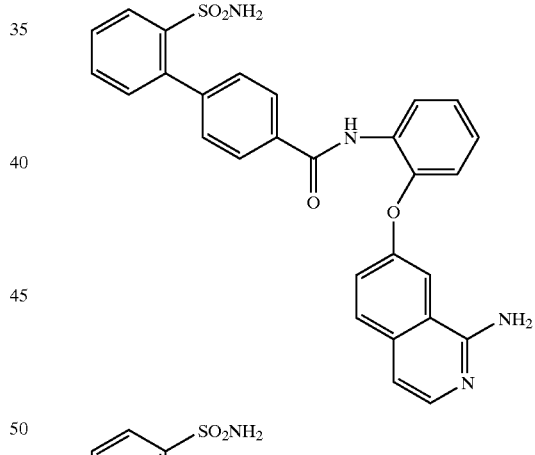
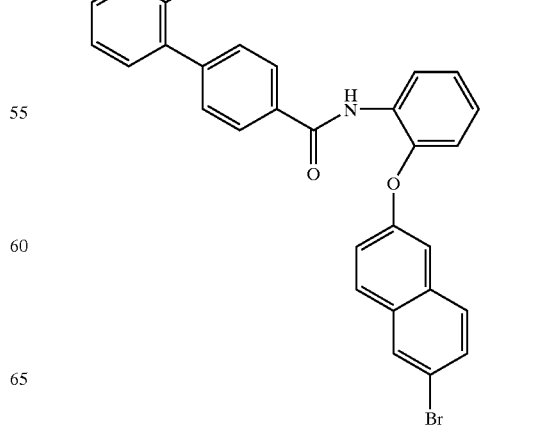

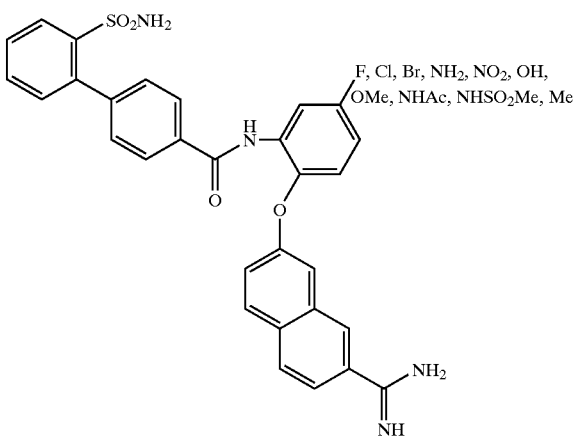

and all pharmaceutically acceptable isomers, salts, hydrates, solvates and prodrug derivatives thereof.

This invention also encompasses all pharmaceutically acceptable isomers, salts, hydrates, solvates, and prodrug derivatives of the preferred compounds. In addition, the preferred compounds can exist in various isomeric and tautomeric forms, and all such forms are meant to be included in the invention, along with pharmaceutically acceptable salts, hydrates, solvates, and prodrug derivatives of such isomers and tautomers.

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, the free acid or free base form of a compound of one of the formulas above can be reacted with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Prodrug Derivatives of Compounds

This invention also encompasses prodrug derivatives of the compounds contained herein. The term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, Design of Prodrugs, pp. 7–9, 21–24, Elsevier, Amsterdam 1985 and Silverman, The Organic Chemistry of Drug Design and Drug Action, pp. 352–401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

As mentioned above, the compounds of this invention find utility as therapeutic agents for disease states in mammals which have disorders of coagulation such as in the treatment or prevention of unstable angina, refractory angina, myocardial infarction, transient ischemic attacks, thrombotic stroke, embolic stroke, disseminated intravascular coagulation including the treatment of septic shock, deep venous thrombosis in the prevention of pulmonary embolism or the treatment of reocclusion or restenosis of reperfused coronary arteries. Further, these compounds are useful for the treatment or prophylaxis of those diseases which involve the production and/or action of factor Xa/prothrombinase complex. This includes a number of thrombotic and prothrombotic states in which the coagulation cascade is activated which include but are not limited to, deep venous thrombosis, pulmonary embolism, myocardial infarction, stroke, thromboembolic complications of surgery and peripheral arterial occlusion.

Accordingly, a method for preventing or treating a condition in a mammal characterized by undesired thrombosis comprises administering to the mammal a therapeutically effective amount of a compound of this invention. In addition to the disease states noted above, other diseases treatable or preventable by the administration of compounds of this invention include, without limitation, occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life-threatening thrombi occurring throughout the microvasculature leading to widespread organ failure, hemorrhagic stroke, renal dialysis, blood oxygenation, and cardiac catheterization.

The compounds of the invention also find utility in a method for inhibiting the coagulation biological samples, which comprises the administration of a compound of the invention.

The compounds of the present invention may also be used in combination with other therapeutic or diagnostic agents. In certain preferred embodiments, the compounds of this invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of the present invention may act in a synergistic fashion to prevent reocclusion following a successful thrombolytic therapy and/or reduce the time to reperfusion. These compounds may also allow for reduced doses of the thrombolytic agents to be used and therefore minimize potential hemorrhagic side-effects. The compounds of this invention can be utilized in vivo, ordinarily in mammals such as primates, (e.g. humans), sheep, horses, cattle, pigs, dogs, cats, rats and mice, or in vitro.

The biological properties of the compounds of the present invention can be readily characterized by methods that are well known in the art, for example by the in vitro protease activity assays and in vivo studies to evaluate antithrombotic efficacy, and effects on hemostasis and hematological parameters, such as are illustrated in the examples.

Diagnostic applications of the compounds of this invention will typically utilize formulations in the form of solutions or suspensions. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be 3–11, more preferably 5–9 and most preferably 7–8. It will be understood that use of certain of the foregoing excipients, carriers, or stabilizers will result in the formation of cyclic polypeptide salts. While the preferred route of administration is by injection, other methods of administration are also anticipated such as orally, intravenously (bolus and/or infusion), subcutaneously, intramuscularly, colonically, rectally, nasally, transdermally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber, or other polymers commercially available.

The compounds of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidyicholines.

The compounds of this invention may also be delivered by the use of antibodies, antibody fragments, growth factors, hormones, or other targeting moieties, to which the compound molecules are coupled& The compounds of this invention may also be coupled with suitable polymers as targetable drug carriers. Such polymers can include polyvinylpyrrolidinone, pyran copolymer, polyhydroxypropyl-methacrylamide-phenol, polyhydroxyethyl-aspartamide-phenol, or polyethyleneoxide-polylysine substituted with palmitoyl residues. Furthermore, compounds of the invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the body's fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of compound are commenced at lower dosage levels, with dosage levels being increased until the desired effect is achieved.

The compounds of the invention can be administered orally or parenterally in an effective amount within the dosage range of about 0.1 to 100 mg/kg, preferably about 0.5 to 50 mg/kg and more preferably about 1 to 20 mg/kg on a regimen in a single or 2 to 4 divided daily doses and/or continuous infusion.

Typically, about 5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Preparation of Compound

The compounds of the present invention may be synthesized by either solid or liquid phase methods described and referenced in standard textbooks, or by a combination of both methods. These methods are well known in the art. See, Bodanszky, "The Principles of Peptide Synthesis", Hafner, et al., Eds., Springer-Verlag, Berlin, 1984.

Starting materials used in any of these methods are commercially available from chemical vendors such as Aldrich, Sigma, Nova Biochemicals, Bachem Biosciences, and the like, or may be readily synthesized by known procedures.

Reactions are carried out in standard laboratory glassware and reaction vessels under reaction conditions of standard temperature and pressure, except where otherwise indicated.

During the synthesis of these compounds, the functional groups of the amino acid derivatives used in these methods are protected by blocking groups to prevent cross reaction during the coupling procedure. Examples of suitable blocking groups and their use are described in "The Peptides: Analysis, Synthesis, Biology", Academic Press, Vol. 3 (Gross, et al., Eds., 1981) and Vol. 9 (1987), the disclosures of which are incorporated herein by reference.

Compounds according to the invention can be synthesized utilizing procedures well known in the art. The reaction products are isolated and purified by conventional methods, typically by solvent extraction into a compatible solvent. The products may be further purified by column chromatography or other appropriate methods.

Compositions and Formulations

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, reaction of the free acid or free base form of a compound of the structures recited above with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Diagnostic applications of the compounds of this invention will typically utilize formulations such as solution or suspension. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinalpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by injection, other methods of administration are also anticipated such as intravenously (bolus and/or infusion), subcutaneously, intramuscularly, colonically, rectally, nasally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of this invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyvinylpyrrolidone, pyran copolymer, polyhydroxypropyl-methacrylamide-phenol, polyhydroxyethylaspartamide-phenol, or polyethyleneoxide-polylysine substituted with palmitoyl residues. Furthermore, the factor Xa inhibitors of this invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For injection by hypodermic needle, it may be assumed the dosage is delivered into the body's fluids. For other routes of administration, the absorption efficiency must be individually determined for each inhibitor by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered several times daily, and other dosage regimens may also be useful.

Typically, about 0.5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin, and excipient such as microcrystalline cellulose, a disintegrating agent like corn starch or alginic acid, a lubricant such as magnesium stearate, a sweetening agent such as sucrose or lactose, or a flavoring agent. When a dosage form is a capsule, in addition to the above materials it may also contain a liquid carrier such as water, saline, a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

In practicing the methods of this invention, the compounds of this invention may be used alone or in combination, or in combination with other therapeutic or diagnostic agents. In certain preferred embodiments, the compounds of this inventions may be coadministered along with other compounds typically prescribed for these conditions according to generally accepted medical practice, such as anticoagulant agents, thrombolytic agents, or other, antithrombotics, including platelet aggregation inhibitors, tissue plasminogen activators, urokinase, prourokinase, streptokinase, heparin, aspirin, or warfarin. The compounds of this invention can be utilized in vivo, ordinarily in mammals such as primates, such as humans, sheep, horses, cattle, pigs, dogs, cats, rats and mice, or in vitro.

The preferred compounds of the present invention are characterized by their ability to inhibit thrombus formation with acceptable effects on classical measures of coagulation parameters, platelets and platelet function, and acceptable levels of bleeding complications associated with their use. Conditions characterized by undesired thrombosis would include those involving the arterial and venous vasculature.

With respect to the coronary arterial vasculature; abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous translumina coronary angioplasty (PTCA).

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The compounds of this present invention, selected and used as disclosed herein, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Anticoagulant therapy is also useful to prevent coagulation of stored whole blood and to prevent coagulation in other biological samples for testing or storage. Thus the compounds of this invention can be added to or contacted with any medium containing or suspected to contain factor Xa and in which it is desired that blood coagulation be inhibited, e.g., when contacting the mammal's blood with material such as vascular grafts, stents, orthopedic prostheses, cardiac stents, valves and prostheses, extra corporeal circulation systems and the like.

Without firer description, it is believed that one of ordinary skill in the art can, using the preceding description and the following illustrative examples, make and utilize the compounds of the present invention and practice the claimed methods.

EXAMPLES

Examples of Chemical Production Process General Reaction Schemes

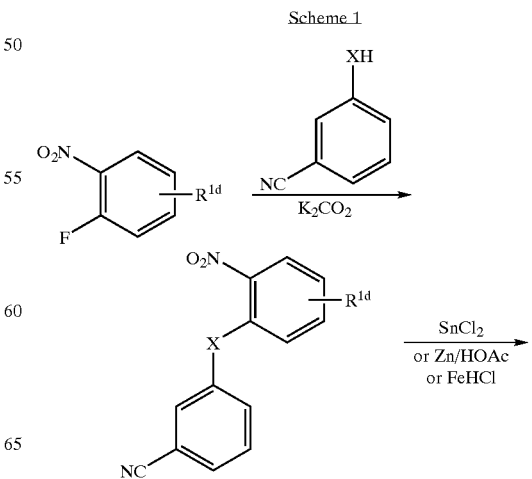

Scheme 1

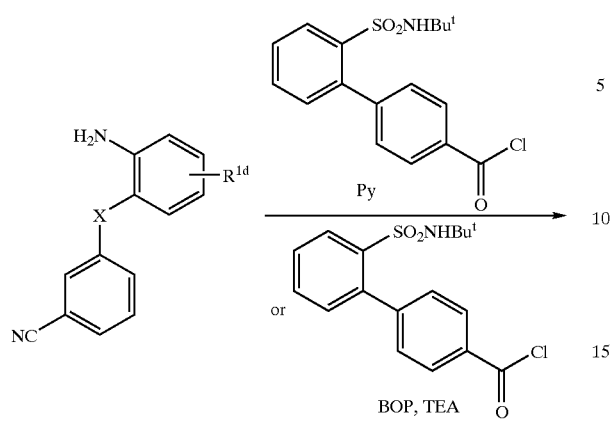
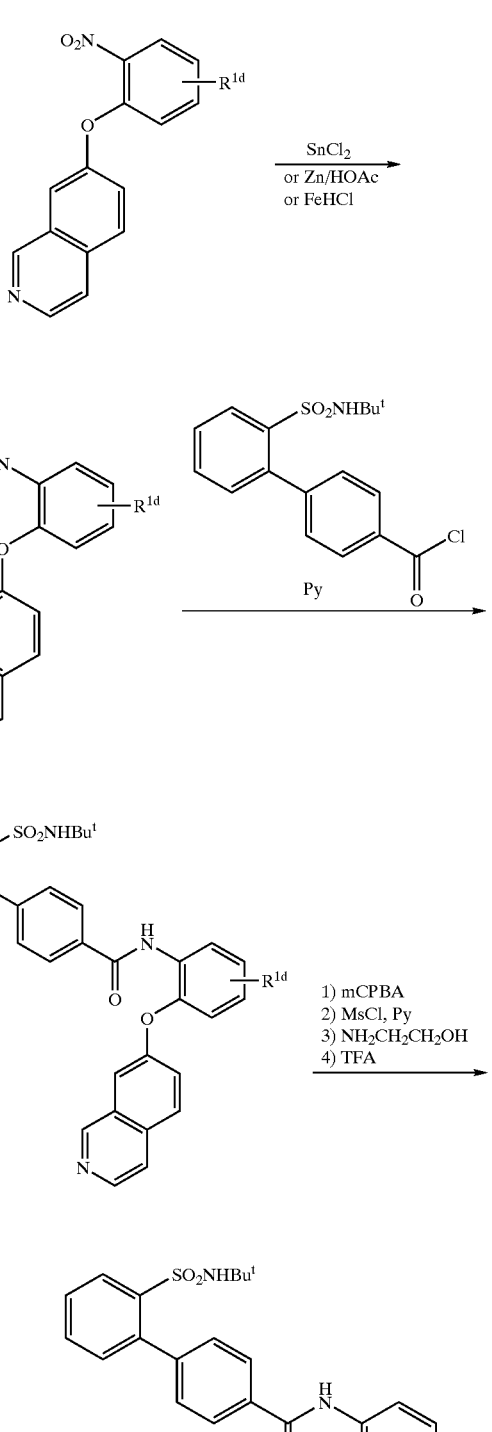
X = O or NH
Scheme 2
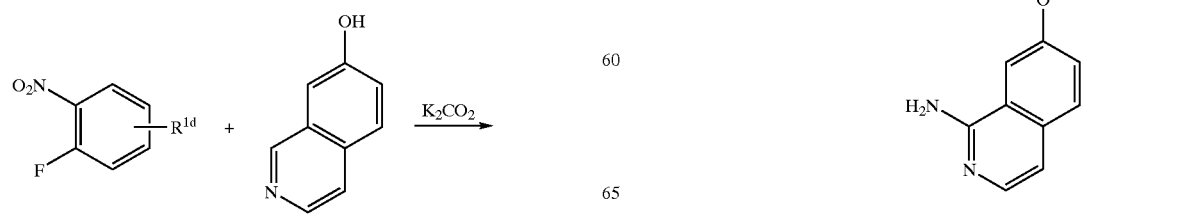

75
Scheme 3
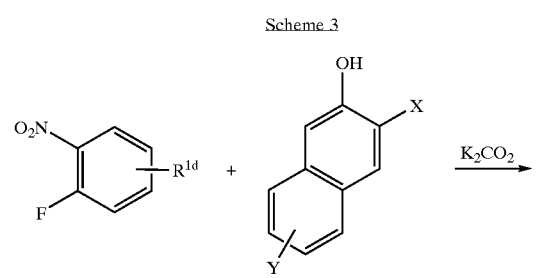
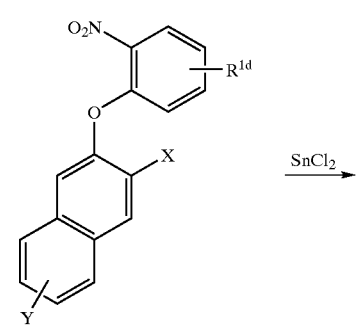
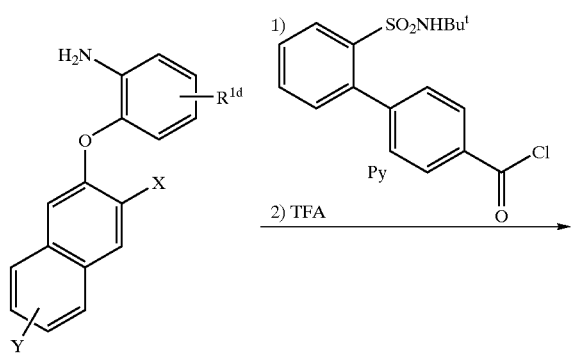
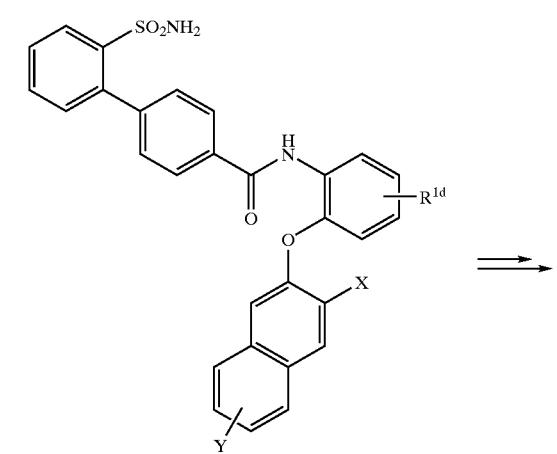
76
-continued
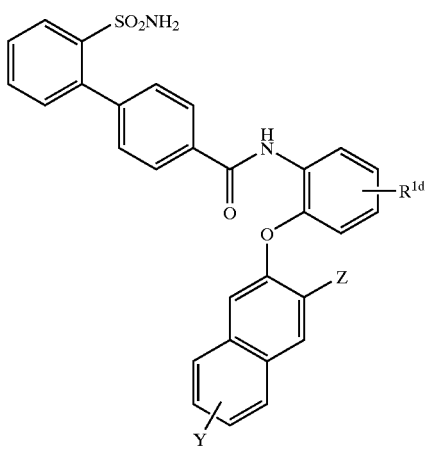
Scheme 4
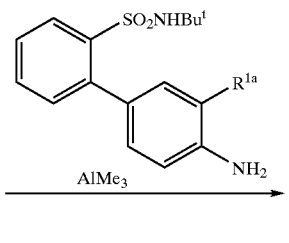
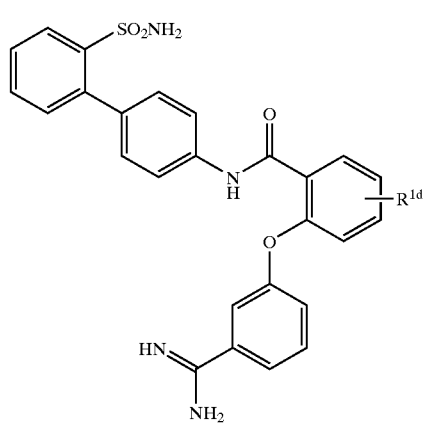

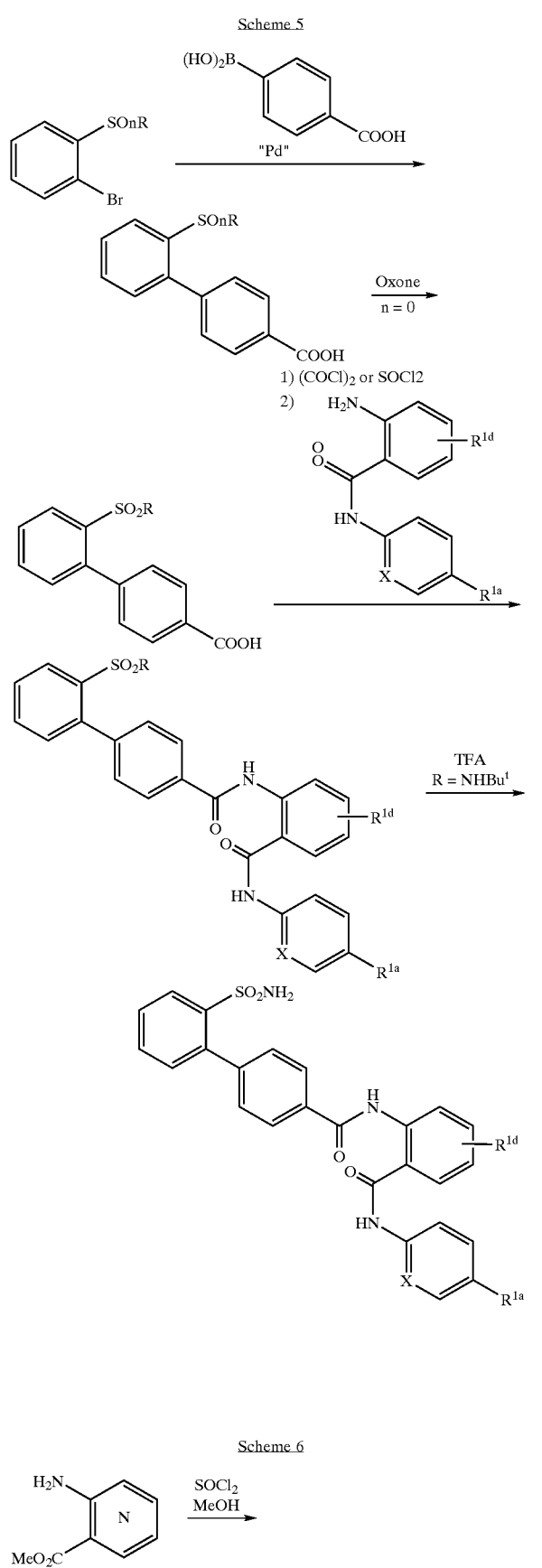

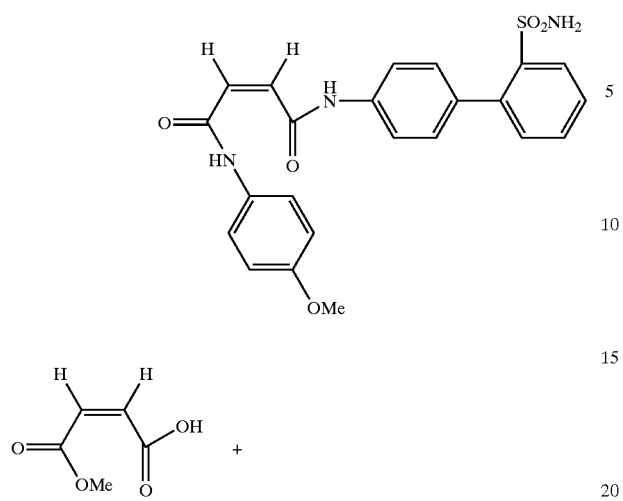
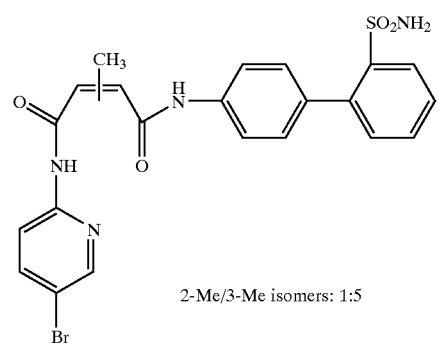
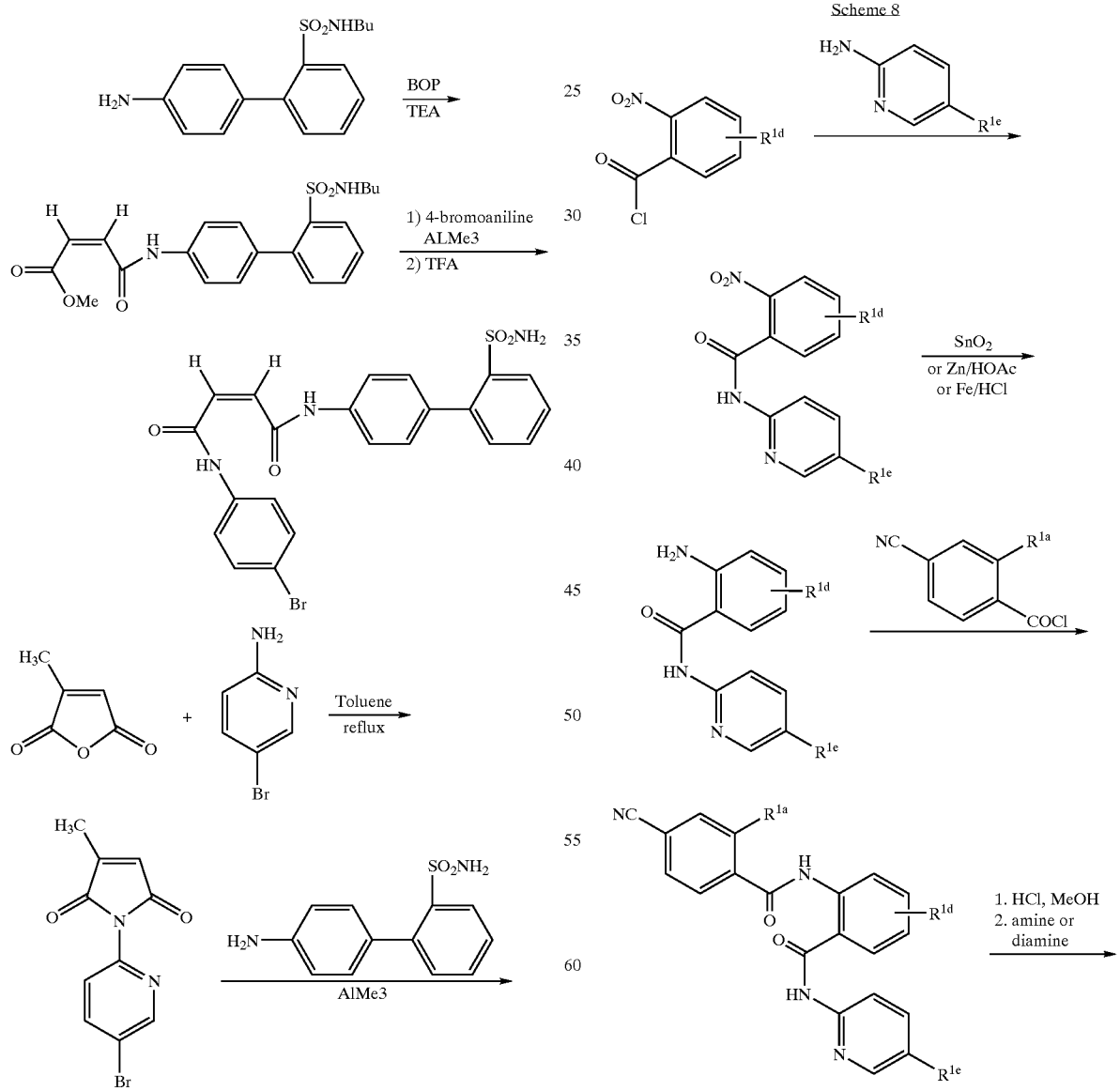
Scheme 8
2-Me/3-Me isomers: 1:5

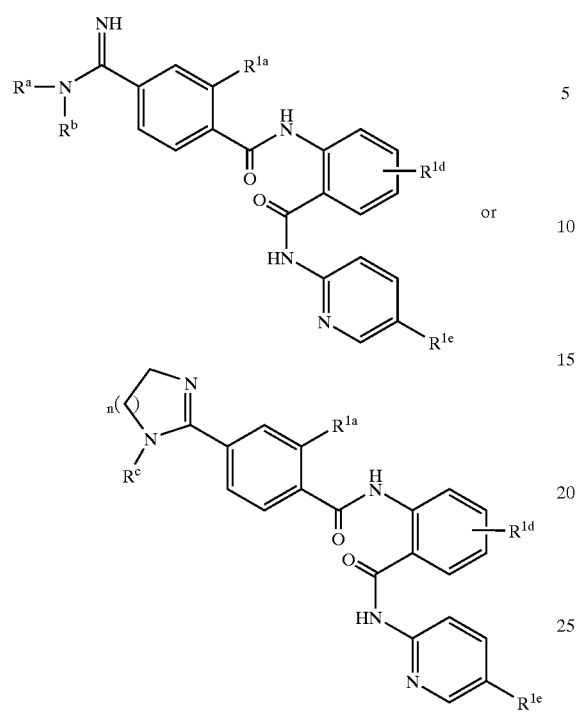
or
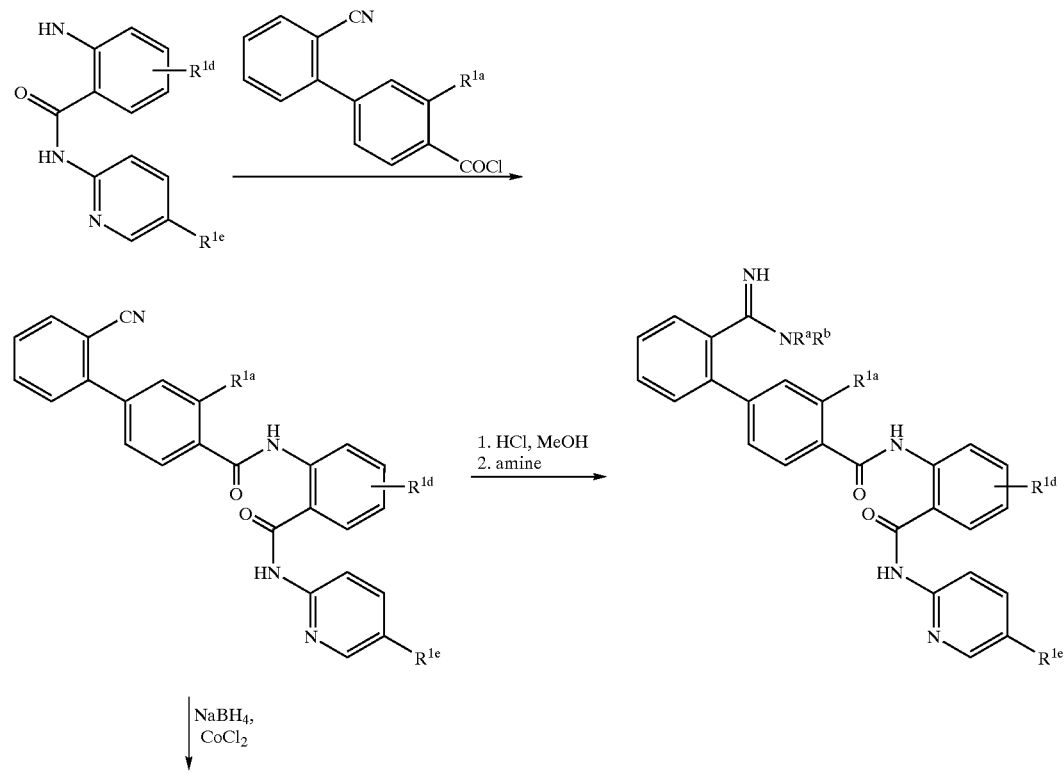
Scheme 9

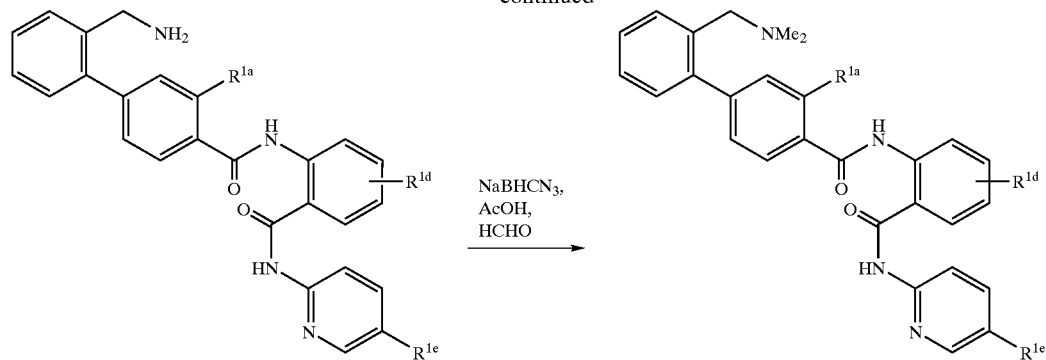
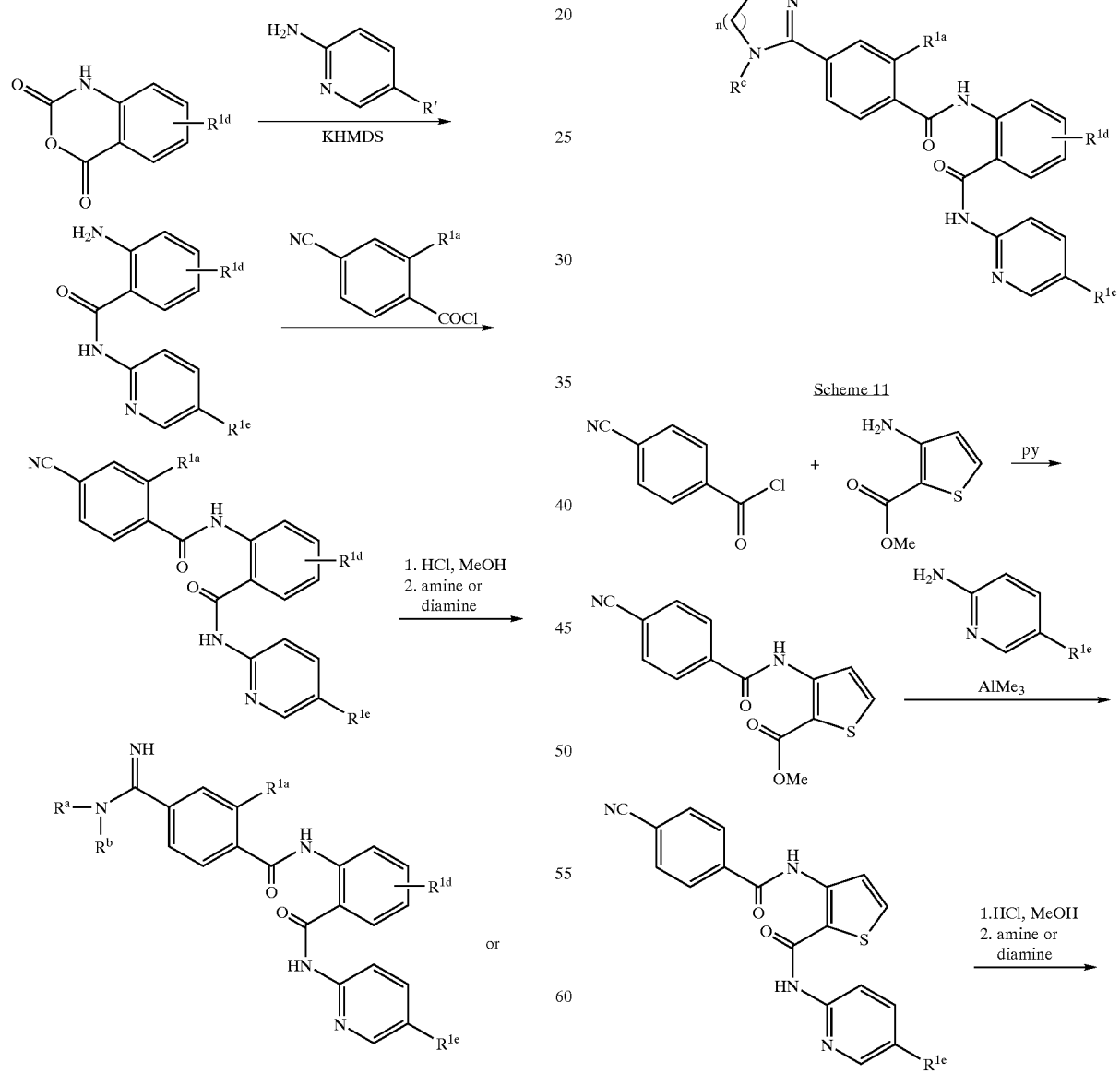

85
-continued
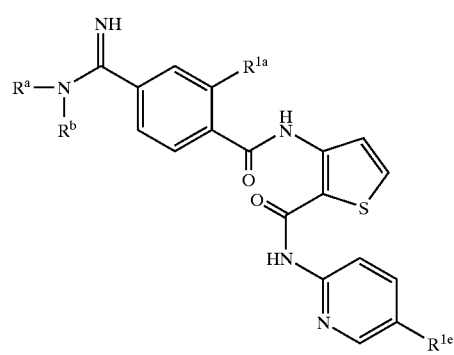
or
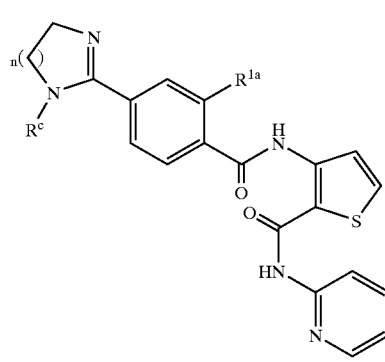
86
-continued
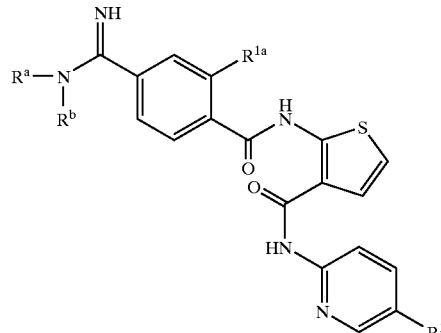
or
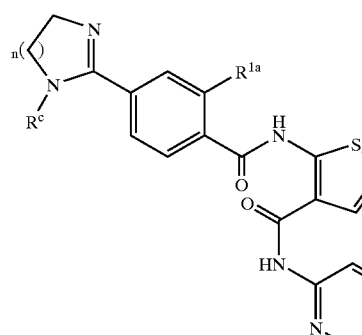
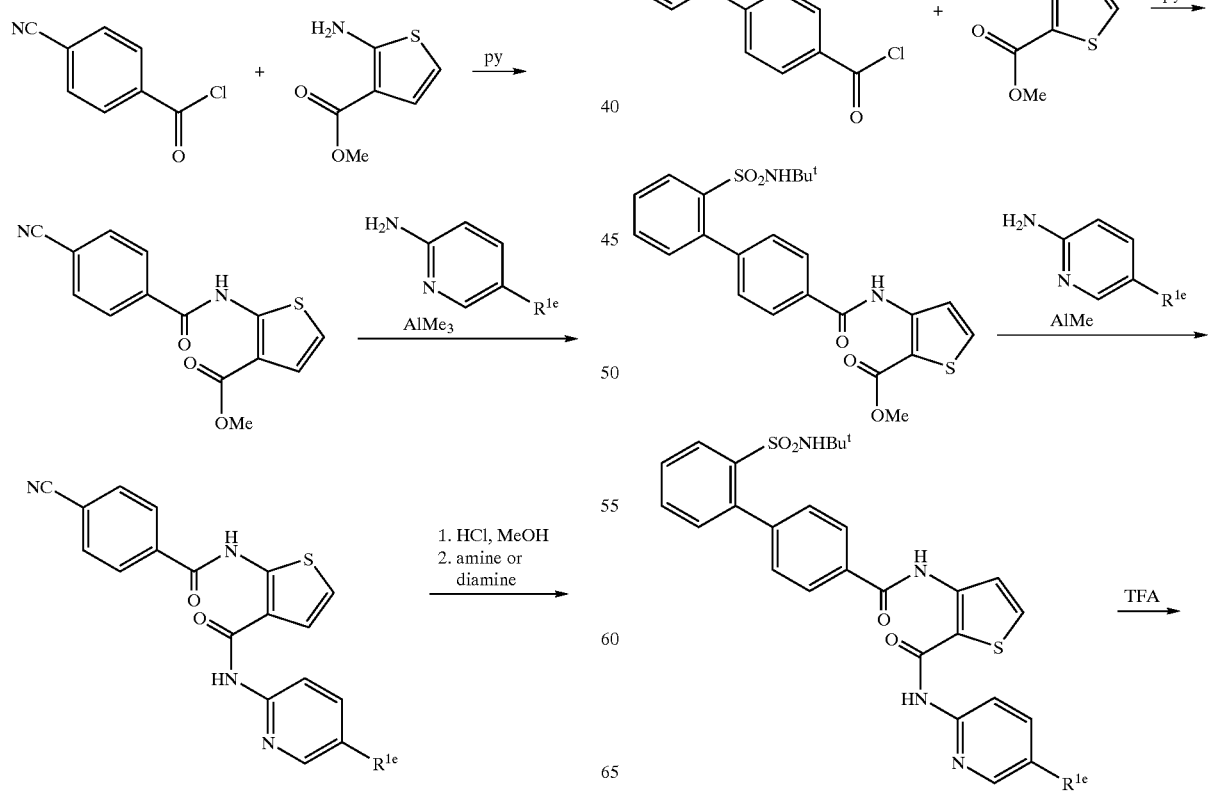

Scheme 15
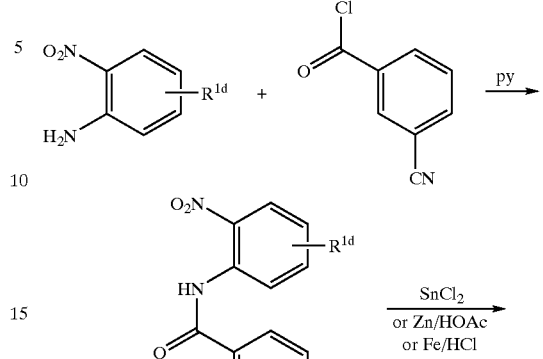
Scheme 14
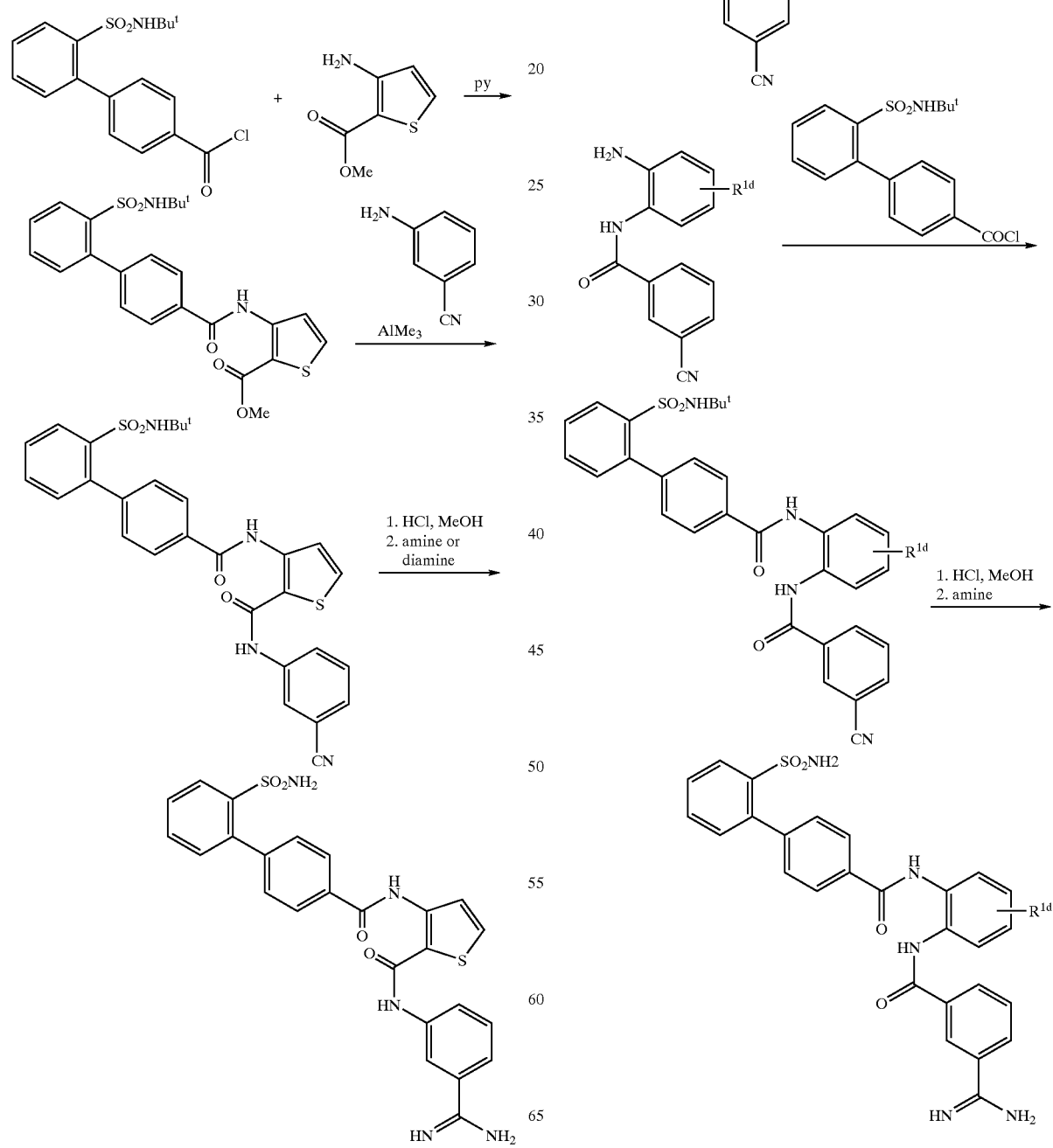

Scheme 16: Transformations of $R^{1d}$
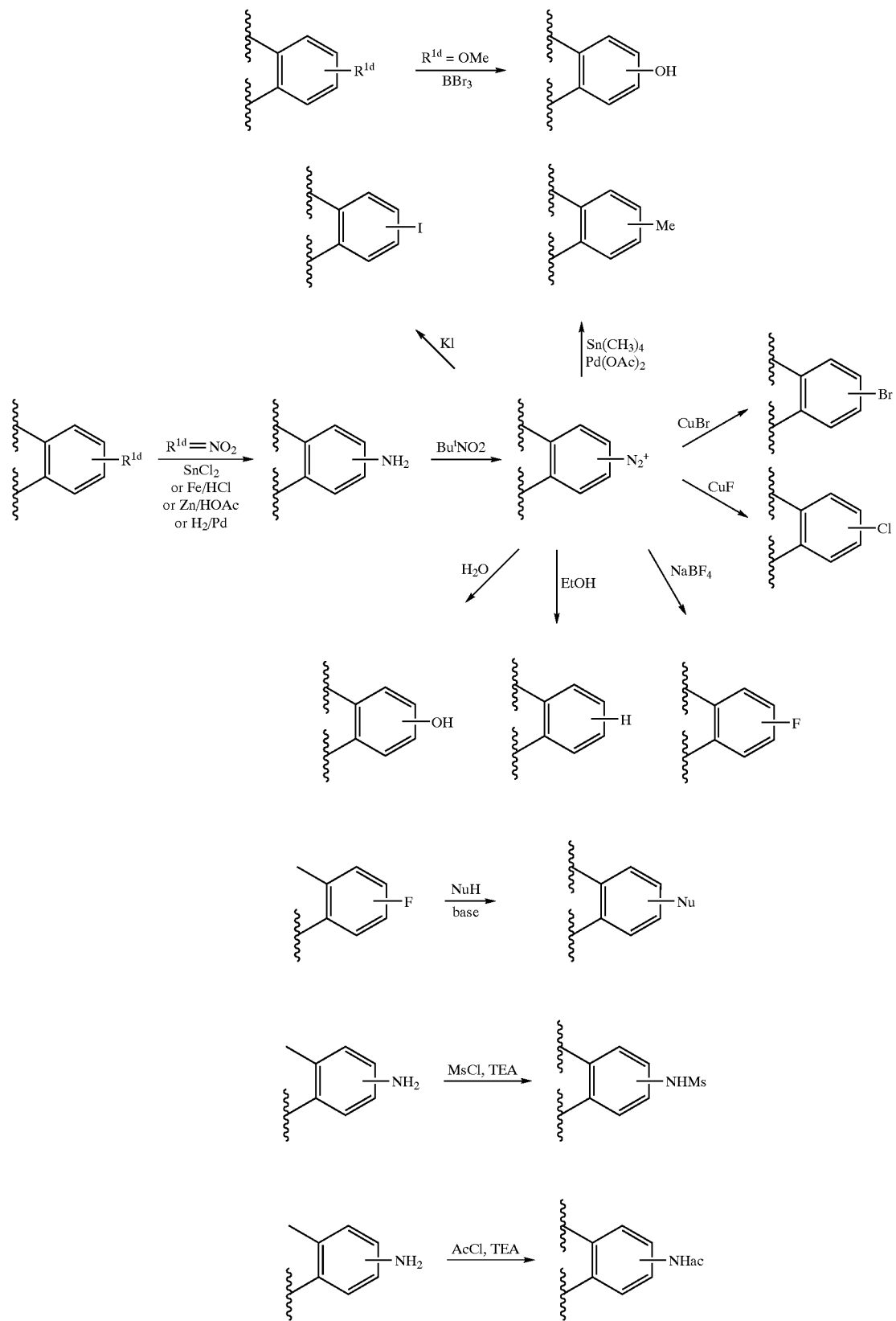

Example 1

3-(2-(4-[(2-aminosulfonyl)phenyl]benzoylamino)phenoxy)benzaridine

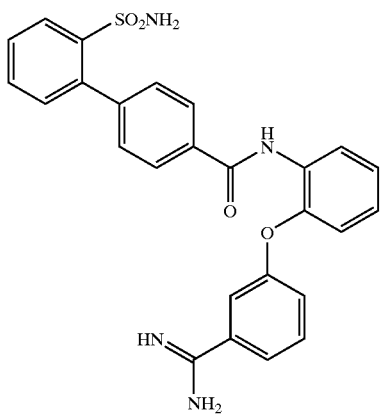

Step 1: To a solution of 2-fluoro nitrobenzene (1.41 g, 10 mmol, 1.0 equiv) and 3-hydroxybenzonitrile (1.19 g, 1.0 equiv) in 10 mL of DMF was added $K_2CO_3$ (2.76 g, 2 equiv). After stirring at 60° C. for 3 h, the mixture was diluted with EtOAc and washed with $H_2O$. The organic layer was dried over $MgSO_4$, filtered and evaporated to give 3-(2-nitrophenoxy)benzonitrile (2.38 g, 99%). MS found for $C_{13}H_9N_2O_3$ (M+H)$^+$: 241.

Step 2: A solution of 3-(2-nitrophenoxy)benzonitrile (1.21 g, 5 mmol, 1.0 equiv) in 30 mL of EtOH was treated with $SnCl_2 2H_2O$ (3.38 g, 3 equiv) at reflux for 4 h. The volatile was evaporated and the residue was redissolved in EtOAc, washed with saturated aqueous $NaHCO_3$ and 1N NaOH. The organic layer was dried over $MgSO_4$, filtered and evaporated to give 3-(2-aminophenoxy)benzonitrile (1.04 g, 99%). MS found for $C_{13}H_{11}N_2O$ (M+H)$^+$: 211.

Step 3: A mixture of 3-(2-aminophenoxy)benzonitrile (210 mg, 1 mmol, 1.0 equiv), 4-[(2-t-butylaminosulfonyl)phenyl] benzoic acid (330 mg, 1 equiv), Bop reagent (880 mg, 2 equiv) and TEA (1.39 mL, 10 equiv) in 3 mL of DMF was stirred at rt overnight. The mixture was diluted with EtOAc, washed with $H_2O$. The organic layer was dried over $MgSO_4$, filtered and evaporated. Flash chromatography on silica gel gave 3-(2-(4-[(2-t-butylaminosulfonyl)phenyl]benzoylamino)phenoxy)benzonitrile (300 mg, 57%). MS found for $C_{30}H_{28}N_3O_4S$ (M+H)$^+$: 526.

Step 4: A stream of HCl(g) was bubbled through a 0° C. solution of 3-(2-(4-[(2-t-butylaminosulfonyl)phenyl] benzoylamino)phenoxy)benzonitrile (53 mg, 0.1 mmol) in 5 mL of methanol until saturation. The mixture was stirred at rt overnight and evaporated. The resulting residue was treated with ammonium acetate (39 mg, 5 equiv) in 10 ml methanol at reflux temperature for 2 h. The solvent was removed at reduced pressure and the crude benzamidine was purified by HPLC (C18 reversed phase) eluting with 0.5% TFA in $H_2O/CH_3CN$ to give 3-(2-(4-[(2-aminosulfonyl) phenyl]benzoylamino)phenoxy)benzamidine (40 mg, 83%). MS found for $C_{26}H_{23}N_4O_4S$ (M+H)$^+$: 487.

Example 2

3-(4-fluoro-2-(4-[(2-aminosulfonyl)phenyl]phenylcarbonylamino)phenoxy)benzamidine

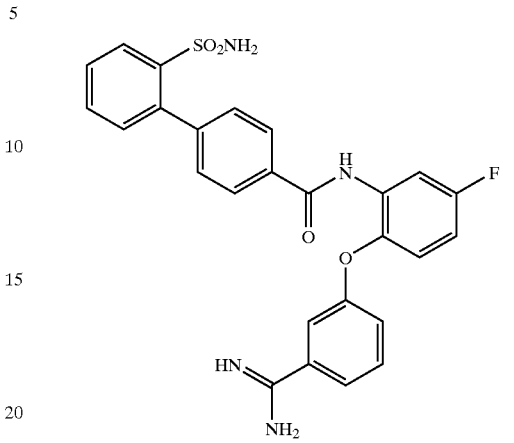

Step 1: A mixture of 3-(2-amino-4-fluorophenoxy)benzonitrile (230 mg, 1 mmol, 1.0 equiv), 4-[(2-t-butylaminosulfonyl)phenyl]benzoic chloride (349 mg, 1 equiv), pyridine (3 mL) in 10 mL of dichloromethane was stirred at rt overnight, washed with $H_2O$. The organic layer was dried over $MgSO_4$, filtered and evaporated. Flash chromatography on silica gel gave 3-(4-fluoro-2-(4-[(2-t-butylaminosulfonyl)phenyl]phenylcarbonylamino) phenoxy)benzonitrile (495 mg, 91%). MS found for $C_{30}H_{27}FN_3O_4S$ (M+H)$^+$: 544.

Step 2: A stream of HCl(g) was bubbled through a 0° C. solution of 3-(4-fluoro-2-(4-[(2-t-butylaminosulfonyl) phenyl]phenylcarbonylamino)phenoxy)benzonitrile (55 mg, 0.1 mmol) in 5 mL of methanol until saturation. The mixture was stirred at rt overnight and evaporated. The resulting residue was treated with ammonium acetate (39 mg, 5 equiv) in 10 ml methanol at reflux temperature for 2 h. The solvent was removed at reduced pressure and the crude benzamidine was purified by HPLC (C18 reversed phase) eluting with 0.5% TFA in $H_2O/CH_3CN$ to give 3(4-fluoro-2-(4-[(2-aminosulfonyl)phenyl]phenylcarbonylamino)phenoxy) benzamidine (39 mg, 77%). MS found for $C_{26}H_{22}FN_4O_4S$ (M+H)$^+$: 505.

Example 3

3-(4-trifluoromethyl-2-(4-[(2-aminosulfonyl)phenyl]phenylcarbonylamino)phenoxy)benzamidine

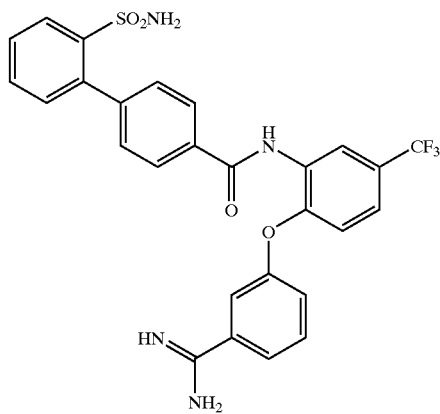

Step 1: A mixture of 3-(2-amino-4-trifluoromethylphenoxy) benzonitrile (280 mg, 1 mmol, 1.0 equiv), 4-[(2-t-butylaminosulfonyl)phenyl]benzoic chloride (349 mg, 1 equiv), pyridine (3 mL) in 10 mL of dichloromethane was stirred at rt overnight, washed with H$_2$O. The organic layer was dried over MgSO$_4$, filtered and evaporated. Flash chromatography on silica gel gave 3-(4-trifluoromethyl-2-(4-[(2-t-butylaminosulfonyl)phenyl]phenylcarbonylamino)phenoxy)benzonitrile (529 mg, 89%). MS found for C$_{31}$H$_{27}$F$_3$N$_3$O$_4$S (M+W)$^+$: 594.

Step 2: A stream of HCl(g) was bubbled through a 0° C. solution of 3-(4-trifluoromethyl-2-(4-[(2-t-butylaminosulfonyl)phenyl]phenylcarbonylamino)phenoxy)benzonitrile (59 mg, 0.1 mmol) in 5 mL of methanol until saturation. The mixture was stirred at rt overnight and evaporated. The resulting residue was treated with ammonium acetate (39 mg, 5 equiv) in 10 ml methanol at reflux temperature for 2 h. The solvent was removed at reduced pressure and the crude benzamidine was purified by HPLC (C18 reversed phase) eluting with 0.5% TFA in H$_2$O/CH$_3$CN to give 3-(4-trifluoromethyl-2-(4-[(2-aminosulfonyl)phenyl]phenylcarbonylamino)phenoxy)benzamidine (35 mg, 63%). MS found for C$_{27}$H$_{22}$F$_3$N$_4$O$_4$S (M+H)$^+$: 555.

Example 4

3-(4-methylsulfonyl-2-(4-[(2-aminosulfonyl)phenyl]phenylcarbonylamino)phenoxy)benzamidine

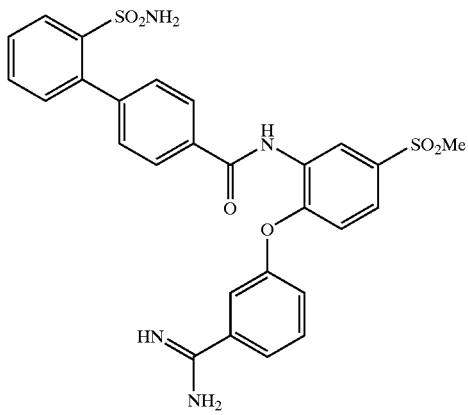

Step 1: A mixture of 3-(2-amino-4-methylsulfonylphenoxy) benzonitrile (290 mg, 1 mmol, 1.0 equiv), 4-[(2-t-butylaminosulfonyl)phenyl]benzoic chloride (349 mg, 1 equiv), pyridine (3 mL) in 10 mL of dichloromethane was stirred at rt overnight, washed with H$_2$O. The organic layer was dried over MgSO$_4$, filtered and evaporated. Flash chromatography on silica gel gave 3-(4-methylsulfonyl-2-(4-[(2-t-butylaminosulfonyl)phenyl]phenylcarbonylamino)phenoxy)benzonitrile (429 mg, 71%). MS found for C$_{31}$H$_{30}$N$_3$O$_6$S$_2$ (M+H)$^+$: 604.

Step 2: A stream of HCl(g) was bubbled through a 0° C. solution of 3-(4-methylsulfonyl-2-(4-[(2-t-butylaminosulfonyl)phenyl]phenylcarbonylamino)phenoxy)benzonitrile (60 mg, 0.1 mmol) in 5 mL of methanol until saturation. The mixture was stirred at rt overnight and evaporated. The resulting residue was treated with ammonium acetate (39 mg, 5 equiv) in 10 ml methanol at reflux temperature for 2 h. The solvent was removed at reduced pressure and the crude benzamidine was purified by HPLC (C18 reversed phase) eluting with 0.5% TFA in H$_2$O/CH$_3$CN to give 3-(4-methylsulfonyl-2-(4-[(2-aminosulfonyl)phenyl]phenylcarbonylamino)phenoxy)benzamidine (27 mg, 47%). MS found for C$_{27}$H$_{25}$N$_4$O$_6$S$_2$ (M+H)$^+$: 565.

Examples 5–8

The following compounds of Examples 5–8 were prepared using the procedure described in Example 1:

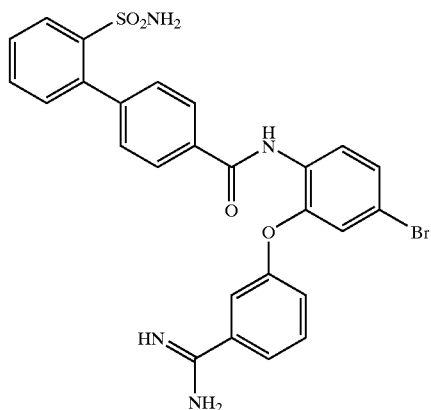

Example 5
MS (M + H):
565

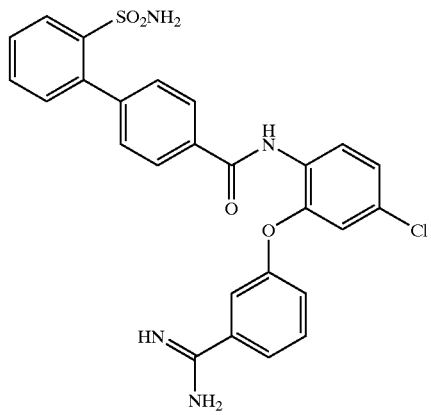

Example 6
MS (M + H):
521

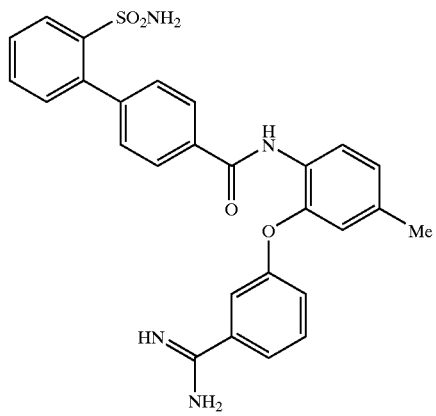

Example 7
MS (M + H):
501

-continued

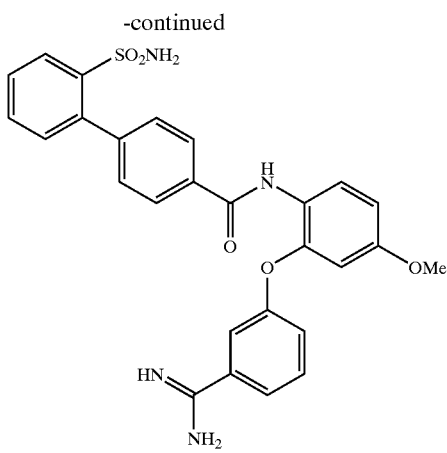

Example 8
MS (M + H): 517

Example 9

3-(5hydroxy-2-(4-[(2-aminosulfonyl)phenyl]phenylcarbonylamino)phenoxy)benzamidine

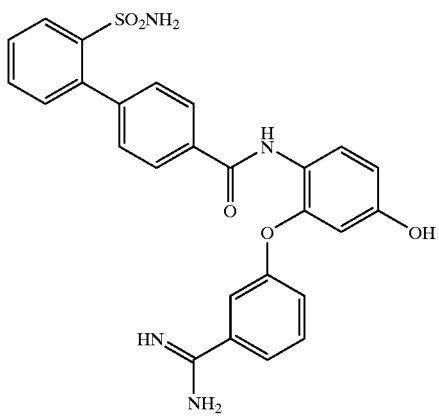

Step 1: A solution of 3-(5-methoxy-2-(4-[(2-aminosulfonyl)phenyl]phenylcarbonylamino)phenoxy)benzamidine (52 mg, 0.1 mmol, 1 equiv) in 5 mL of methylene chloride was treated with BBr$_3$ (1 M in dichloromethane, 0.5 mL, 5 equiv) overnight. The reaction was quenched with water carefully and after the volatile was evaporated, the aqueous residue was purified by HPLC (C18 reversed phase) eluting with 0.5% TFA in H$_2$O/CH$_3$CN to give 3-(5-hydroxy-2-(4-[(2-aminosulfonyl)phenyl]phenylcarbonylamino)phenoxy)benzamidine. (41 mg, 82%). MS found for $C_{26}H_{23}N_4O_6S$ (M+H)$^+$: 503.

Example 10
3-(4-methoxycarbonyl-2-(4-[(2-aminosulfonyl)phenyl]phenylcarbonylamino)phenoxy)benzamidine

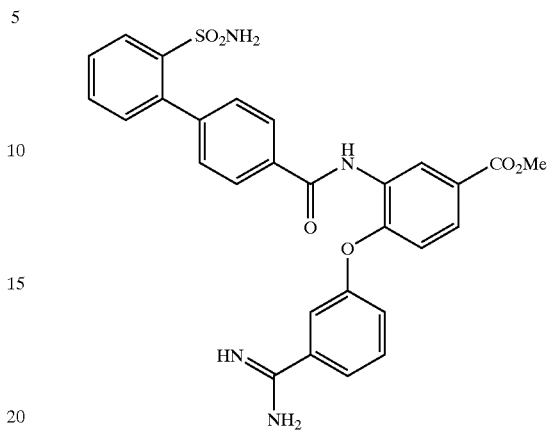

Step 1: A mixture of 3-(2-amino-4-methoxycarbonylphenoxy)benzonitrile (270 mg, 1 mmol, 1.0 equiv), 4-[(2-t-butylaminosulfonyl)phenyl]benzoic chloride (349 mg, 1 equiv), pyridine (3 mL) in 10 mL of dichloromethane was stirred at rt overnight, washed with H$_2$O. The organic layer was dried over MgSO$_4$, filtered and evaporated. Flash chromatography on silica gel gave 3-(4-methoxycarbonyl-2-(4-[(2-t-butylaminosulfonyl)phenyl]phenylcarbonylamino)phenoxy)benzonitrile (502 mg, 86%). MS found for $C_{32}H_{30}N_3O_6S$ (M+H)$^+$: 584.

Step 2: A stream of HCl(g) was bubbled through a ODC solution of 3-(4-methoxycarbonyl-2-(4-[(2-t-butylaminosulfonyl)phenyl]phenylcarbonylamino)phenoxy)benzonitrile (58 mg, 0.1 mmol) in 5 mL of methanol until saturation. The mixture was stirred at rt overnight and evaporated. The resulting residue was treated with ammonium acetate (39 mg, 5 equiv) in 10 ml methanol at reflux temperature for 2 h. The solvent was removed at reduced pressure and the crude benzamidine was purified by HPLC (C18 reversed phase) eluting with 0.5% TFA in H$_2$O/CH$_3$CN to give 3-(4-methoxycarbonyl-2-(4-[(2-aminosulfonyl)phenyl]phenylcarbonylamino)phenoxy)benzamidine (29.5 mg, 54%). MS found for $C_{21}H_{25}N_4O_6S$ (M+H)$^+$: 545.

Example 11
3-(4-hydroxycarbonyl-2-(4-[(2-aminosulfonyl)phenyl]phenylcarbonylamino)phenoxy)benzamidine

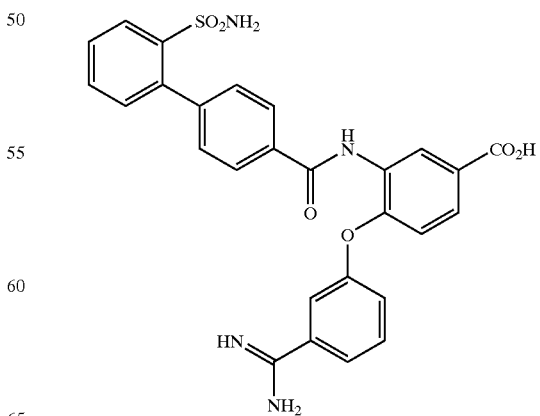

A solution of 3-(4-methoxycarbonyl-2-(4-[(2-aminosulfonyl)phenyl]phenylcarbonylamino)phenoxy)benzamidine (10.9 mg, 0.02 mmol, 1.0 equiv) in 5 mL of methanol was treated with 1N LiOH (2 mL) at rt for 2 h. Methanol was evaporated, the aqueous residue was subjected to HPLC with 0.5% TFA in H$_2$O/CH$_3$CN to give 3-(4-hydroxycarbonyl-2-(4-[(2-aminosulfonyl)phenyl]phenylcarbonylamino)phenoxy)benzamidine (8.9 mg, 84%). MS found for C$_{27}$H$_{23}$N$_4$O$_6$S (M+H)$^+$: 531.

Example 12

3-(2-(4-[(2-aminosulfonyl)phenyl]phenylcarbonylamino)pheylamino)benzamidine

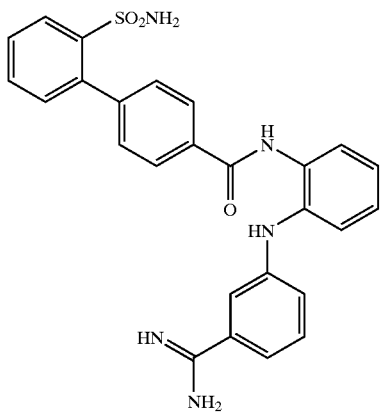

Step 1: A mixture of 3-(2-amino-phenylamino)benzonitrile (196 mg, 1 mmol, 1.0 equiv), 4-[(2-t-butylaminosulfonyl)phenyl]benzoic chloride (349 mg, 1 equiv), pyridine (3 mL) in 10 mL of dichloromethane was stirred at rt overnight, washed with H$_2$O. The organic layer was dried over MgSO$_4$, filtered and evaporated. Flash chromatography on silica gel gave 3-(2-(4-[(2-t-butylaminosulfonyl)phenyl]phenylcarbonylamino)phenylamino)benzonitrile (226 mg, 43%). MS found for C$_{30}$H$_{29}$N$_4$O$_3$S (M+H)$^+$: 525.

Step 2: A stream of HCl(g) was bubbled through a 0° C. solution of 3-(2-(4-[(2-t-butylaminosulfonyl)phenyl]phenylcarbonylamino)pheylamino)benzonitrile (53 mg, 0.1 mmol) in 5 mL of methanol until saturation. The mixture was stirred at rt overnight and evaporated. The resulting residue was treated with ammonium acetate (39 mg, 5 equiv) in 10 ml methanol at reflux temperature for 2 h. The solvent was removed at reduced pressure and the crude benzamidine was purified by HPLC (C18 reversed phase) eluting with 0.5% TFA in H$_2$O/CH$_3$CN to give 3-(2-(4-[(2-aminosulfonyl)phenyl]phenylcarbonylamino)pheylamino)benzamidine (27 mg, 55%). MS found for C$_{26}$H$_{24}$N$_5$O$_3$S (M+H)$^+$: 486.

Example 13
7-(2-(4-[(2-aminosulfonyl)phenyl]benzoylamino)phenoxy)-1-aminoisoquinoline

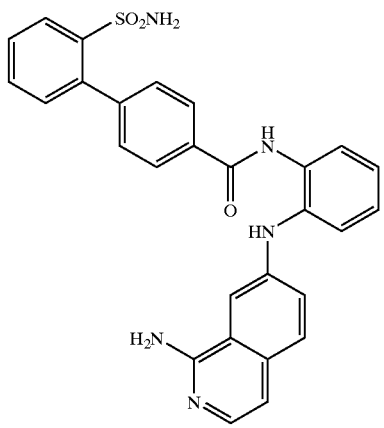

Step 1: A mixture of 7-(2-aminophenoxy)isoquinoline (237 mg, 1 mmol, 1.0 equiv), 4-[(2-t-butylaminosulfonyl)phenyl]benzoic acid (330 mg, 1 equiv), Bop reagent (880 mg, 2 equiv) and TEA (1.39 mL, 10 equiv) in 3 mL of DMF was stirred at rt overnight. The mixture was diluted with EtOAc, washed with H$_2$O. The organic layer was dried over MgSO$_4$, filtered and evaporated. Flash chromatography on silica gel gave 7-(2-(4-[(2-t-butylaminosulfonyl)phenyl]benzoylamino)phenoxy)isoquinoline (469 mg, 85%). MS found for C$_{32}$H$_{24}$N$_3$O$_4$S (M+H)$^+$: 552.

Step 2: A solution of 7-(2-(4-[(2-t-butylaminosulfonyl)phenyl]benzoylamino)phenoxy)isoquinoline (110 mg, 0.2 mmol, 1 equiv) in 5 mL of acetone was treated with mCPBA (113 mg, 577%, 1.5 equiv) until HPLC showed complete reaction. Acetone was evaporated, the residue was partitioned between methylene chloride and saturated aqueous NaHCO$_3$. The organic layer was dried over MgSO$_4$ and used in the next step directly.

Step 3: The compound obtained in step 2 in 5 mL of pyridine was treated with tosyl chloride (46 mg, 1.2 equiv) at rt overnight and pyridine was removed under reduced pressure. The residue was reacted with 5 mL of ethanolamine for 12 h, and partitioned between methylene chloride and water. The organic layer was dried over MgSO$_4$, filtered, evaporated and refluxed in 3 mL of trifluoroacetic acid for 30 min. After removing TFA, the crude was purified by HPLC (C18 reversed phase) eluting with 0.5% TFA in H$_2$O/CH$_3$CN to give 7-(2-(4-[(2-aminosulfonyl)phenyl]benzoylamino)phenoxy)-1-aminoisoquinoline (43 mg, 42%). MS found for C$_{28}$H$_{23}$N$_4$O$_4$S (M+H)$^+$: 511.

Example 14
7-(2-(4-[(2-aminosulfonyl)phenyl]benzoylamino)-4-fluorophenoxy)1-aminoisoquinoline

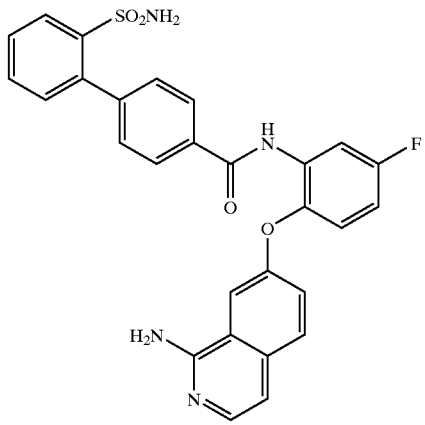

Step 1: A mixture of 7-(2-amino-4-fluorophenoxy)isoquinoline (255 mg, 1 mmol, 1.0 equiv), 4-[(2-t-butylaminosulfonyl)phenyl]benzoic acid (330 mg, 1 equiv), Bop reagent (880 mg, 2 equiv) and TEA (1.39 mL, 10 equiv) in 3 mL of DMF was stirred at rt overnight. The mixture was diluted with EtOAc, washed with H$_2$O. The organic layer was dried over MgSO$_4$, filtered and evaporated. Flash chromatography on silica gel gave 7-(2-(4-[(2-t-butylaminosulfonyl)phenyl]benzoylamino)-4-fluorophenoxy)isoquinoline (467 mg, 82%). MS found for C$_{32}$H$_{29}$FN$_3$O$_4$S (M+H)$^+$: 570.

Step 2: A solution of 7-(2-(4-[(2-t-butylaminosulfonyl)phenyl]benzoylamino)-4-fluorophenoxy)isoquinoline (114, 0.2 mmol, 1 equiv) in 5 mL of acetone was treated with mCPBA (113 mg, 57%, 1.5 equiv) until HPLC showed complete reaction. Acetone was evaporated, the residue was partitioned between methylene chloride and saturated aqueous NaHCO$_3$. The organic layer was dried over MgSO$_4$ and used in the next step directly.

Step 3: The compound obtained in step 4 in 5 mL of pyridine was treated with tosyl chloride (46 mg, 1.2 equiv) at rt overnight and pyrine was removed under reduced pressure. The residue was reacted with 5 mL of ethanolamine for 12 h, and partitioned between methylene chloride and water. The organic layer was dried over MgSO$_4$, filtered, evaporated and refluxed in 3 mL of trifluoroacetic acid for 30 min. After removing TFA, the crude was purified by HPLC (C18 reversed phase) eluting with 0.5% TFA in H$_2$O/CH$_3$CN to give 7-(2-(4-[(2-aminosulfonyl)phenyl]benzoylamino)-4-fluorophenoxy)1-aminoisoquinoline (77 mg, 50%). MS found for C$_{28}$H$_{22}$FN$_4$O$_4$S (M+H)$^+$: 529.

Example 15

7-(2-(4-[(2-aminosulfonyl)phenyl]benzoylamino)-4-trifluoromethylphenoxy)1-aminoisoquinoline

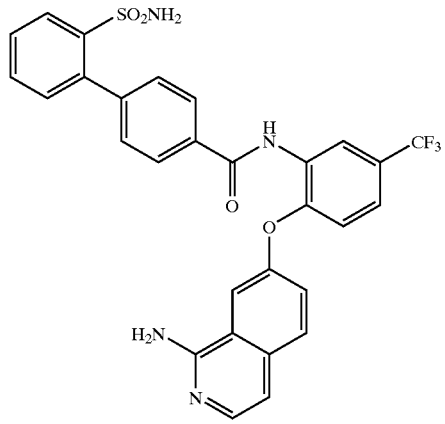

Step 1: A mixture of 7-(2-amino-4-trifluoromethylphenoxy)isoquinoline (305 mg, 1 mmol, 1.0 equiv), 4-[(2-t-butylaminosulfonyl)phenyl]benzoic acid (330 mg, 1 equiv), Bop reagent (880 mg, 2 equiv) and TEA (1.39 mL, 10 equiv) in 3 mL of DMF was stirred at rt overnight. The mixture was diluted with EtOAc, washed with H$_2$O. The organic layer was dried over MgSO$_4$, filtered and evaporated. Flash chromatography on silica gel gave 7-(2-(4-[(2-t-butylaminosulfonyl)phenyl]benzoylamino)-4-trifluoromethylphenoxy)isoquinoline (360 mg, 58%). MS found for C$_{33}$H$_{29}$F$_3$N$_3$O$_4$S (M+H)$^+$: 620.

Step 2: A solution of 7-(2-(4-[(2-t-butylaminosulfonyl)phenyl]benzoylamino)-4-trifluoromethylphenoxy)isoquinoline (124 mg, 0.2 mmol, 1 equiv) in 5 mL of acetone was treated with mCPBA (113 mg, 57%, 1.5 equiv) until HPLC showed complete reaction. Acetone was evaporated, the residue was partitioned between methylene chloride and saturated aqueous NaHCO$_3$. The organic layer was dried over MgSO$_4$ and used in the next step directly.

Step3: The compound obtained in step 4 in 5 mL of pyridine was treated with tosyl chloride (46 mg, 1.2 equiv) at rt overnight and pyrine was removed under reduced pressure. The residue was reacted with 5 mL of ethanolamine for 12 h, and partitioned between methylene chloride and water. The organic layer was dried over MgSO$_4$, filtered, evaporated and refluxed in 3 mL of trifluoroacetic acid for 30 min. After removing TFA, the crude was purified by HPLC (C18 reversed phase) eluting with 0.5% TFA in H$_2$O/CH$_3$CN to give 7-(2-(4-[(2-aminosulfonyl)phenyl]benzoylamino)-4-trifluoromethylphenoxy)1-aminoisoquinoline (64 mg, 52%). MS found for C$_{29}$H$_{22}$F$_3$N$_4$O$_4$S (M+H)$^+$: 579.

Example 16

7-(2-(4-[(2-aminosulfonyl)phenyl]benzoylamino)-4-methylsulfonylphenoxy)1-aminoisoquinoline

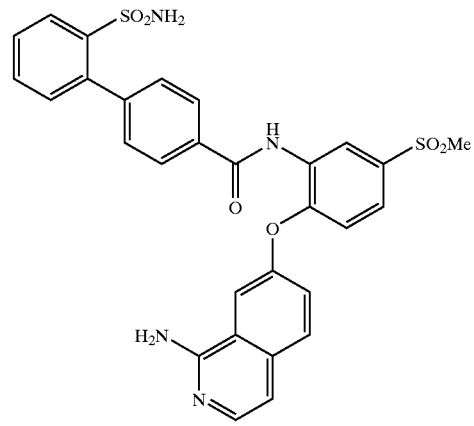

Step 1: A mixture of 7-(2-amino-4-methylsulfonylphenoxy)isoquinoline (315 mg, 1 mmol, 1.0 equiv), 4-[(2-t-butylaminosulfonyl)phenyl]benzoic acid (330 mg, 1 equiv), Bop reagent (880 mg, 2 equiv) and TEA (1.39 mL, 10 equiv) in 3 mL of DUT was stirred at rt overnight. The mixture was diluted with EtOAc, washed with H$_2$O. The organic layer was dried over MgSO$_4$, filtered and evaporated. Flash chromatography on silica gel gave 7-(2-(4-[(2-t-butylaminosulfonyl)phenyl]benzoylamino)-4-methlsulfonylphenoxy) isoquinoline (460 mg, 73%). MS found for C$_{33}$H$_{32}$N$_3$O$_6$S$_2$ (M+H)$^+$: 630.

Step 2: A solution of 7-(2-(4-[(2-t-butylaminosulfonyl)phenyl]benzoylamino)-4-methlsulfonylphenoxy)isoquinoline (126 mg, 0.2mmol, 1 equiv) in 5 mL of acetone was treated with mCPBA (113 mg, 57%, 1.5 equiv) until HPLC showed complete reaction. Acetone was evaporated, the residue was partitioned between methylene chloride and saturated aqueous NaHCO$_3$. The organic layer was dried over MgSO$_4$ and used in the next step directly.

Step 3: The compound obtained in step 4 in 5 mL of pyridine was treated with tosyl chloride (46 mg, 1.2 equiv) at rt overnight and pyrine was removed under reduced pressure. The residue was reacted with 5 mL of ethanolamine for 12 h, and partitioned between methylene chloride and water. The organic layer was dried over MgSO$_4$, filtered, evaporated and refluxed in 3 mL of trifluoroacetic acid for 30 min. After removing TFA, the crude was purified by HPLC (C18 reversed phase) eluting with 0.5% TFA in H$_2$O/CH$_3$CN to give 7-(2-(4-[(2-aminosulfonyl)phenyl]benzoylamino)-4-methylsulfonylphenoxy)1-aminoisoquinoline (94 mg, 80%). MS found for C$_{29}$H$_{29}$N$_4$O$_6$S$_2$ (M+H)$^+$: 589.

Example 17

3-(2-(4-[-(2-aminosulfonyl)phenyl]phenylaminocarbonyl-4-nitrophenoxy)benzamidine

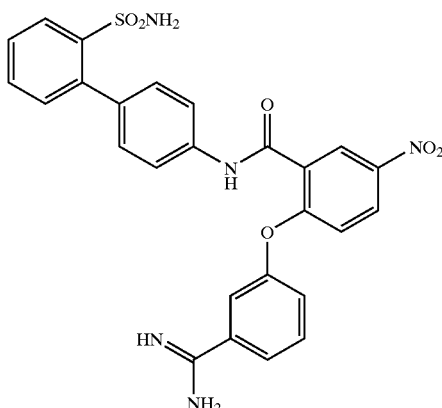

Step 1: A solution of 2-fluoro-5-nitrobenzoic acid (1.85 g, 10 mmol, 1.33 equiv) in thionyl chloride (5 mL) was refluxed for 2 h and evaporated. The residue was redissolved in 20 mL of methylene chloride and to the solution were added 4-[(2-t-butylaminosulfonyl)phenyl]aniline (2.0 g, 1.0 equiv) and 5 mL of pyridine. After stirring at rt ovenight, the volatile was evaporated. Flash chromatography on silica gel 1-(4-[(2-t-butylaminosulfonyl)phenyl]phenylaminocarbonyl)-2-fluoro-5-nitrobenzene (2.9 g, 99%); MS found for C$_{23}$H$_{23}$FN$_3$O$_5$S (M+H)$^+$: 472.

Step 2: To a solution of 1-(4-[(2-t-butylaminosulfonyl)phenyl]phenylaminocarbonyl)-2-fluoro-5-nitrobenzene (1.18 g, 0.25 mmol, 1.0 equiv) and 3-hydroxybenzonitrile (298 mg, 1.0 equiv) in 10 mL of DMF was added K$_2$CO$_3$ (691 mg, 2 equiv). After stirring at 60° C. for 3 h, the mixture was diluted with EtOAc and washed with H$_2$O. The organic layer was dried over MgSO$_4$, filtered, evaporated and chromatographied to give 3-(2-(4-[(2-t-butylaminosulfonyl)phenyl]phenylaminocarbonyl-4-nitrophenoxy)benzonitrile (950 g, 63%). MS found for C$_{30}$H$_{27}$N$_4$O$_6$S (M+H)$^+$: 571.

Step 3: A stream of HCl(g) was bubbled through a 0° C. solution of 3-(2-(4-[(2-t-butylaminosulfonyl)phenyl]phenylaminocarbonyl-4-nitrophenoxy)benzonitrile (57 mg, 0.1 mmol) in 5 mL of methanol until saturation. The mixture was stirred at rt overnight and evaporated. The resulting residue was treated with ammonium acetate (39 mg, 5 equiv) in 10 ml methanol at reflux temperature for 2 h. The solvent was removed at reduced pressure and the crude was purified by HPLC (C18 reversed phase) eluting with 0.5% TFA in H$_2$O/CH$_3$CN to 3-(2-(4-[(2-aminosulfonyl)phenyl]phenylaminocarbonyl-4-nitrophenoxy)benzamidine (24 mg, 45%). MS found for C$_{26}$H$_{22}$N5O$_6$S (M+H)$^+$: 532.

Example 18

3-(2-(4-[(2-aminosulfonyl)phenyl]phenylaminocarbonyl-4-aminophenoxy)benzamidine

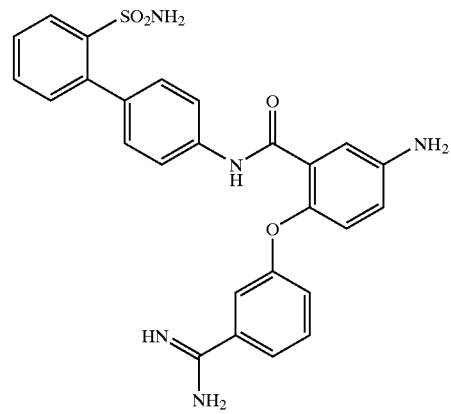

A mixture of 3-(2-(4-[(2-aminosulfonyl)phenyl]phenylaminocarbonyl-4-nitrophenoxy)benzamidine (53 mg, 0.1 mmol, 1 equiv), 5 mL of 1N HCl, 5 mg of Pd/C (10%) in 10 mL of methanol was stirred at rt under 1 atm H$_2$ atmosphere overnight. After filtration through a thin layer of Celite and removal of the volatile, the aqueous residue was purified by HPLC (C18 reversed phase) eluting with 0.5% TFA in H$_2$O/CH$_3$CN to 3-(2-(4-[(2-aminosulfonyl)phenyl]phenylaminocarbonyl-4-aminophenoxy)benzamidine (31 mg, 66%). MS found for C$_{26}$H$_{24}$N$_5$O$_4$S (M+H)$^+$: 502.

Example 19

3-(2-(4-[(2-aminosulfonyl)phenyl]phenylaminocarbonyl-4-chlorophenoxy)benzamidine

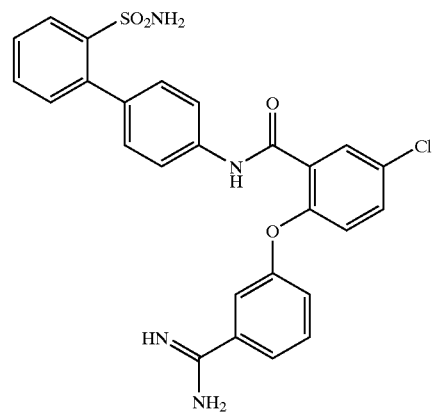

Step 1: A mixture of 3-(2-(4-[(2-t-butylaminosulfonyl)phenyl]phenylaminocarbonyl-4-nitrophenoxy)benzonitrile (570 mg, 1 mmol, 1 equiv) and SnCl$_2$.2H$_2$O (677 mg, 3 equiv) in 25 mL of EtOAc was refluxed for 2 h. The reaction was quenched with sat. NaHCO$_3$. The organic layer was separated and dried over MgSO$_4$, filtered and evaporated to give 3-(2-(4-[(2-t-butylaminosulfonyl)phenyl]phenylaminocarbonyl-4-aminophenoxy)benzonitrile (45 mg, 83%). MS found for C$_{30}$H$_{29}$N$_4$O$_4$S (M+H)$^+$: 541.

Step 2: A mixure of t-BuNO$_2$ (21 mg, 0.1 mmol, 2 equiv), CuCl (20 mg, 2 equiv) in 5 mL of acetonitrile was refluxed for 10 min. To the solution was added 3-(2-(4-[(2-t-butylaminosulfonyl)phenyl]phenylaminocarbonyl-4-aminophenoxy)benzonitrile (54 mg, 0.1 mmol, 1 equiv). The mixture was refluxed for 1 h and evaporated. Flash chromatography with 1:2 EtOAc/hexane to give [(2-t-butylaminosulfonyl)phenyl]phenylaminocarbonyl-4-chlorophenoxy)benzonitrile (43 mg, 77%)MS found for C$_{30}$H$_{27}$ClN$_3$O$_4$S (M+H)$^+$: 561.

Step 3: A stream of HCl(g) was bubbled through a 0° C. solution of 3-(2-(4-[(2-t-butylaminosulfonyl)phenyl]phenylaminocarbonyl-4-chlorophenoxy)benzonitrile (56 mg, 0.1 mmol) in 5 mL of methanol until saturation. The mixture was stirred at rt overnight and evaporated. The resulting residue was treated with ammonium acetate (40 mg, 5 equiv) in 10 ml methanol at reflux temperature for 2 h. The solvent was removed at reduced pressure and the crude was purified by HPLC (C18 reversed phase) eluting with 0.5% TFA in H$_2$O/CH$_3$CN to 3-(2-(4-[(2-aminosulfonyl)phenyl]phenylaminocarbonyl-4-chlorophenoxy)benzamidine (47 mg, 84%). MS found for C$_{26}$H$_{22}$ClN$_4$S (M+H)$^+$: 521.

Example 20

3-(2-(4-[(2-aminosulfonyl)phenyl]phenylaminocarbonyl-4-bromophenoxy)benzamidine

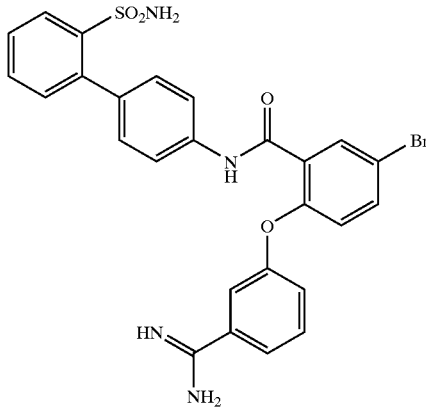

This compound is prepared according to the procedure described in example 19. MS found for C$_{26}$H$_{22}$BrN$_4$O$_4$S (M+H)$^+$: 565.

Example 21
2-bromo-6-(2-(4-1-[(2-aminosulfonyl)phenyl]phenylcarbonylamino)phenoxy naphthalene

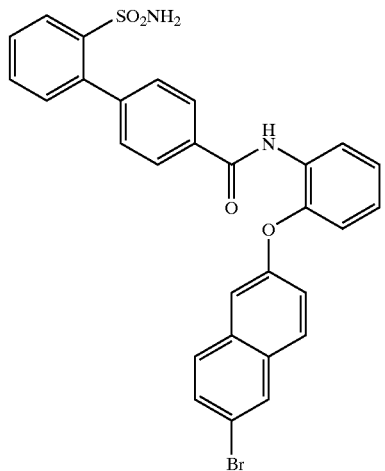

A mixture of 2-bromo-6-(2-aminophenoxy) naphthalene (314 mg, 1 mmol, 1.0 equiv), 4-[(2-t-butylaminosulfonyl)phenyl]benzoyl chloride (349 mg, 1 equiv), pyridine (3 mL) in 10 mL of dichloromethane was stirred at rt overnight, washed with H$_2$O. The organic layer was dried over MgSO$_4$, filtered, evaporated and refluxed in 2 mL of trifluoroacetic acid for 30 min. TFA was then evaporated and HPLC (C18 reversed phase) eluting with 0.5% TFA in H$_2$O/CH$_3$CN gave 2-bromo-6-(2-(4-[(2-aminosulfonyl)phenyl]phenylcarbonylamino)phenoxy naphthalene (378 mg, 66%). MS found for C$_{29}$H$_{22}$BrN$_2$O$_4$S (M+H)$^+$: 573.

Example 22
3-methoxycarbonyl-2-(4-[(2-aminosulfonyl)phenyl]phenylcarbonylamino)phenoxy naphthalene

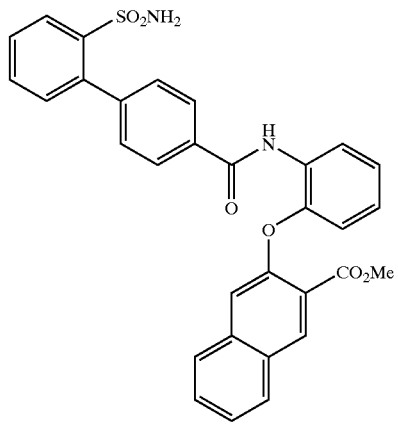

A mixture of 3-methoxycarbonyl-2-(2-aminophenoxy) (294 mg, 1 mmol, 1.0 equiv), 4-[(2-t-butylaminosulfonyl)phenyl]benzoyl chloride (349 mg, 1 equiv), pyridine (3 mL) in 10 mL of dichloromethane was stirred at rt overnight, washed with H$_2$O. The organic layer was dried over MgSO$_4$, filtered, evaporated and refluxed in 2 mL of trifluoroacetic acid for 30 min. TFA was then evaporated and HPLC (C18 reversed phase) eluting with 0.5% TFA in H$_2$O/CH$_3$CN gave 3-methoxycarbonyl-2-(4-[(2-aminosulfonyl)phenyl]phenylcarbonylamino)phenoxy naphthalene (420 mg, 76%). MS found for C$_{31}$H$_{25}$N$_2$O$_6$S (M+H)$^+$: 553.

Example 23
3-hydroxycarbonyl-2-(4-[(2-aminosulfonyl)phenyl]phenylcarbonylamino)phenoxy naphthalene

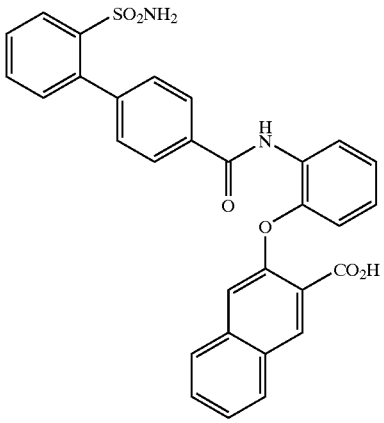

A solution of 3-methoxycarbonyl-2-(4-methylsulfonyl-2-(4-[(2-aminosulfonyl)phenyl]phenylcarbonylamino)phenoxy) naphthalene (55 mg, 0.1 mmol, 1.0 equiv) in 5 mL of methanol was treated with 1N LiOH (2 mL) at rt for 2 h. Methanol was evaporated, the aqueous residue was subjected to HPLC with 0.5% TFA in $H_2O/CH_3CN$ to give 3-hydroxycarbonyl-2-(4-[(2-aminosulfonyl)phenyl]phenylcarbonylamino)phenoxy naphthalene (47 mg, 88%). MS found for $C_{30}H_{23}N_2O_6S$ (M+H)$^+$: 539.

Example 24
3-aminocarbonyl-2-(4-[(2-aminosulfonyl)phenyl]phenylcarbonylamino)phenoxy naphthalene

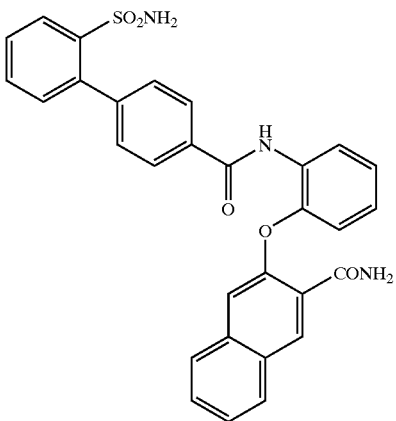

Step 1: A solution of 3-methoxycarbonyl-2-(4-methylsulfonyl-2-(4-[(2-t-butylaminosulfonyl)phenyl]phenylcarbonylamino)phenoxy)naphthalene (40 mg, 0.066 mmol) in 5 mL of methanol was treated with 1N LiOH (2 mL) at rt for 2 h. Methanol was evaporated, and acidified with 1N HCl until PH ~1–2. The product (39 mg, 100%), 3-hydroxycarbonyl-2-(4methylsulfonyl-2-(4-[(2-t-butylaminosulfonyl)phenyl]phenylcarbonylamino)phenoxy)naphthalene, was extracted with EtOAc, dried over $MgSO_4$, filtered and evaporated. MS found for $C_{34}H_{31}N_2O_6S$ (M+H)$^+$: 595.

Step 2: A solution of 3-hydroxycarbonyl-2-(4-methylsulfonyl-2-(4-[(2-t-butylaminosulfonyl)phenyl]phenylcarbonylamino)phenoxy)naphthalene (39 mg, 0.066 mmol) was refluxed in 3 mL of thionyl chloride for 2 h and evaporated. The residue was then stirred in 5 mL of 2M ammonia in methanol overnight. The volatile was evaporated and the residue was refluxed in 2 mL of trifluoroacetic acid overnight to give the product 3-aminocarbonyl-2-(4-[(2-aminosulfonyl)phenyl]phenylcarbonylamino)phenoxy naphthalene (14 mg, 39%) after HPLC (C18 reversed phase, eluting with 0.5% TFA in $H_2O/CH_3CN$). MS found for $C_{30}H_{24}N_3O_5S$ (M+H)$^+$: 538.

Example 25
3-methoxycarbonyl-2-(4-[(2-aminosulfonyl)phenyl]phenylcarbonylamino)phenoxy-6-bromo naphthalene

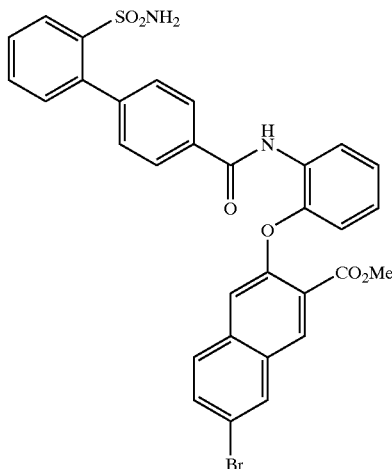

A mixture of 2-(2-aminophenoxy)-3-methoxycarbonyl-6-bromo naphthalene (372 mg, 1 mmol, 1.0 equiv), 4-[(2-t-butylaminosulfonyl)phenyl]benzoyl chloride (349 mg, 1 equiv), pyridine (3 mL) in 10 mL of dichloromethane was stirred at rt overnight, washed with $H_2O$. The organic layer was dried over $MgSO_4$, filtered, evaporated and refluxed in 2 mL of trifluoroacetic acid for 30 min. TFA was then evaporated and HPLC (C18 reversed phase) eluting with 0.5% TFA in $H_2O/CH_3CN$ gave 3-methoxycarbonyl-2-(4-[(2-aminosulfonyl)phenyl]phenylcarbonylamino)phenoxy-6-bromo naphthalene (423 mg, 67%). MS found for $C_{31}H_{24}BrN_2O6S$ (M+H)$^+$: 631.

Example 26
3-hydroxycarbonyl-2-(4-[(2-aminosulfonyl)phenyl]phenylcarbonylamino)phenoxy-6-bromo naphthalene

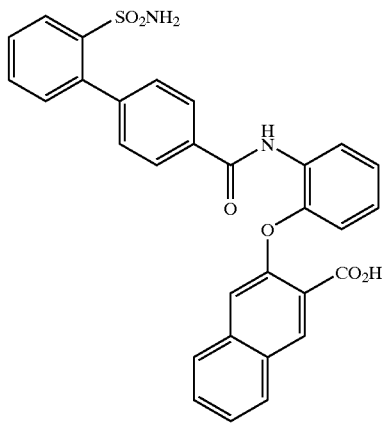

A solution of 3-methoxycarbonyl-2-(4-methylsulfonyl-2-(4-[(2-aminosulfonyl)phenyl]phenylcarbonylamino)phenoxy)6-bromo naphthalene (63 mg, 0.1 mmol, 1.0 equiv) in 5 mL of methanol was treated with 1N LiOH (2 mL) at rt for 2 h. Methanol was evaporated, the aqueous residue was subjected to HPLC with 0.5% TFA in $H_2O/CH_3CN$ to give 3-hydroxycarbonyl-2-(4-[(2-aminosulfonyl)phenyl]phenylcarbonylamino)phenoxy-6-bromo naphthalene (47 mg, 78%). MS found for $C_{30}H_{22}BrN_2O6S$ $(M+H)^+$: 617.

Example 27

N-(5-bromo-2-pyridinyl)(24-[(2-aminosulfonyl)phenyl]phenylcarbonylamino)phenylcarboxamide

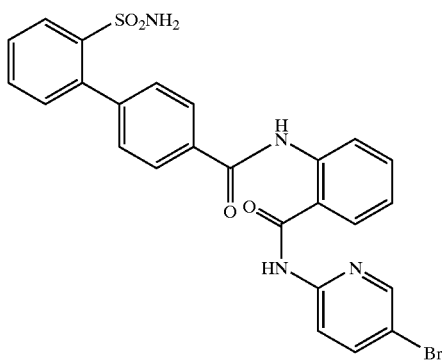

Step 1: A solution of 2-ntrobenzoyl chloride (3.70 g, 20 mmol, 1.0 equiv), 2-amino-5-bromopyridine (3.50 g, 1.0 equiv), pyridine (10 mL) in 25 mL of methylene chloride was stirred overnight. The volatile was evaporated, flash chromatography on silica gel gave N-(5-bromo-2-pyridinyl)-(2-nitro)phenylcarboxamide (5.02 g, 77%). MS found for $C_{12}H_9BrN_3O_3$ $(M+H)^+$: 322.

Step 2: A solution of N-(5-bromo-2-pyridinyl)-(2-nitro)phenylcarboxamide (1.0 g, 3.1 mmol, 1.0 equiv) in 30 mL of EtOAc was treated with $SnCl_2.2H_2O$ (2.80 g, 4 equiv) at reflux for 4 h. The volatile was evaporated and the residue was redissolved in EtOAc, washed with saturated aqueous $NaHCO_3$ and 1N NaOH. The organic layer was dried over $MgSO_4$, filtered and evaporated to N-(5-bromo-2-pyridinyl)-(2-amino)phenylcarboxamide (0.89 g, 98%). MS found for $C_{12}H_{11}BrN_3O$ $(M+H)^+$: 292.

Step 3: A mixture of N-(5-bromo-2-pyridinyl)(2-amino)phenylcarboxamide (292 mg, 1 mmol, 1.0 equiv), 4-[(2-t-butylaminosulfonyl)phenyl]benzoyl chloride (349 mg, 1 equiv), pyridine (3 mL) in 10 mL of dichloromethane was stirred at rt overnight, washed with $H_2O$. The organic layer was dried over $MgSO_4$, filtered, evaporated and refluxed in 2 mL of trifluoroacetic acid for 30 min. TFA was then evaporated and BHPLC (C18 reversed phase) eluting with 0.5% TFA in $H_2O/CH_3CN$ gave N-(5-bromo2-pyridinyl)-(2-4-[(2-aminosulfonyl)phenyl]phenylcarbonylamino) phenylcarboxamide (470 mg, 85%). MS found for $C_{25}H_{20}BrN_4O_4S$ $(M+H)^+$: 551.

Example 28

N-(5-chloro-2-pyridinyl)-(2-4-[(2-aminosulfonyl)phenyl]phenylcarbonylamino)phenylcarboxamide

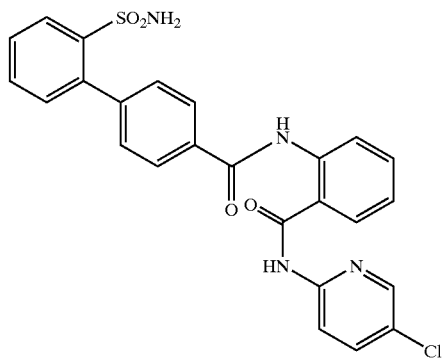

A mixture of N-(5-chloro-2-pyridinyl)-(2-amino)phenylcarboxamide (247 mg, 1 mmol, 1.0 equiv), 4-[(2-t-butylaminosulfonyl)phenyl]benzoyl chloride (349 mg, 1 equiv), pyridine (3 mL) in 10 mL of dichloromethane was stirred at rt overnight, washed with $H_2O$. The organic layer was dried over $MgSO_4$, filtered, evaporated and refluxed in 2 mL of trifluoroacetic acid for 30 min. TFA was then evaporated and HPLC (C18 reversed phase) eluting with 0.5% TFA in $H_2O/CH_3CN$ gave N-(5-chloro-2-pyridinyl)-(2-4-[(2-aminosulfonyl)phenyl]phenylcarbonylamino) phenylcarboxamide (370 mg, 73%). MS found for $C_{25}H_{20}ClN_4O_4S$ $(M+H)^+$: 507.

Example 29

N-(5-bromo-2-pyridinyl)-(2-(4-[(2-methylsulfonyl)phenyl]phenylcarbonyl)amino)phenylcarboxamide

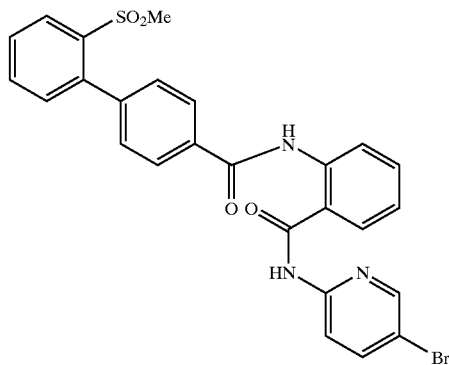

Step 1: To a mixture of 2-bromothioanisole (4.8g, 23.6 mmol), 4-carboxybenzeneboronic acid (3.92g, 23.6 mmol) and 2M $K_2CO_3$ (35.5 mmol, 71 mmol) in dioxane (20 ml) was added dichlorobis(triphenylphosphine)palladium (II) (415 mg, 0.6 mmol) under Ar. It was refluxed for 2 hrs. After the removal of the solvent, the residue was neutralized by 1N HCl and extracted with dichloromethane. The organic layer was dried over $MgSO_4$ and concentrated in vacuo to give 4-[(2-methylthio)phenyl]benzoic acid (5.9g, 100%). ES-MS $(M+H)^+$=245.

Step 2: To a solution of 4-[(2-methylthio)phenyl]benzoic acid (3.43 g, 14 mmol) in $H_2O$ (10 ml) and acetone (20 ml) was added oxone monopersulfate (34.6 g, 56 mmol). The mixture was stirred at r.t. overnight. After the removal of the solvent, the residue was extracted with ethyl acetate. The organic layer was dried over MgSO$_4$ and concentrated in vacuo to give 2.16 g (63%) 4-[(2-methylsulfonyl)phenyl] benzoic acid. ES-MS (M+H)$^+$=277.

Step 3: To a solution of 4-[(2-methylsulfonyl)phenyl] benzoic acid (552 mg, 2 mmol) in dichloromethane (5 ml) was added oxalyl chloride (350 ul, 4 mmol) and 2 drops of DMF. The mixture was stirred at r.t. for 2 hrs. After the removal of the solvent in vacuo, the residue was dissolved in dichloromethane (5 ml), N-(5-bromo-2-pyridinyl)-(2-amino)phenylcarboxamide (700 mg, 2.4 mmol), pyridine (486 ul, 6 mmol) and catalytic amount of DMAP were added. The mixture was stirred at r.t. overnight. After the removal of the solvent, the residue was purified by flash column (30% ethyl acetate/hexane) and then preparative HPLC to get 414 mg (38%) of N-5-bromo-2-pyridinyl)-(2-(4-[(2-methylsulfonyl)phenyl]phenylcarbonyl)amino) phenylcarboxamide. ES-MS M$^+$=550, (M+2)$^+$=552.

Example 30

N-(5-chloro-2-pyridinyl)-(2-(4-[(2-methylsulfonyl) phenyl]phenylcarbonyl)amino)phenylcarboxamide

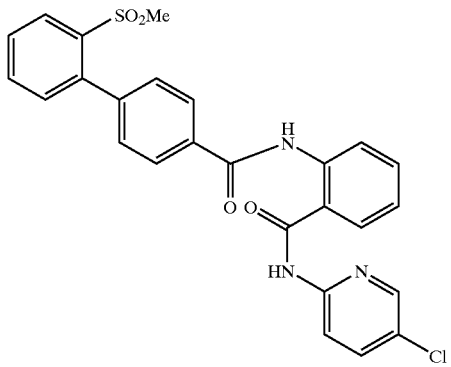

To a solution of 4-[(2-methylsulfonyl)phenyl]benzoic acid (280 mg, 1 mmol) in dichloromethane (5 ml) was added oxalyl chloride (175 ul, 2 mmol) and 2 drops of DMF. The mixture was stirred at r.t. for 2 hrs. After the removal of the solvent in vacuo, the residue was dissolved in dichloromethane (5 ml), N-(5-chloro-2-pyridinyl)-(2-amino) phenylcarboxamide (297 mg, 1.2 mmol), pyridine (243 ul, 3 mmol) and catalytic amount of DMAP were added. The mixture was stirred at r.t. overnight. After the removal of the solvent, the residue was purified by flash column (30% ethyl acetate/hexane) and then preparative HPLC to get 95 mg (20%) of N-(5-chloro-2-pyridinyl)-(2-(4-[(2-methylsulfonyl)phenyl]phenylcarbonyl)amino) phenylcarboxamide. ES-MS M+=505.5, (M+2)+=507.5.

Example 31

N-(4-bromo-2-methoxycarbonyphenyl)-(2-(4-[(2-methylsulfonyl)phenyl]phenylcarbonyl)amino) phenylcarboxamide

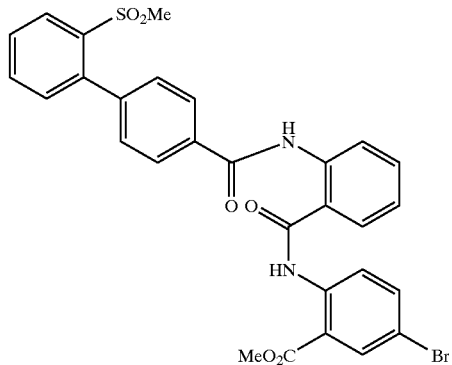

A sample of 4-[(2-methylsulfonyl)phenyl]benzoic acid (280 mg, 1 mmol, 1 equiv) was refluxed with 2 mL of thionyl chloride for 2 h and evaporated. The residue was dissolved in 5 mL of dichloromethane, N-(4-bromo-2-methoxycarbonyphenyl)-2-amino)phenylcarboxamide (348 mg, 1 equiv), pyridine (3 mL) were added. The mixture was stirred at r.t. overnight. After the removal of the solvent, the residue was purified by flash column to give 480 mg (79%) of N-(4-bromo-2-methoxycarbonyphenyl)-(2-(4-[(2-methylsulfonyl)phenyl]phenylcarbonyl)amino) phenylcarboxamide. MS found for $C_{29}H_{24}BrN_2O_6S$ (M+H)$^+$: 607.

Example 32

N-(4-chloro-2-methoxycarbonyphenyl)-(2-(4-[(2-methylsulfonyl)phenyl]phenylcarbonyl)amino) phenylcarboxamide

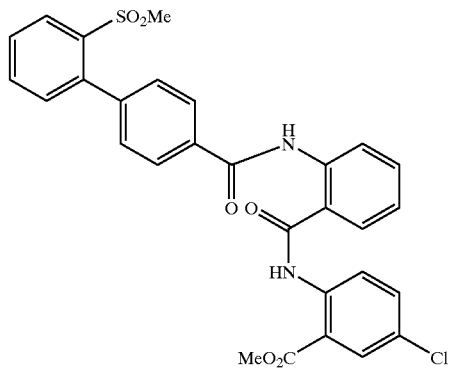

A sample of 4-[(2-methylsulfonyl)phenyl]benzoic acid (280 mg, 1 mmol, 1 equiv) was refluxed with 2 mL of thionyl chloride for 2 h and evaporated. The residue was dissolved in 5 mL of dichloromethane, N-(4-chloro-2-methoxycarbonyphenyl)-(2-amino)phenylcarboxamide (304 mg, 1 equiv), pyridine (3 mL) were added. The mixture was stirred at r.t. overnight. After the removal of the solvent, the residue was purified by flash column to give 479 mg (85%) of N-(4-chloro-2-methoxycarbonyphenyl)-(2-(4-[(2- methylsulfonyl)phenyl]phenylcarbonyl)amino)
phenylcarboxamide. MS found for $C_{29}H_{24}ClN_2O_6S$ (M+H)+: 563.

Example 33

N-(5-bromo-2-pyridinyl)-(2-(4-[(2-aminosulfonyl)
phenyl]phenylcarbonylamino)pyridinyl-3-
carboxamide

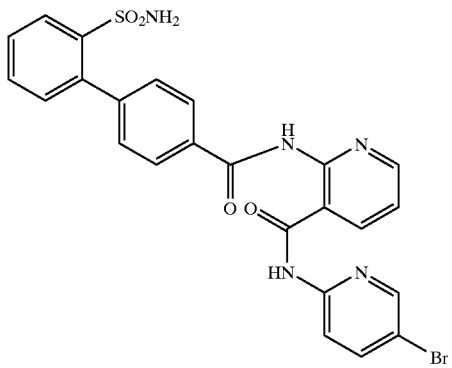

Step 1: A solution of 2-aminopyridine-3-carboxylic acid (138 mg, 1 mmol) in 10 mL of methanol was treated with thionyl chloride in portions until complete reaction. The solvent was evaporated and the residue was dissolved in 10 mL of pyridine. To the solution were added 4-[(2-t-butylaminosulfonyl)phenyl]benzoic acid and POCl₃. The resulting mixture was stirred at rt overnight, quenched by slow addition of water, and extracted with EtOAc. The organic layer was dried over MgSO₄, filtered and flash chromatographied to give methyl 2-(4-[(2-t-butylaminosulfonyl)phenyl]phenylcarbonyl)aminopyridine-3-carboxylate (243 mg, 52%). MS found for $C_{24}H_{26}N_3O_5S$ (M+H)+: 468.

Step 2: To A solution of 2-amino-5-bromopridine (45 mg, 4.0 equiv) in 5 mL of methylene chloride treated with AlMe. (2M in hexane, 0.65 mL, 20 equiv) for 30 min was added methyl 2-(4-[(2-t-butylaminosulfonyl)phenyl]phenylcarbonyl)aminopyridine-3-carboxylate (30 mg, 0.064 mmol, 1 equiv). The mixture was stirred at rt overnight, quenched with saturated aqueous potassium sodium tartrate. The organic layer was dried over MgSO₄, filtered, evaporated and refluxed in 2 mL of trifluoroacetic acid for 30 min. TFA was then evaporated and HPLC (C18 reversed phase) eluting with 0.5% TFA in H₂O/CH₃CN gave N-(5-bromo-2-pyridinyl)-(2-4-[(2-aminosulfonylphenyl]phenylcarbonylamino)pyridinyl-3-carboxamide (17 mg, 48%). MS found for $C_{24}H_{19}BrN_5O_4S$ (M+H)+: 552.

Example 34

N-(5-chloro-2-pyridinyl)-(2-4-[(2-aminosulfonyl)
phenyl]phenylcarbonylamino)pyridinyl-3-
carboxamide

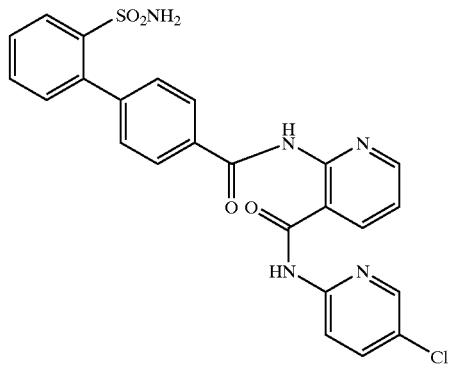

To A solution of 2-amino-5-chloropridine (32 mg, 4.0 equiv) in 5 mL of methylene chloride treated with AlMe. (2M in hexane, 0.65 mL, 20 equiv) for 30 min was added methyl 2-(4-[(2-t-butylaminosulfonyl)phenyl]phenylcarbonyl)aminopyridine-3-carboxylate (30 mg, 0.064 mmol, 1 equiv). The mixture was stirred at rt overnight, quenched with saturated aqueous potassium sodium tartrate. The organic layer was dried over MgSO₄, filtered, evaporated and refluxed in 2 mL of trifluoroacetic acid for 30 min. TFA was then evaporated and HPLC (C18 reversed phase) eluting with 0.5% TFA in H₂/CH₃CN gave N-(5-chloro-2-pyridinyl)-(2-4-[(2-aminosulfonyl)phenyl]phenylcarbonylamino)pyridinyl-3-carboxamide (21 mg, 66%). MS found for $C_{24}H_{19}ClN_5O_4S$ (M+H)+: 508.

Example 35

N-(5-bromo-2-pyridinyl)-(3-4-[(2-aminosulfonyl)
phenyl]phenylcarbonylamino)pyridinyl-2-
carboxamide

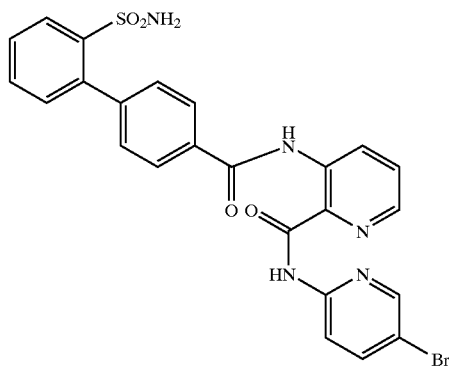

To A solution of 2-amino-5-bromopridine (69.2 mg, 4.0 equiv) in 5 mL of methylene chloride treated with AlMe₃ (2M in hexane, 1 mL, 20 equiv) for 30 min was added 3-(4-[(2-t-butylaminosulfonyl)phenyl]phenylcarbonyl)aminopyridine-2-carboxylate (46.7 mg, 1 equiv). The mixture was stirred at rt ovenight, quenched with saturated aqueous potassium sodium tartrate. The organic layer was dried over MgSO₄, filtered, evaporated and refluxed in 2 mL of trifluoroacetic acid for 30 min. TFA was then evaporated and HPLC (C18 reversed phase) eluting with 0.5% TFA in H$_2$O/CH$_3$CN gave N-(5-bromo-2-pyridinyl)-(3-4-[(2-aminosulfonyl)phenyl]phenylcarbonylamino)pyridinyl-2-carboxamide (29 mg, 53%). MS found for C$_{24}$H$_{19}$BrN$_5$O$_4$S (M+H)$^+$: 552.

Example 36

N-(5-(chloro-2-pyridinyl)-(2-4-[(2-aminosulfonyl)phenyl]phenylcarbonylamino)pyridinyl-3-carboxamide

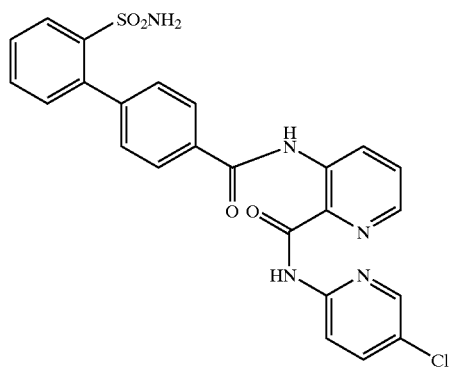

To A solution of 2-amino-5-chloropridine (51.2 mg, 4.0 equiv) in 5 mL of methylene chloride treated with AlMeS (2M in hexane, 1 mL, 20 equiv) for 30 min was added 3-(4-[(2-t-butylaminosulfonyl)phenyl]phenylcarbonyl)aminopyridine-2carboxylate (46.7 mg, 0.1 mmol, 1 equiv). The mixture was stirred at rt overnight, quenched with saturated aqueous potassium sodium tartrate. The organic layer was dried over MgSO$_4$, filtered, evaporated and refluxed in 2 mL of trifluoroacetic acid for 30 min. TFA was then evaporated and HPLC (C18 reversed phase) eluting with 0.5% TFA in H$_2$O/CH$_3$CN gave N-(5-chloro-2-pyridinyl)-2-4-[(2-aminosulfonyl)phenyl]phenylcarbonylamino)pyridinyl-3-carboxamide (33 mg, 64%). MS found for C$_{24}$H$_{19}$ClN$_5$O$_4$S (M+H)$^+$: 508.

Examples 37–40

The following compounds of Examples 37–40 were prepared using the procedure described in Example 36:

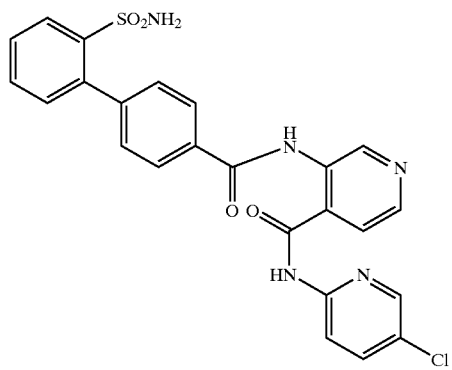

Example 37
MS (M + H): 508

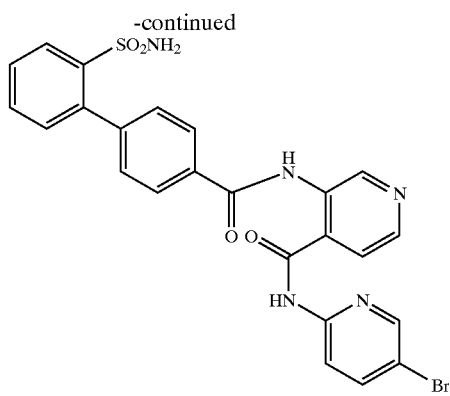

Example 38
MS (M + H): 552

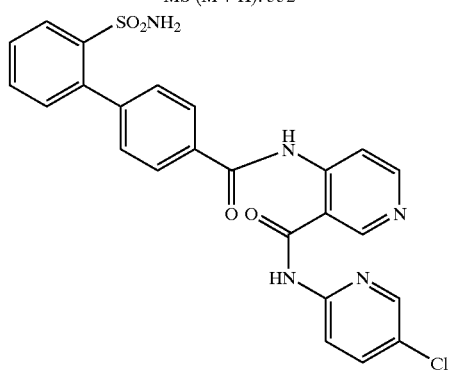

Example 39
MS (M + H): 508

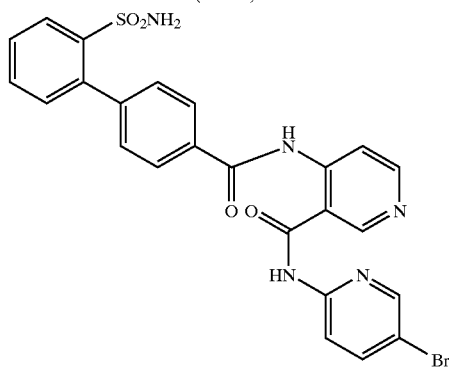

Example 40
MS (M + H): 552

Example 41
N-(4-bromo-2-nitrophenyl)-(2-(4-[(2-methylsulfonyl)phenyl]phenylcarbonyl)amino)phenylcarboxamide

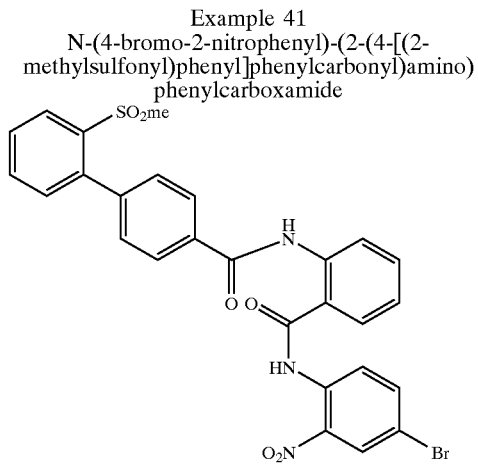

Step 1: A mixture of methyl 2-aminobenzoate (150 mg, 1 mmol, 1.0 equiv), 4-[(2-methylsulfonyl)phenyl]benzoic chloride (294 mg, 1 equiv), pyridine (3 mL) in 10 mL of dichloromethane was stirred at rt overnight, washed with H$_2$O. The organic layer was dried over MgSO$_4$, filtered and evaporated. Flash chromatography on silica gel gave methyl 2-(4-[(2-methylsulfonyl)phenyl]phenylcarbonyl)aminobenzoate (250 mg, 54%). MS found for C$_{25}$H$_{27}$N$_2$O$_5$S (M+H)$^+$: 467.

Step 2: To a solution of 4-bromo-2-ntroaniline (43.4 mg, 0.2 mmol, 2.0 equiv) in 5 mL of methylene chloride treated with AlMe$_3$ (2M in hexane, 0.3 mL, 6 equiv) for 30 min was added methyl 2-(4-[(2-methylsulfonyl)phenyl]phenylcarbonyl)aminobenzoate (46.6 mg, 1 equiv). The mixture was stirred at rt overnight, quenched with saturated aqueous potassium D sodium tartrate. The organic layer was dried over MgSO$_4$, filtered and evaporated. Flash chromatography on silica gel gave N-(4-bromo-2-nitrophenyl)-(2-(4-[(2-methylsulfonyl)phenyl]phenylcarbonyl)amino)phenylcarboxamide (5 mg, 9%). MS found for C$_{27}$H$_{21}$BrN$_3$O$_6$S (M+H)$^+$: 594.

Example 42

N-(4-methoxyphenyl)-N'4-[(2-aminosulfonyl)phenyl]phenyl)-maleamic amide

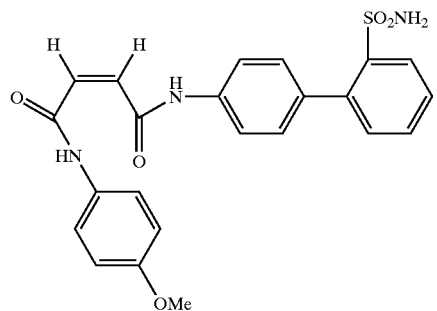

A. Preparation of N-(4-methoxyphenyl)-N'-(4-[(2-tert-butylaminosulfonyl)phenyl]phenyl)-maleamic amide.

To a solution of commercially available N-(4-methoxyphenyl)maleamic acid (100 mg, 0.452 mmol), triethylamine (0.126 mL, 0.906 mmol) and 4-(2-tert-butylaminosulfonylphenyl)aniline (138 mg, 0.454 mmol) in anhydrous DMF (5 mL), BOP (260 mg, 0.588 mmol) was added. The mixture was stirred at room temperature overnight. Water and EtOAc were added. The organic phase was separated, washed with H2O, then with 5% NaHCO3, dried over Na2SO4, concentrated in vacuo. The residue was purified by HPLC using a gradient of 20% CH3CN in H2O (containing 0.1% TFA) to 100% CH3CN over 80 min. Fractions containing the desired product were pooled, and lyophilized to give a powder (70 mg, yield: 31%). MS 508 (M+H).

B. Preparation of N-(4-methoxyphenyl)-N'-(4-[(2-aminosulfonyl)phenyl]phenyl)-maleamic amide.

The compound N-(4-methoxyphenyl)-N'-(4-[(2-tert-butylaminosulfonyl)phenyl]phenyl)-maleamic amide (40 mg, 79 mol) was dissolved in TFA (3 mL). It was allowed to stand at room temperature overnight. TFA was removed in vacuo. The residue was purified by HPLC using a gradient of 5% CH3CN in H2O (containing 0.1% TFA) to 95% CH3CN over 60 min. Fractions containing the desired product w were pooled, and lyophilized to give a powder (18 mg, yield: 51%). MS 452 (M+H) and 474(M+Na). $^1$HNMR (CDCl3) 11.40 (br.s, 1H), 10.28 (br.s, 1H), 8.12 (d, 1H, J=8 Hz), 7.72 (d, 2H, J=8 Hz), 7.60–7.20 (m, 9H), 6.86 (AB type, 2H), 6.45 (br.s, 2H), 3.79 (s, 3H).

Example 43

N-(4-bromophenyl)-N'-(4-[(2-aminosulfonyl)phenyl]phenyl)maleamic amide

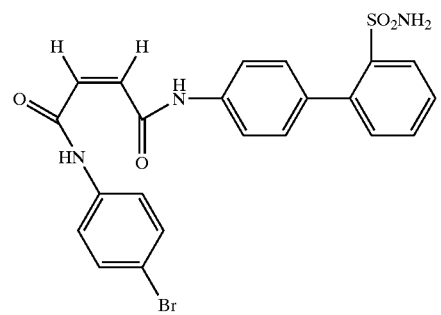

A. Preparation of N-(4-[(2-tert-butylaminosulfonyl)phenyl]phenyl)maleamic methyl ester.

To a solution of commercially available maleic acid monomethyl ester (277 mg, 2.13 mmol), 4-(2-tert-butylaminosulfonylphenyl)aniline (648 mg, 2.13 mmol) and triethylamine (0.593 mL, 4.26 mmol) in CH2Cl2 (20 mL), BOP (1.13 g, 2.55 mmol) was added. The mixture was stirred at room temperature overnight. More maleic acid monomethyl ester (50 mg, 0.385 mmol) was added. It was stirred for 3 hours. The CH2Cl2 solution was then washed with sat. NaHCO3, 1N HCl and sat. NaCl. The solution was dried over Na2SO4, concentrated in vacuo. The residue was purified by a silica gel column using a gradient of 10–40% EtOAc in hexane as solvents, to give the titled compound (360 mg, yield: 41%). MS 361 (M+H–$^t$Bu) and 439 (M+Na).

B. Preparation of N-(4-bromophenyl)-N'-(4-[(2-aminosulfonyl)phenyl]phenyl)-maleamic amide To a solution of 4-bromoaniline (93 mg, 0.543 mmol) in CH2Cl2 (5 mL) at room temperature, trimethylaluminum (0.82 mL, 2.0 M in hexane, 1.64 mmol) was added dropwise. After the solution was stirred for 30 min at room temperature, compound N-(4-[(2-tert-butylaminosulfonyl)phenyl]phenyl)maleamic methyl ester (113 mg, 0.272 mmol) was added. The mixture was stirred at room temperature for 2 days. The solution was neutralized with 1N HCl to pH 2–3. Water and CH2Cl2 were added, and organic phase was separated, dried over Na2SO4, concentrated in vacuo. The residue was dissolved in TFA (4 mL). It was allowed to stand at room temperature overnight. TFA was removed in vacuo. The residue was purified by HPLC using a gradient of 5% CH3CN in H2O (containing 0.1% TFA) to 95% CH3CN over 60 min. Fractions containing the desired product were pooled, and lyophilized to give a powder (8 mg, yield: 6%). MS 500 and 502 (M+H), 522 and 524 (M+Na). $^1$H NMR (CD3OD) 8.09 (d, 1H, J=8 Hz), 7.68 (d, 2H, J=8 Hz), 7.64–7.28 (m, 9H), 6.45 (AB type, 2H).

Examples 44 and 45

Preparation of $N^1$-(5-bromopyridin-2-yl)-$N^4$-(4-[(2-aminosulfonyl)phenyl]phenyl)-2-methylmaleamic amide and $N^1$-(5-bromopyridin-2-yl)-$N^4$-(4-[(2-aminosulfonyl)phenyl]phenyl)-3-methylmaleamic amide

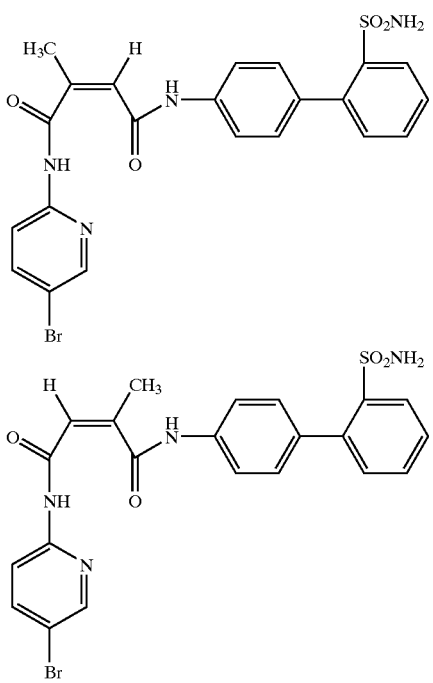

A. Preparation of N-(5-bromopyridin-2-yl)-methylmaleimide. A mixture of citraconic anhydride (1.00 mL, 11.1 mmol) and 2-amino-5-bromopyridine (1.93 g, 11.2 mmol) in toluene (60 mL) was heated to reflux overnight. The solution was cooled down, filtered. The filtrate was concentrated in vacuo to give a solid (2.10 g, yield: 71%). MS 267 and 269 (M+H).

B. Preparation of $N^1$-(5-bromopyridin-2-yl)-$N^4$-(4-[(2-aminosulfonyl)phenyl]phenyl)-2-methylmaleamic amide and $N^1$-(5-bromopyridin-2-yl)-$N^4$-(4-[(2-aminosulfonyl)phenyl]phenyl)-3-methylmaleamic amide.

To the solution of 4-(2-aminosulfonylphenyl)aniline (0.170 g, 0.685 mmol) in CH2Cl2 (10 mL) at room temperature, trimethylaluminum (2.0 M in hexane, 2.00 mL, 4.00 mmol) was added dropwise, during which time, white gel-like precipitates came out the solution. It was stirred for 30 min. A solution of N-(5-bromopyridin-2-yl)-methylmaleimide (0.122 g, 0.457 mmol) in CH2Cl2 (5 mL) was added. It was stirred for 1 hour, during which time the precipitates started to dissolve, and the solution became clear. It was stirred for another 2 hours. IN HCl was added to neutralize the solution to pH 2–3, which resulted in precipitation. The precipitates were collected by filtration, dried on vacuum. The precipitates (75 mg, yield: 32%) were a mixture of 2-methyl and 3-methylmaleamic amide isomers in a ratio of 1:5. MS 515 and 517 (M+H), 537 and 539 (M+Na).

Example 46

N-(5-bromo-2-pyridinyl)-(2-(4-[(2-aminosulfonyl)phenyl]phenylcarbonyl)amino)-4-nitrophenylcarboxamide

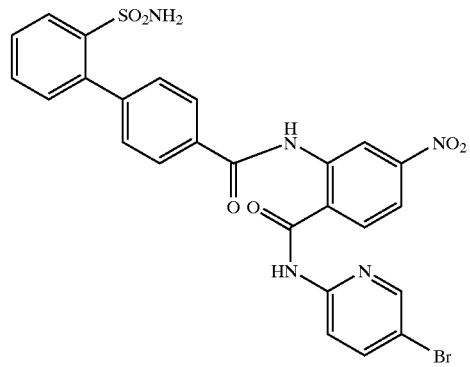

Step 1: A solution of 2-amino-4-nitrobenzoic acid (182 mg, 1 mmol, 1 equiv) in 10 mL of methanol was treated with thionyl chloride in portions until complete reaction. The solvent was evaporated and the residue was dissolved in 10 mL of pyridine. To the solution were added 4-[(2-t-butylaminosulfonyl)phenyl]benzoic acid (330 mg, 1 equiv) and POCl$_3$ (0.93 mL, 10 equiv). The resulting mixture was stirred at rt overnight, quenched by slow addition of water, and extracted with EtOAc. The organic layer was dried over MgSO$_4$, filtered and flash chromatographied to give methyl 2-(4-[(2-t-butylaminosulfonyl)phenyl]phenylcarbonyl)amino-4-nitrobenzoate (430 mg, 84%). MS found for $C_{25}H_{26}N_3O_7S$ (M+H)$^+$: 512.

Step 2: To A solution of 2-amino-5-bromopridine (135 mg, 4.0 equiv) in 5 mL of methylene chloride treated with AlMe$_3$ (2M in hexane, 1 mL, 10 equiv) for 30 min was added methyl 2-(4-[(2-t-butylaminosulfonyl)phenyl]phenylcarbonyl)amino-4-nitrobenzoate (100 mg, 0.2 mmol, 1 equiv). The mixture was stirred at rt overnight, quenched with saturated aqueous potassium sodium tartrate. The organic layer was dried over MgSO$_4$, filtered, evaporated and refluxed in 2 mL of trifluoroacetic acid for 30 min. TFA was then evaporated and HPLC (C18 reversed phase) eluting with 0.5% TFA in H$_2$O/CH$_3$CN gave N-(5-bromo-2-pyridinyl)-(2-(4-[(2-aminosulfonyl)phenyl]phenylcarbonyl)amino)-4-nitrophenylcarboxamide (42 mg, 36%). MS found for $C_{25}H_{19}BrN_5O_6S$ (M+H)$^+$: 596.

Examples 47–49

The following compounds of Examples 47–49 were prepared according to the procedure described in example 46.

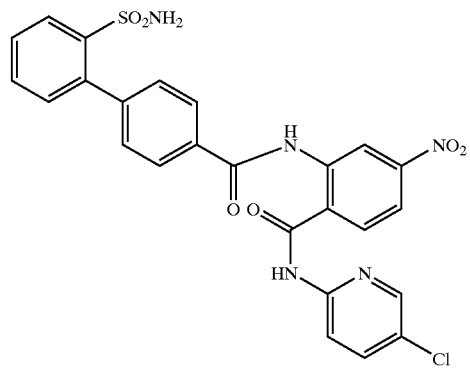

Example 47
MS (M + H): 552

-continued

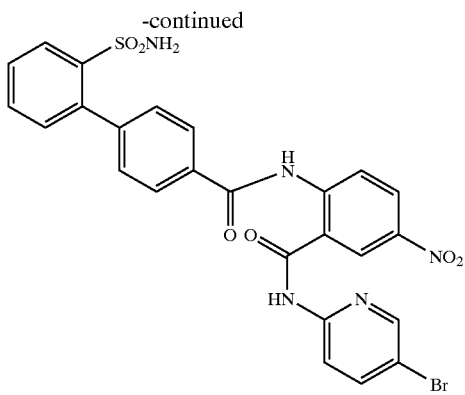

Example 48
MS (M + H): 596

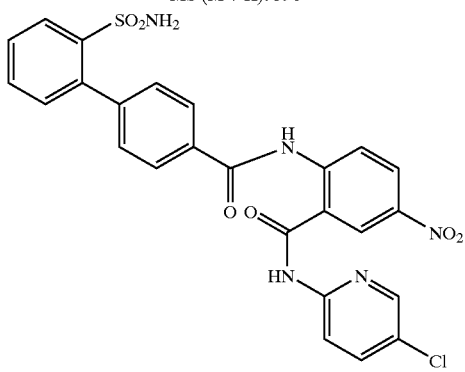

Example 49
MS (M + H): 552

Example 50

N-(5-bromo-2-pyridinyl)-(2-(4-[(2-aminosulfonyl)
phenyl]phenylcarbonyl)amino)-4-
aminophenylcarboxamide

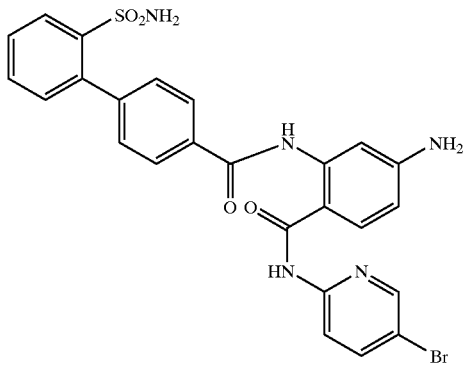

A solution of N-(5-bromo-2-pyridinyl)-(2-(4-[(2-t-butylsulfonyl)phenyl]phenylcarbonyl)amino)-4-nitrophenylcarboxamide (65 mg, 0.1 mmol, 1 equiv) in 10 mL of EtOAc was treated with SnCl$_2$2H$_2$O (90 m g, 4 equiv) at reflux for 4 h. The volatile was evaporated and the residue was redissolved in EtOAc, washed with saturated aqueous NaHCO and 1N NaOH. The organic layer was dried over MgSO$_4$, filtered and evaporated to give N-(5-bromo-2-pyridinyl)-(2-(4-[(2-t-butylsulfonyl)phenyl]phenylcarbonyl)amino)-4-aminophenyl carboxamide, which was refluxed with 2 mL of TEA for 1 h. After removal of TFA by rotavap, the residue was purified by HPLC (C18 reversed phase) eluting with 0.5% TFA in H$_2$O/CH$_3$CN to give N-(5-bromo-2-pyridinyl)-2-(4-[(2-aminosulfonyl) phenyl]phenylcarbonyl)amino)-4-aminophenylcarboxamide (47 mg, 84%). MS found for C$_{25}$H$_{21}$BrN$_5$O$_4$S (M+H)$^+$: 566.

Example 51

N-(5-chloro-2-pyridinyl)-(2-(4-[(2-aminosulfonyl)
phenyl]phenylcarbonyl)amino)-4-
aminophenylcarboxamide

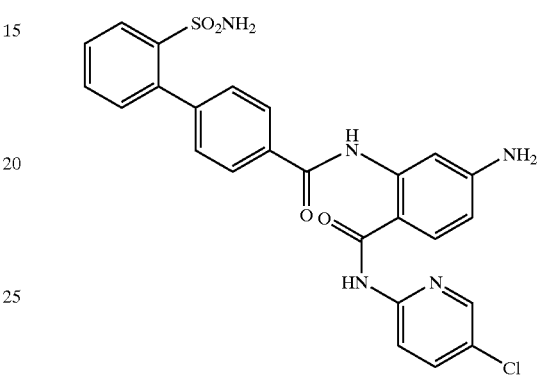

This compound was prepared according to the procedure described in example 50. MS found for C$_{25}$H$_{21}$ClN$_5$O$_4$S (M+H)$^+$: 522.

Example 52

N-(5-bromo-2-pyridinyl)-(2-(4-[(2-aminosulfonyl)
phenyl]phenylcarbonyl)amino)-4-
methylsulfonylaminophenylcarboxamide

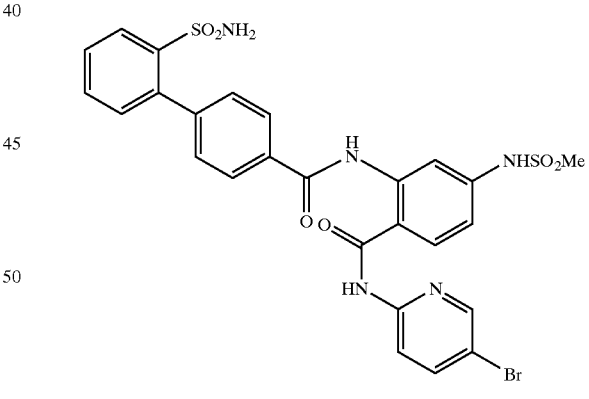

A solution of N-(5-bromo-2-pyridinyl)-(2-(4-[(2-t-butylsulfonyl)phenyl]phenylcarbonyl)amino)-4-aminophenyl carboxamide (62 mg, 0.1 mmol, 1 equiv) in 3 mL of CH$_2$Cl$_2$ was treated with MsCl (23 mg, 2 equiv) and TEA (0.5 mL) at rt for 4 h. The mixture was washed with water and dried over MgSO$_4$, filtered and evaporated. The residue was refluxed with 2 mL of TFA for 1 h. After removal of TFA by rotavap, the residue was purified by HPLC (C18 reversed phase) eluting with 0.5% TFA in H$_2$O/CH$_3$CN to give N-(5-bromo-2-pyridinyl)-(2-(4-[(2-aminosulfonyl)phenyl]phenylcarbonyl)amino)-4- methylsulfonylaminophenylcarboxamide (33 mg, 52%). MS found for $C_{26}H_{23}BrN_5O_6S2$ (M+H)$^+$: 644.

Example 53

N-(5-chloro-2-pyridinyl)-(2-(4-[(2-aminosulfonyl)phenyl]phenylcarbonyl)amino)-4-methylsulfonylaminophenylcarboxamide

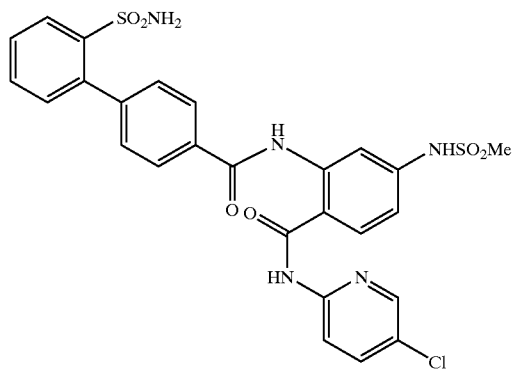

This compound was prepared according to the procedure described in example 53. MS found for $C_{26}H_{23}ClN_5O_6S_2$ (M+H)$^+$: 600.

Example 54

N-(5-bromo-2-pyridinyl)-(2-(4-[(2-aminosulfonyl)phenyl]phenylcarbonyl)amino)-5-aminophenylcarboxamide

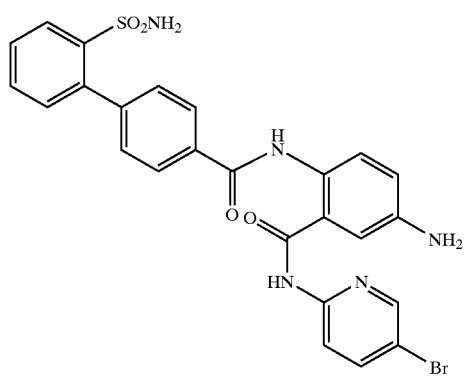

This compound was prepared according to the procedure described in example 50. MS found for $C_{25}H_{21}BrN_5O_4S$ (M+H)$^+$: 566.

Example 55

N-(5-chloro-2-pyridinyl)-2-(4-[(2-aminosulfonyl)phenyl]phenylcarbonyl)amino)-5-aminophenylcarboxamide

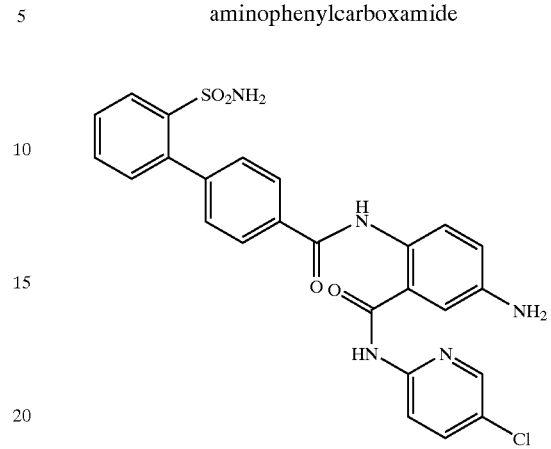

This compound was prepared according to the procedure described in example 50. MS found for $C_{25}H_{21}ClN_5O_4S$ (M+H)$^+$: 522.

Example 56

N-(5-bromo-2-pyridinyl)-(2-(4-amidinophenylcarbonyl)amino)-phenylcarboxamide

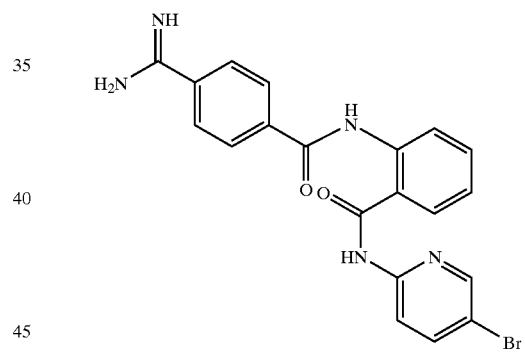

Step 1: A mixture of N-(5-bromo-2-pyridinyl)-(2-amino)phenylcarboxamide (292 mg, 1 mmol, 1.0 equiv), 4-cyano benzoyl chloride (165 mg, 1 equiv), pyridine (3 mL) in 10 mL of dichloromethane was stirred at rt overnight, washed with H$_2$O. The organic layer was dried over MgSO$_4$, filtered, evaporated to give N-(5-bromo-2-pyridinyl)-(2-(4-cyanophenylcarbonyl)amino)-phenylcarboxamide (349 mg, 70%). MS found for $C_{20}H_{14}BrN_4O_2$ (M+H)$^{30}$: 421.

Step 2: A stream of HCl(g) was bubbled through a 0° C. solution of N-(5-bromo-2-pyridinyl)-(2-(4-cyanophenylcarbonyl)amino)-phenylcarboxamide (49 mg, 0.1 mmol) in 5 mL of methanol until saturation. The mixture was stirred at rt overnight and evaporated. The resulting residue was treated with ammonium acetate (40 mg) in 10 ml methanol at reflux temperature for 2 h. The solvent was removed at reduced pressure and the crude benzamidine was purified by HPLC (C18 reversed phase) eluting with 0.5% TFA in H$_2$O/CH$_3$CN to give N-(5-bromo-2-pyridinyl)-(2-(4-amidinophenylcarbonyl)amino)-phenylcarboxamide (31 mg, 70%). MS found for $C_{20}H_{17}BrN_5O_2$ (M+H)$^+$: 438.

Examples 57–86
The following compounds of Examples 57–86 were prepared according to the procedure described in example 56.
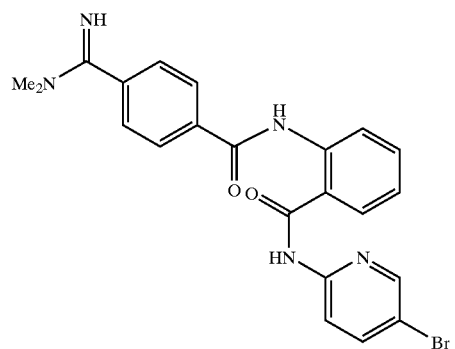
Example 57
MS (M + H):
466
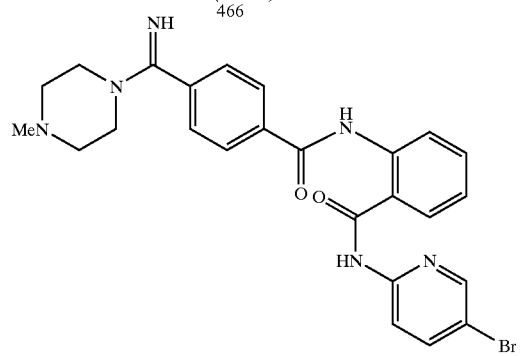
Example 58
MS (M + H):
521
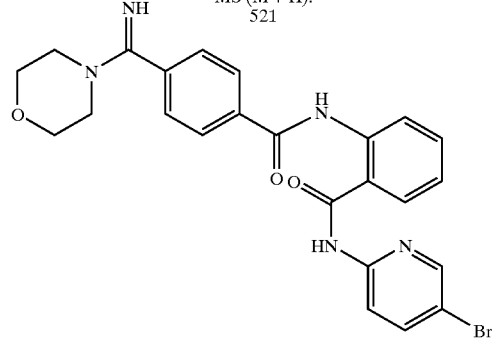
Example 59
MS (M + H):
508
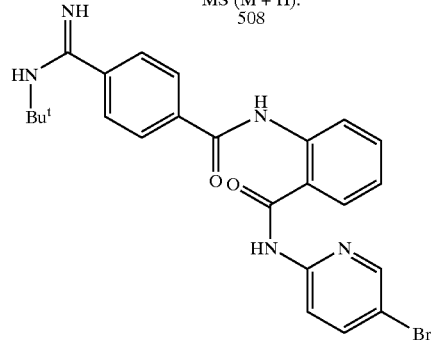
Example 60
MS (M + H):
494
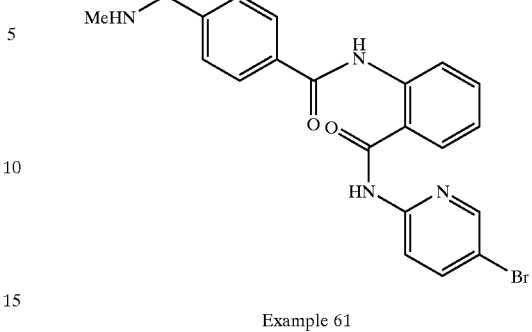
Example 61
MS (M + H):
452
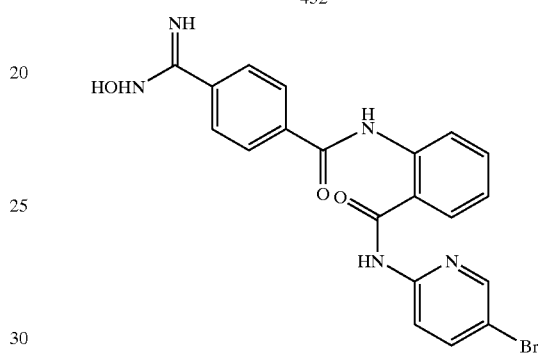
Example 62
MS (M + H):
454
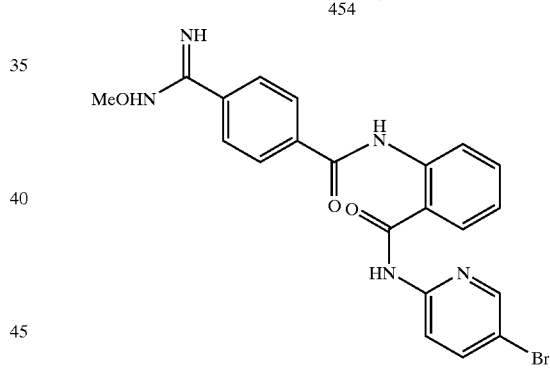
Example 63
MS (M + H):
468
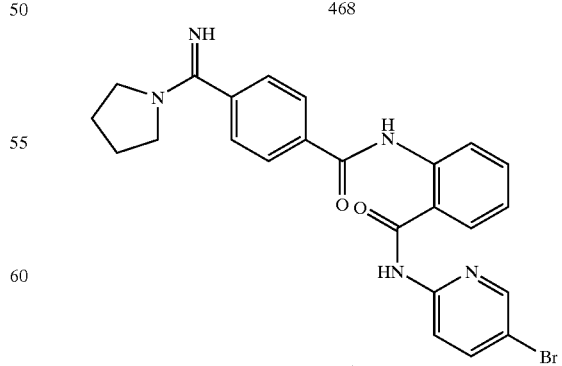
Example 64
MS (M + H):
492

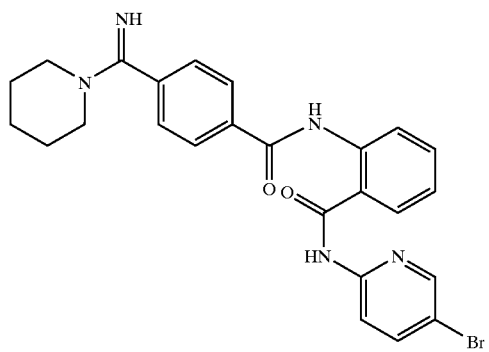
Example 65
MS (M + H):
506
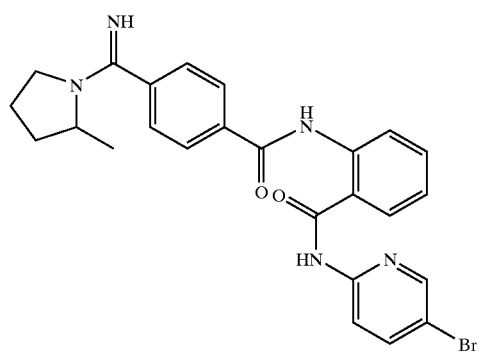
Example 66
MS (M + H):
506
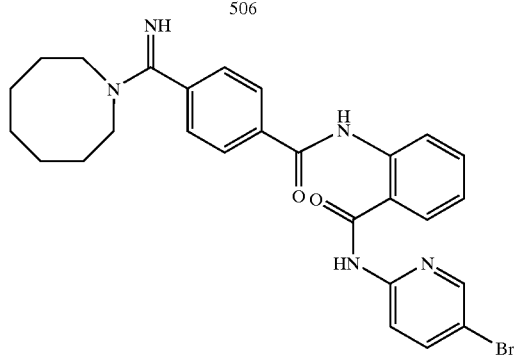
Example 67
MS (M + H):
520
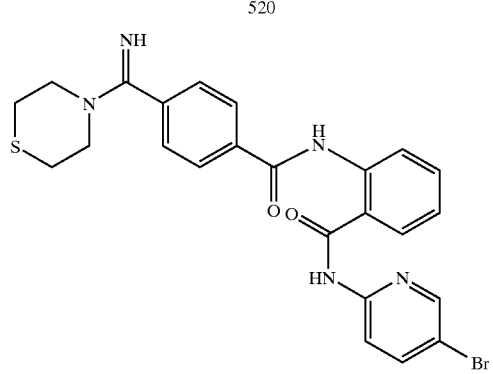
Example 68
MS (M + H):
524
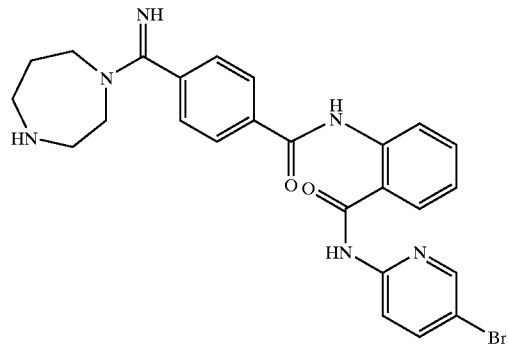
Example 69
MS (M + H):
521
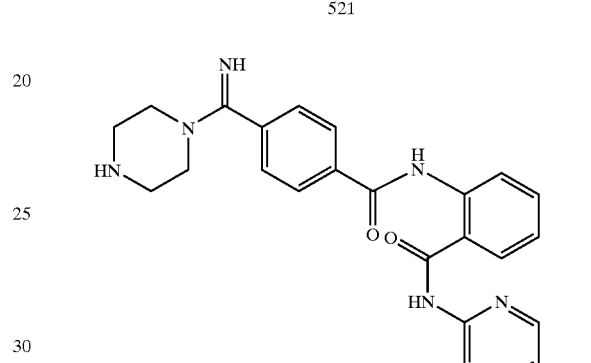
Example 70
MS (M + H):
507
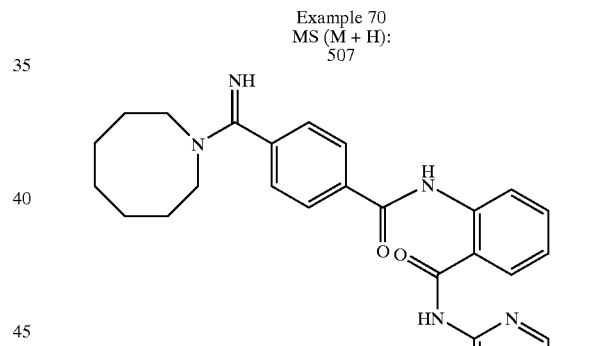
Example 71
MS (M + H):
476
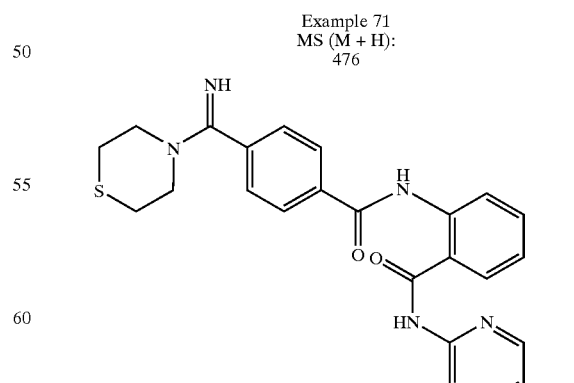
Example 72
MS (M + H):
480

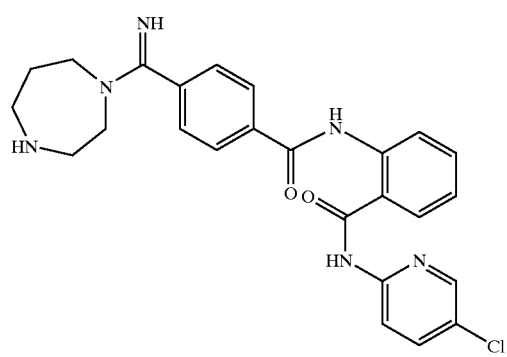
Example 73
MS (M + H):
477
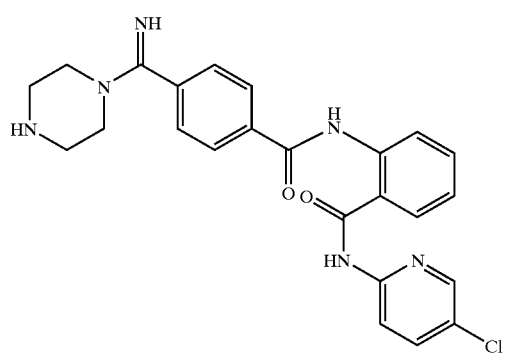
Example 74
MS (M + H):
463
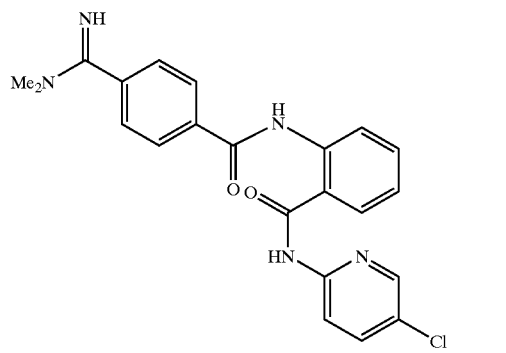
Example 75
MS (M + H):
422
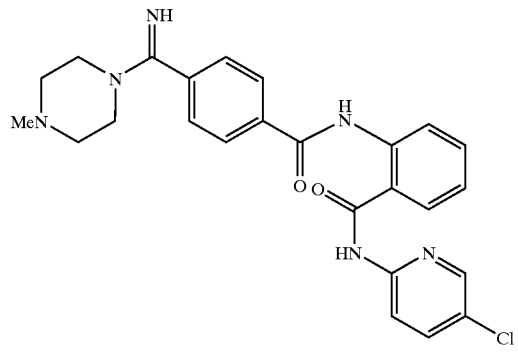
Example 76
MS (M + H):
477
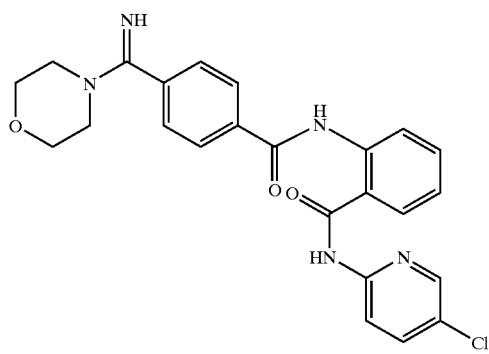
Example 77
MS (M + H):
464
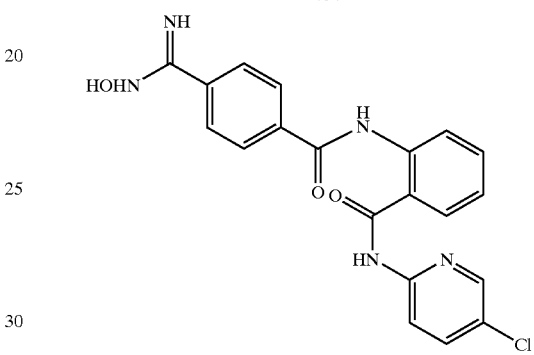
Example 78
MS (M + H):
410
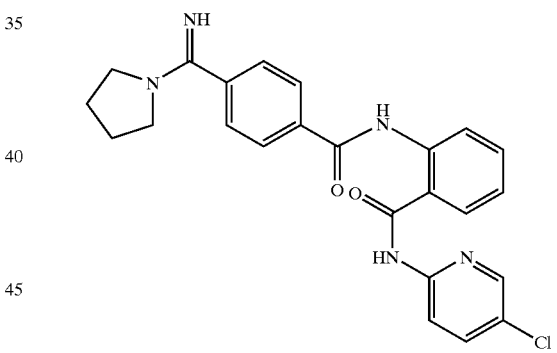
Example 79
MS (M + H):
448
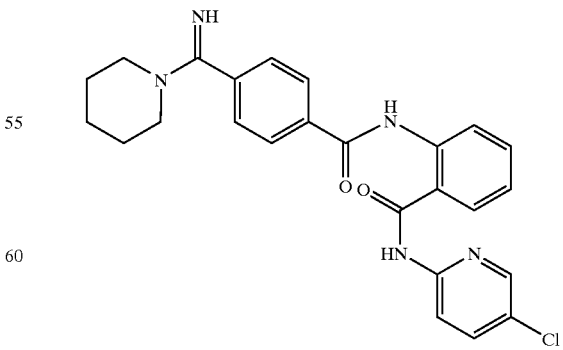
Example 80
MS (M + H):
462

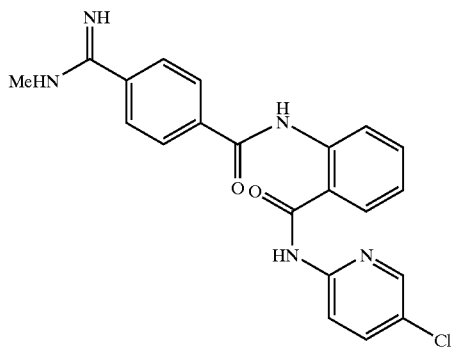
Example 81
MS (M + H):
408
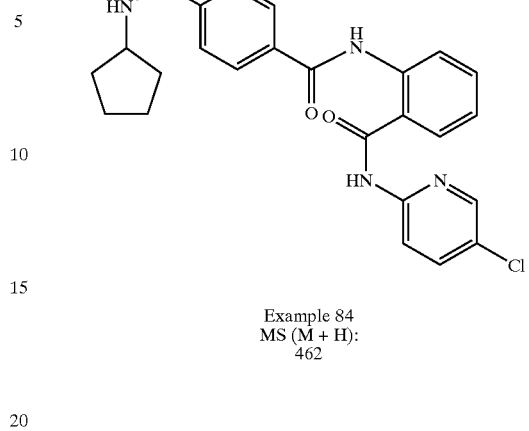
Example 84
MS (M + H):
462
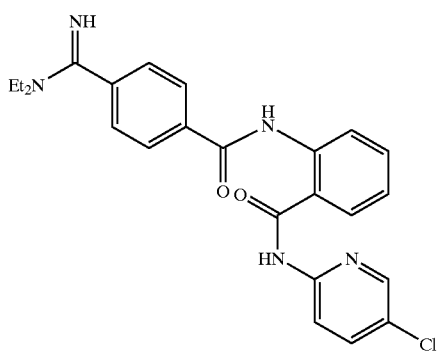
Example 82
MS (M + H):
22
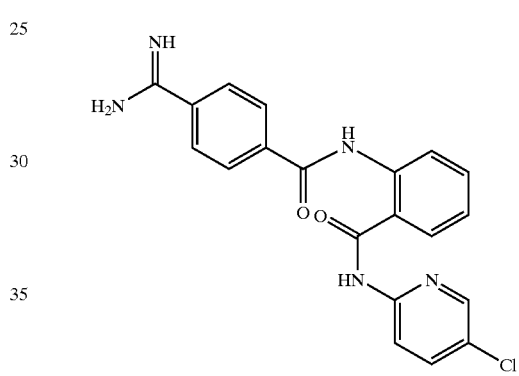
Example 85
MS (M + H):
394
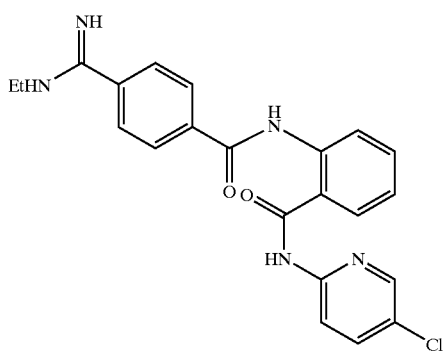
Example 83
MS (M + H):
450
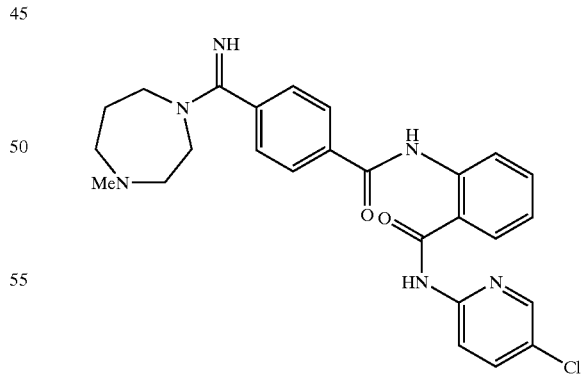
Example 86
MS (M + H):
491

Example 87

N-(5-bromo-2-pyridinyl)-(2-(4-(2-imidazolinyl)phenylcarbonyl)amino)-phenylcarboxamide

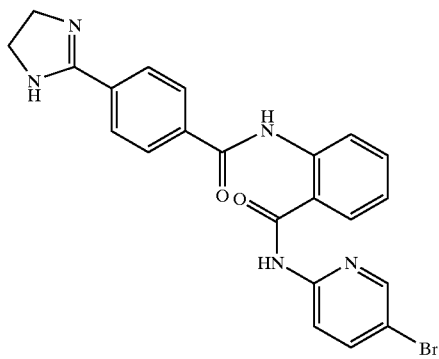

A stream of HCl(g) was bubbled through a 0° C. solution of N-(5-bromo-2-pyridinyl)-(2-(4-cyanophenylcarbonyl)amino)-phenylcarboxamide (49 mg, 0.1 mmol) in 5 mL of methanol until saturation. The mixture was stirred at rt overnight and evaporated. The resulting residue was treated with ethylene diamine (40 mg) in 10 ml methanol at reflux temperature for 2 h. The solvent was removed at reduced pressure and the crude benzamidine was purified by HPLC (C18 reversed phase) eluting with 0.5% TFA in $H_2O$/$CH_3CN$ to give N-(5-bromo-2-pyridinyl)-(2-(4-(2-imidazolinyl)phenylcarbonyl)amino)-phenylcarboxamide (41 mg, 89%). MS found for $C_{22}H_{19}BrN_5O_2$ (M+H)$^+$: 464.

Examples 88–96

The following compounds of Examples 88–96 were prepared according to the procedure described in example 87.

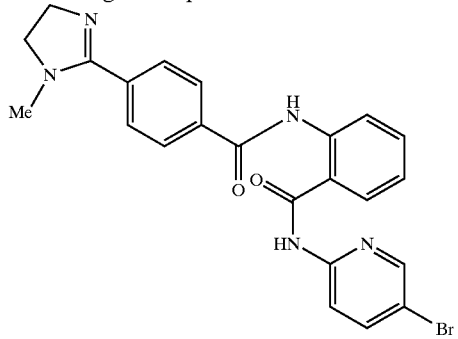

Example 88
MS (M + H):
478

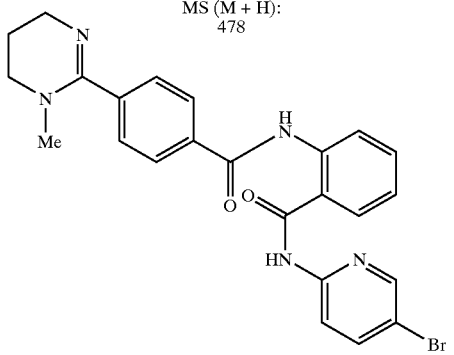

Example 89
MS (M + H):
492

-continued

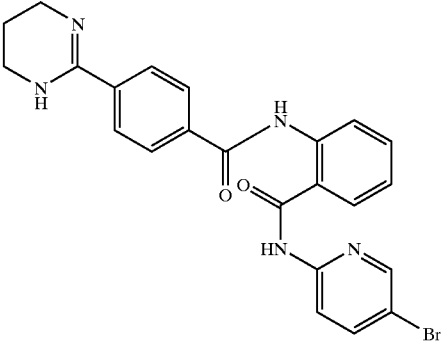

Example 90
MS (M + H):
478

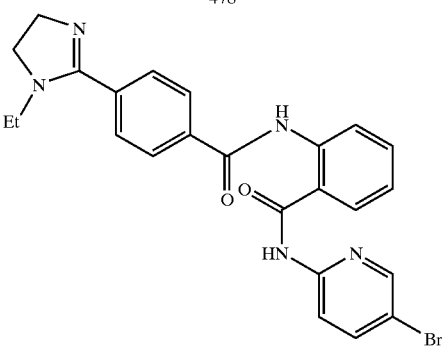

Example 91
MS (M + H):
492

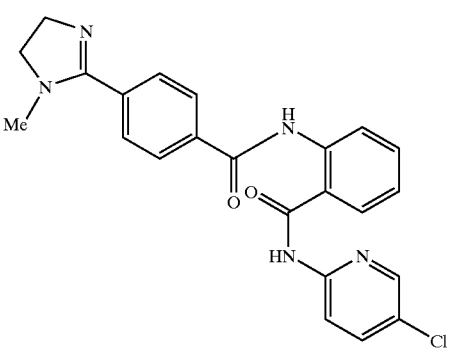

Example 92
MS(M + H):
434

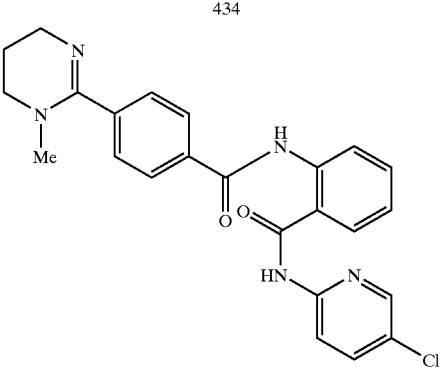

Example 93
MS(M + H):
488

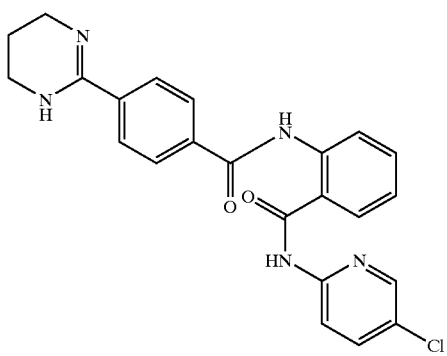

Example 94
MS(M + H):
434

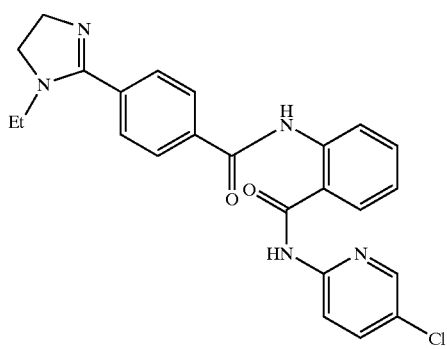

Example 95
MS(M + H):
448

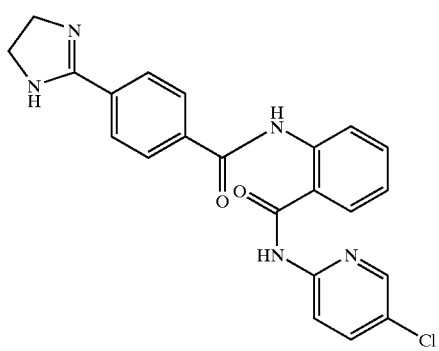

Example 96
MS(M + H):
420

Example 96

MS (M+H): 420

Example 97

N-(5-bromo-2-pyridinyl)-(2-(4-(5-tetrazolyl)phenylcarbonyl)amino)-phenylcarboxamide

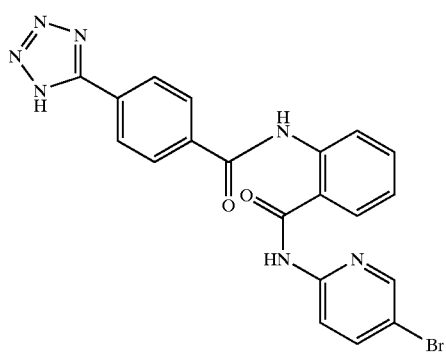

A mixture of N-(5-bromo-2-pyridinyl)-(2-(4-cyanophenylcarbonyl)amino)-phenylcarboxamide (49 mg, 0.1 mmol) and sodium azide (67 mg, 10 equiv) in 5 mL of DMF was heated at 100° C. for 24 h. The reaction mixture was diluted with EtOAc, washed with water, dried, filtered and evaporated. The residue was purified by HPLC (C18 reversed phase) eluting with 0.5% TFA in $H_2O/CH_3CN$ to give N-(5-bromo-2-pyridinyl)-(2-(4-(5-tetrazolyl)phenylcarbonyl)amino)-phenylcarboxamide (33 mg, 65%). MS found for $C_{20}H_{15}BrN_7O_2$ $(M+H)^+$: 464.

Example 98 and Example 99

N-(5-bromo-2-pyridinyl)-(2-(4-[-[1,1-doxo(1,4-thiazaperhydroin-4-yl))iminimethy]phenylcarbonyl)amino)-phenylcarboxamide and N-(5-bromo-2-pyridinyl)-(2-(4-[1-oxo(1,4-thiazaperhydroin-4-yl))iminimethy]phenylcarbonyl)amino)-phenylcarboxamide

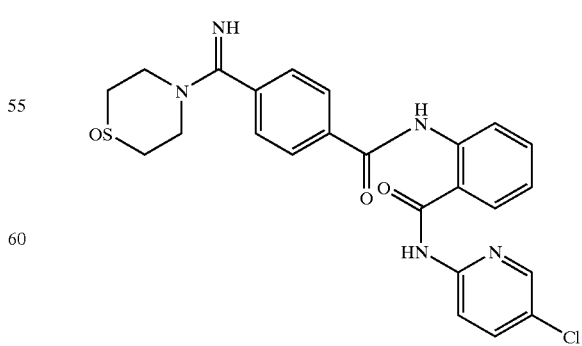

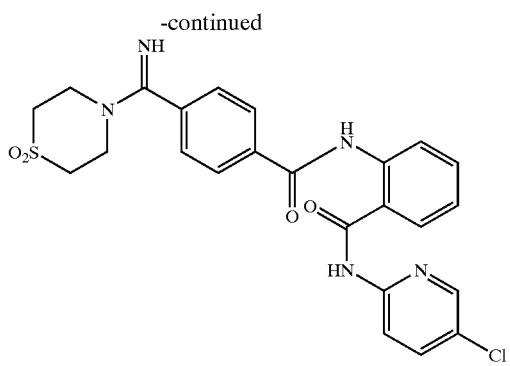

A mixture of N-(5-bromo-2-pyridinyl)-(2-(4-(1,4-thiazaperhydroin-4-yl)iminimethyl]phenylcarbonyl)amino)-phenylcarboxamide (48 mg, 0.1 mmol) and and 3 mL of 30% hydrogen doxide was stirred at rt for 12 h. The reaction was quenched with solid Na$_2$S$_2$O$_3$. Purification by HPLC (C18 reversed phase) eluting with 0.5% TFA in H$_2$O/CH$_3$CN gave N-(5-bromo-2-pyridinyl)-(2-(4-[-[1,1-doxo(1,4-thiazaperhydroin-4-yl))iminimethyl]phenylcarbonyl)amino)-phenylcarboxamide (15 mg, 31%), MS found for C$_{24}$H$_{23}$ClN$_5$O$_4$S (M+H)$^+$: 512 and N-(5-bromo-2-pyridinyl)-(2-(4-[1-oxo(1,4-thiazaperhydroin-4-yl))iminimethyl]phenylcarbonyl)amino)-phenylcarboxamide (20 mg, 41%). MS found for C$_{24}$H$_{23}$ClN$_5$O$_3$S (M+H)$^+$: 496.

Examples 100–105

The following compounds were prepared according to the procedure described in example 56 and example 87.

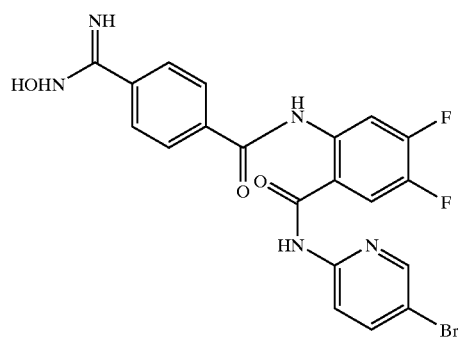

Example 102
MS (M + H):
490

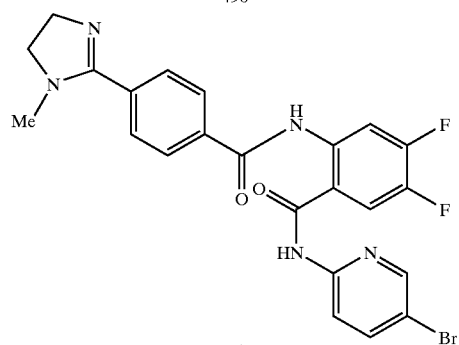

Example 103
MS (M + H):
514

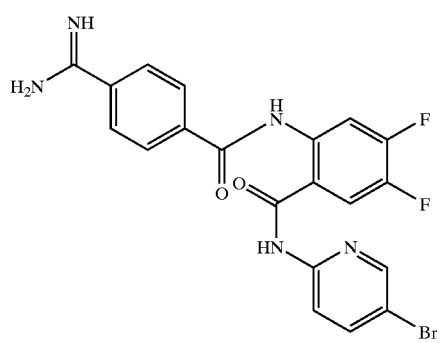

Example 100
MS (M + H):
474

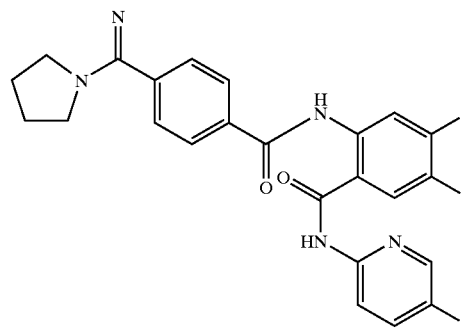

Example 104
MS (M + H):
528

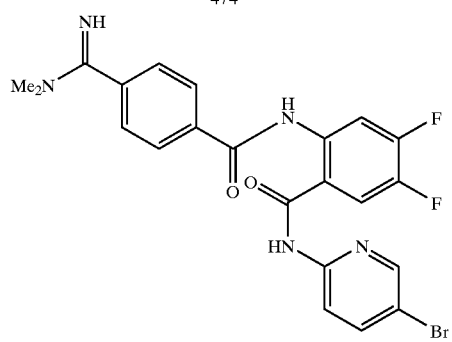

Example 101
MS (M + H):
502

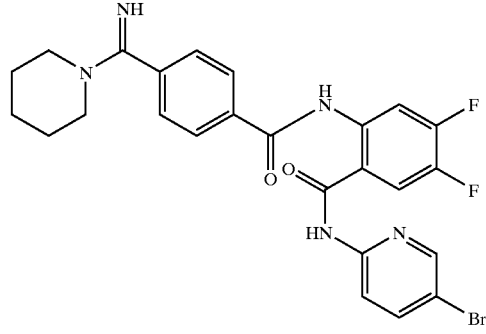

Example 105
MS (M + H):
542

Example 106

N-(5-bromo-2-pyridinyl)-(2-4-[(2-aminosulfonyl)phenyl]phenylcarbonylamino)-4,5-difluorophenylcarboxamide

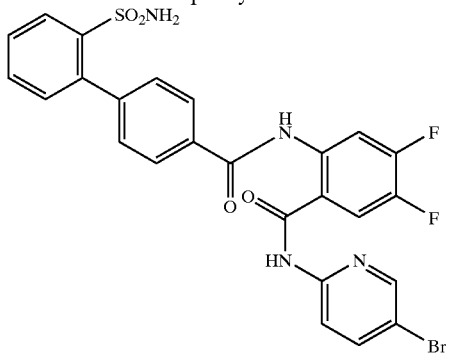

This compound is prepared according to the procedure described in example 27. MS found for $C_{25}H_{18}BrF_2N_4O_4S$ (M+H)$^+$: 587.

Example 107

3-(2-(4-[(2-aminosulfonyl)phenyl]-2-fluorophenylaminocarbonyl-4-aminophenoxy)benzamidine

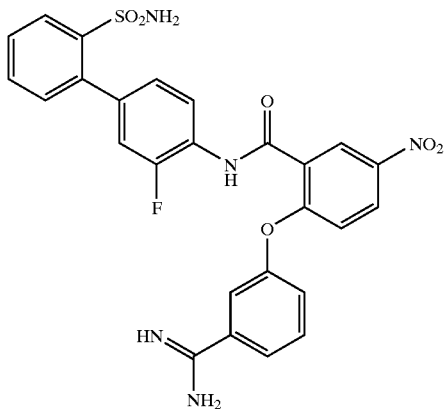

This compound is prepared according to the procedure described in example 17. MS found for MS found for $C_{26}H_{21}FN_5O_6S$ (M+H)$^+$: 550.

Example 108

3-(2-(4-[(2-aminosulfonyl)phenyl]-2-fluorophenylaminocarbonyl-4-aminophenoxy)benzamidine

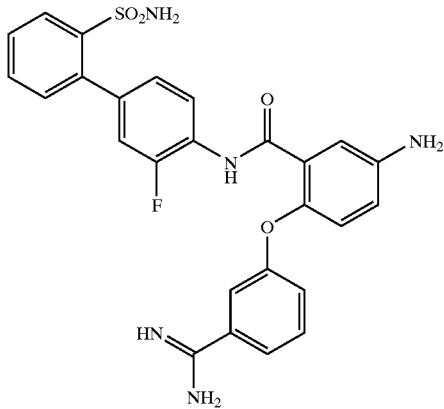

This compound is prepared according to the procedure described in example 18. MS found for $C_{26}H_{23}FN_5O_4S$ (M+H)$^+$: 520.

Examples 109–114

The following compounds were prepared according to the procedure described in example 1 except that in step 4, NH$_2$OH was used instead of NH$_4$OAc.

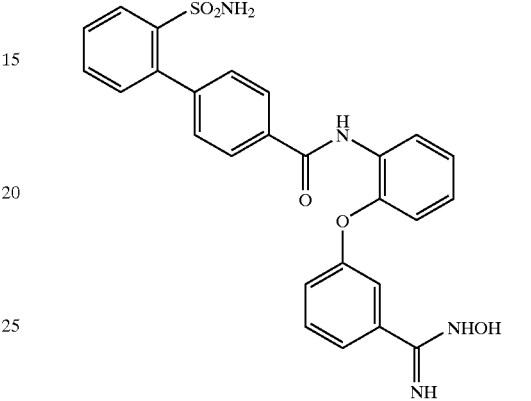

Example 109
MS (M + H):
502

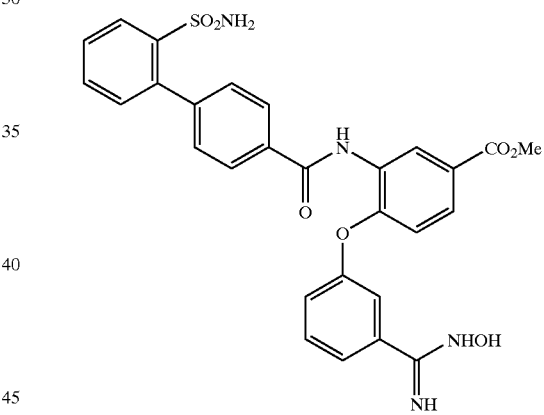

Example 110
MS (M + H):
560

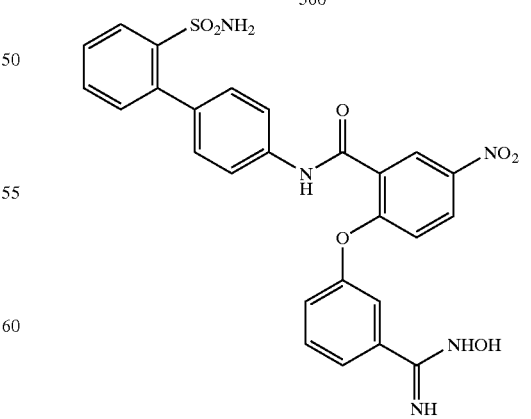

Example 111
MS (M + H):
547

-continued

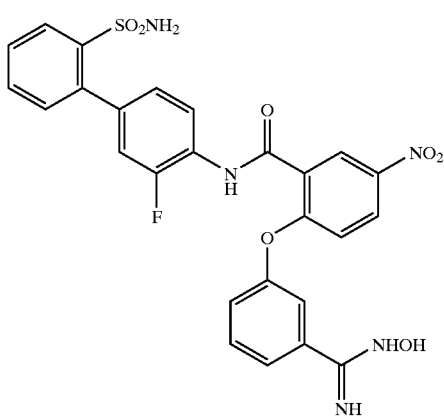

Example 112
MS (M + H):
547

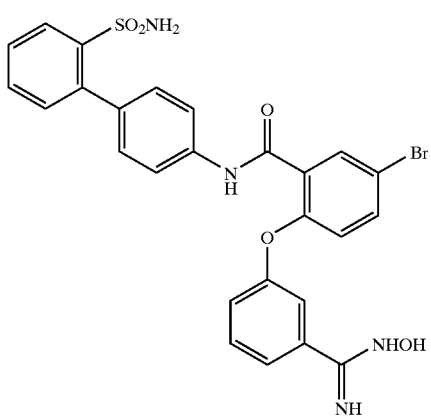

Example 113
MS (M + H):
581

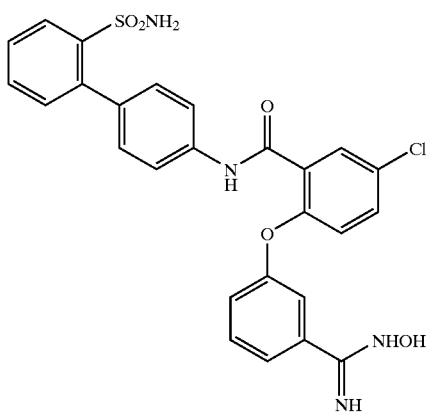

Example 114
MS (M + H):
537

Example 115

3-(2-(4-[(2-aminosulfonyl)phenyl]benzoylamino)phenoxy)benzylamine

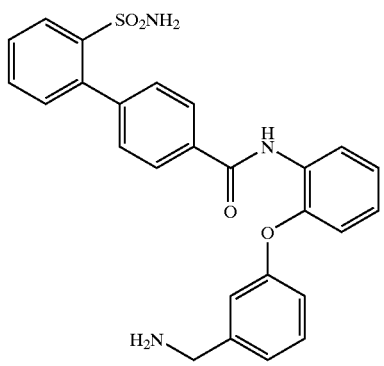

A mixure of 3-(2-(4-[(2-t-butylaminosulfonyl)phenyl]benzoylamino)phenoxy)benzonitrile (53 mg, 0.1 mmol) (53 mg, 0.1 mmol, 1 equiv), 5 mg of Pd/C (10%) in 10 mL of methanol was stirred at rt under 1 atm $H_2$ atomosphere overnight. After filtration through a thin layer of Celite and removal of the volatile, residue was refluxed in 2 mL of TFA for 1 h, and purified by HPLC (C18 reversed phase) eluting with 0.5% TFA in $H_2O/CH_3CN$ to 3-(2-(4-[(2-aminosulfonyl)phenyl]benzoylamino)phenoxy)benzylamine (13 mg, 27%). MS found for $C_{26}H_{24}N_3O_4S$ $(M+H)^+$: 474.

Example 116

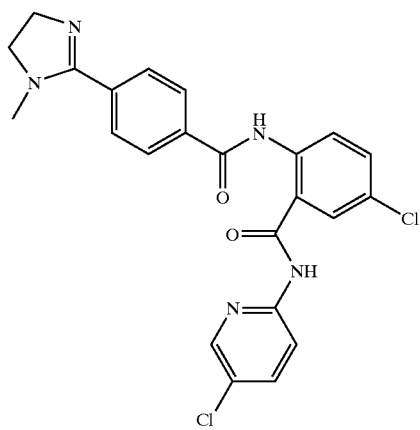

Step 1: To a solution of 2-amino-5-chloropyridine (328 mg, 2.55 mmol) in tetrahydrofuran (5 ml) was 0.5M potassium bis(trimethylsilyl)amide in toluene (10 ml, 5.05 mmol) dropwise at −78° C. After stirred for additional 0.5 hr at −78° C., the mixture was added 5-chloroisatoic anhydride (0.5 g, 2.55 mmol) at −78° C. The mixture was warmed up to r.t gradually and stirred overnight. After quenched by saturated ammonium chloride solution, the mixture was extracted by ethyl acetate. The organic layer was dried over magnesium sulfate and concentrated to give (2-amino-5-chlorophenyl)-N-(5-chloro(2-pyridyl))carboxamide (0.71 g. 100%). MS found for C12H9Cl2N3O $M^+$=282, $(M+2)^+$=284.

Step 2: To a solution of the compound of (2-amino-5-chlorophenyl)-N-(5-chloro(2-pyridyl))carboxamide (0.71 g, 2.52 mmol) in dichloromethane (10 ml) was added 3-cyanobenzoyl chloride (417 mg, 2.52 mmol) and pyridine (0.611 ml, 7.55 mmol). The mixture was stirred at r.t. overnight. The precipitate was filtered and washed with dichloromethane to give N-{4-chloro-2-[N-(5-chloro(2-pyridyl))carbamoyl]phenyl}(4-cyanophenyl)carboxamide as a solid (683 mg, 66%). MS found for C20H12Cl2N4O2 $M^+$=411, $(M+2)^+$=413.

Step 3: To a solution of the compound of N-{4-chloro-2-[N-(5-chloro(2-pyridyl))carbamoyl]phenyl}(4-cyanophenyl)carboxamide (683 mg, 1.66 mmol) in anhydrous pyridine (10 ml) and triethyl amine (1 ml) was saturated with hydrogen sulfide gas at 0° C. The mixture was stirred at r.t. overnight. After the evaporated the solvent, the residue was dissolved in anhydrous acetone (5 ml) and iodomethane (1 ml, 16.6 mmol) was added. The mixture was stirred under reflux condition for 2 hrs. After the evaporation of solvent, the residue was dissolved in anhydrous methanol (5 ml) and added a solution of N-methylethylenediamine (0.732 ml, 8.3 mmol) and acetic acid (1.5 ml) in anhydrous methanol (5 ml). The mixture was stirred under reflux condition for 2 hrs. After the evaporation of solvent, the crude residue was purified by RP-HPLC to give N-{4-chloro-2-[N-(5-chloro(2-pyridyl))carbamoyl]phenyl}[4-(1-methyl(2-imidazolin-2-yl))phenyl]carboxamide as a white powder. MS found for C23H19Cl2N5O2 $M^+$=468 $(M+2)^+$= 470.

Examples 117–141

The following compounds were prepared according to the procedure described in example 116.

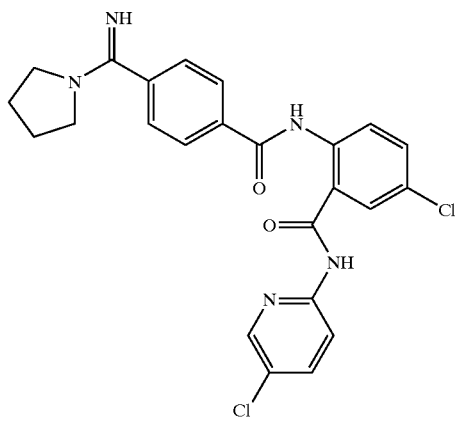

$C_{24}H_{21}Cl_2N_5O_2$
$M^+ = 482$
$(M + 2)^+ = 484$
Example 118

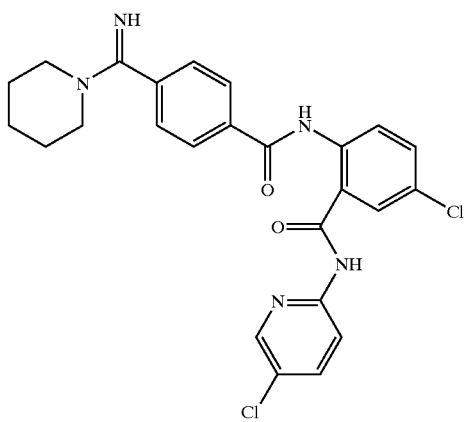

$C_{25}H_{25}Cl_2N_5O_2$
$M^+ = 496$
$(M + 2)^+ = 498$
Example 119

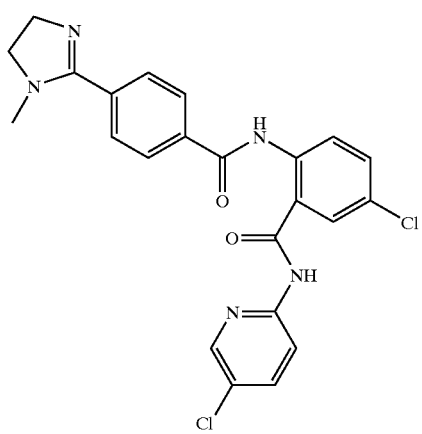

$C_{23}H_{19}Cl_2N_5O_2$
$M^+ = 488$
$(M + 2)^+ = 470$
Example 117

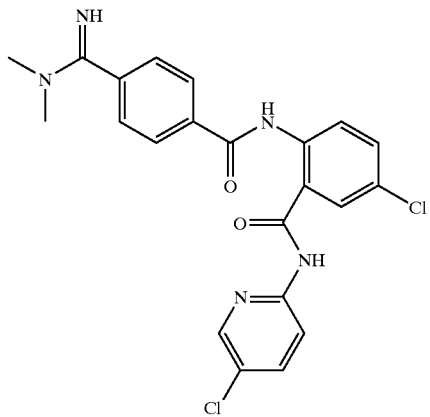

$C_{22}H_{19}Cl_2N_5O_2$
$M^+ = 456$
$(M + 2)^+ = 458$
Example 120

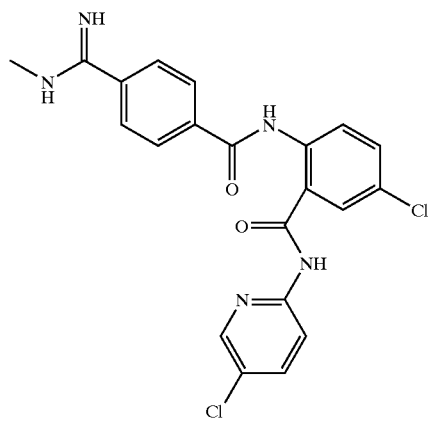
Example 121
C₂₁H₁₇Cl₂N₅O₂
M⁺ = 442
(M + 2)⁺ = 444
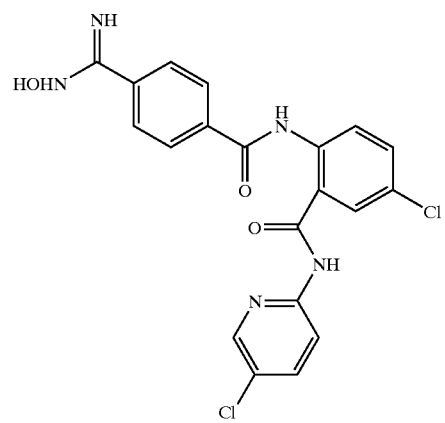
Example 124
C₂₀H₁₅Cl₂N₅O₃
M⁺ = 444
(M + 2)⁺ = 446
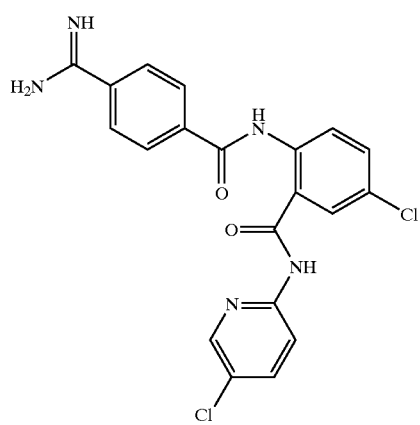
Example 122
C₂₀H₁₅Cl₂N₅O₂
M⁺ = 428
(M + 2)⁺ = 430
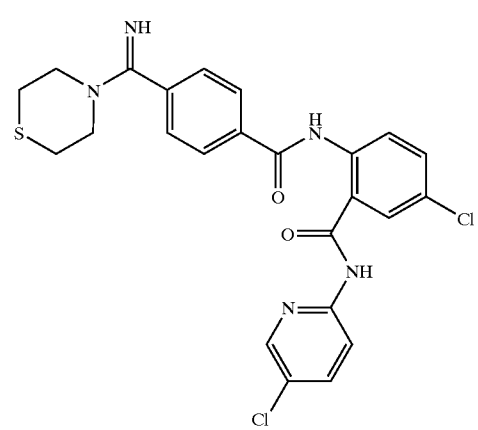
Example 125
C₂₄H₂₁Cl₂N₅O₂S
M⁺ = 514
(M + 2)⁺ = 516
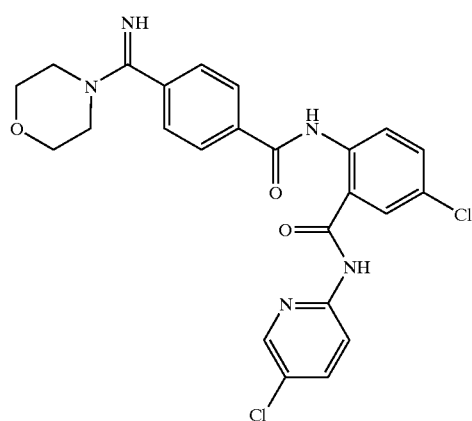
Example 123
C₂₄H₂₁Cl₂N₅O₃
M⁺ = 498
(M + 2)⁺ = 500
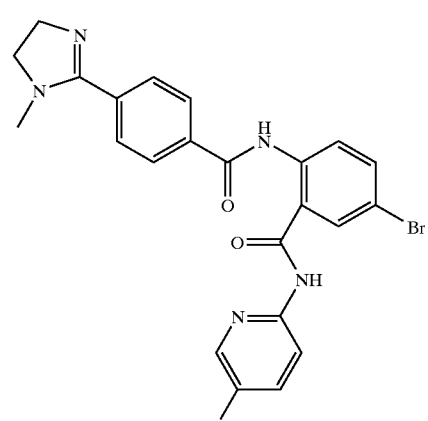
Example 126
C₂₃H₁₉BrClN₅O₂
M⁺ = 512
(M + 2)⁺ = 514

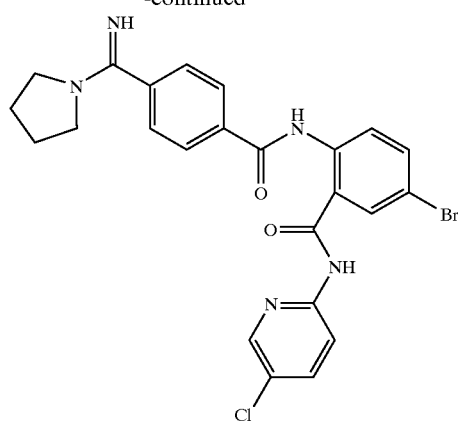
Example 127
C$_{24}$H$_{21}$Cl$_2$N$_5$O$_2$S
M$^+$ = 526
(M + 2)$^+$ = 528
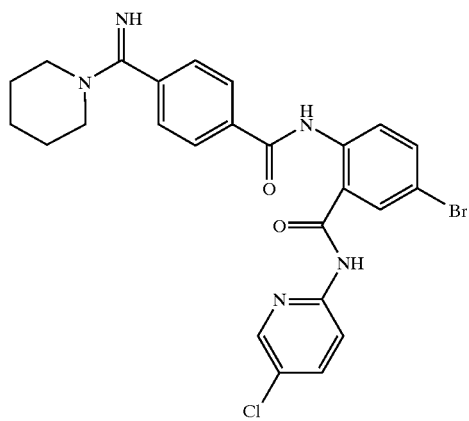
Example 128
C$_{24}$H$_{21}$Cl$_2$N$_5$O$_2$S
M+ = 540
(M + 2)+ = 542
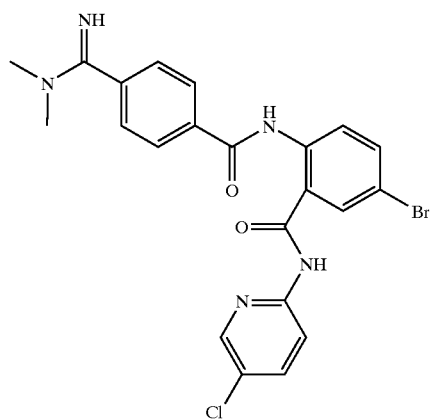
Example 129
C$_{22}$H$_{19}$BrClN$_5$O$_2$
M$^+$ = 500
(M + 2)$^+$ = 502
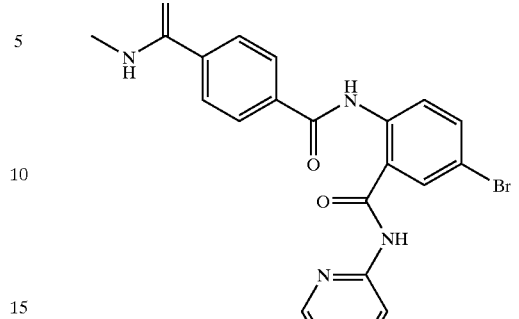
Example 130
C$_{21}$H$_{17}$BrClN$_5$O$_2$
M$^+$ = 486
(M + 2)$^+$ = 488
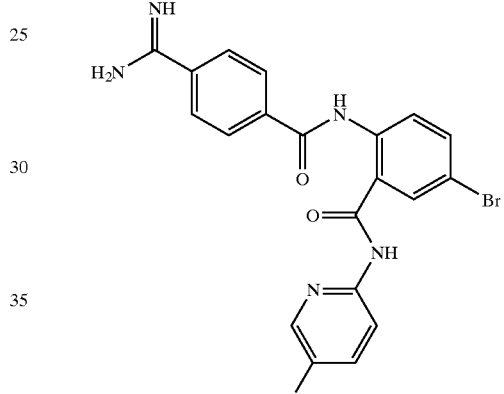
Example 131
C$_{20}$H$_{15}$BrClN$_5$O$_2$
M$^+$ = 472
(M + 2)$^+$ = 474
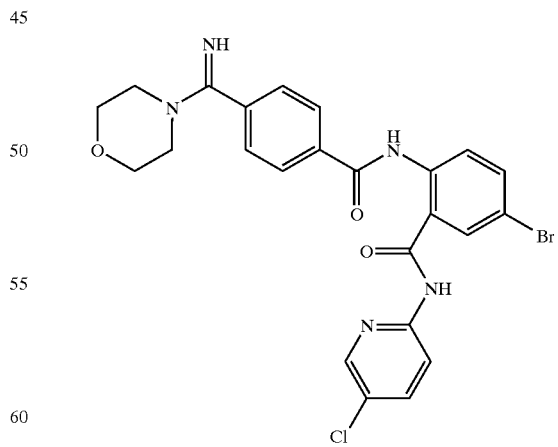
Example 132
C$_{24}$H$_{21}$BrClN$_5$O$_2$S
M$^+$ = 542
(M + 2)$^+$ = 544

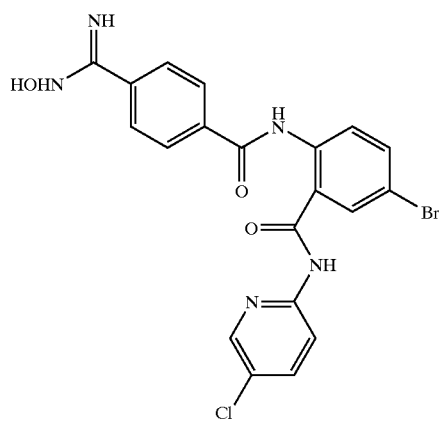
Example 133
$C_{20}H_{15}BrClN_5O_3$
$M^+ = 488$
$(M + 2)^+ = 490$
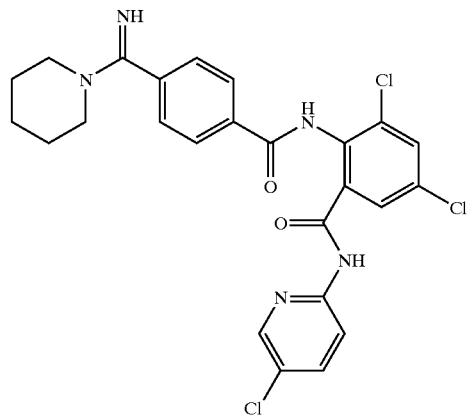
Example 136
$C_{25}H_{22}Cl_3N_6O_2$
$M^+ = 530$
$(M + 2)^+ = 532$
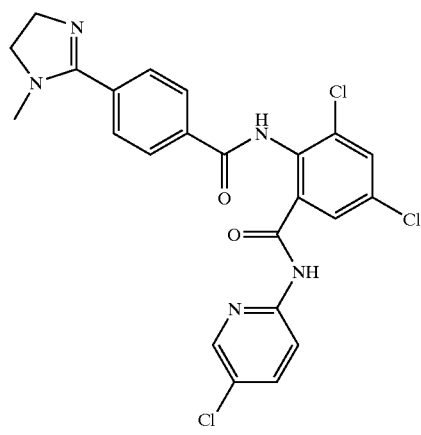
Example 134
$C_{23}H_{18}Cl_3N_6O_2$
$M^+ = 502$
$(M + 2)^+ = 504$
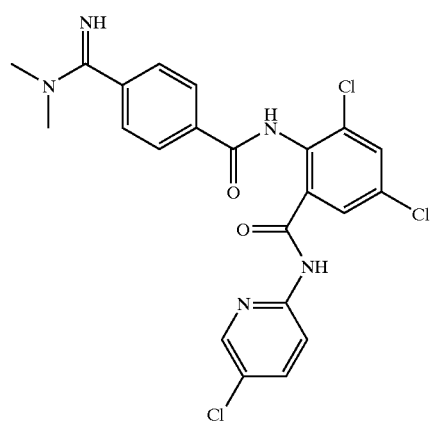
Example 137
$C_{22}H_{18}Cl_3N_6O_2$
$M^+ = 490$
$(M + 2)^+ = 492$
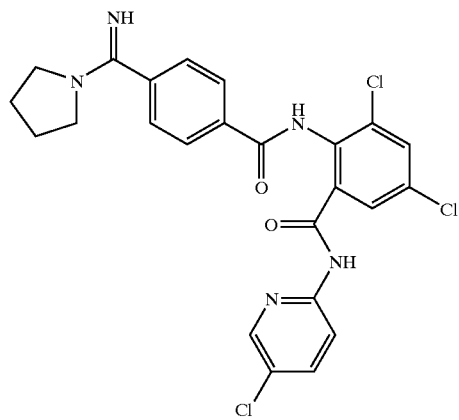
Example 135
$C_{24}H_{20}Cl_3N_6O_2$
$M^+ = 516$
$(M + 2)^+ = 518$
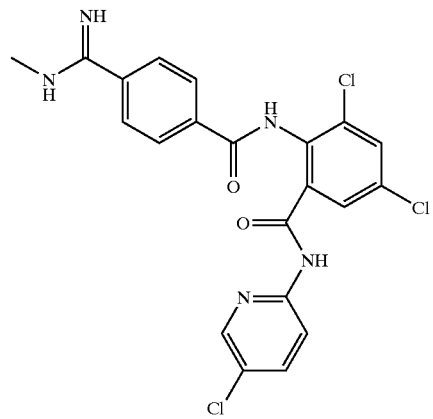
Example 138
$C_{21}H_{16}Cl_3N_6O_2$
$M^+ = 476$
$(M + 2)^+ = 478$

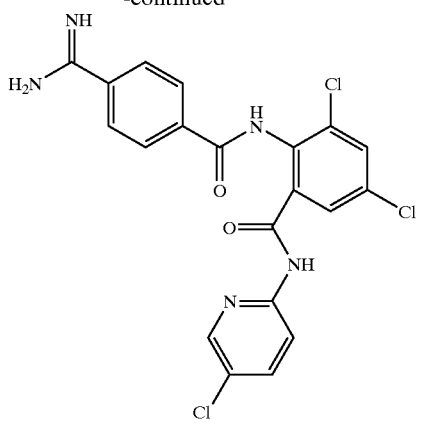

Example 139
C₂₀H₁₄Cl₃N₆O₂
M⁺ = 482
(M + 2)⁺ = 484

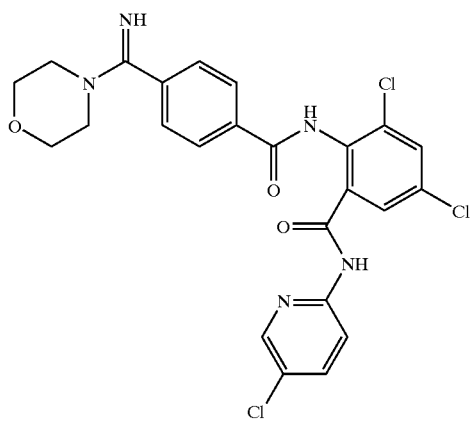

Example 140
C₂₄H₂₀Cl₃N₆O₂
M⁺ = 532
(M + 2)⁺ = 534

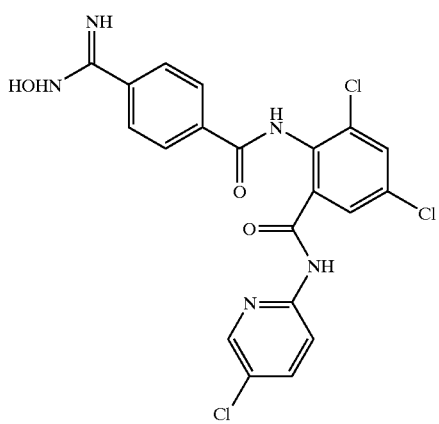

Example 141
C₂₀H₁₄Cl₃N₆O₂
M⁺ = 478
(M + 2)⁺ = 480

Example 142

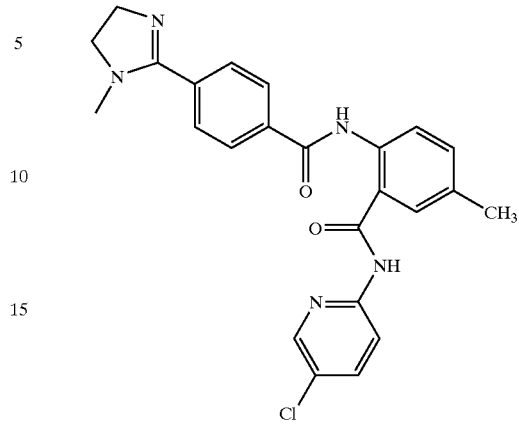

Step 1: To a solution of 5-methyl-2-nitrobenzoic acid (1 g, 5.52 mmol) in dichloromethane (5 ml) was added oxalyl chloride (0.964 ml, 11.04 mmol) and a few drops of dimethylformamide. The mixture was stirred at r.t. for 2 hrs. After the evaporation of the solvent, the residue was dissolved in dichloromethane (5 ml). 2-amino-5-chloropyridine (852 mg, 6.62 mmol) and pyridine (1.34 ml, 16.56 mmol) were added to the solution. The mixture was stirred at r.t. overnight. After the evaporation of the solvent, the crude residue was purified by silica gel column chromatography using solvent system 25% ethyl acetate in hexane as eluent to give N-(5-chloro(2-pyridyl))(5-methyl-2-nitrophenyl) carboxamide as a solid (1.48 g, 92%). MS found for C13H10ClN3O3 M⁺=291, (M+2)⁺=293.

Step 2: To a solution of the compound of N-(5-chloro(2-pyridyl))(5-methyl-2-nitrophenyl)carboxamide (1.48 g, 5.1 mmol) in methanol (10 ml) was added 5% Pt/C (1.48 g, 0.19 mmol). The mixture was applied hydrogen balloon at r.t. for 2 hrs. After the filtration by Celite, the filtrate was concentrated to give (2-aminophenyl)-N-(2-pyridyl)carboxamide, C, chloride, N (1.36 g, 100%). MS found for C13H12ClN3O M⁺=262, (M+2)⁺=264.

Step 3: To a solution of the compound of (2-aminophenyl)-N-(2-pyridyl)carboxamide, C, chloride, N (1.36 g, 5.2 mmol) in dichloromethane (10 ml) was added 3-cyanobenzoly chloride (860 mg, 5.2 mmol) and pyridine (1.26 ml, 15.6 mmol). The mixture was stirred at r.t. overnight. After the evaporation of the solvent, the crude residue was purified by silica gel column chromatography using solvent system 25% ethyl acetate in hexane as eluent to give N-{2-[N-(5-chloro(2-pyridyl))carbamoyl]-4-methylphenyl}(4-cyanophenyl)carboxamide as a solid (830 mg, 41%). MS found for C21H15ClN4O2 M⁺=390, (M+2)⁺=392.

Step 4: To a lotion of the compound of N-{2-[N-(5-chloro (2-pyridyl))carbamoyl]-4-methylphenyl}(4-cyanophenyl) carboxamide (830 mg, 2.1 mmol) in anhydrous methanol (5 ml) and ethyl acetate (10 ml) was saturated with hydrogen chloride gas at 0° C. The mixture was stirred at r.t. overnight. After the evaporated the solvent, the residue was dissolved in anhydrous methanol (5 ml) and N-methylethylenediamine (0.926 ml, 10.5 mmol) was added. The mixture was stirred under reflux condition for 2 hrs. After the evaporation of solvent, the crude residue was purified by RP-HPLC to give N-{2-[N-(5-chloro(2-pyridyl))carbamoyl]-4-methylphenyl} [4-(1-methyl(2-imidazolin-2-yl))phenyl]carboxamide as a white powder. MS found for C24H22ClN5O2 M⁺=448, (M+2)⁺=450.

Examples 143–148
The following compounds were prepared according to the procedure described in Example 142
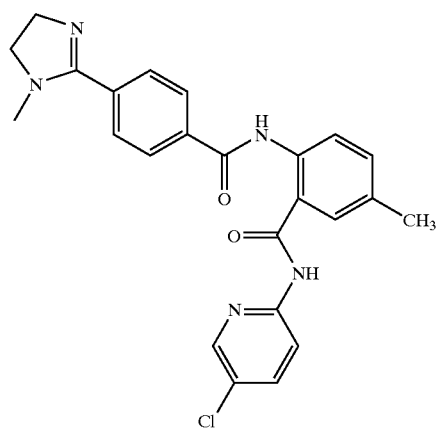
Example 143
$C_{24}H_{22}ClN_5O_2$
$M^+ = 448$
$(M + 2)^+ = 450$
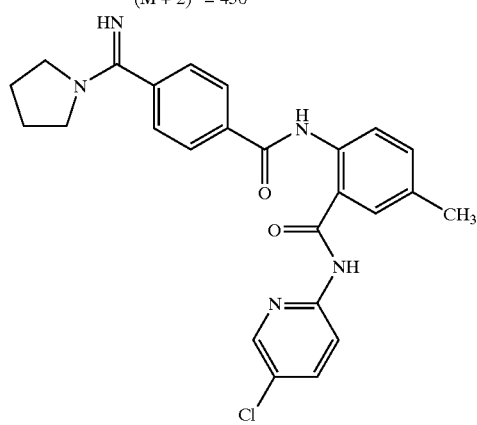
Example 144
$C_{25}H_{24}ClN_5O_2$
$M^+ = 462$
$(M + 2)^+ = 464$
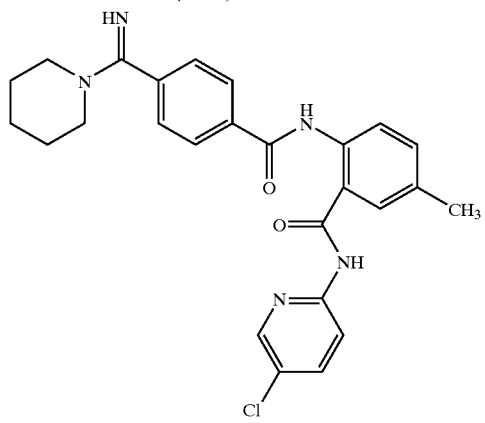
Example 145
$C_{26}H_{25}ClN_5O_2$
$M^+ = 476$
$(M + 2)^+ = 478$
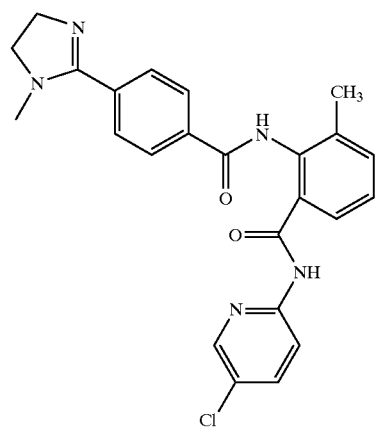
Example 146
$C_{24}H_{22}Cl_3N_6O_2$
$M^+ = 448$
$(M + 2)^+ = 450$
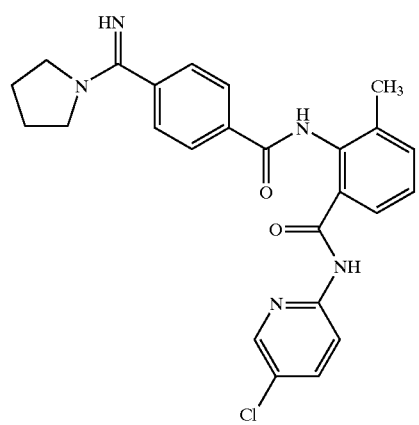
Example 147
$C_{25}H_{24}Cl_3N_6O_2$
$M^+ = 462$
$(M + 2)^+ = 464$
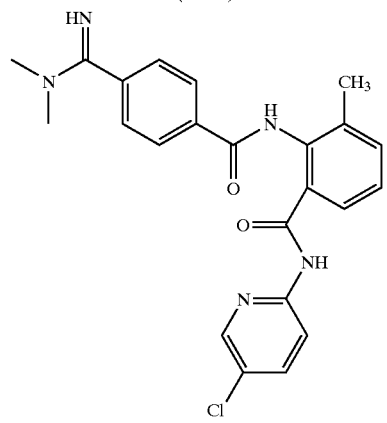
Example 148
$C_{23}H_{22}Cl_3N_6O_2$
$M^+ = 436$
$(M + 2)^+ = 438$

Example 149

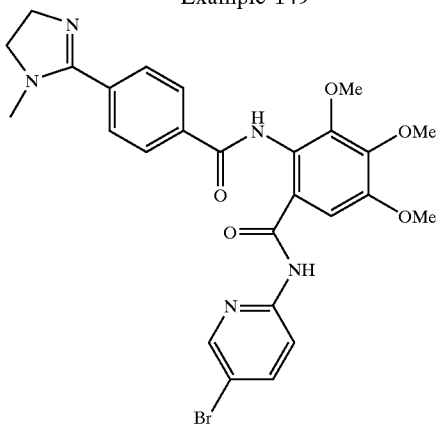

Step 1: To a solution of 3,4,5-trimethoxy-2-nitrobenzoic acid (0.5 g, 1.95 mmol) in dichloromethane (5 ml) was added oxalyl chloride (0.34 ml, 3.9 mmol) and a few drops of dimethylformamide. The mixture was stirred at r.t. for 2 hrs. After the evaporation of the solvent, the residue was dissolved in dichloromethane (5 ml). 2-amino-5-bromopyridine (0.81 g, 4.7 mmol) and pyridine (0.94 ml, 11.7 mmol) were added to the solution. The mixture was stirred at r.t. overnight. After the evaporation of the solvent, the crude residue was purified by silica gel column chromatography using solvent system 25% ethyl acetate in hexane as eluent to give N-(5-bromo(2-pyridyl))(3,4,5-trimethoxy-2-nitrophenyl)carboxamide as a solid (790 mg, 98%). MS found for C15H14BrN3O6 $M^+$=412, $(M+2)^+$=414.

Step 2: To a solution of the compound of N-(5-bromo(2-pyridyl))(3,4,5-trimethoxy-2-nitrophenyl)carboxamide (790 mg, 1.92 mmol) in ethyl acetate (5 ml) was added tin chloride (II) hydrate (1.73 g, 7.67 mmol). The mixture was stirred under reflux condition for 2 hrs. After filtered by Celite, the filtrate was added 1N sodium hydroxide solution and extracted with ethyl acetate. The organic layer was dried over magnesium sulfate and concentrated to give (2-amino-3,4,5-trimethoxyphenyl)-N-(5-bromo(2-pyridyl))carboxamide (570 mg, 77%). MS found for C15H16BrN3O4 $M^+$=382, $(M+2)^+$=384.

Step 3: To a solution of the compound of (2-amino-3,4,5-trimethoxyphenyl)-N-(5-bromo(2-pyridyl))carboxamide (570 mg, 1.49 mmol) in dichloromethane (5 ml) was added 3-cyanobenzoly chloride (247 mg, 1.49 mmol) and pyridine (0.362 ml, 4.48 mmol). The mixture was stirred at r.t. overnight. After the evaporation of the solvent, the crude residue was purified by silica gel column chromatography using solvent system 25% ethyl acetate in hexane as eluent to give N-{6-[N-(5-bromo(2-pyridyl))carbamoyl]-2,3,4-trimethoxyphenyl}(4-cyanophenyl)carboxamide as a solid (680 mg, 69%). MS found for C23H19BrN4O5 $M^+$=511, $(M+2)^+$=513.

Step 4: To a slotion of the compound of N-{6-[N-(5-bromo(2-pyridyl))carbamoyl]-2,3,4-trimethoxyphenyl}(4-cyanophenyl)carboxamide (680 mg, 1.33 mmol) in anhydrous methanol (5 ml) and ethyl acetate (10 ml) was saturated with hydrogen chloride gas at 0° C. The mixture was stirred at r.t. overnight. After the evaporated the solvent, the residue was dissolved in anhydrous methanol (5 ml) and N-methylethylenediamine (0.586 ml, 6.65 mmol) was added. The mixture was stirred under reflux condition for 2 hrs. After the evaporation of solvent, the crude residue was purified by RP-HPLC to give N-{6-[N-(5-bromo(2-pyridyl))carbamoyl]-2,3,4-trimethoxyphenyl}[4-(1-methyl(2-imidazolin-2-yl))phenyl]carboxamide as a white powder (240 mg, 32%). MS found for C26H26BrN5O5 $M^+$=568, $(M+2)^+$=570.

Examples 150–153

The following compounds were prepared according to the procedure described in Example 149

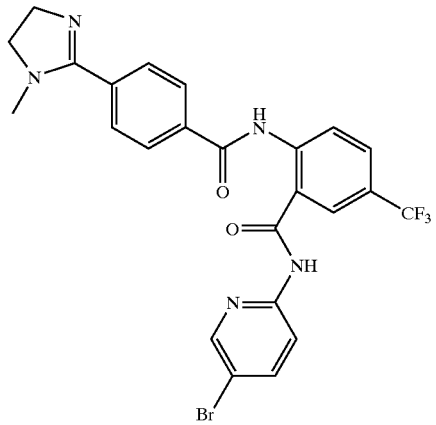

Example 150
$C_{24}H_{19}BrF_3N_5O_2$
$M^+ = 546$
$(M + 2)^+ = 548$

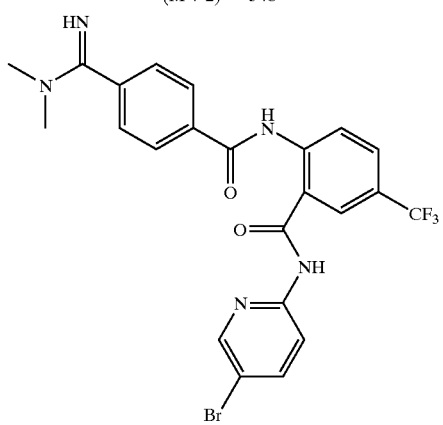

Example 151
$C_{23}H_{19}BrF_3N_5O_2$
$M^+ = 534$
$(M + 2)^+ = 536$

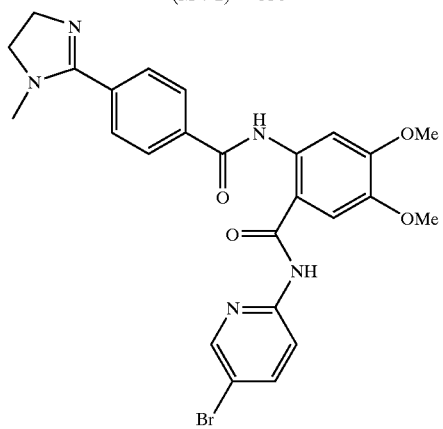

Example 152
$C_{25}H_{24}Br_3N_5O_2$
$M^+ = 494$
$(M + 2)^+ = 496$

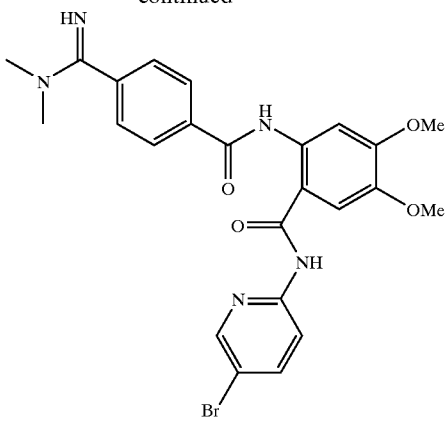

Example 153
C25H24Br3N5O2
M+ = 482
(M + 2)+ = 484

Example 154

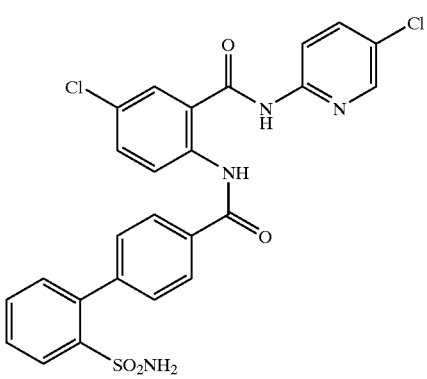

Step 1: To a solution of 4-{2-{[(tert-butyl)amino}sulfonyl}phenyl}benzoic acid (167 mg, 0.5 mmol) in dichloromethane (5 ml) was added oxalyl chloride (0.09 ml, 1 mmol) and a few drops of dimethylformamide. The mixture was stirred at r.t. for 2 hrs. After the evaporation of the solvent, the residue was dissolved in dichloromethane (5 ml). The compound of (2-amino-5-chlorophenyl)-N-(5-chloro(2-pyridyl))carboxamide (0.17 g, 0.6 mmol) and pyridine (0.122 ml, 1.5 mmol) were added to the solution. The mixture was stirred at r.t. overnight. The solvent was evaporated to give (2-{[4-(2-{[(tert-butyl)amino]sulfonyl}phenyl)phenyl]-carbonylamino}-5-chlorophenyl)-N-(5-chloro(2-pyridyl))carboxamide. MS found for C29H26Cl2N4O4S M+=597, (M+2)+=599.

Step 2: The mixture of the compound of (2-{[4-(2-{[(tert-butyl)amino]sulfonyl}phenyl)phenyl]carbonylamino}-5-chlorophenyl)-N-(5-chloro(2-pyridyl))carboxamide example 12 (0.5 mmol) in trifluoroacetic acid (5 ml) was stirred at r.t. for 5 hrs. After the evaporation of solvent, the crude residue was purified by RP-HPLC to give N-(5-chloro(2-pyridyl))(5-chloro-2-{[4-(2-sulfamoylphenyl)-phenyl]carbonylamino}phenyl)-carboxamide as a white powder (68 mg, 25%). MS found for C25H18Cl2N4O4S M+=541, (M+2)+=543.

Example 155

2-[4-(N-{2-[N-(5-chloro-2-pyridyl)carbamoyl]phenyl}carbamoyl)phenyl]-benzenecarboxamidine

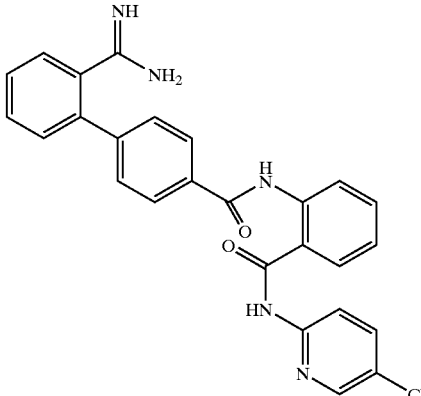

C26H20ClN5O2
Exact Mass: 469.13
Mol. Wt: 469.92

A steam of H2S (g) was bubbled through a 0° C. solution of N-{2-[N-(5-chloro(2-pyridyl))carbamoyl]phenyl}[4-(2-cyanophenyl)phenyl]carboxamide (100 mg, 0.22 mmol, 1.0 equiv.) in 9 mL pyridine and 1 mL NEt3 until saturation. The mixture was stirred at rt for 1 day and evaporated. The resulting residue was treated with MeI (94 mg, 0.663 mmol, 3.0 equiv.) in 10 mL acetone at reflux temperature for 1 hr and concentrated to dryness. The resulting residue was treated with a mixture of NH4OAc (340 mg, 4.42 mmol, 20 equiv.) in 0.5 mL acetic acid and 2 mL methanol at 50° C. for 2 days. The solvent was removed at reduced pressure and the crude benzamidine was purified by HPLC (C18 reversed phase) eluting with 0.1% TFA in H2O/CH3CN to give 2-[4-(N-{2-[N-(5-chloro-2-pyridyl)carbamoyl]phenyl}carbamoyl)phenyl]benzenecarboxamidine (15 mg, 15%). MS found for C26H20ClN5O2 (M+H)+: 470.

Example 156

(4-{2-[(dimethylamino)iminomethyl]phenyl}phenyl)-N-{2-[N-(5-chloro(2-pyridyl))carbamoyl]phenyl}carboxamide

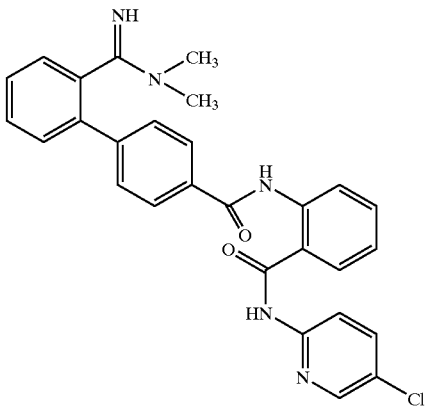

C28H24ClN5O2
Exact Mass: 497.16
Mol. Wt: 497.98

This compound was prepared according to the procedure described in Example 155. MS found for $C_{28}H_{24}ClN_5O_2$ (M+H)⁺: 498.

Example 157

N-{2-[N-(5-chloro(2-pyridyl))carbamoyl]phenyl}{4-[2-((hydroxyamino)iminomethyl)-phenyl]phenyl}carboxamide

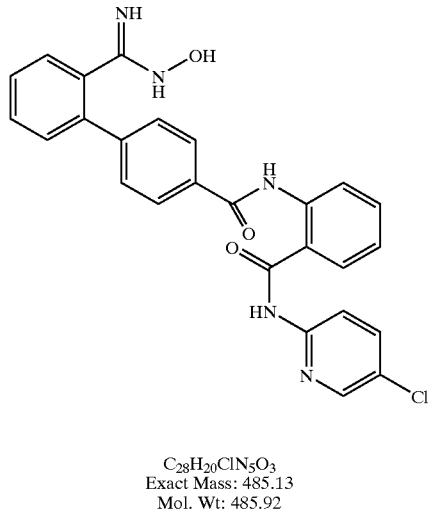

$C_{28}H_{20}ClN_5O_3$
Exact Mass: 485.13
Mol. Wt: 485.92

A mixture of N-{2-[N-(5-chloro(2-pyridyl))carbamoyl]phenyl}[4-(2-cyanophenyl)phenyl]carboxamide (14 mg, 0.03 mmol, 1.0 equiv.), hydroxyamine hydrochloride (6.25 mg, 0.09 mmol, 3.0 equiv.) and triethyl amine (0.03 mL, 0.3 mmol, 10.0 equiv.) in ethanol (3 mL) was stirred at rt for 6 days, concentrated and HPLC (C18 reversed phase) eluting with 0.1% TFA in $H_2O/CH_3CN$ to give N-{2-[N-(5-chloro(2-pyridyl))carbamoyl]phenyl}{4-[2-((hydroxyamino)iminomethyl)phenyl]phenyl}carboxamide (4 mg, 27.5%). MS found for $C_{26}H_{20}ClN_5O_3$ (M+H)⁺: 486.

Example 158

2-[4-(N-{2-[N-(5-chloro-2-pyridyl)carbamoyl]phenyl}carbamoyl)phenyl]benzamide

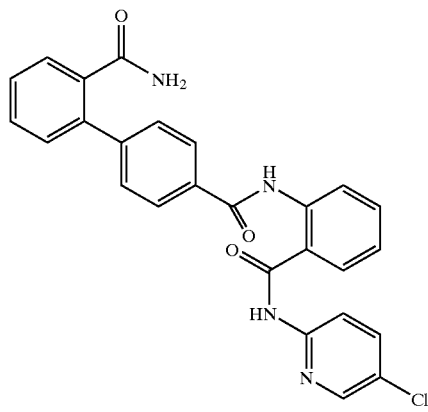

$C_{26}H_{19}ClN_4O_3$
Exact Mass: 470.11
Mol. Wt: 470.91

This compound was ontained as on of the side product in Example 157. MS found for $C_{26}H_{19}ClN_4O_3$ (M+H)⁺: 471.

Example 159

{4-[2-(aminomethyl)phenyl]phenyl}-N-{2-[N-(5-chloro(2-pyridyl))carbamoyl]-phenyl}carboxamide

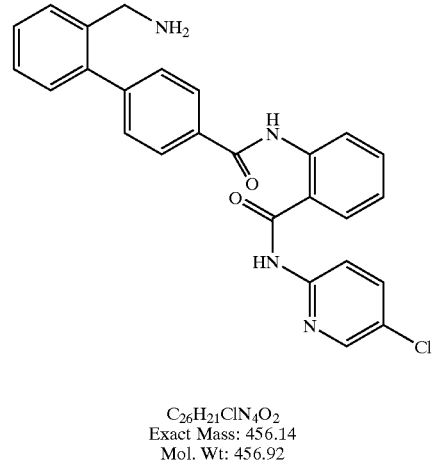

$C_{26}H_{21}ClN_4O_2$
Exact Mass: 456.14
Mol. Wt: 456.92

A mixture of N-{2-[N-(5-chloro(2-pyridyl))carbamoyl]phenyl}[4-(2-cyanophenyl)phenyl]carboxamide (200 mg, 0.442 mmol, 1.0 equiv.), cobalt chloride (86 mg, 0.664 mmol, 1.5 equiv.) and sodium borohydride (50 mg, 1.33 mmol, 3.0 equiv.) in DMF (15 mL) was stirred at 0° C. to rt for 3 days. The reaction was quenched with ice cubes, diluted with DCM (100 mL) and filtered through celite. The filtrate was washed with saturated aqueous $NaHCO_3$. The organic layer was dried over $MgSO_4$, filtered, evaporated and HPLC (C18 reversed phase) eluting with 0.1% TFA in $H_2O/CH_3CN$ gave {4-[2-(aminomethyl)phenyl]phenyl}-N-{2-[N-(5-chloro(2-pyridyl))carbamoyl]phenyl}carboxamide (87 mg, 43%). MS found for $C_{26}H_{21}ClN_4O2$ (M+H)⁺: 457.

Example 160

[4-(aminomethyl)phenyl]-N-{2-[N-(5-chloro(2-pyridyl))carbamoyl]phenyl}carboxamide

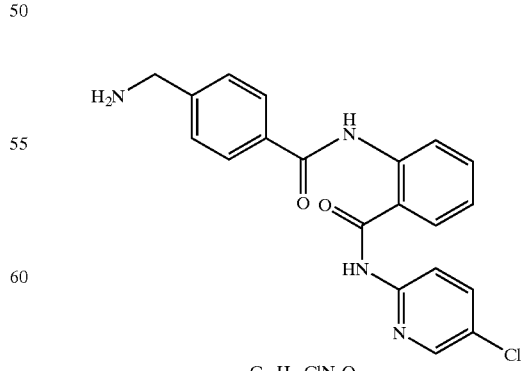

$C_{20}H_{17}ClN_4O_2$
Exact Mass: 380.10
Mol. Wt.: 380.83

A mixture of N-{2-[N-(5-chloro(2-pyridyl))carbamoyl] phenyl}(4-cyanophenyl)carboxamide (1 g, 2.6 mmol, 1.0 equiv.), cobalt chloride (0.5 g, 3.85 mmol, 1.5 equiv.) and sodium borohydride (0.295 g, 7.8 mmol, 3.0 equiv.) in DMF (20 mL) was stirred at 0° C. to rt for 2.5 hr. The reaction was quenched with ice cubes, diluted with ethyl acetate (100 mL) and filtered through celite. The filtrate was washed with saturated aqueous NaHCO$_3$. The organic layer was dried over MgSO$_4$, filtered, evaporated and HPLC (C18 reversed phase) eluting with 0.1% TFA in H$_2$O/CH$_3$CN gave [4-(aminomethyl)phenyl]-N-{2-[N-(5-chloro(2-pyridyl)) carbamoyl]phenyl}carboxamide (320 mg, 30%). MS found for $C_{20}H_{17}ClN_4O_2$ (M+H)$^+$: 381.

Example 161

N-{2-[N-(5-chloro(2-pyridyl))carbamoyl]phenyl}{4-[(2-imidazolin-2-ylamino)methyl]-phenyl}carboxamide

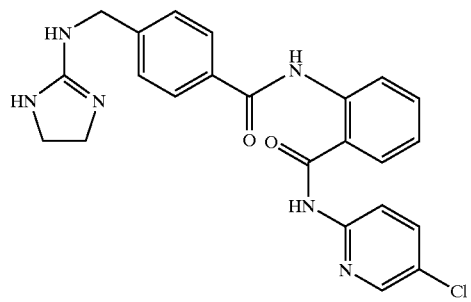

$C_{23}H_{21}ClN_6O_2$
Exact Mass:448.14
Mol. Wt.:448.90

A mixture of [4-(aminomethyl)phenyl]-N-{2[N-(5-chloro (2-pyridyl))carbamoyl]phenyl}carboxamide (80 mg, 0.21 mmol), 2-methylthio-2-imidazoline hydriodide (77 mg, 0.315 mmol, 1.5 equiv.) and triethyl amine (0.5 mL) in 1 mL DMF was stirred at room temperature overnight, concentrated to dryness and HPLC (C18 reversed phase) eluting with 0.1% TFA in H$_2$O/CH$_3$CN gave N-{2-[(5-chloro(2-pyridyl))carbamoyl]phenyl}{4-[(2-imidazolin-2-ylamino) methyl]phenyl}carboxamide (13.5 mg, 15%). MS found for $C_{23}H_{21}ClN_6O2$ (M+H)$^+$: 449.

Example 162

N-{2-[N-(5-chloro(2-pyridyl))carbamoyl]phenyl} (4{[(1-methyl(2-imidazolin-2-yl))amino] methyl}phenyl)carboxamide

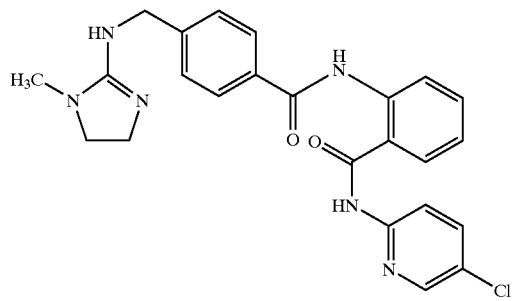

$C_{24}H_{23}ClN_6O_2$
Exact Mass:462.16
Mol. Wt.:462.93

Step 1: To the boiling solution of 2-methylthio-2-imidazoline hydriodide (1 g, 8.4 mmol) in methanol (10 mL) was added MeI (0.78 mL, 12.6 mmol, 1.5 equiv.) dropwise. The reaction mixture was stirred at reflux temperature for 1 hr, concentrated and crystallized with ether to give 1-methyl-2-methylthio-2-imidazoline (1.1 g, 100%). MS found for $C_5H_{10}N_2S$ (M+H)$^+$: 131.

Step 2: A mixture of [4-(aminomethyl)phenyl]-N-{2-[N-(5-chloro(2-pyridyl))carbamoyl]phenyl}carboxamide (74 mg, 0.195 mmol), 1-methyl-2-methylthio-2-imidazoline (25 mg, 0.195 mmol), NEt3 (2 mL) and pyridine (5 mL) was stirred at 80° C. overnight, concentrated and HPLC (C18 reversed phase)eluting with 0.1% TFA in H2O/CH3CN gave N-{2-[N-(5-chloro(2-pyridyl))carbamoyl]phenyl}(4-{[(1-methyl (2-imidazolin-2-yl))amino]methyl}phenyl)carboxamide (52 mg, 65%). MS found for $C_{24}H_{23}ClN_6O_2$ (M+H)$^+$: 463.

Example 163

N-{2-[N-(5-chloro(2-pyridyl))carbamoyl](3-thienyl)} [4-(1-methyl(2-imidazolin-2-yl))phenyl] carboxamide

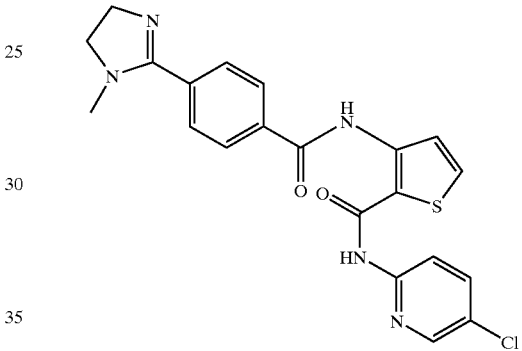

Preparation of methyl 3-[(4-cyanophenyl)carbonylamino] thiophene-2-carboxylate

A mixture of 4-cyanobenzoyl chloride (1.0500 g, 6.4 mmol), methyl 3-aminothiophenecarboxylate (1.0000 g, 6.4 mmol), and triethylamine (1 mL, 7.0 mmol) in dichloromethane was stirred at room temperature for 18 hours. The mixture was poured into a separatory funnel and washed by 1 N HCl. The organic layers were combined, dried over MgSO4, concentrated in vacuo, and chromatographed through a silica gel column to give the title compound 1.6588 g (91%). ES-MS 287 (M+1).

Preparation of N-{2-[N-(5-chloro(2-pyridyl))carbamoyl](3-thienyl)}(4-cyanophenyl)carboxamide A portion of 2-amino-5-chloropyridine (68.6 mg, 0.5 mmol) was treated with AlMe3 (0.8 mL, 1.6 mmol), followed by adding the product from step A (160 mg, 0.5 mmol). The mixture was stirred at room temperature for 18 hours. The excess of AlMe3 was killed by 1N HCl solution. The organic layers were combined, dried over MgSO$_4$, concentrated in vacuo, and chromatographed through a silica gel column to give the title compound 0.1528 g (80%). ES-MS 383 (M+1).

Preparation of Example 163

A mixture of the product from step B (0.1528 g, 0.4 mmol) and EtOH saturated with HCl was stirred at room temperature for 18 hours. The solvent was removed by a rotovap. The crude oil was treated with 2 mL N-methylethylenediamine for 2 hours until the reaction was complete. Prep HPLC was used to purity the final product. It gave 0.1537 g (88%). ES-MS 440 (M+1).

Example 164

{4-[(dimethylamino)iminomethyl]phenyl}-N-{2-[N-(5-chloro(2-pyridyl))carbamoyl](3-thienyl)}carboxamide

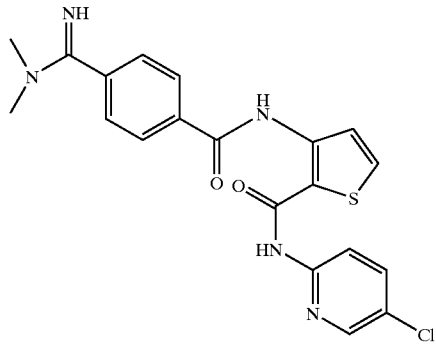

Example 164 was made by the procedure of Example 163. ES-MS 428 (M+1).

Example 165

4-(N-{2-[N-(5-chloro-2-pyridyl)carbamoyl]-3-thienyl}carbamoyl)benzenecarboxamidine

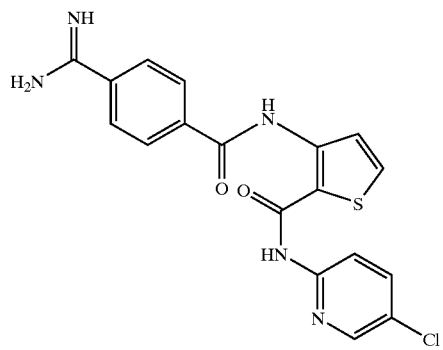

Example 165 was made by the procedure of Example 163. ES-MS 400 (M+1).

Example 166

N-{2-[N-(5-chloro(2-pyridyl))carbamoyl](3-thienyl)}[4-(iminopiperidylmethyl)-phenyl]carboxamide

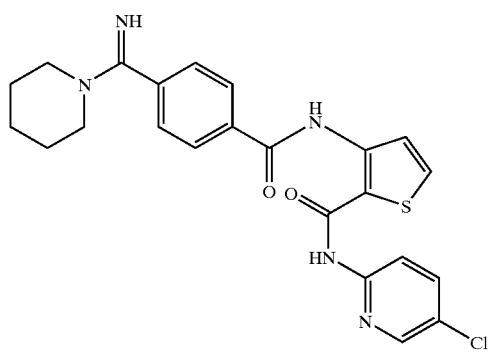

Example 166 was made by the procedure of Example 163. ES-MS 468 (M+1).

Example 167

N-{2-[N-(5-chloro(2-pyridyl))carbamoyl](3-thienyl)}[4-(iminopyrrolidinylmethyl)-phenyl]carboxamide

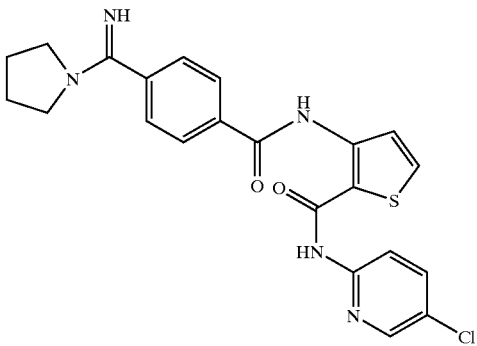

Example 167 was made by the procedure of Example 163. ES-MS 454 (M+1).

Example 168

N-{2-[N-(5-chloro(2-pyridyl))carbamoyl](3-thienyl)}[4-(iminomorpholin-4-ylmethyl)phenyl]carboxamide

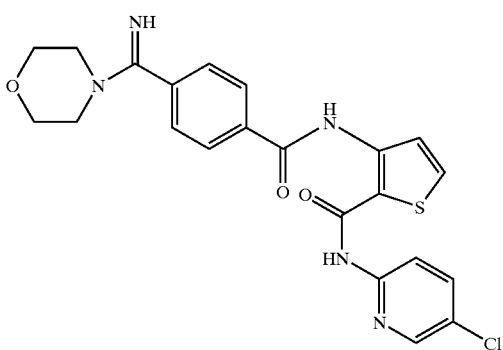

Example 168 was made by the procedure of Example 163. ES-MS 470(+1).

Example 169

N-{2-[N-(5-chloro(2-pyridyl))carbamoyl](3-thienyl)}{[4-(imino-1,4-thiazaperhydroin-4-ylmethyl)phenyl]carboxamide

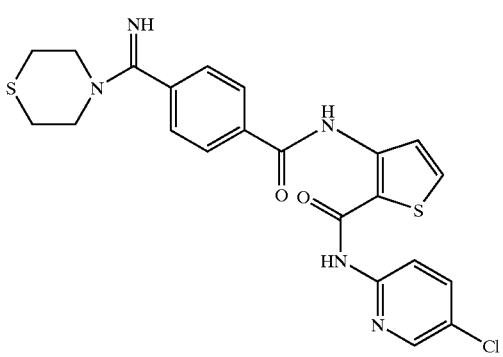

Example 169 was made by the procedure of Example 163. ES-MS 486 (M+1).

Example 170

[4-(azaperhydroepinyliminomethyl)phenyl]-N-{2-[N-(5-chloro(2-pyridyl))carbamoyl](3-thienyl)}carboxamide

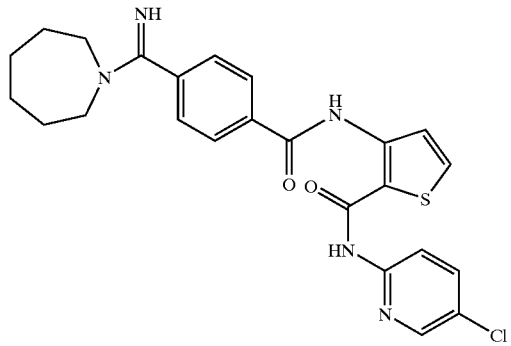

Example 170 was made by the procedure of Example 163. ES-MS 482 (M+1).

Example 171

N-{2-[N-(5-chloro(2-pyridyl))carbamoyl](3-thienyl)}{-4-[imino(2-methylpyrrolidinyl)methyl]phenyl}carboxamide

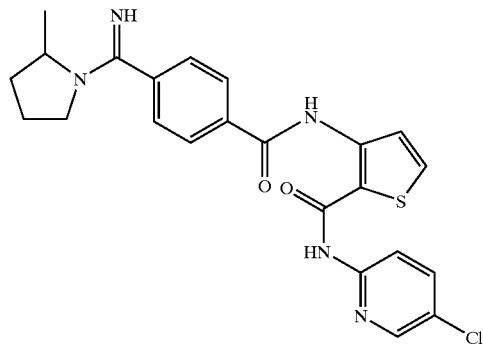

Example 171 was made by the procedure of Example 163. ES-MS 468 (M+1).

Example 172

N-{2-[N-(5-chloro(2-pyridyl))carbamoyl](3-thienyl)}{4-[imino(methylamino)methyl]phenyl}carboxamide

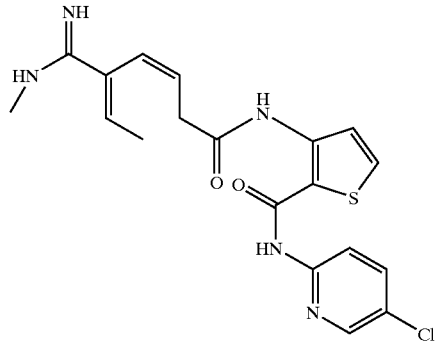

Example 172 was made by the procedure of Example 163.

Example 173

N-{2-[N-(5-chloro(2-pyridyl))carbamoyl](3-thienyl)}[4-(3-methyl(3,4,5,6-tetrahydropyrimidin-2-yl))phenyl]carboxamide

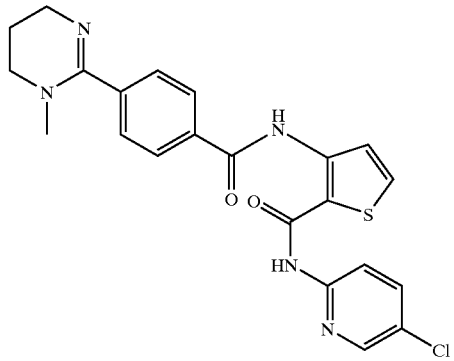

Example 173 was made by the procedure of Example 163. ES-MS 414 (M+1).

Example 174

N-{2-[N-(5-chloro(2-pyridyl))carbamoyl](3-thienyl)}[4-((hydroxyamino)iminomethyl)-phenyl]carboxamide

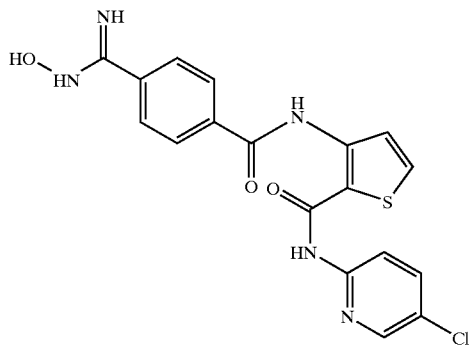

Example 174 was made by the procedure of Example 163. ES-MS 416 (M+1).

Example 175

1-{[4(N-{2-[N-(5-chloro(2-pyridyl))carbamoyl](3-thienyl)}carbamoyl)phenyl]-iminomethyl}pyrrolidine-2-carboxylic acid

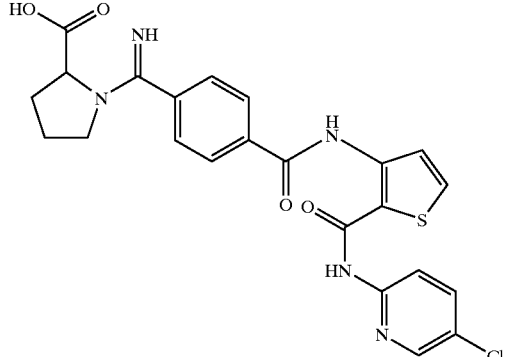

Example 175 was made by the procedure of Example 163. ES-MS 498 (M+1).

Example 176

N-{2-[N-(5-bromo(2-pyridyl))carbamoyl](3-thienyl)}[4-(1-methyl(2-imidazolin-2-yl))phenyl]carboxamide

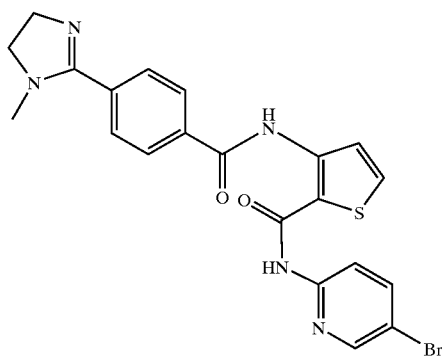

Example 176 was made by the procedure of Example 163. ES-MS 484 (M+1).

Example 177

4-(N-{2-[N-(5-bromo-2-pyridyl)carbamoyl]-3-thienyl}carbamoyl)benzenecarboxamidine

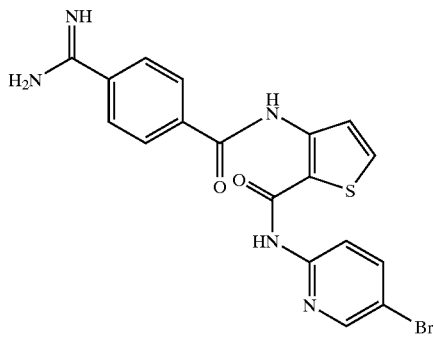

Example 177 was made by the procedure of Example 163. ES-MS 444 (M+1).

Example 178

N-{2-[N-(5-bromo(2-pyridyl))carbamoyl](3-thienyl)}[4-(iminopyrrolidinylmethyl)phenyl]carboxamide

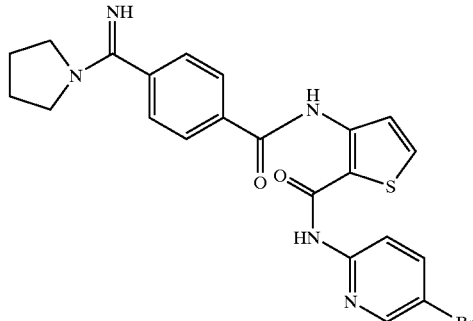

Example 178 was made by the procedure of Example 163. ES-MS 494 (M+1).

Example 179

N-{2-[N-(5-bromo(2-pyridyl))carbamoyl](3-thienyl)}[4-(iminopiperidylmethyl)phenyl]carboxamide

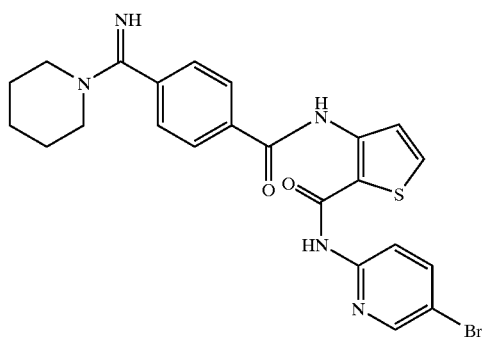

Example 179 was made by the procedure of Example 163. ES-MS 512 (M+1).

Example 180

N-{2-[N-(5-bromo(2-pyridyl))carbamoyl](3-thienyl)}[4-(iminomorpholin-4-ylmethyl)phenyl]carboxamide

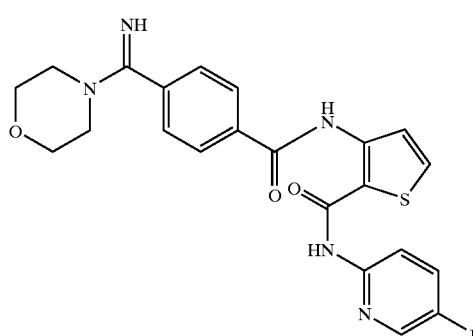

Example 180 was made by the procedure of Example 163. ES-MS 514 (M+1).

Example 181

N-{2-[N-(5-bromo(2-pyridyl))carbamoyl](3-thienyl)}[4-(imino-1,4-thiazaperhydroin-4-ylmethyl)phenyl]carboxamide

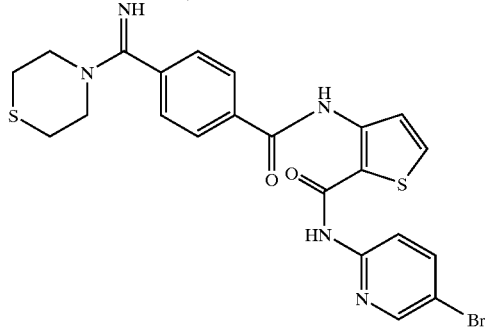

Example 181 was made by the procedure of Example 163. ES-MS 530 (M+1).

Example 182

N-{3-[N-(5-chloro(2-pyridyl))carbamoyl](2-thienyl)}[4-(iminopyrrolidinylmethyl)phenyl]carboxamide

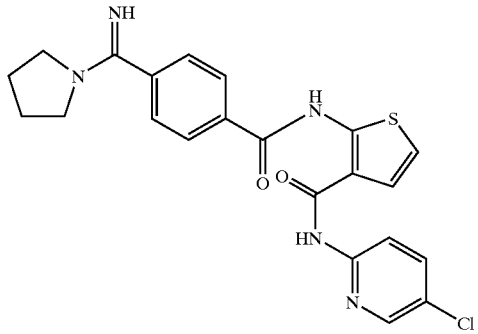

Example 182 was made by the procedure of Example 163. ES-MS 454 (M+1).

Example 183

N-{3-[N-(5-chloro(2-pyridyl))carbamoyl](2-thienyl)}[4-(1-methyl(2-imidazolin-2-yl))phenyl]carboxamide

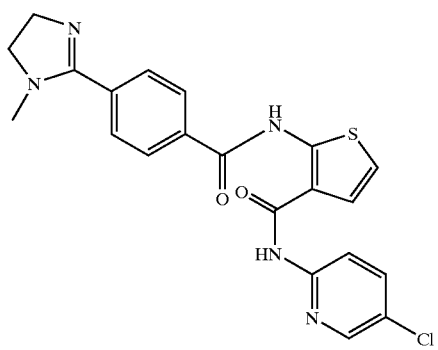

Example 183 was made by the procedure of Example 163. ES-MS 440 (M+1).

Example 184

3-[(3-{[4-(2-sulfamoylphenyl)phenyl]carbonylamino}-2-thienyl)carbonylamino]benzenecarboxamidine

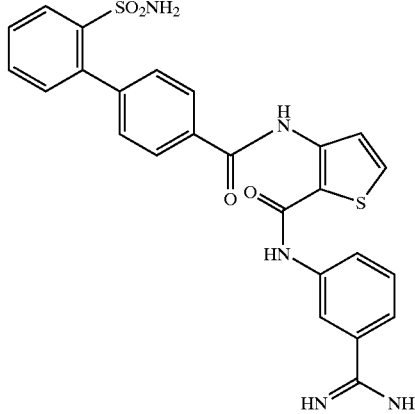

Example 184 was made by the procedure of Example 163 (step A, B, C) followed by a final step of trifluoroacetic acid removal of the t-butyl group. 4-(2-{[(tert-butyl)amino]sulfonyl}phenyl)benzoyl chloride was used to replace 4-cyanobenzoyl chloride in Example 1. ES-MS 520 (M+1).

Example 185

N-{2-[N-(5-chloro(2-pyridyl))carbamoyl](3-thienyl)}[4-(2-sulfamoylphenyl)phenyl]carboxamide

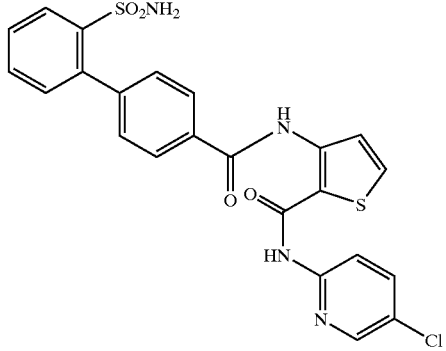

Example 185 was made by the procedure of Example 163 except using 4-(2-{[(tert-butyl)amino]sulfonyl}phenyl)benzoyl chloride instead of 4-cyanobenzoyl chloride. ES-MS 513 (M+1).

Example 186

N-{2-[N-(5-bromo(2-pyridyl))carbamoyl](3-thienyl)}[4-(2-sulfamoylphenyl)phenyl]carboxamide

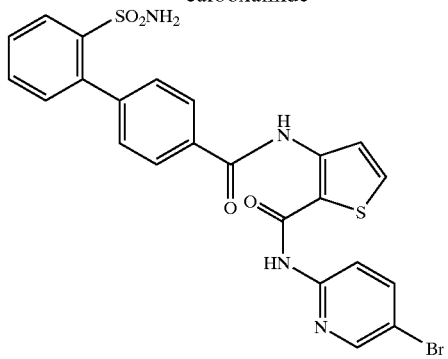

Example 186 was made by the procedure of Example 185. ES-MS 556(M+1).

Example 187

N-(5-bromo-2-pyridinyl)-(2-4-[(2-aminosulfonyl)phenyl]phenylaminocarbonyl)5-methyl-pyrazoicarboxamide.

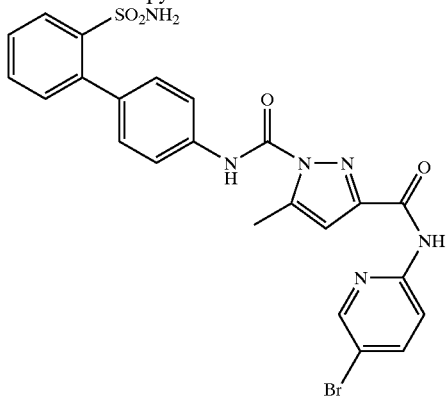

Step 1: A solution of 2-amino-5-bromopyridine (0.200 g, 1.16 mmol 1.0 equiv), in 5 mls of methylene chloride, under argon, was treated with trimethylaluminum (0.312 mL, 2.0 N in hexanes, 4.0 equiv) at room temperature for 30 min. To the solution was added ethyl-3-methylpyrazole-5-carboxylate (0.356 g, 2.0 equiv). After 4 hrs, the volatile was evaporated, and the residue was redissolved into EtOAc, washed with 0.5N HCl, 0.2 N $K_2CO_3$, and saturated aqueous NaCl. The organic layer was dried over Na2SO4, filtered, evaporated and purified via flash chromatography on silica gel to give N-(5-bromo-2-pyridinyl)-(3-methyl)5-pyrazolecarboxamide (0.160 g, 49%). MS found for $C_{10}H_9BrN_4O$ $(M+H)^+$: 281, 283.

Step 2: A solution of N-(5-bromo-2-pyridinyl)-(3-methyl)5-pyrazolecarboxamide (0.060 g, 0.213 mmol, 1.0 equiv) in 2 mL of acetonitrile was treated with triphosgene (0.063 g, 1.0 equiv) at room temperature for 5 min under argon. To the solution was added 4-[(2-t-butylaminosulfonyl)phenyl]phenylamine (0.071 g, 1.1 equiv) After 1 hr, the volatile was evaporated and the residue was redissolved into EtOAc, washed with 0.5N HCl, 0.2 N $K_2CO_3$, and saturated aqueous NaCl. The organic layer was dried over $Na_2SO_4$, filtered, evaporated, purified via flash chromatography on silica gel and then reacted in 2 mL of trifluoroacetic acid for 16 hrs at room temperature. TFA was then evaporated and the residue was redissolved into EtOAc, washed with 0.5N HCl, 0.2 N $K_2CO_3$, and saturated aqueous NaCl. The organic layer was dried over $Na_2SO_4$, filtered, evaporated, and triturated with diethyl ether to give N-(5-bromo-2-pyridinyl)-(2-4-[(2-aminosulfonyl)phenyl]phenylaminocarbonyl)5-methyl-pyrazolcarboxamide (0.0024 g, 2%). MS found for $C_{23}H_{19}BrN_6O_4S$ $(M+H)^+$: 555, 557.

Example 188

N-(5-bromo-2-pyridinyl)-(2-4-[(2-aminosulfonyl)phenyl]phenylcarbonylamino)-5-fluorophenylcarboxamide

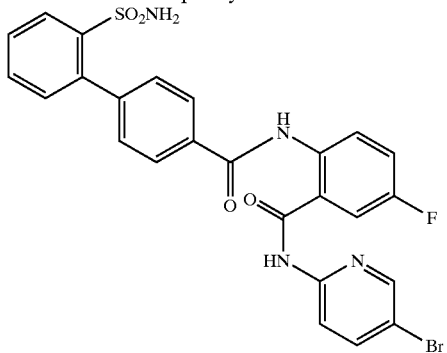

Step 1: A solution of 5-fluoro-2-nitrobenzoic acid (10.0 g, 54 mmol, 1.0 equiv), 2-amino-5-bromopyridine (12.2 g, 1.3 equiv), in 80 mL of pyridine was treated with phosphorous oxychloride (25.3 g, 3.0 equiv) for 30 min. The volatile was evaporated and the residue was redissolved into EtOAc, washed with 1N HCl, saturated aqueous $NaHCO_3$ and saturated aqueous NaCl. The organic layer was dried over $Na_2SO_4$, filtered, and evaporated. The volatile was evaporated, and the product was triturated with diethyl ether to give N-(5-bromo-2-pyridinyl)-(2-nitro)-5-fluorophenylcarboxamide (12.5 g, 68%). MS found for $C_{12}H_7BrFN_3O_3$ $(M+H)^+$: 340, 342.

Step 2: A solution of N-(5-bromo-2-pyridinyl)-(2-nitro)-5-flurophenylcarboxamide (2.0 g, 5.88 mmol, 1.0 equiv) in 30 mL of EtOAc was treated with $SnCl_2H_2O$ (5.90 g, 4 equiv) at reflux for 4 h. The volatile was evaporated and the residue was redissolved in EtOAc, washed with saturated aqueous $NaHCO_3$ and 1N NaOH. The organic layer was dried over $MgSO_4$, filtered and evaporated to N-(5-bromo-2-pyridinyl)-(2-amino)-5-fluorophenylcarboxamide (1.79 g, 98%). MS found for $C_{12}H_9BrFN_3O$ $(M+H)^+$: 310, 312.

Step 3: A mixture of N-(5-bromo-2-pyridinyl)-(2-amino)-5-fluorophenylcarboxamide (0.310 g, 1 mmol, 1.0 equiv), 4-[(2-t-butylaminosulfonyl)phenyl]benzoyl chloride (0.430 g, 1.3 equiv), pyridine (2 mL) in 10 mL of dichloromethane was stirred at rt overnight. The volatile was evaporated and the residue was redissolved into EtOAc, washed with 1N HCl, saturated aqueous $NaHCO_3$ and saturated aqueous NaCl. The organic layer was dried over $Na_2SO_4$, filtered, and evaporated. The intermediate was reacted into 5 mL of trifluoroacetic acid at rt overnight. TFA was then evaporated and the product was triturated with diethyl ether, and then with chloroform to give N-(5-bromo-2-pyridinyl)-(2-4-[(2-aminosulfonyl)phenyl]phenylcarbonylamino)-5-fluorophenylcarboxamide (120 mg, 21%). MS found for $C_{25}H_{18}BrFN_4O_4S$ $(M+H)^+$: 569, 571.

Example 189

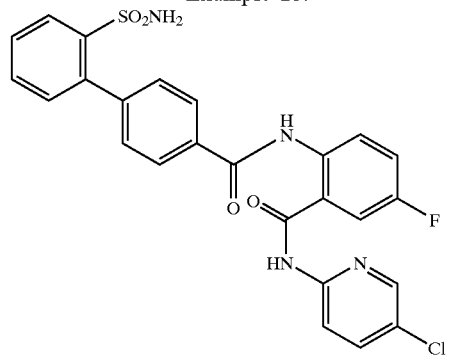

This compound is prepared according to the procedure described in example 2 with the exception of using zinc in acetic acid to reduce nitro-intermediate in step 2. The final product was purified by HPLC (C18 reversed phase) eluting with 0.5% TFA in $H_2O/CH_3CN$. MS found for $C_{25}H_{18}ClFN_4O_4S$ $(M+H)^+$: 525, 527.

Example 190

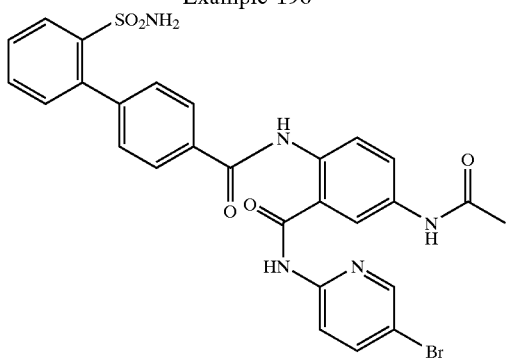

This compound is prepared according to the procedure described in example 2 with the exception of using 5-acetamido-2-nitrobenzoic acid as the starting material in step 1. The final product was purified by HPLC (C18 reversed phase) eluting with 0.5% TFA in $H_2O/CH_3CN$ MS found for $C_{27}H_{22}BrN_5O_5S$ (M+H)$^+$: 608, 610.

Example 191

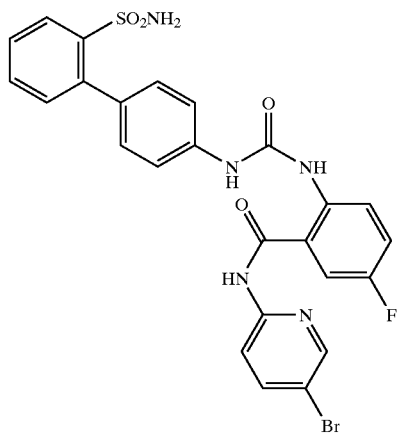

This compound is prepared according to the procedure described in example 2 with the exception of the following step 1b performed on the nitro-intermediate from step 1. The final product was purified by HPLC (C18 reversed phase) eluting with 0.5% TFA in $H_2O/CH_3CN$ MS found for $C_{30}H_{29}BrN_6O_4S$ (M+H)$^+$: 649, 651.

Step 1b: A mixture of N-(5-bromo-2-pyridinyl)-(2-nitro)-5-fluorophenylcarboxamide (0.68 g, 2 mmol, 1.0 equiv), N-methylpiperazine (0.60 g, 3 equiv), and $Cs_2CO_3$ (1.30 g, 2 equiv) in 5 mL of dimethylformamide was stirred at 90° C. overnight Ethyl acetate was added and washed with $H_2O$. The organic layer was dried over $Na_2SO_4$, filtered, evaporated, purified via flash chromatography on silica gel to give N-(5-bromo-2-pyridinyl)-(2-nitro)-5-(4-N-methylpiperazine)phenylcarboxamide (0.54 g, 65%). MS found for $C_{17}H_{18}BrN_5O_3$ (M+H)$^+$: 419, 421.

Example 192

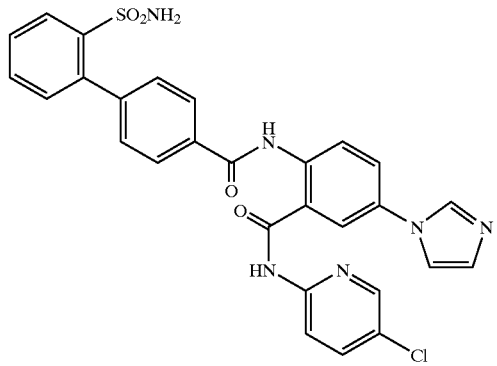

This compound is prepared according to the procedure described in example 5. The final product was purified by HPLC (C18 reversed phase) eluting with 0.5% TFA in $H_2O/CH_3CN$ MS found for $C_{28}H_{21}ClN_6O_4S$ (M+H)$^+$: 573, 575.

Example 193

N-(5-bromo-2-pyridinyl)-(2-4-[(2-aminosulfonyl) phenyl]phenylaminocarbonylamino)5-fluorophenylcarboxamide Step 3: A mixture of 4-[(2-t-butylaminosulfonyl)phenyl] phenylamine (0.180 g, 1.2 equiv), N,N'-disuccinimidyl carbonate (0.154 g, 1.2 equiv), 4-methylmorpholine (0.5 mL) in 10 mL of acetonitrile was stirred at rt for 30 min. N-(5-bromo-2-pyridinyl)-(2-amino)-5-fluorophenylcarboxamide (0.155 g, 0.5 mmol, 1.0 equiv) was added and the solution was stirred at rt for 3 hrs. The volatile was evaporated and the residue was redissolved into EtOAc, washed with 1N HCl, saturated aqueous $NaHCO_3$ and saturated aqueous NaCl. The organic layer was dried over $Na_2SO_4$, filtered, and evaporated. The intermediate was reacted into 5 mL of trifluoroacetic acid at rt overnight. TFA was then evaporated and the product was purified by HPLC (C18 reversed phase) eluting with 0.5% TFA in $H_2O/CH_3CN$ to give N-(5-bromo-2-pyridinyl)-(2-4-[(2-aminosulfonyl)phenyl] phenylaminocarbonylamnino)-5-fluorophenylcarboxamide (0.053 g, 188%). MS found for $C_{25}H_{19}BrFN_5O_4S$ (M+H)$^+$: 584, 586.

Examples 194–195

N-(5-bromo-2-pyridinyl-(2-4-amidinophenylcarbonyl)amino)5-fluorophenylcarboxamide

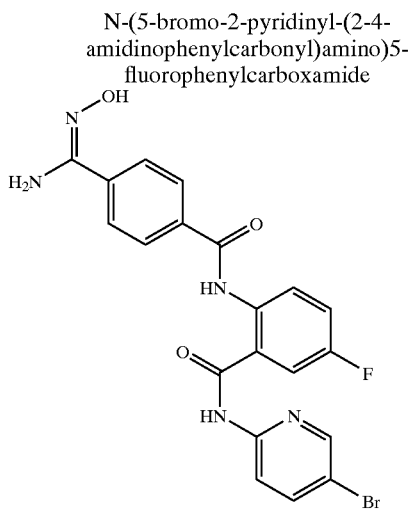

Example 194

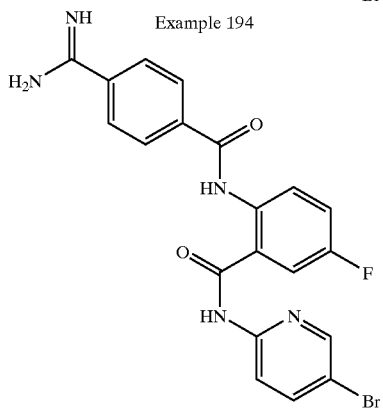

Example 195

Step 1: A mixture of N-(5-bromo-2-pyridinyl)-(2-amino)5-fluorophenylcarboxamide (1.24 g, 4 mmol, 1.0 equiv), 4-cyano benzoyl chloride (0.792 g, equiv), and pyridine (3 mL) in 15 mL of dichloromethane was stirred at rt overnight. The volatile was evaporated and the residue was redissolved into EtOAc, washed with 1N HCl, saturated aqueous NaHCO$_3$ and saturated aqueous NaCl. The organic layer was dried over Na$_2$SO$_4$, filtered, and evaporated to give N-(5-bromo-2-pyridinyl)-(2-(4-cyanophenylcarbonyl)amino)5-fluorophenylcarboxamide (1.14 g, 65%). MS found for C$_{20}$H$_{12}$BrFN$_4$O$_2$ (M+H)$^+$: 439, 441.

Step 2: A mixture of N-(5-bromo-2-pyridinyl)-(2-(4-cyanophenylcarbonyl)amino)5-fluorophenylcarboxamide (1.12 g, 2.56 mmol, 1.0 equiv), hydroxylamine-HCl (0.213 g, 1.2 equiv), and triethylamine (1 mL) in 15 mL of ethyl alcohol was stirred at 50° C. overnight. The volatile was evaporated and the residue was redissolved into EtOAc, washed with 1N HCl, saturated aqueous NAHCO$_3$ and saturated aqueous NaCl. The organic layer was dried over Na$_2$SO$_4$, filtered, and evaporated to give N-(5-bromo-2-pyridinyl)-(2-(4-hydroxyaindinophenylcarbonyl)amino)5-fluorophenylcarboxamide (compound Example 194) (0.84 g, 70%). One third of this material was purified by HPLC (C18 reversed phase) eluting with 0.5% TFA in H$_2$O/CH$_3$CN to yield 0.20 grams (71%). MS found for C$_{20}$H$_{15}$BrFN$_5$O$_3$ (M+H)$^+$: 472, 474.

Step 3: A mixture of N-(5-bromo-2-pyridinyl)-(2-(4-hydroxyamidinophenylcarbonyl)amino)5-fluorophenylcarboxamide (0.56 g, 1.19 mmol, 1.0 equiv) and zinc dust (0.39 g, 5.0 equiv), in 10 mL of acetic acid was stirred at rt for 45 min. The volatile was filtered and evaporated. The residue was purified by HPLC (C18 reversed phase) eluting with 0.5% TFA in H$_2$O/CH$_3$CN give N-(5-bromo-2-pyridinyl)-(2-(4-amidinophenylcarbonyl)amino)5-fluorophenyl-carboxamide (compound Example 195) (0.24 g, 44%). MS found for C$_{20}$H$_{15}$BrFN$_5$O$_2$ (M+H)$^+$: 456,458.

Example 196

N-(5-bromo-2-pyridinyl)-(2-(4-(1-methyl-2-imadazolin-2-yl)phenylcarbonyl)amino)5-fluorophenylcarboxamide

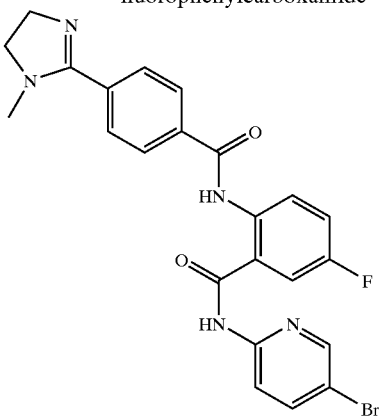

Step 1: A stream of HCl(g) was bubbled through a 0° C. solution of N-(5-bromo-2-pyridinyl)-(2-4-cyanophenylcarbonyl)amino)5-fluorophenylcarboxamide (1.0 g, 2.3 mmol) in 30 mL of methanol until saturation. The mixture was stirred at rt overnight and evaporated. One-fifth of the resulting residue was treated with (2-aminoethyl)methylamine (0.10 g) in 10 ml methanol at rt overnight. The solvent was removed at reduced pressure and the crude product was purified by HPLC (C18 reversed phase) eluting with 0.5% TFA in H$_2$O/CH$_3$CN to give N-(5-bromo-2-pyridinyl)-(2-4-(1-methyl-2-imadazolin-2-yl)phenylcarbonyl)amino)5-fluorophenylcarboxamide (0.082 g, 37%). MS found for C$_{23}$H$_{19}$BrFN$_5$O$_2$ (M+H)$^+$: 496, 498.

Examples 197–267

The following compounds were prepared generally according to the procedure described in Example 196.

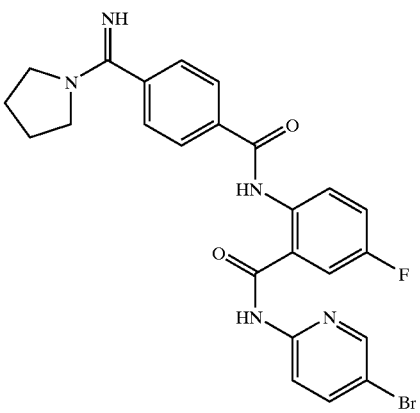

Example 197
MS (M + H):
510, 512

-continued
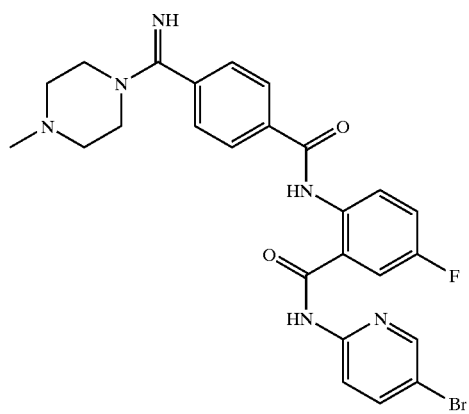
Example 198
MS (M + H):
539, 541
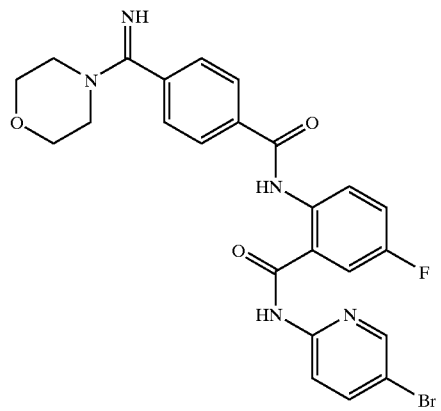
Example 199
MS (M + H):
526, 528
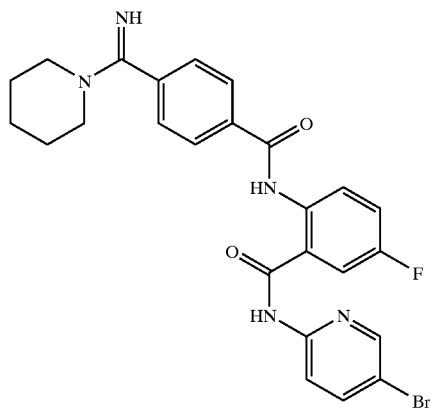
Example 200
MS (M + H):
524, 526
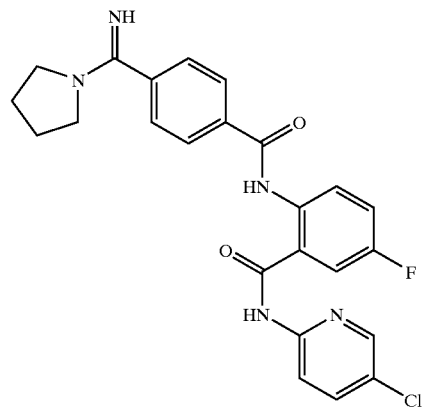
Example 201
MS (M + H):
466, 468
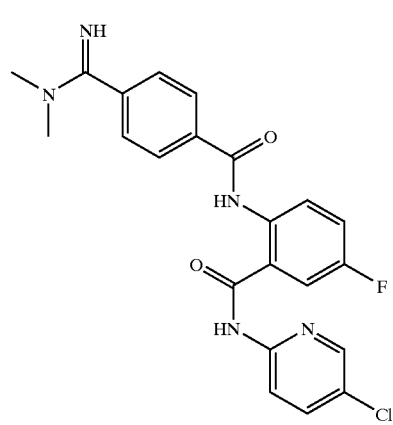
Example 202
MS (M + H):
440, 442
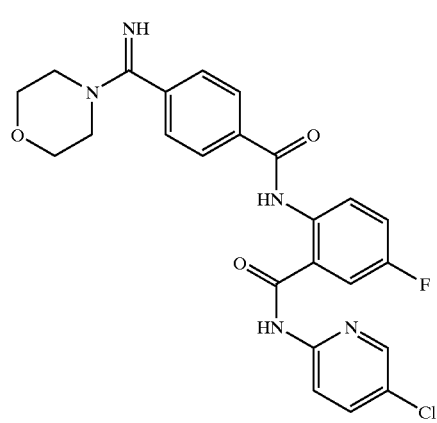
Example 203
MS (M + H):
482, 484

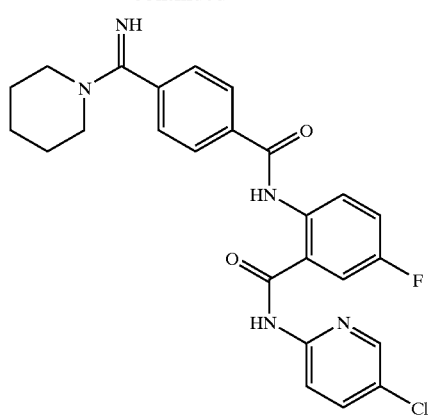
Example 204
MS (M + H):
480, 482
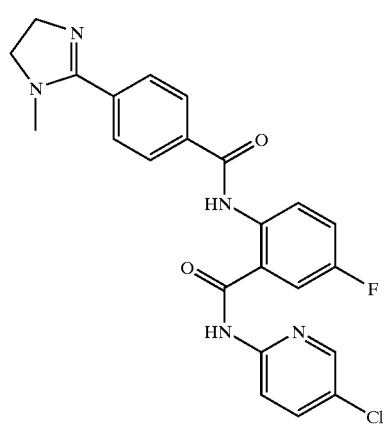
Example 205
MS (M + H):
452, 454
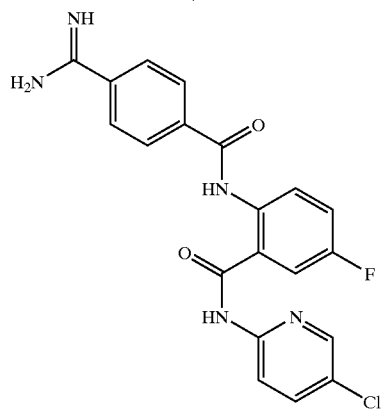
Example 206
MS (M + H):
412, 414
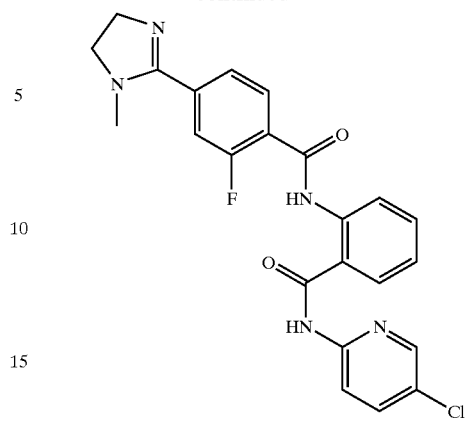
Example 207
MS (M + H):
452, 454
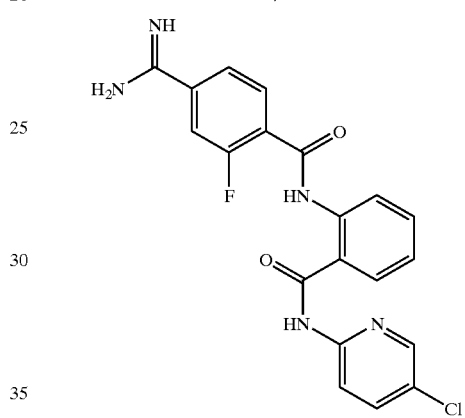
Example 208
MS (M + H):
412, 414
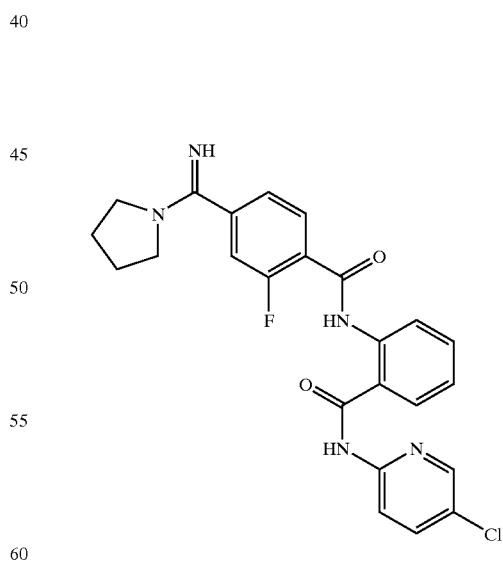
Example 209
MS (M + H):
466, 468

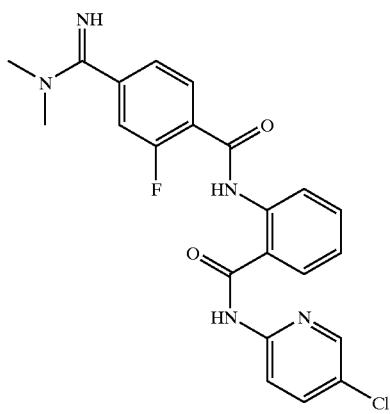
Example 210
MS (M + H):
440, 442
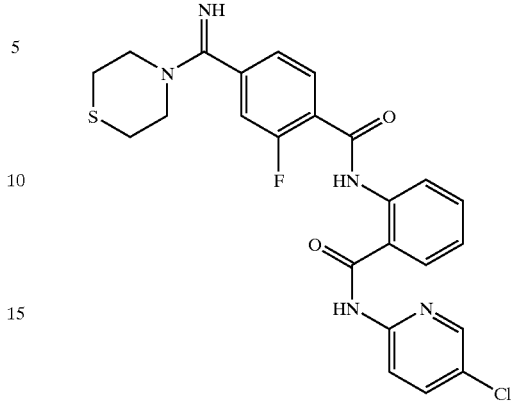
Example 213
MS (M + H):
498, 500
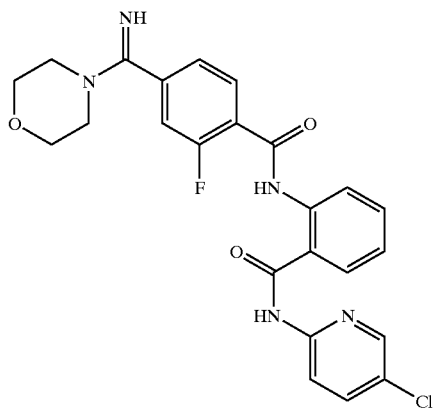
Example 211
MS (M + H):
482, 484
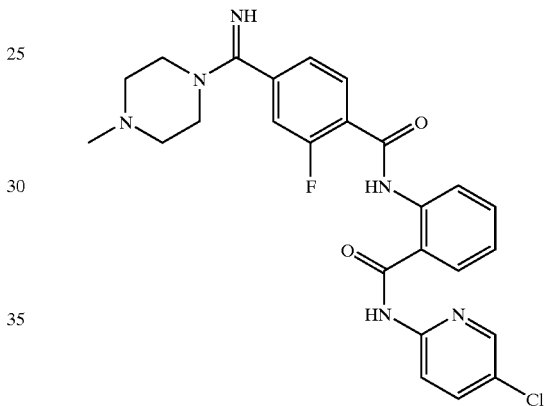
Example 214
MS (M + H):
495, 497
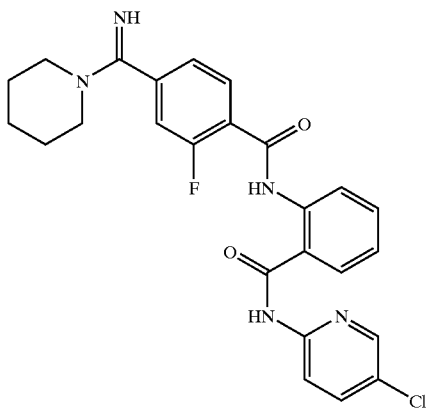
Example 212
MS (M + H):
480, 482
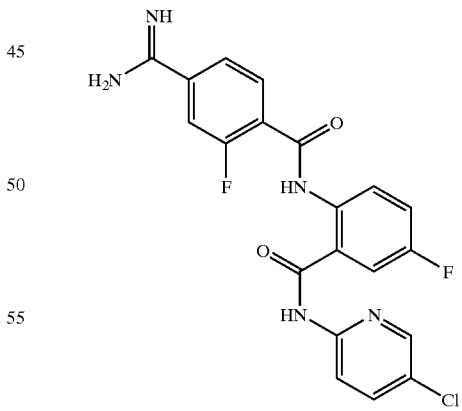
Example 215
MS (M + H):
430, 432

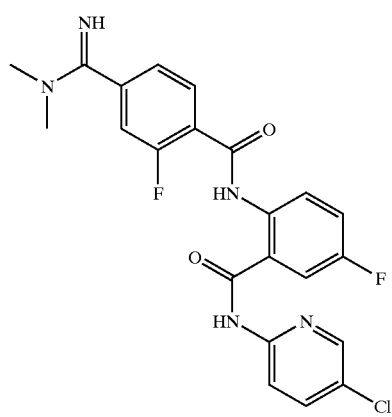
Example 216
MS (M + H):
458, 460
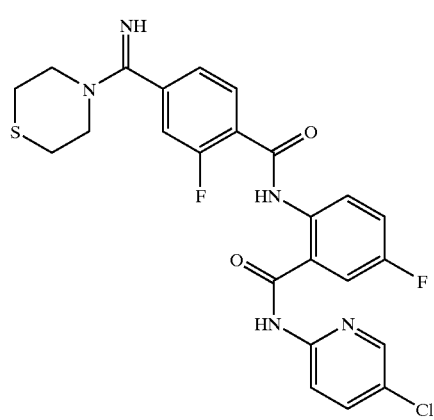
Example 217
MS (M + H):
516, 518
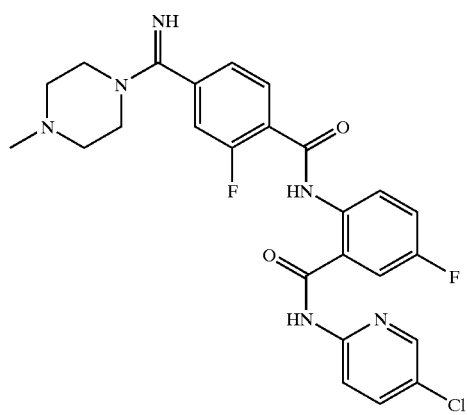
Example 218
MS (M + H):
513, 515
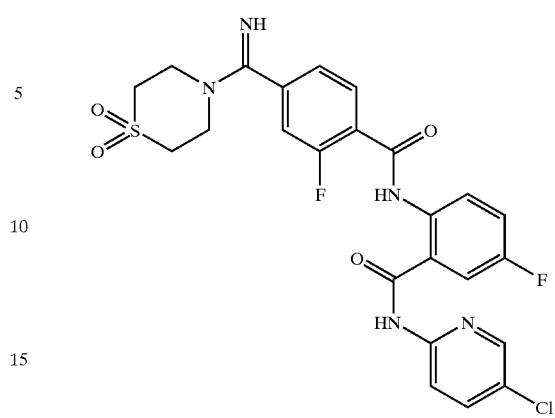
Example 219
MS (M + H):
548, 550
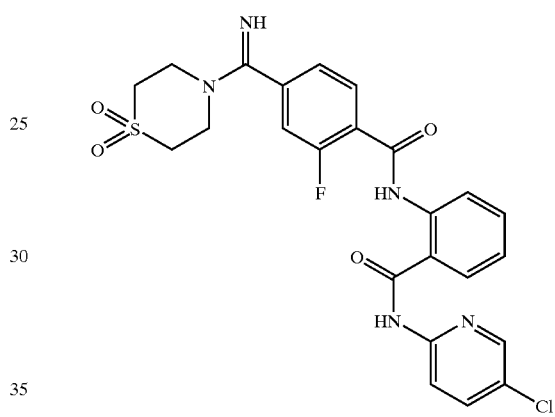
Example 220
MS (M + H):
530, 532
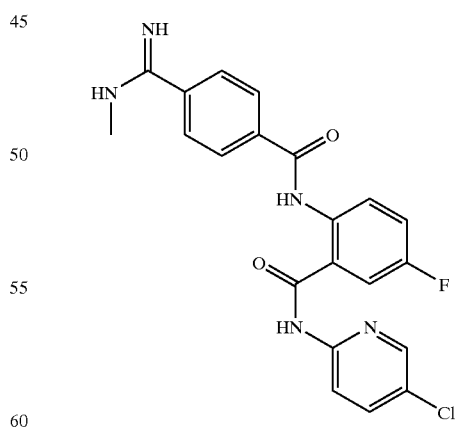
Example 221
MS (M + H):
426, 428

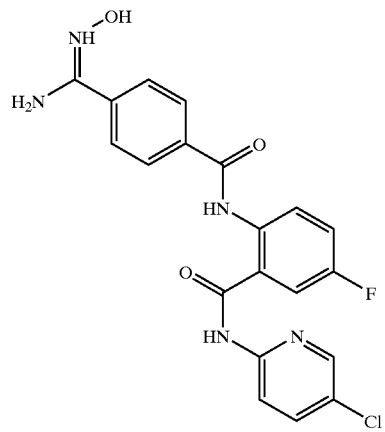
Example 222
MS (M + H):
428, 430
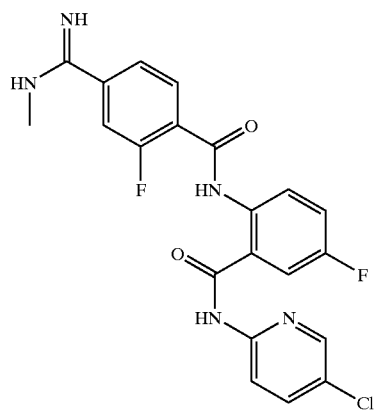
Example 223
MS (M + H):
426, 428
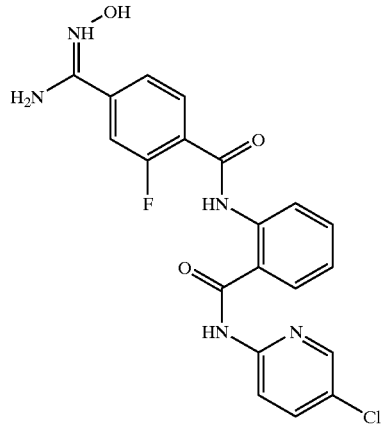
Example 224
MS (M + H):
428, 430
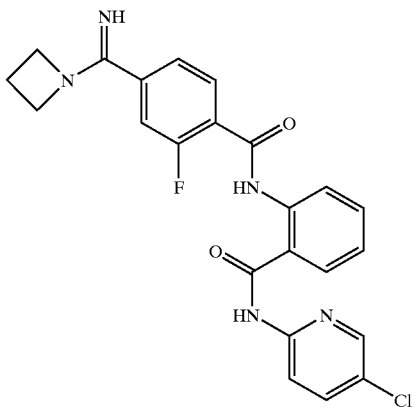
Example 225
MS (M + H):
452, 454
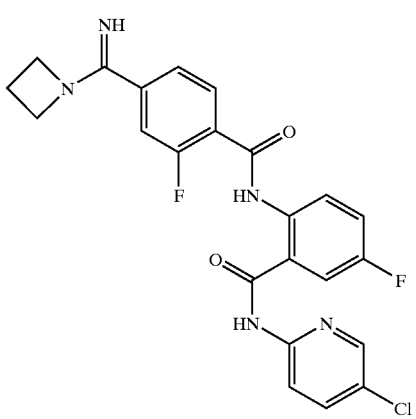
Example 226
MS (M + H):
470, 472
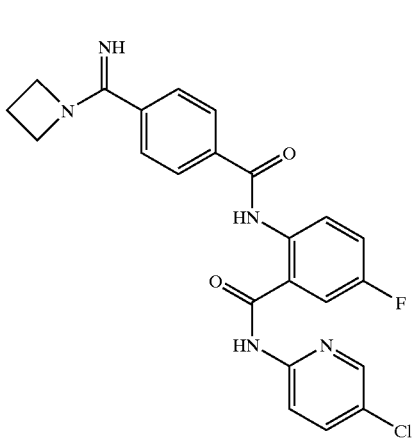
Example 227
MS (M + H):
452, 454

-continued
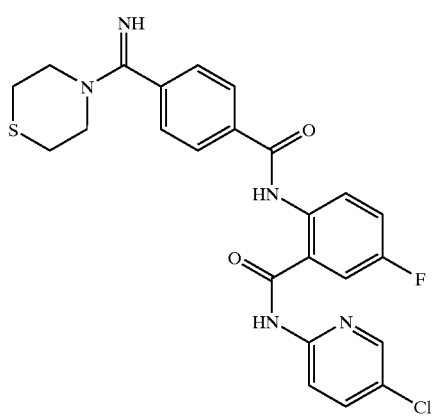
Example 228
MS (M + H):
498, 500
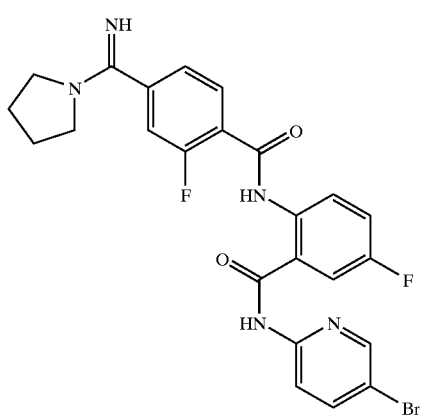
Example 229
MS (M + H):
528, 530
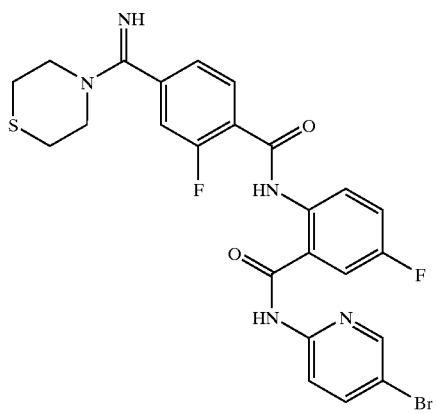
Example 230
MS (M + H):
560, 562
-continued
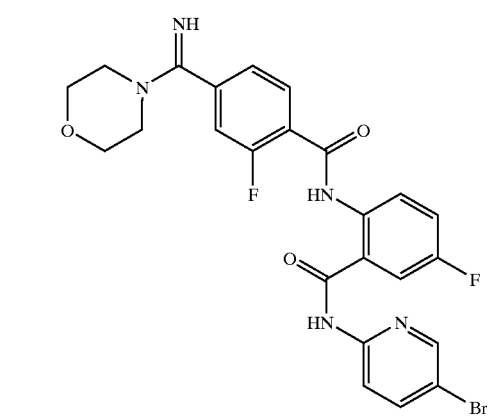
Example 231
MS (M + H):
544, 546
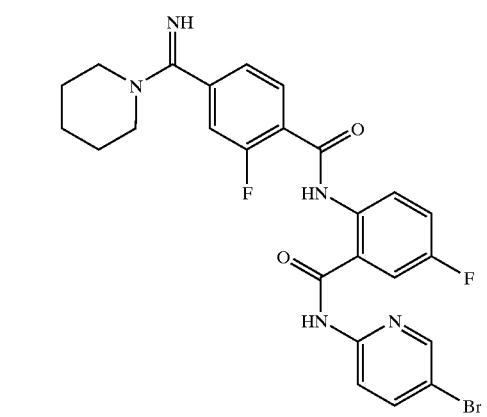
Example 232
MS (M + H):
542, 544
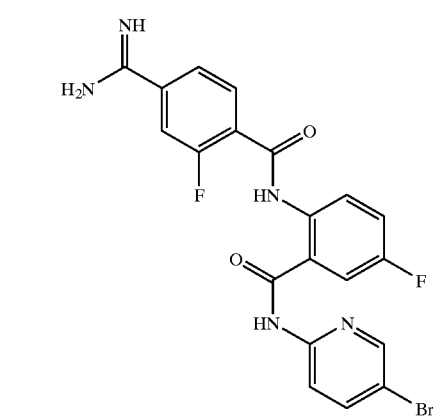
Example 233
MS (M + H):
474, 476

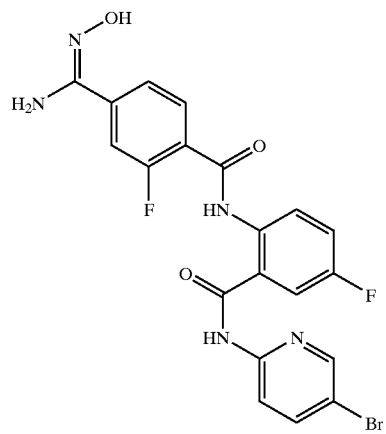
Example 234
MS (M + H):
490, 492
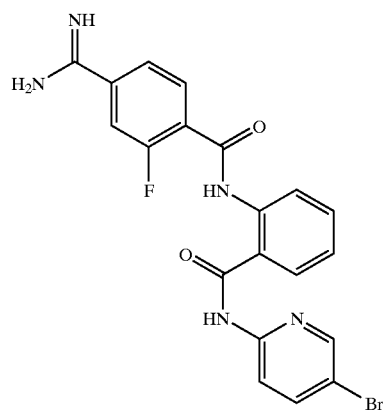
Example 235
MS (M + H):
456, 458
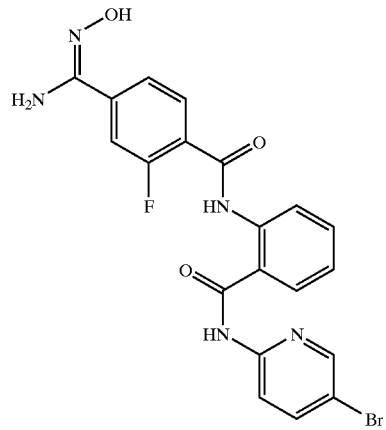
Example 236
MS (M + H):
472, 474
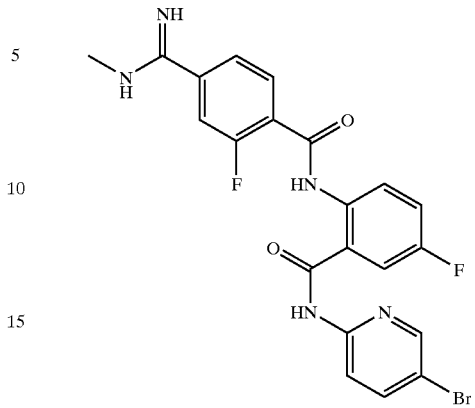
Example 237
MS (M + H):
488, 490
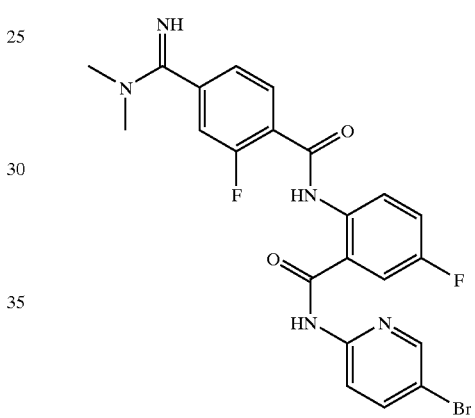
Example 238
MS (M + H):
502, 504
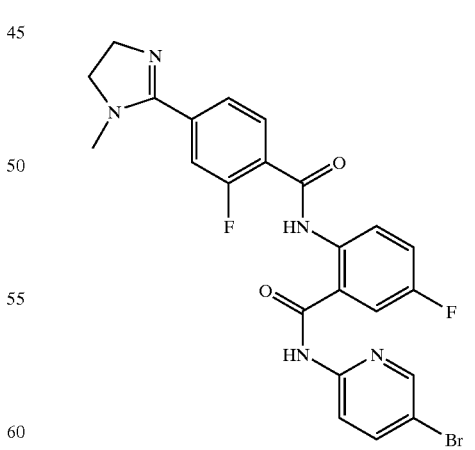
Example 239
MS (M + H):
514, 516

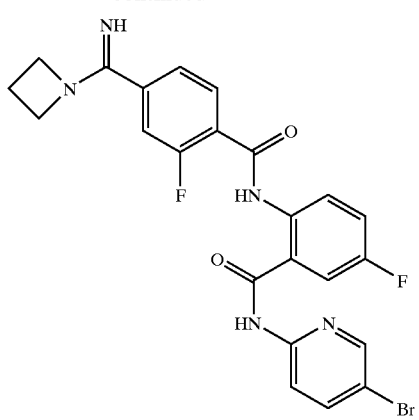
Example 240
MS (M + H):
514, 516
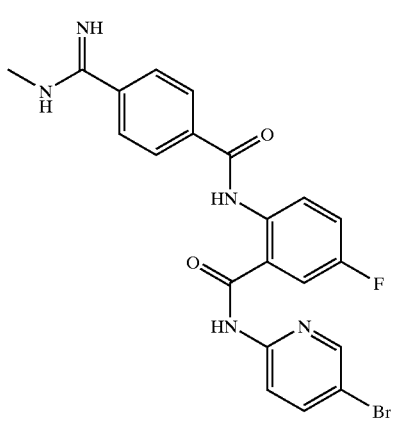
Example 241
MS (M + H):
470, 472
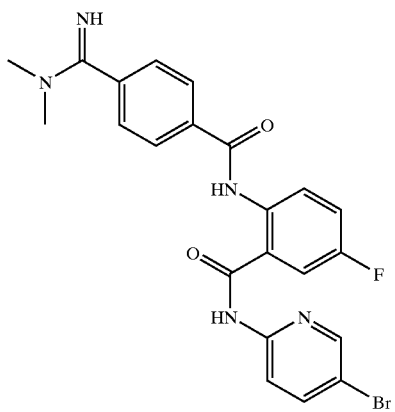
Example 242
MS (M + H):
484, 486
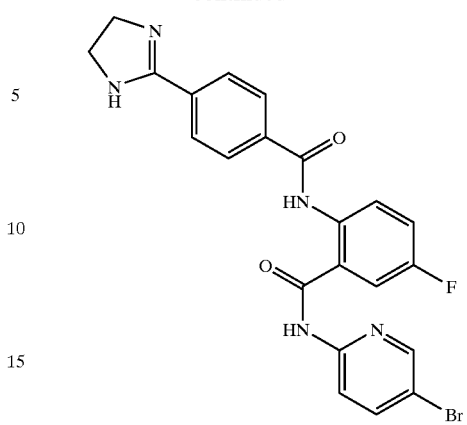
Example 243
MS (M + H):
482, 484
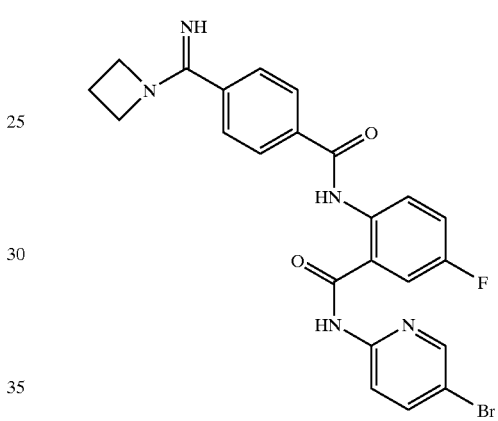
Example 244
MS (M + H):
496, 498
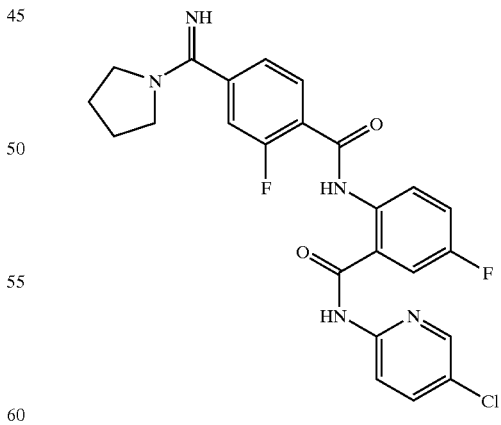
Example 245
MS (M + H):
484, 486

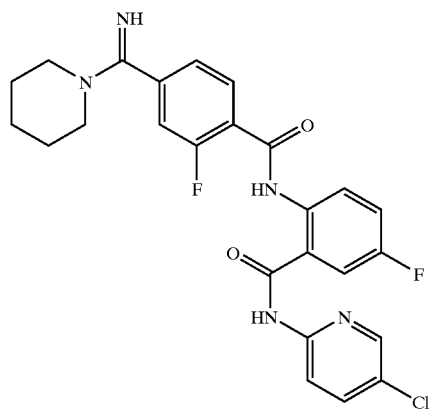
Example 246
MS (M + H):
498, 500
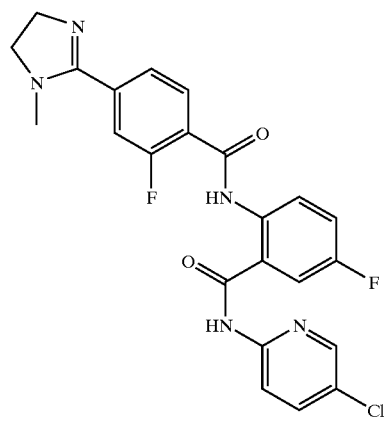
Example 247
MS (M + H):
470, 472
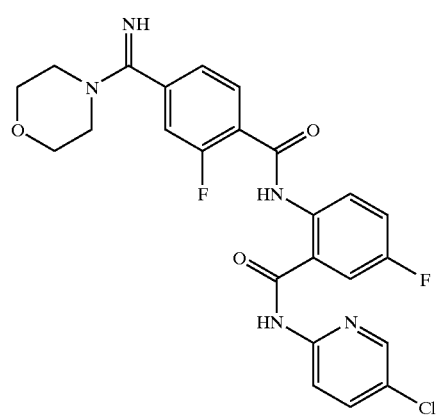
Example 248
MS (M + H):
500, 502
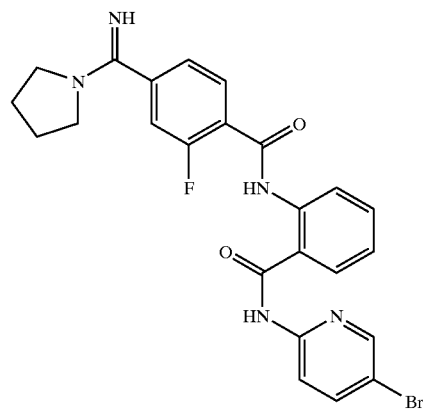
Example 249
MS(M + H):
510, 512
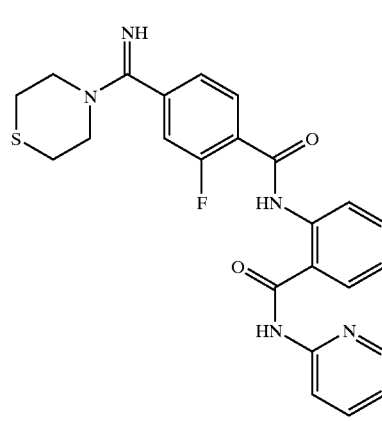
Example 250
MS(M + H):
542, 544
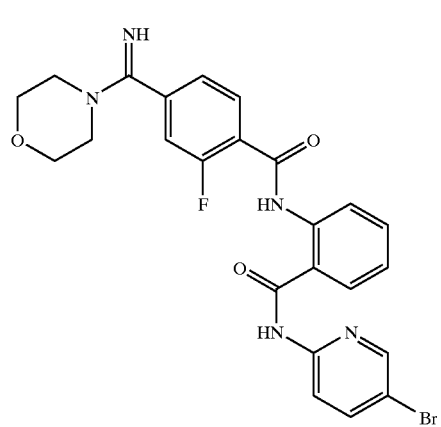
Example 251
MS(M + H):
526, 528

-continued
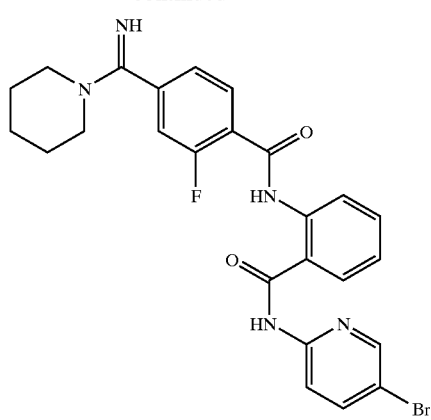
Example 252
MS(M + H):
524, 526
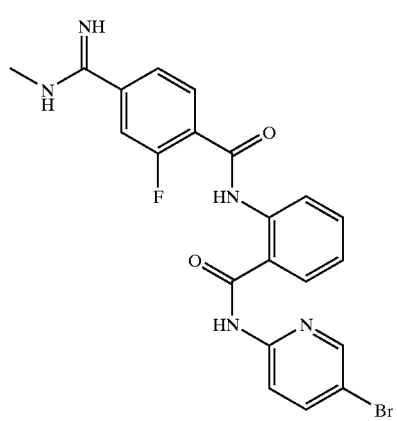
Example 253
MS(M + H):
470, 472
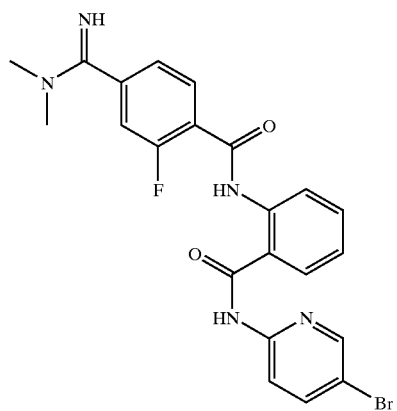
Example 254
MS(M + H):
484, 486
-continued
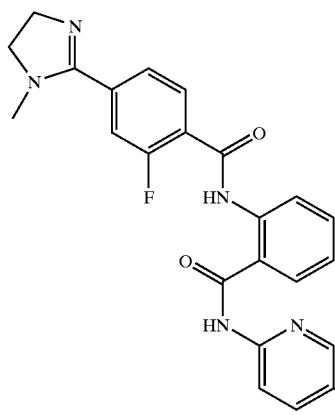
Example 255
MS(M + H):
496, 498
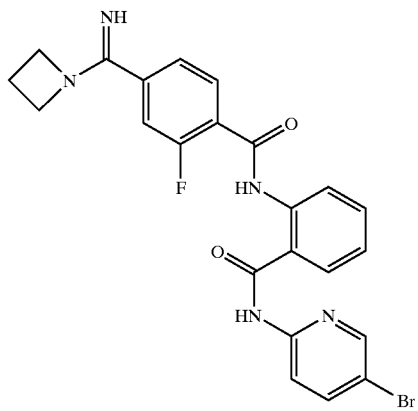
Example 256
MS(M + H):
496, 498
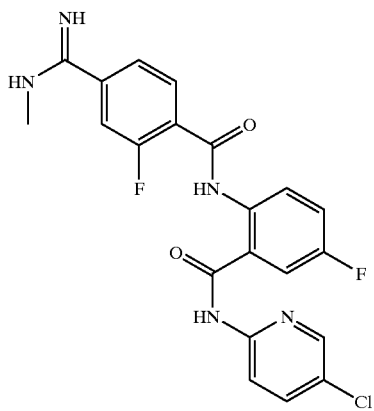
Example 257
MS(M + H):
444, 446

195

-continued

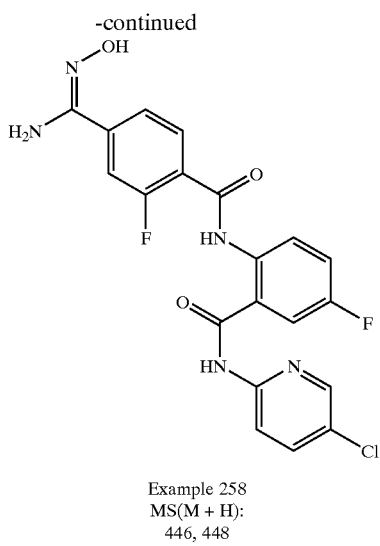

Example 258
MS(M + H):
446, 448

Example 259

N-{2-[N-(5-bromo(2-pyridyl))carbamoyl]-4,5-dimethoxyphenyl}4-cyanophenyl)carboxamide

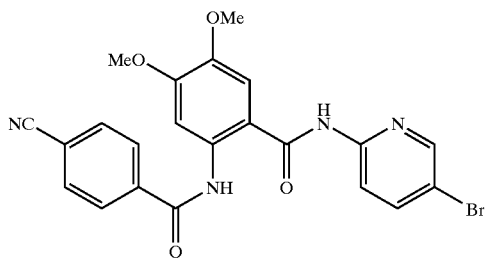

To a solution of 4,5-dimethoxy-2-nitrobenzoic acid (2.2 gm, 10 mmol) and 2-amino-5-bromopyridine (2.4 gm, 14 mmol) in anhydrous pyridine (50 mL) at 0° C. was added POCl$_3$ (1.9 mL, 20 mmol). After stirring at room temperature for 30 min, the reaction was complete. The mixture was concentrated and diluted with EtOAc (200 mL). The organic solution was washed with brine, dried and evaporated to give intermediate compound 1 (3.0 gm, 80%). MS found for C$_{14}$H$_{12}$BrN$_3$O$_5$ (M+H)$^+$: 382.00, 383.95.

A mixture of intermediate compound 1 (320 mg, 0.83 mmol) and SnCl$_2$.2H$_2$O (900 mg, 4.0 mmol) in EtOAc (10 mL) was refluxed for 1 hour. Reduction completed. The solid was filtered through a celite bed. The filtrate was diluted with EtOAc (50 mL), and the red solution was washed with 1N aq. NaOH solution (×3) and brine, dried and evaporated to give intermediate compound 2 (230 mg, 78%). MS found for C$_{14}$H$_{14}$BrN$_3$O$_3$ (M+H)$^+$: 352.00, 354.05.

To a solution of intermediate compound 2 (200 mg, 0.57 mmol) in a mixture of pyridine (3 mL) and DCM (10 mL) was added 4-cyanobenzoyl chloride (140 mg, 0.85 mmol). Precipitate formed immediately and the reaction was complete. The solid was collected by filtration and washed with DCM. After drying in vacco, the titled compound was obtained as a yellow solid in 70% yield (190 mg). MS found for C$_{22}$H$_{17}$BrN$_4$O$_4$ (M+H)$^+$: 481.00, 483.00.

196

Example 260

(4,5-dimethoxy-2-{[4-(1-methyl(2-imidazolin-2-yl))phenyl]carbonylamino}phenyl)-N-(5-bromo(2-pyridyl))carboxamide

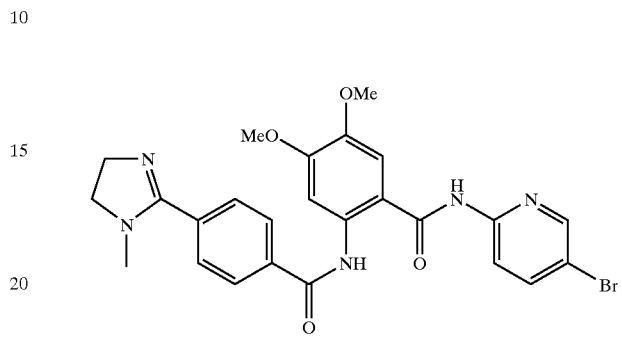

To a solution of compound obtained in Example 259 (100 mg, 0.20 mmol) in 10% Et$_3$N/pyridine (10 mL) at 0° C. was bubbled dry H$_2$S gas to saturation. The mixture was stirred at ambient temperatures overnight, and the conversion was complete. The solvent was removed to dryness, and the residue was suspended in anhydrous acetone (10 mL), followed by addition of MeI (1 mL). The reaction mixture was refluxed for 1 hour. The solvent was removed by rotary evaporation. To the residue was added anhydrous MeOH (10 mL) and N-methylethylenediamine (1 mL). The resulting mixture was refluxed for 1 hour, concentrated and subjected to RP-HPLC purification to give the title compound. MS found for C$_{25}$H$_{24}$BrN$_5$O$_4$ (M+H)$^+$: 538.1, 540.1.

Example 261

4-(N-{2-[N-(5-bromo(2-pyridyl))carbamoyl]-4,5-dimethoxyphenyl}carbamoyl)benzenecarboxamidine

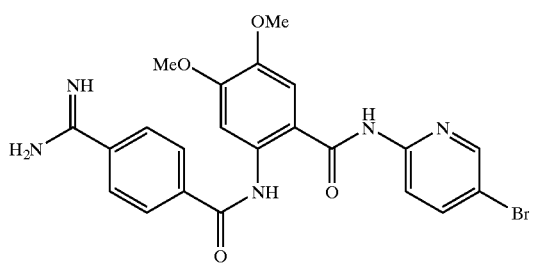

The title compound was obtained from the Example 259 compound according to the procedure described in Example 2. MS found for C$_{22}$H$_{20}$BrN$_5$O$_4$ (M+H)$^+$: 498.1, 500.0.

Example 262

N-(5-chloro(2-pyridyl)){2-[(4-cyanophenyl)carbonylamino]-5-methoxyphenyl}carboxamide

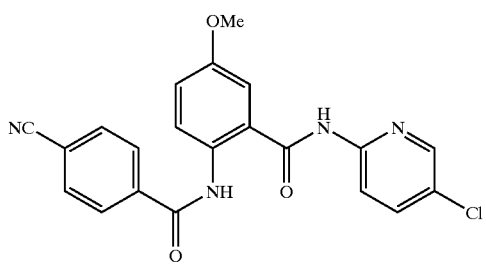

This compound was obtained from 5-methoxy-2-nitrobenzoic acid and 2-amino-5-chloro-pyridine according to the procedure described in Example 259. MS found for $C_{21}H_{15}ClN_4O_3$ (M+H)$^+$: 407.0.

Example 263

N-(5-chloro(2-pyridyl))-(5-methoxy-2-{[4-(1-methyl(2-imidazolin-2-yl))phenyl]-carbonylamino}phenyl)carboxamide

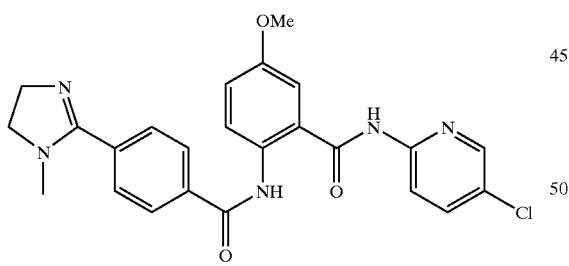

To the suspension of the compound Example 262 (100 mg) in a mixture of anhydrous MeOH (5 mL) and EtOAc (5 mL) at 0° C. was bubbled anhydrous HCl gas to saturation. The mixture was stirred at ambient temperatures overnight. The conversion completed. The solvent was evaporated to dryness. The residue was dissolved in anhydrous MeOH (10 mL), followed by addition of N-methylethylenediamine (1 mL). The resulting mixture was refluxed for 1 hour, concentrated and subjected to RP-HPLC purification to give the title compound 263. MS found for $C_{24}H_{22}ClN_5O_3$ (M+H)$^+$: 464.

Example 264

4-(N-{2-[N-(5-chloro(2-pyridyl))carbamoyl]-4-methoxyphenyl}carbamoyl)benzene-carboxamidine

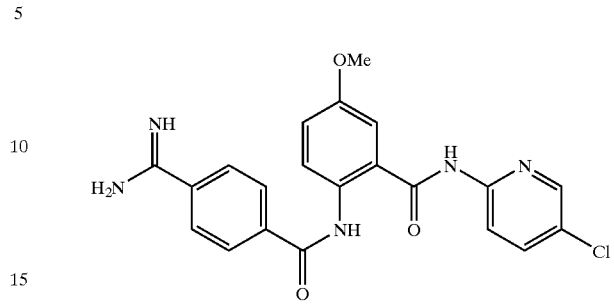

The title compound was obtained from the Example 262 compound by procedures according to Example 262. MS found for $C_{21}H_{18}ClN_5O_3$ (M+H)$^+$: 424.

Example 265

N-(5-chloro(2-pyridyl))[2-({4-[imino(methylamino)methyl]phenyl}carbonylamino)-5-methoxyphenyl]carboxamide

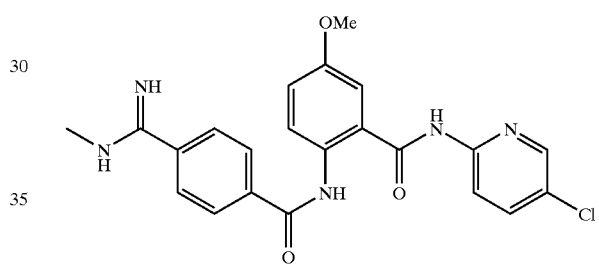

The title compound was obtained from N-(5-chloro(2-pyridyl)){(2-[(4-cyanophenyl)carbonylamino]-5-methoxyphenyl}carboxamide and methylamine according to the procedure described in Example 262. MS found for $C_{22}H_{20}ClN_5O_3$ (M+H)$^+$: 438.

Example 266

[2-({4-[(dimethylamino)iminomethyl]phenyl}carbonylamino)-5-methoxyphenyl]-N-(5-chloro(2-pyridyl))carboxamide

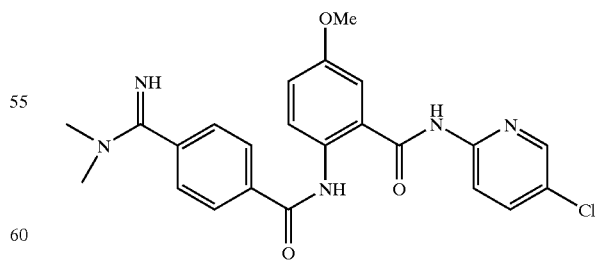

The title compound was obtained from N-(5-chloro(2-pyridyl)){2-[(4-cyanophenyl)carbonylamino]-5-methoxyphenyl}carboxamide and dimethylamine according to the procedure described in example 263. MS found for $C_{23}H_{22}ClN_5O_3$ (M+H)$^+$: 452.

Example 267

N-(5-chloro(2-pyridyl))(2-{[4-(iminopyrrolidinylmethyl)phenyl]carbonylamino}-5-methoxyphenyl)carboxamide

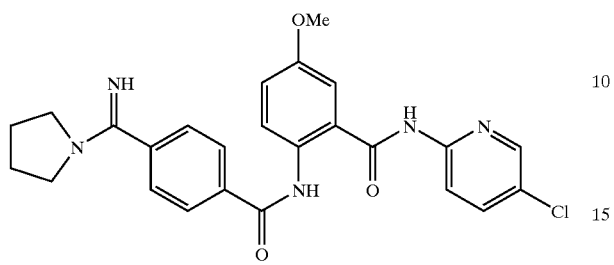

The title compound was obtained from N-(5-chloro(2-pyridyl)){2-[(4-cyanophenyl)carbonylamino]-5-methoxyphenyl}carboxamide and pyrrolidine according to the procedure described in Example 263. MS found for $C_{25}H_{24}ClN_5O_3$ (M+H)$^+$: 478.

Example 268

N-(5-chloro(2-pyridyl))(2-{[4-(iminopiperidylmethyl)phenyl]carbonylamino}-5-methoxyphenyl)carboxamide

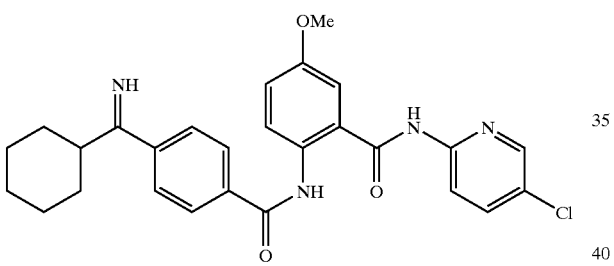

The title compound was obtained from N-(5-chloro(2-pyridyl)){2-[(4-cyanophenyl)carbonylamino]-5-methoxyphenyl}carboxamide and piperidine according to the procedure described in Example 263. MS found for $C_{26}H_{26}ClN_5O_3$ (M+H)$^+$: 492.

Example 269

N-(5-chloro(2-pyridyl))(2-{[4-(iminomorpholin-4-ylmethyl)phenyl]carbonylamin}-5-methoxyphenyl)carboxamide

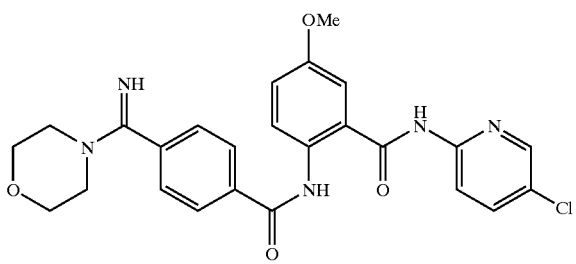

The title compound was obtained from N-(5-chloro(2-pyridyl)){(2-[(4-cyanophenyl)carbonylamino]-5-methoxyphenyl}carboxamide and morpholine according to the procedure described in Example 263. MS found for $C_{25}H_{24}ClN_5O_4$ (M+H)$^+$: 494.1.

Example 270

N-(5-chloro(2-pyridyl)(2-{[4-(imino-1,4-thiazaperhydroin-4-ylmethyl)phenyl]carbonylamino}-5-methoxyphenyl)carboxamide

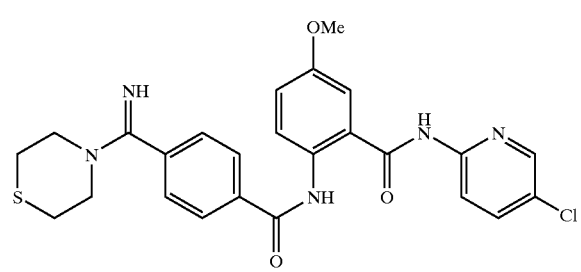

The title compound was obtained from N-(5-chloro(2-pyridyl)){2-[(4-cyanophenyl)carbonylamino]-5-methoxyphenyl}carboxamide and thiomorpholine according to the procedure described in Example 263. MS found for $C_{25}H_{24}ClN_5O_3S$ (M+H)$^+$: 510.

Example 271

(2-{[4-(amino(hydroxyimino)methyl)phenyl]carbonylamino}-5-methoxyphenyl)-N-(5-chloro(2-pyridyl))carboxamide

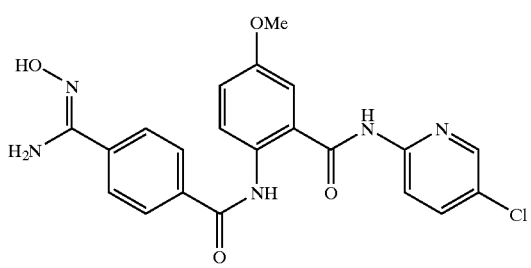

To a suspension of compound N-(5-chloro(2-pyridyl)){2-[(4-cyanophenyl)carbonylamino]-5-methoxyphenyl}carboxamide (150 mg) in EtOH (10 mL) was added hydroxyamine hydrochloride (80 mg) and Et$_3$N (200 μL). The mixture was stirred at 60° C. overnight and the reaction was complete. The solvent was evaporated and the crude material was purified by RP-HPLC to give the title compound. MS found for $C_{21}H_{18}ClN_5O_4$ (M+H)$^+$: 440.1.

Example 272

N-(5-bromo(2-pyridyl)){2-[(4-cyanophenyl)carbonylamino]5-methoxyphenyl}carboxamide

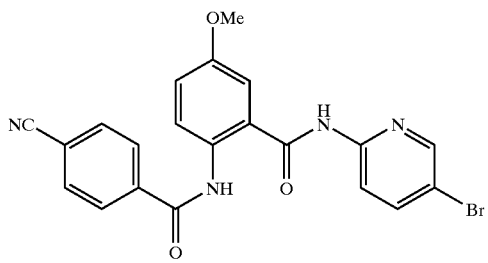

This compound was obtained from 5-methoxy-2-nitrobenzoic acid and 2-amino-5-bromo-pyridine according to the procedure described in Example 259. MS found for $C_{21}H_{15}BrN_4O_3$ (M+H)$^+$: 451.00, 453.00.

Example 273

N-(5-bromo(2-pyridyl))(5-methoxy-2-{[4-(1-methyl(2-imidazolin-2-yl))phenyl]carbonylamino}phenyl)carboxamide

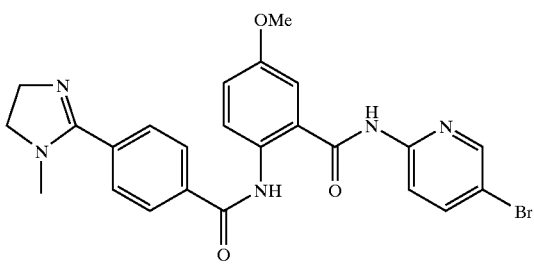

The title compound was obtained according to the procedure described Example 263. MS found for $C_{24}H_{22}BrN_5O_3$ (M+H)$^+$: 508, 510.

Example 274

4-(N-{2-[N-(5-bromo(2-pyridyl))carbamoyl]-4-methoxyphenyl}carbamoyl)benzenecarboxamidine

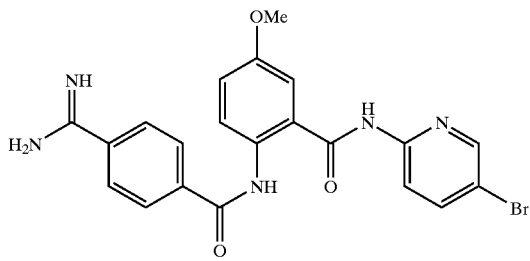

The title compound was obtained according to the procedure described in Example 263. MS found for $C_{21}H_{18}BrN_5O_3$ (M+H)$^+$: 468.05, 470.00.

Example 275

N-(5-bromo(2-pyridyl))[2-({4-[imino(methylamino)methyl]phenyl}carbonylamino)-5-methoxyphenyl]carboxamide

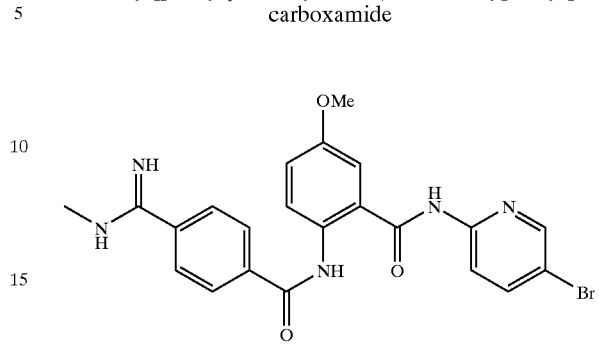

The title compound was obtained according to the procedure described in Example 263. MS found for $C_{22}H_{20}BrN_5O_3$ (M+H)$^+$: 482, 484.

Example 276

[2-({4-[(dimethylamino)iminomethyl]phenyl}carbonylamino)-5-methoxyphenyl]-N-(5-bromo(2-pyridyl))carboxamide

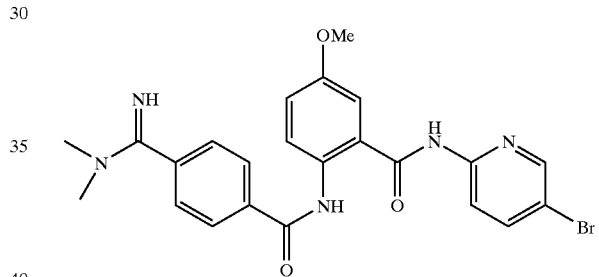

The title compound was obtained according to the procedure described in Example 263. MS found for $C_{23}H_{22}BrN_5O_3$ (M+H)$^+$: 496.1, 498.1.

Example 277

N-(5-chloro(2-pyridyo)(2-{[4-(iminopyrrolidinylmethyl)phenyl]carbonylamino}-5-methoxyphenyl)carboxamide

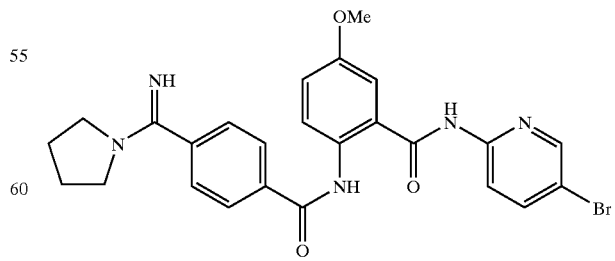

The title compound was obtained according to the procedure described in Example 263. MS found for $C_{25}H_{24}BrN_5O_3$ (M+H)$^+$: 522, 524.

Example 278

N-(N-(5-bromo(2-pyridyl))(2-{[4-(iminopiperidylmethyl)phenyl]carbonylamino)-}5-methoxyphenyl)carboxamide

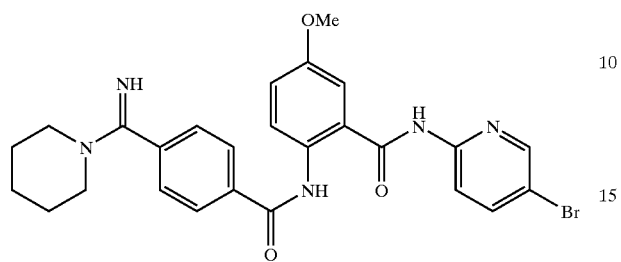

The title compound was obtained according to the procedure described in Examnple 263. MS found for $C_{26}H_{26}BrN_5O_3$ (M+H)$^+$: 536.1, 538.1.

Example 279

N-(5-bromo(2-pyridyl))(2-{[4-(iminomorpholin-4-ylmethyl)phenyl]carbonylamino}-5-methoxyphenyl)carboxamide

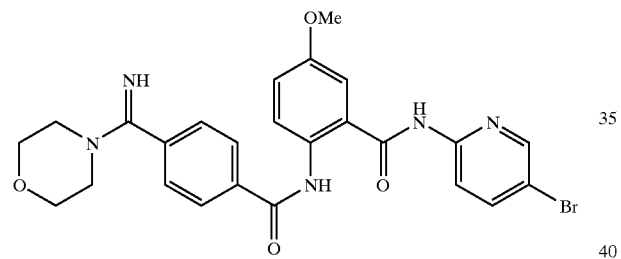

The title compound was obtained according to the procedure described in Example 263. MS found for $C_{25}H_{24}BrN_5O_4$ (M+H)$^+$: 538.1, 540.1.

Example 280

N-(5-bromo(2-pyridyl))(2-{[4-(imino-1,4-thiazaperhydroin-4-ylmethyl)phenyl]carbonylamino}-5-methoxyphenyl)carboxamide

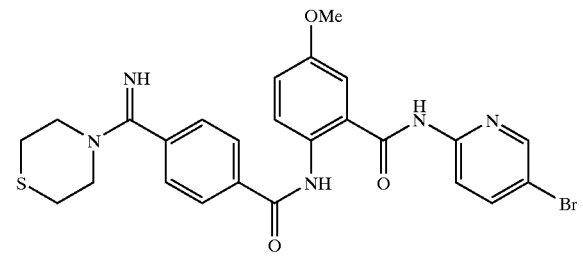

The title compound was obtained according to the procedure described in Example 263. MS found for $C_{25}H_{24}BrN_5O_3S$ (M+H)$^+$: 554.1, 556.05.

Example 281

(2-{[4-(amino(hydroxyimino)methyl)phenyl]carbonylamino}-5-methoxyphenyl)-N-(5-bromo(2-pyridyl))carboxamide

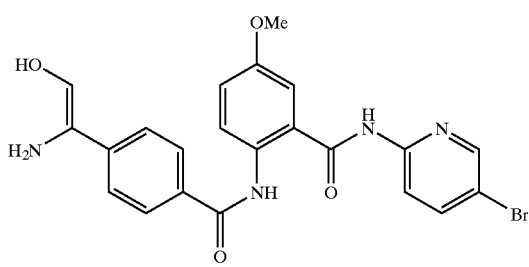

The title compound was obtained according to the procedure described in Example 270. MS found for $C_{21}H_{18}BrN_5O_4$ (M+H)$^+$: 484.1, 486.0.

Example 282

N-(chloro(2-pyridyl)){6-[(4-cyanophenyl)carbonylamino]-3-hydroxyphenyl}carboxamide

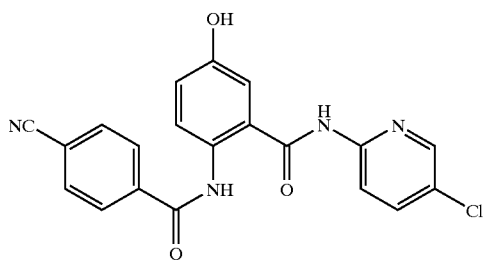

To a suspension of compound N-(5-chloro(2-pyridyl)){2-[(4-cyanophenyl)-carbonylamino]-5-methoxyphenyl}carboxamide (500 mg, 1.2 mmol) in DCM (100 mL) at −78° C. was added BBr$_3$ (2 mL). The mixture was stirred at ambient temperatures for 72 hours. The solid was collected by filtration and was washed by DCM and water, dried under vacuum. The filtrate was concentrated and extracted with EtOAc. The organic extract was washed with brine, dried and evaporated. The resulting solid was combined with the solid obtained from filtration to give the title compound. Total yield is 90% (430 mg). MS found for $C_{20}H_{13}ClN_4O_3$ (M+H)$^+$: 393.0.

Example 283 ethyl 2-{3-[N-(5-chloro(2-pyridyl))carbamoyl]-4-[(4-cyanophenyl)carbonylamino]-phenoxy}acetate

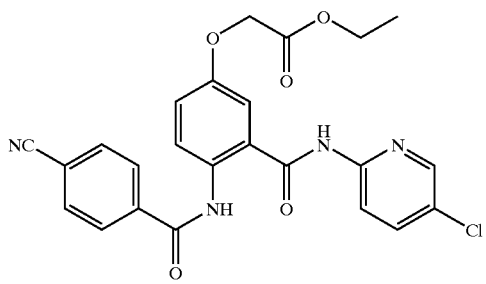

To a mixture of compound N-(5-chloro(2-pyridyl)){6-[(4-cyanophenyl)-carbonylamino]-3-hydroxyphenyl}carboxamide (50 mg, 0.13 mmol) and $Cs_2CO_3$ (83 mg, 0.25 mmol) in DMF (1 mL) at room temperature was added ethyl bromoacetate (15 μL, 0.13 mmol). The mixture was stirred for 1 hour before diluted with EtOAc (20 mL) and water (10 mL). The organic layer was washed with brine dried and evaporated to give 70 mg of the crude compound, which was used without farther purification. MS found for $C_{24}H_{19}ClN_4O_5$ $(M+H)^+$: 479.0.

Example 284 methyl 2-[4-({4-[(dimethylamino)iminomethyl]phenyl}carbonylamino)-3-[N-(5-chloro(2-pyridyl))carbamoyl]phenoxy]acetate

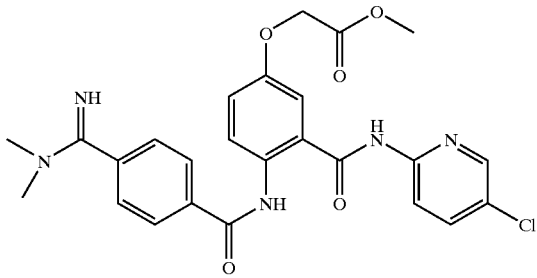

The title compound was obtained according to the procedure described Example 263. MS found for $C_{25}H_{24}ClN_5O_5$ $(M+H)^+$: 510.1.

Example 285

(6-{[4-(amino(hydroxyimino)methyl)phenyl]carbonylamino}-3-hydroxyphenyl)-N-(5-chloro(2-pyridyl))carboxamide

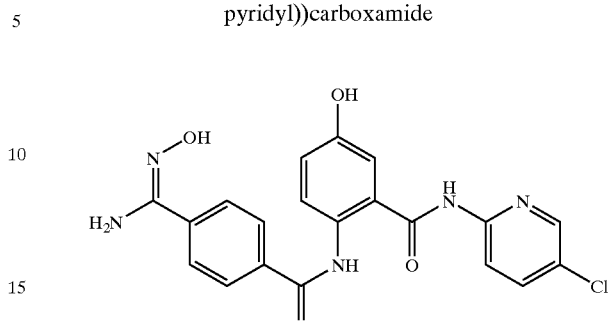

The title compound was obtained according to the procedure described in Example 270. MS found for $C_{20}H_{16}ClN_5O_4$ $(M+Na)^+$: 448.0.

Example 286

4-(N-{2-[N-(5-chloro(2-pyridyl))carbamoyl]-4-hydroxyphenyl}carbamoyl)benzenecarboxamidine

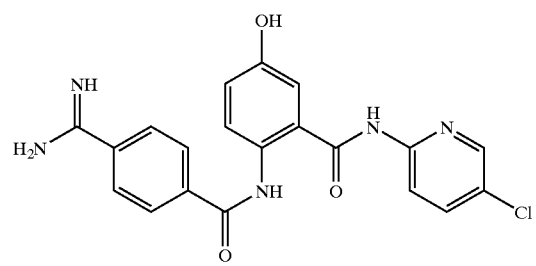

The title compound was obtained according to the procedure described in Example 282. MS found for $C_{20}H_{16}ClN_5O_3$ $(M+H)^+$: 410.1.

Example 287

4-(N-{2-[N-(5-chloro(2-pyridyl))carbamoyl]hydroxyphenyl}carbamoyl)benzenecarboxamidine

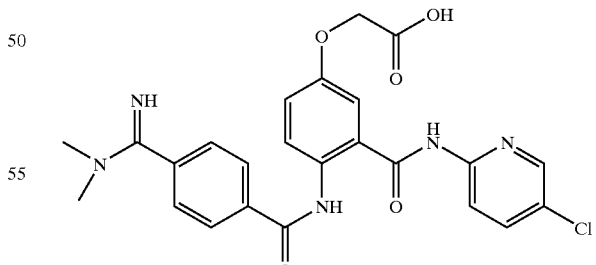

To a solution of Example 284 (10 mg) in MEOH (1 mL) was added 50 μL of 1N aq. LiOH solution. The mixture was stirred for 1 hour and purified by RP-HPLC to give the title compound. MS found for $C_{24}H_{22}ClNO_5$ $(M+H)^+$: 496.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound of the following formula:

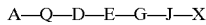

wherein:

A is $N(R^1,R^2)$—$C(=NR^3)$—, wherein;

$R^1$, $R^2$ and $R^3$ are independently selected from the group consisting of:

H, —$OR^5$, —$N(-R^5, -R^6)$, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$; or $R^1$ and $R^2$, or $R^2$ and $R^3$ taken together can form a 3–8 membered cycloalkyl or a heterocyclic ring system, wherein the heterocyclic ring system may have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, $C_1$–$C_4$-alkyl, —CN —$C_{1-4}$ alkyl, —$C_{2-6}$alkenyl, —$C_{2-6}$alkynyl, —$C_{3-8}$-cycloalkyl, —$C_{0-4}$alkyl$C_{3-8}$cycloalkyl and —$NO_2$;

$R^5$ and $R^6$ are independently selected from the group consisting of:

H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$ alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$ cycloalkyl, —CN, and —$NO_2$; or $R^5$ and $R^6$ taken together can form a 3–8 membered cycloalkyl or a heterocyclic ring system, wherein the heterocyclic ring system may have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, $C_1$–$C_4$-alkyl, —CN —$C_{1-4}$alkyl, —$C_{2-6}$alkenyl, —$C_{2-6}$alkynyl, —$C_{3-8}$-cycloalkyl, —$C_{0-4}$alkyl$C_{3-8}$cycloalkyl and —$NO_2$;

Q is a direct link;

D is phenylene, wherein Q and E are attached to D to form a 1,4-disubstituted phenylene ring, and wherein D is further substituted with 0–2 $R^{1a}$ substituents, wherein $R^{1a}$ is selected from:

halo, —$C_{1-4}$alkyl, —$C_{2-6}$alkenyl, —$C_{2-6}$alkynyl, —$C_{3-8}$ cycloalkyl, —$C_{0-4}$alkyl$C_{3-8}$cycloalkyl, —CN, —$NO_2$, —$(CH_2)_n NR^{2a}R^{3a}$, —$(CH_2)_n CO_2R^{2a}$, —$(CH_2)_n CONR^{2a}R^{3a}$, —$SO_2NR^{2a}R^{3a}$, —$SO_2R^{2a}$, —$CF_3$, —$OR^{2a}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, —$C_{1-4}$alkyl, —$C_{2-6}$alkenyl, —$C_{2-6}$alknyl, —$C_{3-8}$-cycloalkyl, —$C_{0-4}$alkyl$C_{3-8}$cycloalkyl, —CN and —$NO_2$;

$R^{2a}$ and $R^{3a}$ are independently selected from the group consisting of:

H, —$C_{1-4}$alkyl, —$C_{2-6}$alkenyl, —$C_{2-6}$alkynyl, —$C_{3-8}$ cycloalkyl, —$C_{0-4}$alkyl$C_{3-8}$cycloalkyl, —$C_{0-4}$ alkylphenyl and —$C_{0-4}$alkylnaphthyl, wherein from 1–4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN and —$NO_2$;

n is an integer of 0–2;

E is —$C(=O)$—$N(-R^8)$—, wherein $R^8$ is a member selected from the group consisting of:

H; —$C_{1-4}$-alkyl; —$C_{0-4}$-alkylaryl; —$C_{0-4}$-alkylheteroaryl; —$C_{1-4}$-alkyl-$C(=O)$—OH, —$C_{1-4}$-alkyl-$C(=O)$—O—$C_{1-4}$-alkyl, and —$C_{1-4}$-alkyl-$C(=O)$—$N(R^{2b}, -R^{3b})$;

$R^{2b}$ and $R^{3b}$ are each a member independently selected from the group consisting of:

H, —$C_{1-4}$alkyl, —$C_{0-4}$-alkyl-aryl; —$C_{0-4}$-alkyl-heterocyclic group, and $R^{2b}$ and $R^{3b}$ together with the N atom to which they are attached can form a 5–8 membered heterocyclic ring containing 1–4 heteroatoms selected from N, O and S, wherein the heterocyclic ring may be substituted with 0–2 $R^{1c}$ groups;

$R^{1c}$ is a member selected from the group consisting of:

Halo; —$C_{1-4}$-alkyl; —CN, —$NO_2$; —$C(=O)$—$N(-R^{2c}, -R^{3c})$; —$C(=O)$—$OR^{2c}$; —$(CH_2)_q$—$N(-R^{2c}, -R^{3c})$; —$SO_2$—$N(-R^{2c}, -R^{3c})$; —$SO_2R^{2c}$; —$CF_3$ and —$(CH_2)_q$—$OR^{2c}$;

$R^{2c}$ and $R^{3c}$ are each independently a member selected from the group consisting of:

H; —$C_{1-4}$-alkyl and —$C_{1-4}$-alkyl-aryl;

q is an integer of 0–2;

G is phenylene group, wherein E and J are attached to G to form a 1,2-disubstituted phenylene group; and wherein G is further substituted with 0–4 $R^{1d}$ groups, wherein;

$R^{1d}$ is a member selected from the group consisting of:

H, halo; $C_{1-6}$alkyl, carbocylic aryl, —CN; —$NO_2$; —$(CH_2)_{0-6}$—$NR^{2d}R^{3d}$; —$SO_2NR^{2d}R^{3d}$; —$SO_2R^{2d}$; —$CF_3$; —$(CH_2)_{0-6}$—$OR^{2d}$; —O—$(CH_2)_{1-6}OR^{2d}$; —O—$(CH_2)_{1-6}$—$C(=O)$—O—$R^{2d}$; —O—$(CH_2)_{1-6}$—$C(=O)$—$N(R^{2d},R^{3d})$; —$N(R^{5a})$—$(CH_2)_{1-6}$—$OR^{2d}$; —$N(R^{5a})$—$(CH_2)_{1-6}$—$N(R^{2d},R^{3d})$; —$C(=O)$—$N(R^{2d},R^{3d})$; —$N(R^{5a})$—$(CH_2)_{1-6}$—$C(=O)$—$N(R^{2d},R^{3d})$; —$N(-(CH_2)_{1-6}$—$OR^{2d})_2$; —$N(R^{5a})$—$(CH_2)_{1-6}$—$OR^{2d}$; —$N(R^{5a})$—$C(=O)$—$R^{2d}$; —$N(R^{5a})$—$SO_2$—$R^{2d}$; —$(CH_2)_{0-6}$—$C(=O)$—O—$R^{2d}$; —$(CH_2)_{0-6}$—$C(=O)$—$N(R^{2d},R^{3d})$; —$(CH_2)_{0-6}$—$C(=NR^{2d})$—$N(R^{3d},R^{4d})$; —$(CH_2)_{0-6}$—$N(R^{5a})C(=NR^{2d})$—$N(R^{3d},R^{4d})$; a —$(CH_2)_{0-6}$—$N(R^{3d})C_{5-6}$ membered saturated, partially unsaturated or aromatic heterocyclic ring containing 1–4 heteroatoms selected from N, O and S, and a —(CH$_2$)$_{0-6}$-5–6 membered saturated, partially unsaturated or aromatic heterocyclic ring containing 1–4 heteroatoms selected from N, O and S;

R$^{5a}$, R$^{2d}$, R$^{3d}$ and R$^{4d}$ are each independently a member selected from the group consisting of:

H, C$_{1-6}$-alkyl and C$_{1-6}$-alkylaryl, —CN; —NO$_2$; carbocyclic aryl, —CN; —NO$_2$; or R$^{2d}$ and R$^{3d}$ taken together with the N atoms they are independently attached form a 5–7 membered saturated, partially unsaturated or aromatic heterocyclic ring; or R$^{3d}$ and R$^{4d}$ taken together with the N atom to which they are attached form a 5–8 membered saturated, partially unsaturated or aromatic heterocyclic ring containing 1–4 heteroatoms selected from N, O and S;

J is —C(=O)—N(—R$^9$)—, wherein

R$^9$ is a member selected from the group consisting of:

H; —C$_{1-4}$-alkyl; —C$_{0-4}$-alkyl-carbocyclic aryl; —(CH$_2$)$_{0-4}$-5–6 membered saturated, partially unsaturated or aromatic heterocyclic ring containing 1–4 heteroatoms selected from N, O and S; —(CH$_2$)$_{1-6}$—C(=O)—O—C$_{1-4}$-alkyl; and —(CH$_2$)$_{1-6}$—C(=O)—N(R$^{6a}$,R$^{6b}$);

R$^{6a}$ and R$^{6b}$ are each a member independently selected from the group consisting of:

H and —C$_{1-6}$-alkyl;

X is a phenyl substituted with 0–3 R$^{1e}$ groups, wherein R$^{1e}$ is a member independently selected from the group consisting of:

Halo; CF$_3$; —C$_{1-4}$-alkyl; carbocyclic aryl; —C$_{0-2}$-alkyl-CN; —O—R$^{2e}$; —C$_{0-2}$-alkyl-C(=O)—O—R$^{2e}$; —C$_{0-2}$-alkyl-C(=O)—N(R$^{2e}$,R$^{3e}$); —C$_{0-2}$-alkyl-NO$_2$; —C$_{0-2}$-alkyl-N(R$^{2e}$,R$^{3e}$; —C$_{0-2}$-alkyl-SO$_2$-N(R$^{2e}$,R$^{3e}$); —C$_{0-2}$-alkyl-SO$_2$—R$^{2e}$; trihaloalkyl; —O—C$_{0-2}$-alkyl-O—R$^{2e}$; —C$_{0-2}$-alkyl-O—R$^{2e}$; —O—C$_{1-4}$-alkyl-C(=O)—N(R$^{2e}$, R$^{3e}$); —O—C$_{1-4}$-alkyl-C(=O)—O—R$^{2e}$; —C$_{0-2}$-alkyl-N(R$^{2e}$)—C(=O)—R$^{3e}$; —C$_{0-2}$-alkyl-N(—R$^{2e}$)—SO$_2$—R$^{3e}$; —CH$_2$—N(R$^{2e}$)—C(=O)—R$^{3e}$; —CH$_2$—N(R$^{2e}$)—SO$_2$—R$^{3e}$; —(CH$_2$)$_{0-6}$—NR$^{2e}$R$^{3e}$; —C(=O)—N(R$^{2e}$,R$^{3e}$); —N(—CH$_2$)$_{1-6}$—OR$^{2e}$)$_2$; —N(R$^{10}$)—(CH$_2$)$_{1-6}$—OR$^{2e}$; —N(R$^{10}$)—C(=O)—R$^{2e}$; —N(R$^{10}$)—SO$_2$—R$^{2e}$; —C(=N(R$^{10}$))—N(R$^{2e}$,R$^{3a}$); and a —(CH$_2$)$_{0-6}$-5–6 membered saturated, partially unsaturated or aromatic heterocyclic ring containing 1–4 heteroatoms selected from N, O and S;

R$^{10}$, R$^{2e}$ and R$^{3e}$ are each independently a member selected from the group consisting of:

H; —C$_{1-4}$-alkyl; —C$_{0-2}$-alkyl-O—R$^{1g}$; —C$_{0-2}$-alkyl-N(—R$^{1g}$, —R$^{2g}$); —C$_{1-4}$-alkyl-carbocyclic aryl; —C$_{1-4}$-alkyl-heterocyclic; and R$^{10}$ and R$^{2e}$, or R$^{2e}$ and R$^{3e}$ together with the N atom to which they are attached can form 5–8 membered heterocyclic ring containing 1–4 heteroatoms selected from N, O and S which can be substituted with 0–2 R$^{1g}$ groups;

R$^{1g}$ and R$^{2g}$ are independently a member selected from the group of:

H; halo; —C$_{1-4}$-alkyl, a carbocyclic aryl group; a saturated, partially unsaturated or aromatic heterocyclic group; —CN; —C(=O)—N(R$^{3g}$)R$^{4g}$; —C(=O)—OR$^{3g}$; —NO$_2$; —(CH$_2$)$_p$—NR$^{3g}$R$^{4g}$; —SO$_2$NR$^{3g}$R$^{4g}$; —SO$_2$R$^{3g}$; —CF$_3$; and —(CH$_2$)$_p$OR$^{3g}$;

p is an integer of 0–2;

R$^{3g}$ and R$^{4g}$ are each independently selected from the group consisting of:

H; C$_{1-4}$-alkyl and —C$_{0-4}$-alkyl-carbocyclic aryl;

and all pharmaceutically acceptable isomers, salts, hydrates, solvates and prodrug derivatives thereof.

2. A compound of claim 1, wherein:

E is —C(=O)—NH—; and

J is —C(=O)—NH—.

3. A pharmaceutical composition for preventing or treating a condition in a mammal characterized by undesired thrombosis comprising a pharmaceutically acceptable carrier and a pharmaceutically effective amount of a compound of claim 1.

4. A method for preventing or treating a condition in a mammal characterized by undesired thrombosis comprising administering to said mammal a therapeutically effective amount of a compound of claim 1.

5. The method of claim 4, wherein the condition is selected from the group consisting of:

acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation, and thrombotic complications associated with the fitting of prosthetic devices.

6. A method for inhibiting the coagulation of biological samples, comprising the step of administering a compound of claim 1.

7. A pharmaceutical composition for preventing or treating a condition in a mammal characterized by undesired thrombosis comprising a pharmaceutically acceptable carrier and a pharmaceutically effective amount of a compound of claim 2.

8. A method for preventing or treating a condition in a mammal characterized by undesired thrombosis comprising administering to said mammal a therapeutically effective amount of a compound of claim 2.

9. The method of claim 8, wherein the condition is selected from the group consisting of:

acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instumentation, and thrombotic complications associated with the fitting of prosthetic devices.

10. A method for inhibiting the coagulation of biological samples, comprising the step of administering a compound of claim 2.

* * * * *